United States Patent
Nikolaev et al.

(10) Patent No.: US 8,889,425 B2
(45) Date of Patent: Nov. 18, 2014

(54) MEANS AND METHODS FOR THE DETERMINATION OF CAMP IN VITRO AND IN VIVO

(75) Inventors: Viacheslav Nikolaev, Würzburg (DE); Moritz Bünemann, Waldbüttelbrunn (DE); Martin J. Lohse, Würzburg (DE)

(73) Assignee: Bayerische Julius-Maximilians-Universität Würzburg, Würzberg (DE)

( * ) Notice: Subject to any disclaimer, the term of this patent is extended or adjusted under 35 U.S.C. 154(b) by 1615 days.

(21) Appl. No.: 10/580,027

(22) PCT Filed: Nov. 26, 2004

(86) PCT No.: PCT/EP2004/013449
§ 371 (c)(1),
(2), (4) Date: Jul. 26, 2006

(87) PCT Pub. No.: WO2005/052186
PCT Pub. Date: Jun. 9, 2005

(65) Prior Publication Data
US 2008/0286760 A1    Nov. 20, 2008

(30) Foreign Application Priority Data
Nov. 26, 2003   (EP) .................................. 03027311

(51) Int. Cl.
| | | |
|---|---|---|
| *G01N 33/533* | (2006.01) | |
| *G01N 33/52* | (2006.01) | |
| *A61K 49/00* | (2006.01) | |
| *C07K 19/00* | (2006.01) | |
| *C07K 14/47* | (2006.01) | |
| *C07K 14/435* | (2006.01) | |
| *C12Q 1/44* | (2006.01) | |
| *G01N 33/573* | (2006.01) | |
| *C12Q 1/527* | (2006.01) | |
| *G01N 33/542* | (2006.01) | |

(52) U.S. Cl.
CPC .......... *G01N 33/533* (2013.01); *G01N 2500/04* (2013.01); *C07K 14/4702* (2013.01); *G01N 2500/02* (2013.01); *C07K 2319/20* (2013.01); *C12Q 1/44* (2013.01); *G01N 33/5735* (2013.01); *C07K 14/43595* (2013.01); *C12Q 1/527* (2013.01); *A61K 49/0017* (2013.01); *G01N 33/542* (2013.01)
USPC ............... 436/501; 530/350; 424/9.6; 436/63

(58) Field of Classification Search
None
See application file for complete search history.

(56) References Cited

U.S. PATENT DOCUMENTS

| 6,573,059 B1 | 6/2003 | Reymond |
| 2002/0110890 A1 | 8/2002 | Reymond |
| 2004/0053328 A1 | 3/2004 | Matsuda et al. |

FOREIGN PATENT DOCUMENTS

| CA | 2419503 | 8/2001 |
| WO | WO 00/49183 A1 | 8/2000 |
| WO | WO 02/02630 A2 | 1/2002 |
| WO | WO 02/14373 A1 | 2/2002 |

OTHER PUBLICATIONS

Whisstock et al. Quaterly Reviews of Biophysics, 2003, "Prediction of protein function from protein sequence and structure", 36(3): 307-340.*
Chica et al. Semi-rational approaches to engineering enzyme activity: combining the benefits of directed evolution and rational design, Curr Opin Biotechnol. Aug. 2005;16(4):378-84. Review.*
Witkowski et al. Conversion of a beta-ketoacyl synthase to a malonyl decarboxylase by replacement of the active-site cysteine with glutamine, Biochemistry. Sep. 7, 1999;38(36):11643-50.*
Rehmann et al, Ligand-mediated activation of the cAMP-responsive guanine nucleotide exchange factor Epac, J. Biol. Chem., 2003, 278, 38548-56.*
Miyawaki et al., Fluorescent indicators for Ca2+ based on green fluorescent proteins and calmodulin, Nature, 1997, 388, 882-87.*
Porumb et al., A calmodulin-target peptide hybrid molecule with unique calcium-binding properties, Protein Eng., 1994, 7, 109-15.*
Ozaki et al., "cAMP-GEFII is a direct target of cAMP in regulated exocytosis," *Nature Cell Biology*, vol. 2, No. 11, pp. 805-811, Nov. 2000.
Pollok et al., "Using GFP in FRET-based applications," *Trends in Cell Biology*, vol. 9, pp. 57-60, Feb. 1999.
Rehmann et al., "Structure and regulation of the cAMP-binding domains of Epac2," *Nature Structural Biology*, vol. 10, No. 1, pp. 26-32, Dec. 9, 2002.
Zaccolo et al., "A genetically encoded, fluorescent indicator for cyclic AMP in living cells," *Nature Cell Biology*, vol. 2, No. 1, pp. 25-29, Jan. 2000.
Fagan et al., "Adenovirus encoded cyclic nucleotide-gated channels: a new methodology for monitoring cAMP in living cells," *FEBS Letters*, vol. 500, No. 1-2, pp. 85-90, Jun. 29, 2001.
Vinogradova, et al., "High Basal Protein Kinase A-Dependent Phosphorylation Drives Rhythmic Internal $Ca^{2+}$ Store Oscillations and Spontaneous Beating of Cardiac Pacemaker Cells", *Circulation Research*, Mar. 3, 2006, 98, pp. 505-514.

(Continued)

*Primary Examiner* — Rebecca Prouty
*Assistant Examiner* — Todd M Epstein
(74) *Attorney, Agent, or Firm* — Foley & Lardner LLP

(57) ABSTRACT

Described is a chimeric peptide, comprising, in order, (a) a first detectable label (b) a cAMP binding moiety having only one cAMP binding site and (c) a second detectable label least two detectable labels is describe. The chimeric peptide is useful for direct determination of cAMP concentration in vitro and/or in vivo. Also described are nucleic acids encoding the chimeric peptide, methods of making and modifying the chimeric peptide, a method for determining the cAMP concentration, and kits.

5 Claims, 14 Drawing Sheets

(56) References Cited

OTHER PUBLICATIONS

Figure 2:
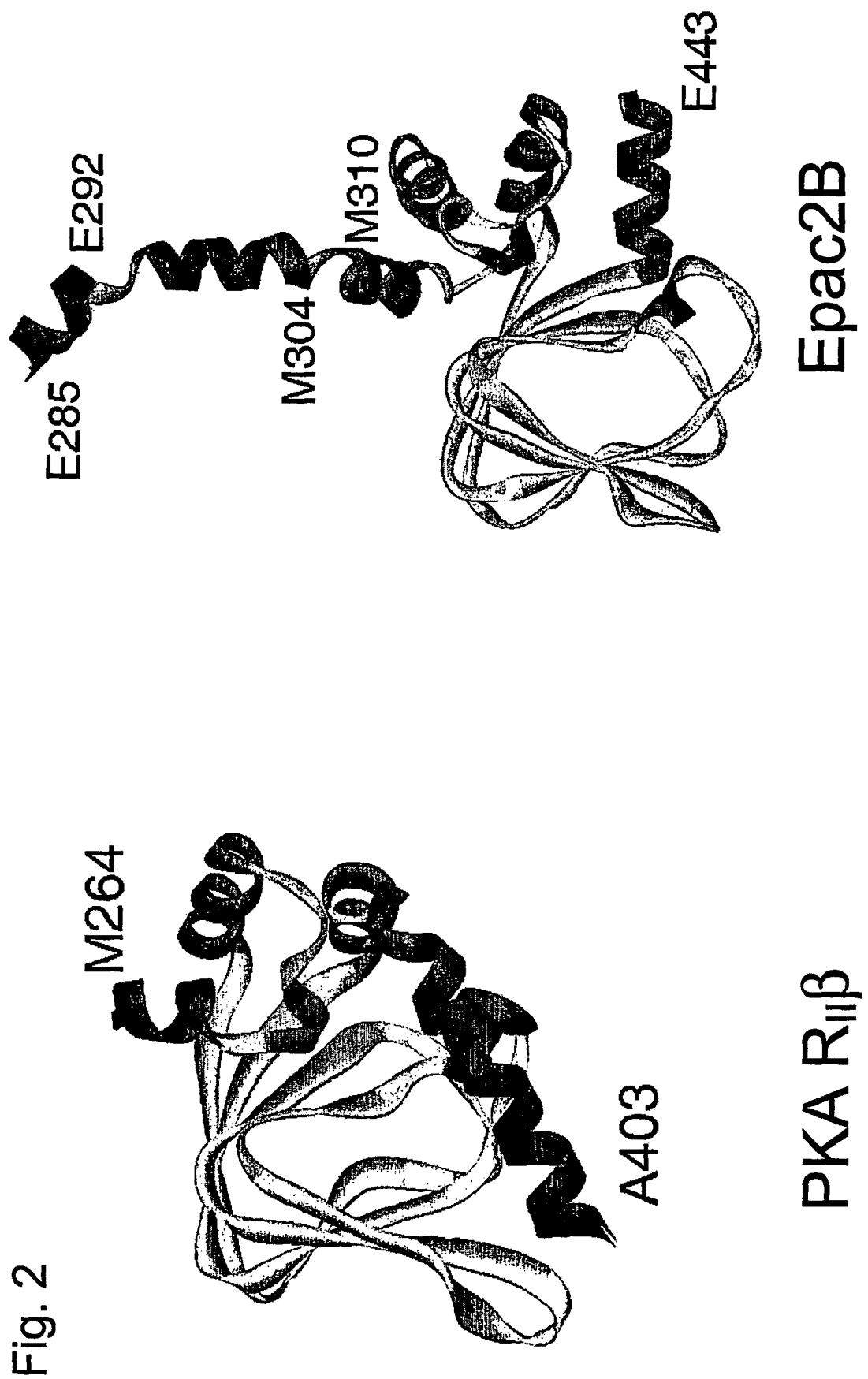

Hohl, et al., "Compartmentation of cAMP in Adult Canine Ventricular Myocytes Relation to Single-Cell Free Ca2+ Transients", *Circulation Research*, 1991, vol. 69, pp. 1369-1379.

The Notice of Reasons for Rejection (w/English Translation) received in the related Japanese Patent Application No. JP 2006-540398, dated Aug. 23, 2010. (3 pgs.).

Ponsioen, et al., "Detecting cAMP-induced Epac activation by fluorescence resonance energy transfer: Epac as a novel cAmP indicator", *EMBO Reports*, 2004, vol. 5, No. 12, pp. 1176-1180.

Polit, et al., "Steady-state and time-resolved fluorescence studies of conformational changes induced by cyclic AMP and DNA binding to cyclic AMP receptor protein from *Escherichia coli*", *Eur. J. Biochem*, 2003, vol. 270, pp. 1413-1423.

Zhang, et al., "Genetically encoded reporters of protein kinase A activity reveal impact of substrate tethering", *PNAS*, 2001, vol. 98, No. 26, pp. 14997-15002.

DiPilato, et al., "Fluorescent indicators of cAMP and Epac activation reveal differential dynamics of cAMP signatling within discrete subcellular compartments", *PNAS*, 2004, vol. 101, No. 47, pp. 16513-16518.

* cited by examiner

PKA constructs  Fig. 1
FRET signal
EcoRI — HindIII
—
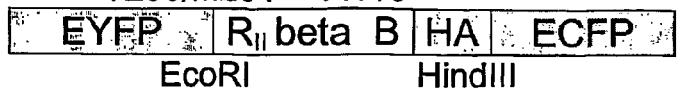
EcoRI — HindIII
+
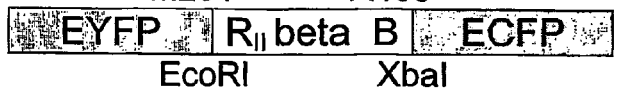
EcoRI — XbaI
+++
NheI   EcoRI   XbaI
++
Epac constructs
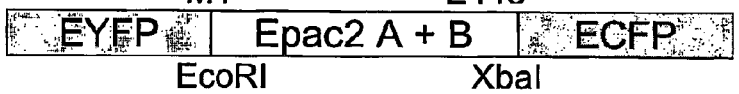
EcoRI — XbaI
—
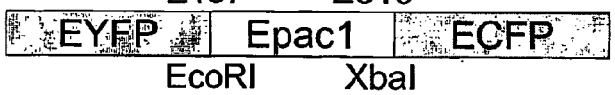
EcoRI — XbaI
+++
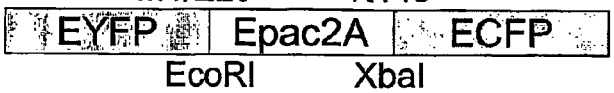
EcoRI — XbaI
—
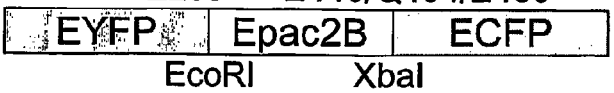
EcoRI — XbaI
+++/+/+
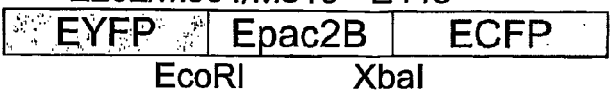
EcoRI — XbaI
+++/+++/+++
NheI   EcoRI   XbaI
+++/+

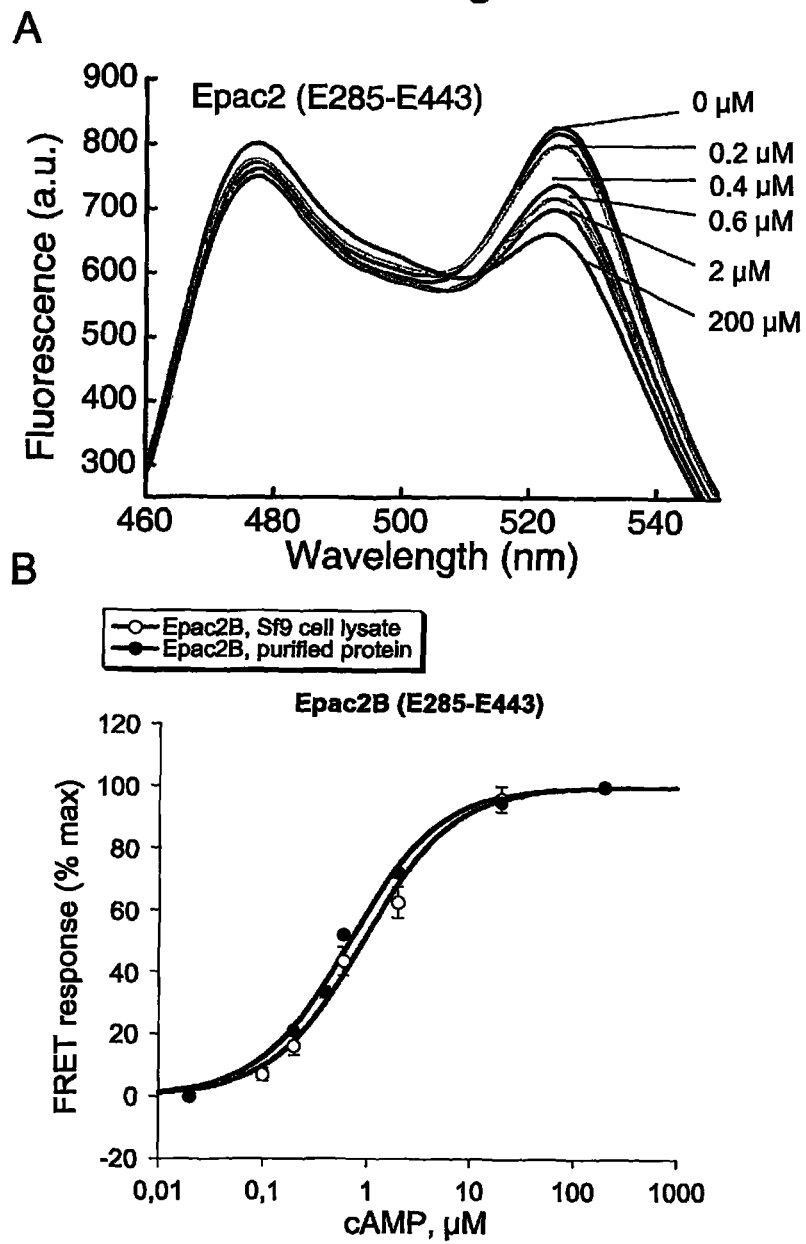

Fig. 8
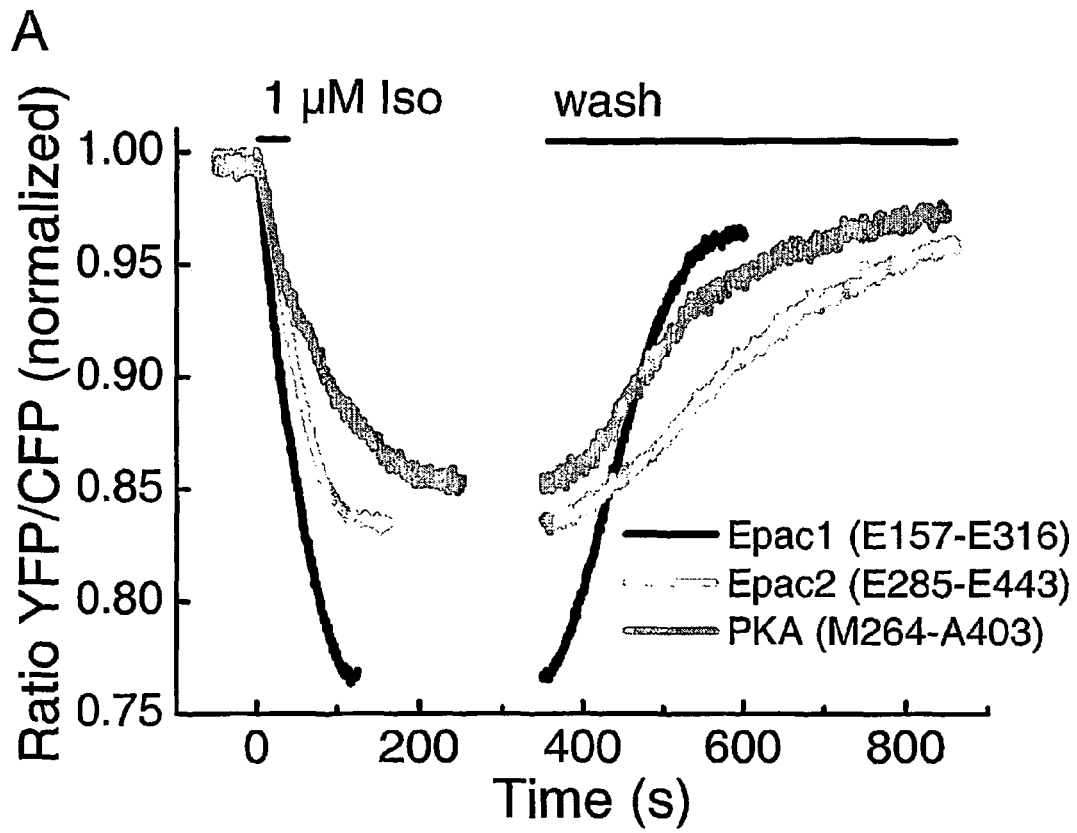
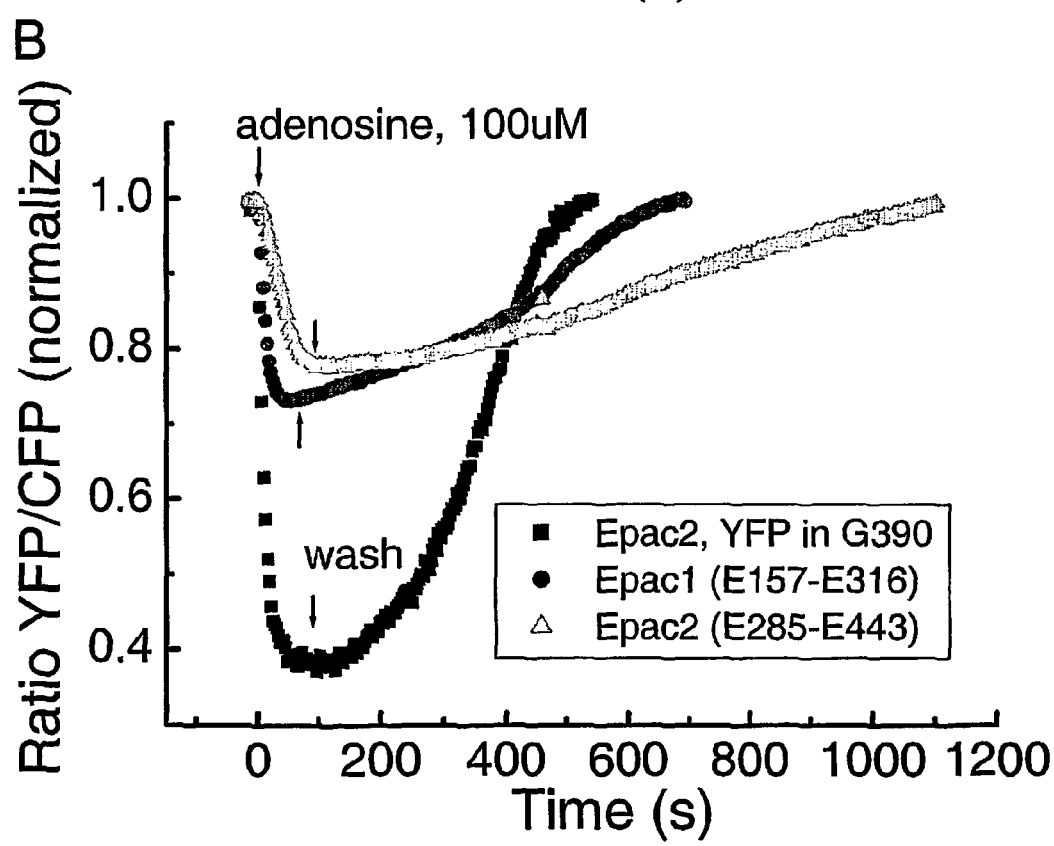

Fig. 12
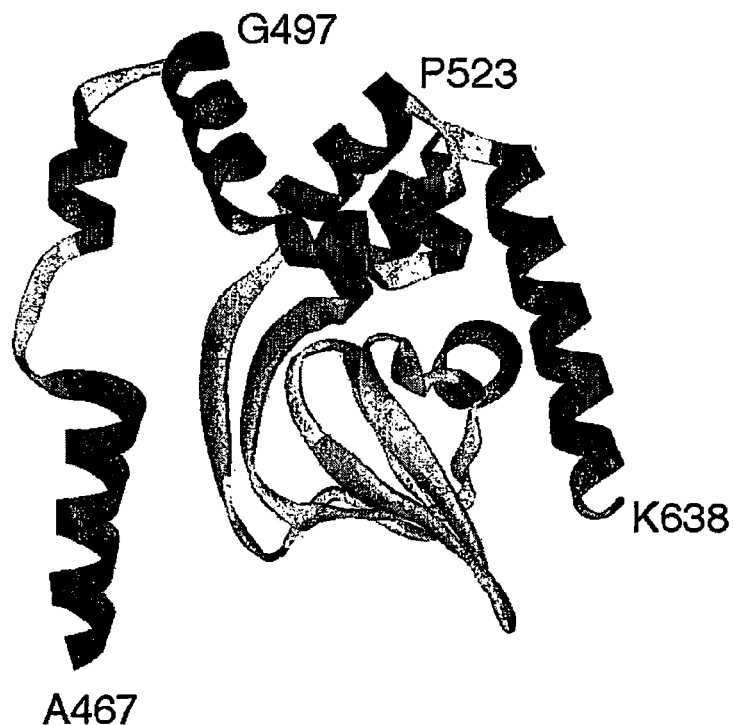
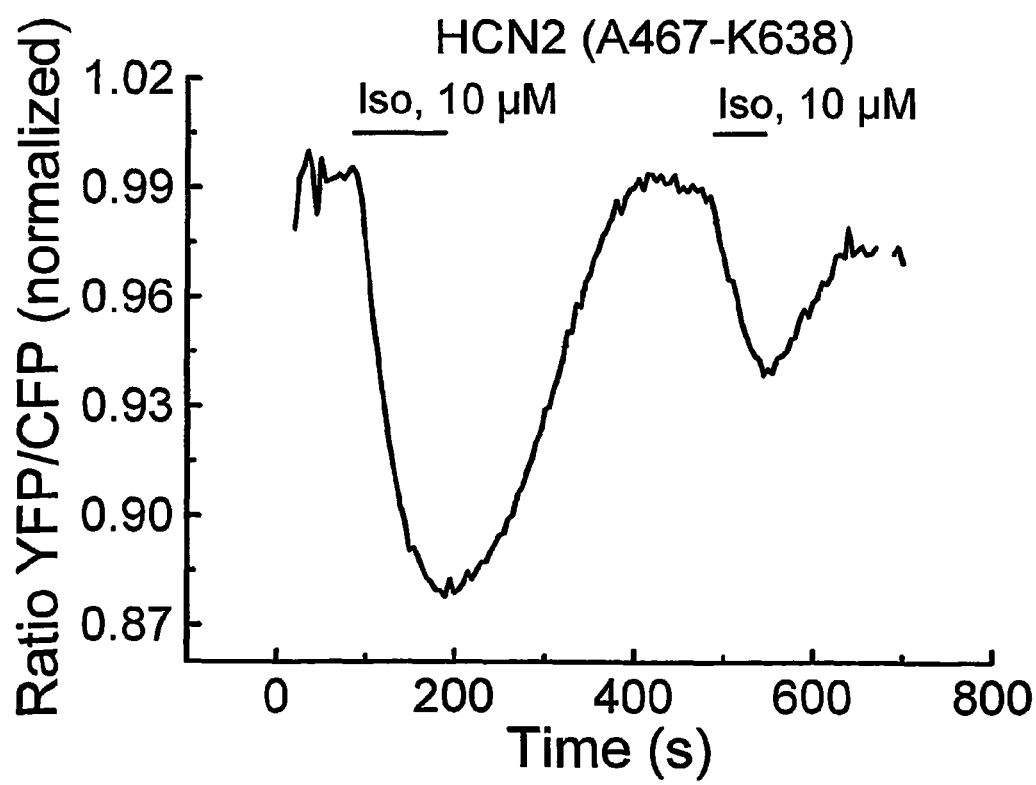

Fig. 14

```
EPAC1     ------EELAEAVALLSQRGPDALLTVALRKPPGQRTDEELDLIFEELLHIKAVAHLSN
EPAC2     EEKKECDEELQDTMLLLSQMGPDAHMRMILRKPPGQRTVDDLEIIYDELLHIKALSHLST
PKA IIβ   ----MYESFIESLPFLKS------LEVSER-----------------LKVVDVIGT
HCN2      ---ADFRQKIHDYYEHRYQGKMFDEDSILGELNGPLREEIVNFNCRKLVASMPLFANADP

αA         β1
EPAC1     SVKRELAAVLLFEPHSKAGTVLFSOQGDKGTSWYIIWKGSVNVVTHGKGLVTTLHEGDDFG
EPAC2     TVKRELAGVLIFESHAKGGTVLFNQGEEGTSWYIILKGSVNVVIYGKGVVCTLHEGDDFG
PKA IIβ   KVYND-GEQIIAQGDSADSFFIVESGE--VRITMKRKGKSDIEENGAVEIARCLRGOYFG
HCN2      NFVTAMLTKLKFEVFQPG-DYIIREGTIGKKMYFIQHGVVSVLTKGN-KEMKLSDGSYFG

α-B
EPAC1     QLALVNDAPRAATIILREDNCHFLRVDKQDFNRII-------KDVEAKTMRLEE----
EPAC2     KLALVNDAPRAASIVLREDNCHFLRVDKEDFNRIL-------RDVE----------
PKA IIβ   ELALVTNKPRAASAHAIG-TVKCLAMDVQAFERLLGPCMEIMKRNIATYEEQLVA----
HCN2      EICLLTRGRRTASVRADT-YCRLYSLSVDNFNEVLEEYP-MMRRAFETVAIDRLDRIGK
```

MEANS AND METHODS FOR THE DETERMINATION OF CAMP IN VITRO AND IN VIVO

The present invention relates to a chimeric peptide, comprising a cAMP binding moiety having only one cAMP binding site and at least two detectable labels, whereby the first of said two detectable labels is located at the carboxy terminus and the second of said two detectable labels is located at the amino terminus of said cAMP binding moiety. Said chimeric peptide of the invention is particularly useful in/for direct determination of cAMP concentration(s) in vitro and/or in vivo. Furthermore, nucleic acid molecules encoding said chimeric proteins are described as well as vectors and host cells comprising the same. The present invention also provides methods for producing the chimeric protein of the invention and methods for identification and screening of molecules or compounds which are capable of modifying cAMP binding to the chimeric peptide of the invention or the biological and/or pharmacological function of adenylyl cyclases or phosphodiesterases. In addition, a method for cAMP determination in a sample and a method for the detection of cAMP in the living cell or tissue is described. Finally, a kit comprising the compounds of the present invention is disclosed.

Signalling via the large family of G protein-coupled receptors (GPCRs) can lead to many cellular responses, ranging from regulation of intracellular levels of cAMP to stimulation of gene transcription. Members of this receptor family have been grouped into different categories dependent on the particular G protein subtypes that they predominantly interact with. For example, receptors that couple to Gs proteins will stimulate adenylate cyclase in many cells, while $G_{a/11}$-coupled receptors can mobilize intracellular $Ca^{2+}$ via activation of phospholipase C. A variety of physiological signals such as neurotransmitter, hormones and light are detected by members of the seven transmembrane domain receptor family. These G protein-coupled receptors (GPCRs) activate G proteins by promoting binding of GTP in exchange for GDP. Both, Gα and Gβγ subunits of activated G proteins can regulate downstream effectors such as adenylyl cyclases, phospholipases or ion channels.

Gene disruption studies have shown that the $Ca^{2+}$ stimulated adenylyl cyclases, AC1 and AC8 are critical for some forms of synaptic plasticity, including long-term potentiation as well as long-term memory formation (LTM). It is hypothesized that these enzymes are required for LTM to support the increased expression of a family of genes regulated through the cAMP/$Ca^{2+}$ response element-binding protein/cAMP response element transcriptional pathway. In contrast to AC1 and AC8, AC3 is a $Ca^{2+}$-inhibited adenylyl cyclase that plays an essential role in olfactory signal transduction. Coupling of odorant receptors to AC3 stimulates cAMP transients that function as the major second messenger for olfactory signaling. These cAMP transients are caused, at least in part, by $Ca^{2+}$ inhibition of AC3, which is mediated through calmodulin-dependent protein kinase II. The unique structure and regulatory properties of these adenylyl cyclases make them attractive drug target sites for modulation of a number of physiological processes including memory formation and olfaction. (Hongbing Wang and Daniel R. Storm. Calmodulin-Regulated Adenylyl Cyclases: Cross-Talk and Plasticity in the Central Nervous System. Mol. Pharmacol. Vol. 63, Issue 3, 463-468, March 2003; Miles D. HOUSLAY and David R. ADAMS. PKA-mediated activation of PDE4, ERK mediated phosphorylation inhibits PDE4. Biochem. J. (2003) 370 (1-18); Donald H. Maurice, Daniel Palmer, Douglas G. Tilley, Heather A. Dunkerley, Stuart J. Netherton, Daniel R. Raymond, Hisham S. Elbatarny, and Sandra L. Jimmo. Cyclic Nucleotide Phosphodiesterase Activity, Expression, and Targeting in Cells of the Cardiovascular System. Mol Pharmacol 64:533-546, 2003).

Cyclic AMP is a ubiquitous intracellular second messenger that transmits information to several proteins including cyclic nucleotide-gated ion channels, protein kinase A (PKA) and EPAC. In turn, these effectors regulate such diverse cellular functions as $Ca^{2+}$ influx, excitability, and gene expression, as well as cell-specific processes such as glycogenolysis and lipolysis. The enzymes known to regulate cAMP levels, adenylyl cyclase and phosphodiesterase, have been studied in detail (Hepler J R, Gilman A G. G proteins. Trends Biochem Sci. 1992 October; 17 (10):383-7; Exton J H. Regulation of phosphoinositide phospholipases by hormones, neurotransmitters, and other agonists linked to G proteins. Annu Rev Pharmacol Toxicol. 1996; 36:481-509; Beavo J A, Brunton L L. Cyclic nucleotide research—still expanding after half a century. Nat Rev Mol Cell Biol. 2002 September; 3(9):710-8; Ishikawa Y. Isoform-targeted regulation of cardiac adenylyl cyclase. Cardiovasc. Pharmacol. 2003; 41: 1-4).

Apart from calcium, cAMP is deemed to be a universal mediator (second messenger) for intracellular signals of a variety of G-coupled receptors, which are known to play an important role for biological processes, such as metabolism, cell growth and migration, immune defense, or contraction of myocardial cells (McKnight G S, Cummings D E, Amieux P S, Sikorski M A, Brandon E P, Planas J V, Motamed K, Idzerda R L. Recent Prog Horm Res. 1998; 53:139-59; 160-1; Prasad K N, Cole W C, Yan X D, Nahreini P, Kumar B, Hanson A, Prasad J E. Defects in cAMP-pathway may initiate carcinogenesis in dividing nerve cells: A review. Apoptosis. 2003 December; 8(6):579-86; Torgersen K M, Vang T, Abrahamsen H, Yaqub S, Tasken K. Molecular mechanisms for protein kinase A-mediated modulation of immune function. Cell Signal. 2002 January; 14(1):1-9; Bailey C H, Bartsch D, Kandel E R Toward a molecular definition of long-term memory storage. Proc Natl Acad Sci USA. 1996 Nov. 26; 93(24):13445-52; Wang H and Storm D R Calmodulin-Regulated Adenylyl Cyclases: Cross-Talk and Plasticity in the Central Nervous System Mol. Pharmacol. Vol. 63, Issue 3, 463-468, March 2003 Evans D B. Modulation of cAMP: mechanism for positive inotropic action. J Cardiovasc Pharmacol. 1986; 8 Suppl 9:S22-9).

Up until five years ago, protein kinase A (PKA) was thought to be the only effector of cAMP. In 1998, the family of EPAC (exchange factor directly activated by cAMP) was discovered, the cAMP binding domains of which show a high degree of homology to domain B of the regulatory subunit of PKA (de Rooij, J., et al., EPAC is a RAP1 guanine-nucleotide-exchange factor directly activated by cyclic AMP. Nature 396, 474-477 (1998)). In the past few years, many of the effects of cAMP which have been considered PKA-dependent earlier could be attributed to the activation of EPAC, which characterized this protein as another important cAMP target in the cell (Bos, J. L., EPAC: a new cAMP target and new avenues in cAMP research. *Nat. Rev. Molecule. Cell. Biol.* 4(9), 733-738 (2003)). In January 2003, the structure of the EPAC2 cAMP binding domain was published (Rehmann, H. et al., Structure and regulation of the cAMP binding domains of EPAC2. *Nat. Struct. Biol.* 10(1), 26-32 (2003)). The crystallographic data suggested a strong cAMP-dependent change in conformation which is said to lead to a change in the distance between α-helix-4 and 6:B.

EPAC proteins are expressed in various tissues including brain, adrenal gland, kidney, heart, ovary, thyroid, spleen, spinal cord, lung, liver and pancreas (Kawasaki H, Springett G M, Mochizuki N, Toki S, Nakaya M, Matsuda M, Housman D E, Graybiel A M. A family of cAMP-binding proteins that directly activate Rap1. Science. 1998 Dec. 18; 282(5397): 2275-9; Ueno H, Shibasaki T, Iwanaga T, Takahashi K, Yokoyama Y, Liu L M, Yokoi N, Ozaki N, Matsukura S, Yano H, Seino S. Characterization of the gene EPAC2: structure, chromosomal localization, tissue expression, and identification of the liver-specific isoform. Genomics. 2001 November; 78(1-2):91-8).

EPAC has been found to regulate integrin proteins which play an important role in cell adhesion, e.g. of some tumor cells, B-cells and lymphocytes migration (Kinbara, K. et al., Ras GTPase intergrins friends or foes? *Nat. Rev. Mol. Cell. Biol.* 4(10), 767-776 (2003)). Furthermore, the secretion of insulin in β-cells of the pancreas is directed by EPAC2 and ryanodin-sensitive channels (Ozaki N, Shibasaki T, Kashima Y, Miki T, Takahashi K, Ueno H, Sunaga Y, Yano H, Matsuura Y, Iwanaga T, Takai Y, Seino S. cAMP-GEFII is a direct target of cAMP in regulated exocytosis. Nat Cell Biol. 2000 November; 2(11):805-11; Kang G, Joseph J W, Chepurny O G, Monaco M, Wheeler M B, Bos J L, Schwede F, Genieser H G, Holz G G. Epac-selective cAMP analog 8-pCPT-2'-O-Me-cAMP as a stimulus for $Ca^{2+}$-induced $Ca^{2+}$ release and exocytosis in pancreatic beta-cells. J Biol. Chem. 2003 Mar. 7; 278(10):8279-85). Furthermore, EPAC regulates the ERK cascade (extracellular signal regulated kinase) which is of particular importance for the proliferation of cells (Fujita T, Meguro T, Fukuyama R, Nakamuta H, Koida M. New signaling pathway for parathyroid hormone and cyclic AMP action on extracellular-regulated kinase and cell proliferation in bone cells. Checkpoint of modulation by cyclic AMP. J Biol. Chem. 2002 Jun. 21; 277(25):22191-200; Lin S L, Johnson-Farley N N, Lubinsky D R, Cowen D S. Coupling of neuronal 5-HT7 receptors to activation of extracellular-regulated kinase through a protein kinase A-independent pathway that can utilize Epac. J. Neurochem. 2003 December; 87(5):1076-85). Additionally, EPAC1 plays a possible role in mitosis (Qiao J, Mei F C, Popov V L, Vergara L A, Cheng X. Cell cycle-dependent subcellular localization of exchange factor directly activated by cAMP. J Biol. Chem. 2002 Jul. 19; 277(29):26581-6). Finally, the regulation of potassium channels in kidney cells is also an important function of EPAC (Laroche-Joubert N, Marsy S, Michelet S, Imbert-Teboul M, Doucet A. Protein kinase A-independent activation of ERK and H,K-ATPase by cAMP in native kidney cells: role of Epac I. J Biol. Chem. 2002 May 24; 277(21):18598-604).

In view of the importance of the cAMP second messenger system, several in vitro approaches to determine the cAMP levels have been developed. Some of these assays are (anti-cAMP-) antibody based techniques, such as the radio immuno-assay (RIA) which is a method for indirect detection of cAMP (Kariv I I, Stevens M E, Behrens D L, Oldenburg K R. High Throughput Quantitation of cAMP Production Mediated by Activation of Seven Transmembrane Domain Receptors. J Biomol Screen. 1999; 4(1):27-32.). However, RIA is time consuming and requires expensive radioactive materials. Furthermore, RIA is not applicable for the use in living cells and tissues. Competitive in vitro immuno-assays with high affinity anti-cAMP antibodies have also been applied for detecting or determining cAMP (Golla R, Seethala R. A homogeneous enzyme fragment complementation cyclic AMP screen for GPCR agonists. J Biomol Screen. 2002 December; 7(6):515-25; Gabriel D, Vernier M, Pfeifer M J et al. High throughput Screening technologies for Direct cyclic AMP Measurments. ASSAY and Drug Development Technologies. 2003, 1(2): 291-303; Sportsman J R, Daijo J, Gaudet E A. Fluorescence polarization assays in signal transduction discovery. Comb Chem High Throughput Screen. 2003 May; 6(3):195-200). This method comprises the addition of anti-cAMP antibodies to cell lysates containing cAMP. The binding of anti-cAMP antibody with cAMP leads either to an activation of a fluorescent/chemiluminescent compound activating enzyme (e.g. cAMP-Screen™ assay, Hit Hunter™ Enzyme Fragment Complementation Assay, cyclic AMP EIA kit), degradation of fluorescent complex (Alpha Screen™ Assay) or to a change of fluorescence polarization of fluorescent labeled tracers (Fluorescent Polarization cAMP Assay) (Golla R, Seethala R. A homogeneous enzyme fragment complementation cyclic AMP screen for GPCR agonists. J Biomol Screen. 2002 December; 7(6):515-25; Gabriel D, Vernier M, Pfeifer M J et al. High throughput Screening technologies for Direct cyclic AMP Measurments. ASSAY and Drug Development Technologies. 2003, 1(2): 291-303; Sportsman J R, Daijo J, Gaudet E A. Fluorescence polarization assays in signal transduction discovery. Comb Chem High Throughput Screen. 2003 May; 6(3):195-200). However, as indicated, the above methods are suitable only for the detection of cAMP in vitro.

In order to try establishing methods which allow monitoring cAMP in vivo, some limited approaches have been undertaken to employ fluorescence resonance energy transfer (FRET)-based test systems utilizing cAMP binding proteins, such as bacterial cAMP receptor protein or PKA. These systems use fluorescence resonance energy transfer between fluorescent proteins (cyan fluorescent protein (CFP) and yellow fluorescent protein (YFP)) inserted in a DNA fragment which associates with bacterial cAMP receptor proteins (in vitro Bridge IT Assay; http://www.biocompare.com/itemdetails.asp?List=2263,173277) or with protein kinase A (PKA) (Zaccolo et. al., Nat. Cell. Biol. 2000).

However, until now it is only the above described PKA method which is able to detect the activation of the signal cascade of cAMP in a living cell. Briefly discussed, said sensor for cAMP has been produced by genetically linking the catalytic (C) subunits of PKA to GFP and the regulatory (R) subunit of PKA to the blue variant of GFP (EBFP). GFP and EBFP show spectral characteristics that made them a suitable pair for FRET. By measuring FRET changes it was possible to monitor cAMP changes in single cells. Although this new methodology is suited for temporal and topographical mapping of cAMP/PKA signaling, this approach shows some major drawbacks. For instance, the sensor used for the PKA process possesses catalytic activity due to the catalytic subunits of PKA and, therefore, intervenes in several intracellular processes. For example, the induction of apoptosis has been observed (Myklebust J H, Josefsen D, Blomhoff H K, Levy F O, Naderi S, Reed J C, Smeland E B. Activation of the cAMP signaling pathway increases apoptosis in human B-precursor cells and is associated with downregulation of Mcl-1 expression. J Cell Physiol. 1999 July; 180(1):71-80). Thus, many cells can not tolerate increased PKA activity and even die when PKA is overexpressed. In addition, it is well described in the art that catalytic activity of PKA initiates PKA mediated desensibilization, which leads to a rapid decrease of cAMP concentration (Houslay M D, Adams D R. PDE4 cAMP phosphodiesterases: modular enzymes that orchestrate signalling cross-talk, desensitization and compartmentalization. Biochem J. 2003 Feb. 15; 370(Pt 1):1-18; Conti M, Richter W, Mehats C, Livera G, Park J Y, Jin C. Cyclic AMP-specific PDE4 phosphodiesterases as critical components of cyclic AMP signaling. J Biol. Chem. 2003 Feb. 21; 278(8):5493-6; Kohout T A, Lefkowitz R J. Regulation of G protein-coupled receptor kinases and arrestins during receptor desensitization. Mol. Pharmacol. 2003 January;

63(1):9-18). Furthermore, the PKA sensor consists of two relatively big proteins which have to be individually labeled. Said proteins have to be expressed in equal concentrations to quantify cAMP concentrations. Finally, PKA contains four binding sites for cAMP with different affinity levels, wherein cAMP binding occurs in a complex cooperative manner. Thus, due to cooperative binding of cAMP, the accurate quantification of cAMP levels is complicated. Additionally, all of the four binding sites must be bound by cAMP to activate the PKA sensor, which causes a delay of the signal.

Due to these disadvantages of the cAMP assays described in the art, there is a need for means and methods for providing a novel generation of cAMP sensors having improved properties such as sensitivity, affinity, and detectability and which allow real-time optical cAMP determination in vitro and in vivo. Such measurements have not been provided for or are not yet accessible by prior art techniques.

This technical problem is solved by the provision of the embodiments as characterized in the claims.

Accordingly, the present invention relates to a chimeric peptide, comprising a cAMP binding moiety having only one cAMP binding site and at least two detectable labels, whereby a first of said two detectable labels is located at the carboxy terminus and a second of said two detectable labels is located at the amino terminus of the cAMP binding moiety. The term "chimeric peptide" relates, in accordance with this invention to a proteinaeous fusion construct comprising a cAMP binding moiety with a single cAMP binding site and two detectable labels as described herein. The inventive chimeric peptide/construct is particularly useful in the direct determination of cAMP concentration(s) in vitro and/or in vivo.

cAMP binding induces a conformational change in the cAMP binding domains of EPAC2 (Rehmann, H. et al., Structure and regulation of the cAMP binding domains of EPAC2. Nat. Struct. Biol. 10(1), 26-32 (2003). Based on this suggestion, the inventors have investigated whether said conformational change in the cAMP binding moieties can be utilized to produce a novel generation of cAMP sensors having improved sensitivity, affinity, and detectability and which allow real-time optical cAMP determination in vitro and/or in vivo. To this end, a novel monomolecular cAMP sensor has been generated by flanking the cAMP binding domains with fluorophores. It was suspected that upon cAMP binding, said change in the conformation of the cAMP binding moiety should induce a change in fluorescence resonance energy transfer (FRET) between the fluorophores, i.e. intramolecular FRET. In a first series of experiments, chimeric peptides in which both A and B cAMP-binding domains of protein kinase A or EPAC2 were sandwiched between two variants of green fluorescent protein (EYFP and ECFP) have been analysed. However, upon activation of cAMP signaling or by adding cAMP, said constructs failed to produce a change in FRET in cells expressing said constructs. Surprisingly, and in contrast to the teaching of the prior art chimeric peptides containing only one cAMP binding moiety flanked by two fluorophores at the C- and N-terminus exhibited a rapid loose in FRET after stimulation of the cAMP pathway or the addition of cAMP, as measured by fluorometry in vitro. Consequently, after having optimized the length of cAMP sensing sequence and position of fluorophores, several highly sensitive cAMP sensor proteins for both in vitro and in vivo applications have been generated, as shown in the following Examples and Figures. The fusion constructs provided herein (comprising only a single cAMP binding domain with one cAMP binding site) are highly sensitive cAMP sensors, which are particularly useful in the determination of spatio-temporal and/or regulatory patterns of receptor-mediated responses of cAMP. As documented below and in particular in FIG. 1, said "single cAMP binding domain" may also be split/separated by one of the at least two detectable labels; see also appended SEQ ID Nos: 14, 15 or 20, etc. The herein provided constructs, "the single-domain sensors", demonstrate a particularly high temporal resolution. The inventive constructs are based on a single cAMP binding domain (comprising only a single cAMP binding site) and reveal a fast speed of activation and are, therefore, suitable for measuring cAMP with said high temporal and spatial resolution. As documented below, the inventive constructs are useful in the study of cellular regulation processes and the biological function of cAMP in living cells. A particular preferred use of the inventive chimeric constructs is pharmacological research and/or drug screening approaches.

As illustrated herein, and in particular in the Examples and Figures, the term "cAMP binding moiety having only one cAMP binding site" relates to a cAMP binding moiety which is rather small (approximately 100 to 200 amino acids, preferably about 120 to 200, most preferably about 130 to 180 amino acids) and which comprises only one cAMP binding site (comprising approximately 10 to 20 amino acid residues, preferably 12 to 18 amino acid residues and particularly preferred 13 to 15 amino acid residues). It is also envisaged that the cAMP binding moiety comprised in the inventive constructs merely comprises a limited and small amount of additional amino acid residues besides the therein comprised cAMP binding site. Accordingly, also a "cAMP moiety" of about 20 amino acid residues, preferably about 40 amino acid residues and most preferably of about 50 amino acid residues is also envisaged in accordance with this invention to be comprised in the chimeric constructs provided herein. The illustrative constructs provided in the Examples comprise a "cAMP binding moiety/domain" of about 130 to about 180 amino acid residues. Most importantly, the chimeric construct has to comprise the single "cAMP binding site". Illustratively, FIG. 14 shows corresponding cAMP binding domains comprising one cAMP binding site of the illustrative examples.

Accordingly, the cAMP binding domain as employed in a chimeric peptide/construct of the present invention comprises only one cAMP binding site, which is also easily detectable by the skilled artisan. As pointed out above, a preferred cAMP binding site comprises 10 to 20 amino acids, more preferably 13 to 15 amino acids. An illustrative example is also shown in FIG. 14. As detailed below, the person skilled in the art may employ techniques for the deduction of cAMP binding moieties and/or cAMP binding sites which comprise the use of computer programs (like TBLASTN) and biochemical/biological assays, like restriction enzyme digestion analysis binding assays, competition-assays and the like.

In particular, novel monomolecular cAMP sensors containing only one cAMP binding site have been generated in which fluorophores (GFP variants) were inserted at particular positions of the cAMP binding domains of human EPAC1, murine EPAC2 or murine PKA regulatory II subunit cDNA. To analyse the activation kinetics of these novel cAMP-sensor proteins, cells stably expressing adenosine A2B receptor, coupling to Gs protein and activating cAMP production via adenylyl cyclase were transiently transfected with plasmids encoding for these sensor proteins (Volpini R, Costanzi S, Vittori S, Cristalli G, Klotz K N. Medicinal chemistry and pharmacology of A2B adenosine receptors. Curr Top Med. Chem. 2003; 3(4):427-43). After transfection, FRET was measured in single living cells as described in more detail below. Addition of adenosine to the cells resulted in decrease of FRET between the fluorophores, implying a cAMP-induced conformational change that led to an increase in the distance between the fluorophores.

Fluorophores, like GFP variants show a cylindrical or rod-like structure with a diameter of 30 Ångstrom and, thus, are known to be relatively big proteins. Therefore, it was expected that flanking of the single cAMP binding moiety by two fluorophores would cover the surface of said cAMP binding moiety, thereby preventing interaction with cAMP. Here, it was surprisingly found that the use of two GFP analoga or fluorophores did not constrain or alter the cAMP binding moiety. Unexpectedly, the moiety was still functional and even provides for a test system wherein intramolecular movements can be monitored in a millisecond range. Therefore, it was surprisingly found that despite the fact that the size of even one GFP variant (diameter of 30 Ångstrom; Tsien, Annu. Rev. Biochem. 1998. 67:509-544) may cover the cAMP binding moiety said cAMP binding moiety fused to two GFP variants is still capable of binding to cAMP. Accordingly, it could not have been expected that the preparation of the chimeric peptide as described herein provides for a fast-kinetic, functional and reliable tool for the direct measurements of cAMP in vitro and in vivo.

In accordance with the above, the detectable labels present in the chimeric peptide of the invention facilitate the detection of a conformational change within the chimeric peptide of the invention upon cAMP binding, which, in turn, leads to a change of the energy emitted by the detectable labels. Thus, the chimeric peptide of the invention provides a monomolecular tool particularly feasible to directly determine the cAMP levels in vitro, e.g. in a cell lysate. For example, the chimeric peptide as defined above, may be added to a cell lysate and by recording FRET or BRET (bioluminescence resonance energy transfer), the cAMP concentration in said sample can be measured by comparing values of the fluorescence emission with a standard curve obtained with defined concentrations of cAMP as set forth in more detail below. The present invention also provides a generally applicable fluorescence-based technique for real-time monitoring of cAMP in single living cells or even in tissues. Furthermore, the present invention provides methods for identification and screening of molecules or compounds which are capable of modifying cAMP binding to the chimeric peptide of the invention or the biological and/or pharmacological function of adenylyl cyclases or phosphodiesterases as set forth below.

Particularly, the inventors developed a chimeric protein for optical cAMP determination which overcomes the drawbacks of the cAMP assays and detection systems described in the prior art.

First, and as discussed above, the chimeric peptide of the invention is relatively short and does not contain any catalytic activity or binding site(s) to other molecules, except for cAMP. Therefore, the protein does not interfere with other intracellular processes such as desensibilization or phosphorylization of other proteins. As illustrated in the Examples and Figures, the constructs of the present invention comprise a cAMP binding domain, comprising approximately 100 to 200 amino acid residues and having only one cAMP binding site which comprises between 10 and 20, preferably 13 to 15 and most preferably 14 amino acids residues.

Second, in contrast to the PKA system (Zaccolo et al., loc. cit), the chimeric protein of the invention is a monomolecular system which can be easily expressed in living cells.

Third, the chimeric peptide of the present invention contains only one cAMP binding site with high affinity, which enables direct determination of cAMP in vitro and/or in vivo. A further consequence of the single cAMP binding site is that kinetics of cAMP detection are much faster than in the previously available cAMP detection systems described in the art. As demonstrated in the following Examples, activation kinetics of cAMP-sensor proteins based on a single binding domain of EPAC2 compared to that of the previously described PKA-sensor (Zaccolo et. al., Nat. Cell. Biol. 2000) reveal that the novel EPAC2-sensor shows a more rapid activation signal. This is most likely due to the presence of only one high-affinity cAMP-binding domain and the absence of catalytic activity (induction of desensitization via phosphodiesterase activation) of the chimeric peptide of the invention. In comparison, PKA has 4 cooperatively acting binding sites and exhibits phosphodiesterase activating properties.

Fourth, the chimeric protein of the invention enables real-time detection of cAMP in vivo and in vitro without using radioactive compounds.

The "resonance energy transfer (RET)" as used herein refers to a non-radiative transfer of excitation energy from a donor (first detection portion) to an acceptor molecule (second detection portion). The conformational change of the cAMP binding moiety upon cAMP binding results in a detectable change of RET between the detection portions. If, for example, RET is increased, the emission peak of the acceptor is raised and the emission peak of the donor is diminished. Thus, the ratio of the emission intensity of the acceptor to that of the donor is indicative for the degree of RET between the detection portions. The conformational change of the chimeric peptide of the invention upon binding of cAMP may result either in a decrease or an increase of the distance between the detection portions.

The term "chimeric" as defined herein relates to a molecule containing sequences derived from two, three or more different genes, which can be derived from one, two, three or more different species.

The term "peptide" as used herein refers to a polypeptide or protein which can be composed of amino acids joined to each other by peptide bonds or modified peptide bonds, i.e., peptide isosteres, and may contain amino acids other than the 20 gene-encoded amino acids. The polypeptides may be modified by either natural processes, such as posttranslational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched, for example, as a result of ubiquitination, and they may be cyclic, with or without branching. Cyclic, branched, and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, PROTEINS—STRUCTURE AND MOLECULAR PROPERTIES, 2nd Ed., T. E. Creighton, W. H. Freeman and Company, New York (1993); POSTTRANSLATIONAL COVALENT MODIFICATION OF PROTEINS, B. C. Johnson, Ed., Academic Press, New York, pgs. 1-12 (1983); Seifter et al., Meth Enzymol 182:626-646 (1990); Rattan et al., Ann NY Acad Sci 663:48-62 (1992).).

The term "chimeric peptide" as used herein refers to polypeptide or protein constructs that are the result of combining multiple proteins, protein domains and/or linker sequences for the purpose of gaining the combined functions of the domains and/or linker sequences as set forth in more detail below. This may be accomplished by molecular cloning of the nucleotide sequences encoding such domains to produce a new polynucleotide sequence that encodes the desired chimeric peptide as used herein. Alternatively, creation of a chimeric peptide may be accomplished by chemically joining two or more proteins.

Particularly, the term "chimeric peptide" as defined herein may comprise the structure A-B-C wherein A represents a first detectable label, B represents a cAMP binding moiety having only one cAMP binding site, and C represents a second detectable label. For example, the cAMP binding moiety may be from the regulatory subunit (R) of a cAMP dependent protein kinase (such as PKA), a guanine nucleotide exchange factor (e.g. EPAC), catabolic gene activator protein from *E. coli*, cAMP gated ion channel, a cyclic nucleotide gated channel (e.g. HCN), neuropathy target esterase (NTE) or cAMP receptor of Dictyostelium. Preferably, the cAMP dependent protein kinase is PKA, the guanine nucleotide exchange factor is EPAC1 or EPAC2, the cyclic nucleotide gated channel is HCN2 (hyperpolarization-activated, cyclic nucleotide-gated $K^+$ channel), the catabolic gene activator protein is derived from *E. coli*, the cAMP gated ion channel is from human, neuropathy target esterase (NTE) is from human and the cAMP receptor is from Dictyostelium. For PKA, the regulatory subunits of PKAIalpha-A or B; PKAIbeta A or B; PKAIIalphaA or B; or PKAIIbeta A or B may be used. Even more preferably, PKA, EPAC1 or EPAC2 is of human, mouse, or rat origin.

A cAMP-binding moiety or domain as used herein refers to a cAMP binding domain/moiety containing either only the single cAMP-binding site (cassette) or the single cAMP-binding site (cassette) and additional adjacent sequences such as alpha helices as exemplified in the following Figures. The cAMP binding moiety as used herein preferably corresponds to the amino acid sequences shown in the following sequences of the sequence listing: amino acid residues 281-445, or preferably 284 to 443 of EPAC2 (domain B) (SEQ ID NO: 3), amino acid residues 203-323, or preferably 157 to 316 of EPAC1 (SEQ ID NO: 2), amino acid residues 274-416, or preferably 255 to 416 or preferably 264 to 416 of regulatory II beta subunit of PKA (SEQ ID NO: 1), amino acid residues 544-661 of cyclic-gated potassium channel 2 (SEQ ID NO: 4), amino acid residues 12-98 of catabolite gene activating protein (SEQ ID NO: 6), amino acid residues 473-568 of neuropathy target esterase (SEQ ID NO: 7), amino acid residues 628-767 of cyclic nucleotide gated cation channel 4 (CNG) (SEQ ID NO: 5) or amino acid residues 467 to 638, or 497 to 638, or 523 to 638, or 517 to 625 of hyperpolarization-activated, cyclic nucleotide-gated $K^+$ channel 2 (HCN2; SEQ ID NO: 72).

The cAMP binding site as used herein can be easily deduced by the person skilled in the art and preferably corresponds to amino acid residues 403-417 of EPAC2 (NP_062662), amino acid residues 258-285, preferably 268 to 281 of EPAC1 (O95398), amino acid residues 348-362 of regulatory II beta subunit of PKA (P12369), amino acid residues 607-621 of cyclic-gated potassium channel 2 (Q9UL51), amino acid residues 71-86 of catabolite gene activating protein (AAN82570), amino acid residues 649-663 of neuropathy target esterase (AAH50553), or amino acid residues 580 to 593 of HCN2 (NP_032252). Corresponding preferred constructs/chimeric peptides of the invention are provided as illustrative examples in appended FIG. 1 or FIG. 11. The constructs as shown in FIG. 1 are also provided in SEQ ID Nos: 8 to 20. The constructs as provided in FIG. 11 (relating to illustrative examples comprising the cAMP binding moiety/domain of HCN2) are also provided by the coding sequences (SEQ ID Nos. 66, 68, and 70) and their corresponding amino acid sequences shown in SEQ ID Nos: 67, 69 and 71. A (mouse) HCN2 polypeptide is defined in SEQ ID NO: 74. The person skilled in the art is easily in the position to deduce cAMP-binding domain (having only one cAMP binding side) from the information given herein. Accordingly, cAMP-binding domains in the sense of this invention may comprise the amino acid stretch L219 to F300 of EPAC1 (as shown in SEQ ID NO: 27, encoded, inter alia, by SEQ ID NO: 26); the amino acid stretch L354 to F435 of Epac2 (as shown in SEQ ID NO: 29, encoded, inter alia, by SEQ ID NO: 28); the amino acid stretch I290 to F379 of PKA (as shown in SEQ ID NO: 31; encoded, inter alia, by SEQ ID NO: 30); or the amino acid stretch L533 to I636 of HCN2 (as shown in SEQ ID NO: 33, encoded, inter alia, by SEQ ID NO: 32). The corresponding cAMP binding moieties are also and additionally illustrated in appended FIGS. 1 and 14.

Figure 11:
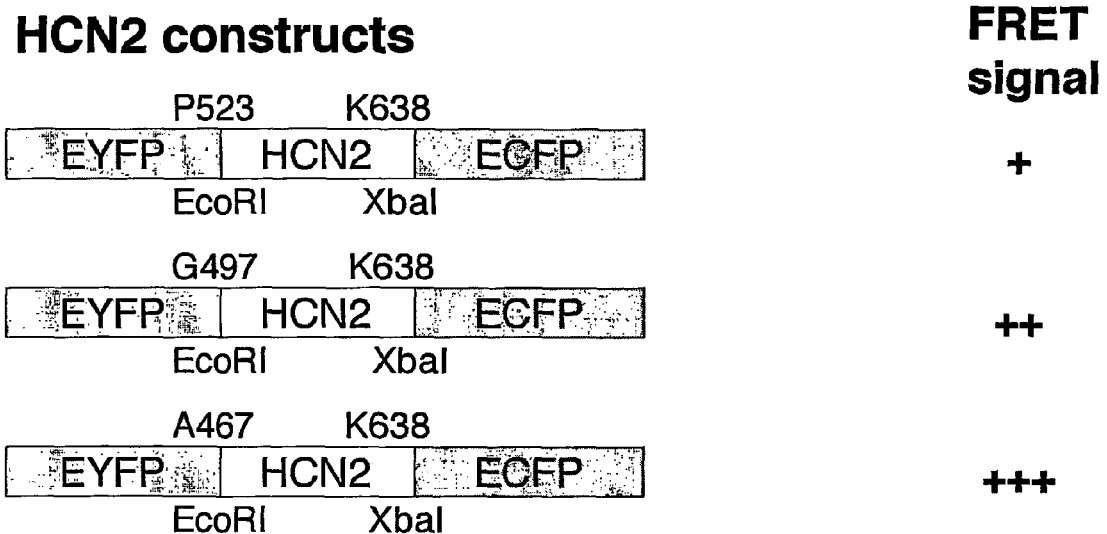

Furthermore, cAMP binding domains in accordance with this invention also schematically illustrated in appended FIGS. 1 and 11 are also comprised in the herein appended sequences, like SEQ ID Nos: 8 to 20, or in the amino acid sequences as shown in SEQ ID Nos: 39, 41, 43, 45, 47, 49, 51, 53, 55, 57, 59, 61, 63, 65, 67, 69, 71 and 73.

Particularly preferred chimeric constructs of the present invention are constructs, wherein the cAMP binding moiety is selected from the group consisting of:

(a) a cAMP binding moiety of a polypeptide as shown (and comprised) in SEQ ID Nos:1 to 7 and 74;

(b) a cAMP-binding moiety as shown or as comprised in any one of SEQ ID Nos: 27, 29, 31, 33, 34, 35, 36 and 37;

(c) a cAMP-binding moiety as comprised in any one of SEQ ID Nos: 8 to 20;

(d) a cAMP-binding moiety as comprised in any one of SEQ ID Nos: 39, 41, 43, 45, 47, 49, 51, 53, 55, 57, 59, 61, 63, 65, 67, 69, 71 and 73; and (e) a cAMP binding moiety which is at least 70%, 80%, 90% or 95% identical to a cAMP binding moiety as defined herein or to the cAMP-binding moiety of (a) to (d).

The inventive chimeric peptide is preferably selected from the group consisting of:

(a) a chimeric peptide as encoded by a nucleic acid molecule as shown in any one of SEQ ID Nos: 38, 40, 42, 44, 46, 48, 50, 52, 54, 56, 58, 70 and 72;

(b) a chimeric peptide comprising an amino acid sequence as shown in any one of SEQ ID Nos: 39, 41, 43, 45, 47, 49, 51, 53, 55, 57, 59, 61, 63, 65 (corresponding to SEQ ID NO: 73), 67, 69, 71 and 73;

(c) a chimeric peptide encoded by a nucleic acid molecule which encodes a polypeptide which is at least 70% identical to a polypeptide as defined in (a) or (b) and which can be used for direct determination of cAMP concentration in vitro and/or in vivo; and (d) a chimeric peptide which is encoded by a nucleic acid molecule which is degenerate to a DNA sequence as defined in (a) and (c).

The illustrative, exemplified chimeric peptides/constructs of the invention as shown in FIGS. 1 and 11 are also documented in the appended sequence protocol. Accordingly, SEQ ID NO: 8 relates to a chimeric construct in accordance with this invention which comprises a cAMP binding moiety comprising only one cAMP binding site and being derived from EPAC2 (amino acids E285 to E443). SEQ ID NO: 9 relates to a chimeric construct in accordance with this invention which comprises a cAMP binding moiety comprising only one cAMP binding site and being derived from EPAC2 (amino acids E292 to E443). SEQ ID NO: 10 relates to a chimeric construct in accordance with this invention which comprises a cAMP binding moiety comprising only one cAMP binding site and being derived from EPAC2 (amino acids M304 to E443). SEQ ID NO: 11 relates to a chimeric construct in accordance with this invention which comprises a cAMP binding moiety comprising only one cAMP binding site and being derived from EPAC2 (amino acids M310 to E443). SEQ ID NO: 12 relates to a chimeric construct in accordance with this invention which comprises a cAMP binding moiety comprising only one cAMP binding site and being derived from EPAC2 (amino acids E285 to Q454). SEQ ID NO: 13 relates to a chimeric construct in accordance with this invention which comprises a cAMP binding moiety comprising only one cAMP binding site and being derived from EPAC2 (amino acids E285 to E460). SEQ ID NO: 16 relates to a chimeric construct in accordance with this invention which comprises a cAMP binding moiety comprising only one cAMP binding site and being derived from EPAC2 (comprising also the membrane anchor; amino acids E285 to E443; see also SEQ ID NO: 57). SEQ ID NO: 17 relates to a chimeric construct in accordance with this invention which comprises a cAMP binding moiety comprising only one cAMP binding site and being derived from EPAC1 (amino acids E157 to E316). SEQ ID NO: 18 relates to a chimeric construct in accordance with this invention which comprises a cAMP binding moiety comprising only one cAMP binding site and being derived from PKA (RII beta) (amino acids M264 to A416, HA; see also SEQ ID NO: 63). SEQ ID NO: 19 relates to a chimeric construct in accordance with this invention which comprises a cAMP binding moiety comprising only one cAMP binding site and being derived from PKA (RII beta) (amino acids M264 to A403, without HA; see also SEQ ID NO: 59). SEQ ID NO: 39 relates to a chimeric construct in accordance with this invention which comprises a CAMP binding moiety comprising only one cAMP binding site and being derived from EPAC1 (amino acids E157 to E316). SEQ ID NO: 41 relates to a chimeric construct in accordance with this invention which comprises a cAMP binding moiety comprising only one cAMP binding site and being derived from EPAC2 (amino acids E285 to E443; see also SEQ ID NO: 8). SEQ ID NO: 43 relates to a chimeric construct in accordance with this invention which comprises a cAMP binding moiety comprising only one cAMP binding site and being derived from EPAC2 (amino acids E292 to E443; see also SEQ ID NO: 9). SEQ ID NO: 45 relates to a chimeric construct in accordance with this invention which comprises a cAMP binding moiety comprising only one cAMP binding site and being derived from EPAC2 (amino acids E304 to E443; see also SEQ ID NO: 10). SEQ ID NO: 47 relates to a chimeric construct in accordance with this invention which comprises a cAMP binding moiety comprising only one cAMP binding site and being derived from EPAC2 (amino acids M310 to E443; see also SEQ ID NO: 11). SEQ ID NO: 49 relates to a chimeric construct in accordance with this invention which comprises a cAMP binding moiety comprising only one cAMP binding site and being derived from EPAC2 (amino acids E285 to Q454; see also SEQ ID NO: 12). SEQ ID NO: 51 relates to a chimeric construct in accordance with this invention which comprises a cAMP binding moiety comprising only one cAMP binding site and being derived from EPAC2 (amino acids E285 to E460; see also SEQ ID NO: 13). SEQ ID NO: 61 relates to a chimeric construct in accordance with this invention which comprises a cAMP binding moiety comprising only one cAMP binding site and being derived from PKA (amino acids V255 to A416 and hemagglutinin antigen (HA)).

SEQ ID Nos: 14, 15, 20, 53, 55, 65 (being the same as 73) are constructs in accordance with this invention, whereby one of the detectable labels are located between the carboxy-terminus and the amino terminus of the cAMP binding moiety/domain having only one cAMP binding site. Said constructs comprise further amino acid residues of the cAMP binding moiety/domain without a cAMP binding site on the carboxy-terminal end (see also FIG. 1). Accordingly, the chimeric construct of the present invention also comprises constructs whereby one of the at least two detectable labels is intercalated/inserted in said cAMP binding domain/moiety. Non-limiting examples are the above recited constructs shown in SEQ ID Nos: 14, 15, 20, 53, 55 and 65 (being the same as 73). Accordingly, SEQ ID NO: 14 and 53 describe a construct comprising an EPAC2 cAMP binding domain/moiety with only cAMP binding site in the format E285 to I388—(detectable label; EYFP)—G390 to E443—(detectable label; ECFP). SEQ ID NO: 15 and 55 describe a construct comprising an EPAC2 cAMP binding domain/moiety with only cAMP binding site in the format E285 to I388—(detectable label; EYFP)—G390 to E460—(detectable label; ECFP). SEQ ID NO: 20 describes a construct comprising a PKA cAMP binding domain/moiety with only cAMP binding site in the format M264 to I331—(detectable label; EYFP)—E333 to A403—(detectable label; ECFP). SEQ ID NO: 65 and 73 describe a construct comprising a PKA cAMP binding domain/moiety with only cAMP binding site in the format V255 to I331—(detectable label; EYFP)—E333 to A403—(detectable label; ECFP).

The fusion between above recited parts/cassettes A, B, and C does not necessarily need to be direct, but may occur through linker sequences. Accordingly, the chimeric peptide may also have the structure A-D-B-C, A-B-E-C or A-D-B-E-C, wherein D and E represents a linker positioned between the detectable label and the cAMP binding moiety. The term "linker" or "linker sequence" as used herein refers to polynucleotide or polypeptide sequence that are used in the construction of the chimeric peptide of the invention. Functions of a linker region can include introduction of cloning sites into the nucleotide sequence, introduction of a flexible component or space-creating region between two protein domains, or creation of an affinity tag for specific molecule interaction. A linker region may be introduced into the chimeric peptide resulting from choices made during polypeptide or nucleotide sequence construction. Said linker as used herein may be 1, 2, 3, 4, 5, 10, 15, 30, or even 50 amino acid residues in length, wherein the linker sequences D and E may or may not have the same length. Preferably, short linkers consist of 1, 2, 3, 4 or 5 amino acid residues. The chimeric peptide as used herein may also be engineered to improve characteristics of the polypeptide of the present invention. For instance, a region of additional amino acids, particularly charged amino acids, may be added to the N-terminus or C-terminus of the chimeric peptide to improve stability and persistence during purification from the host cell or subsequent handling and storage. Also, peptide moieties may be added to the chimeric peptide to facilitate purification. Such regions may be removed prior to final preparation of the polypeptide. The addition of peptide moieties, also called "tags", to facilitate handling of polypeptides are familiar and routine techniques in the art. The term "tag" as used herein refers to an amino acid sequence or a nucleotide sequence that encodes an amino acid sequence, that facilitates isolation, purification and/or detection of the chimeric peptide as used herein containing the tag. A wide variety of such tags are known to those skilled in the art, and are suitable for the chimeric peptide, methods or uses of the present invention. Suitable tags include, but are not limited to, HA peptide, polyhistidine peptides, biotin/avidin, flag tag or other antibody epitope binding sites. For example, the marker amino acid sequence may be a hexa-histidine peptide (SEQ ID NO: 79), such as the tag provided in a pQE vector (QIAGEN, Inc., 9259 Eton Avenue, Chatsworth, Calif., 91311), which, among others, are commercially available. As described in Gentz et al., Proc. Natl. Acad. Sci. USA 86:821-824 (1989), for instance, hexa-histidine (SEQ ID NO: 79) provides for convenient purification of the fusion protein. Another peptide tag useful for purification, the "HA" tag, corresponds to an epitope derived from the influenza hemagglutinin protein. (Wilson et al., Cell 37:767 (1984). Alternatively, the chimeric peptide of the invention may be fused with the constant domain of immunoglobulins (IgA, IgE, IgG, IgM) or portions thereof (CH1, CH2, CH3, or any combination thereof). Furthermore, the chimeric peptide as used herein can be targeted to specific cellular locations, i.e. particular compartments of the cells, based on trafficking signals. The chimeric peptide may be expressed as a soluble protein in the cytoplasm of a cell, or may be inserted into a biological membrane of a cell and/or artificial membrane, like a cellular membrane, a crude membrane preparation, liposomes as well as artificial membranes comprising micelles, lipid monolayers or lipid bilayers. For instance, the chimeric peptide as defined herein may be located in cellular membranes, e.g., membranes of cultured cells or membranes of oocytes. The chimeric peptide can also be targeted to other particular compartments of the cell such as the nucleus, mitochondria, endoplasmic reticulum, chloroplasts or the like, e.g. by using signal sequences or location signals, such as nuclear location sequences or location sequences which target to the Golgi apparatus, mitochondria, endoplasmatic reticulum, or cytosceleton. These are well described in the art.

As detailed herein below, it is also envisaged that the chimeric peptide of the invention is expressed in transgenic non-human animals. Accordingly, also cells, tissues and organs of said non-human transgenic animal may express the chimeric peptide of the present invention and may be in particular useful in drug screenings as explained in detail below.

The chimeric peptide as used herein may be recombinantly produced by methods known in the art; see, inter alia, Sambrook et al., Molecular Cloning: A Laboratory Manual, Cold Spring Harbor Laboratory Press, Cold Spring Harbor, N.Y., 2001. In addition, the chimeric peptide of the invention can be chemically synthesized using techniques known in the art.

The term "and/or" wherever used herein includes the meaning of "and", "or" all or any other combination of the elements connected by said term.

The term "membrane" as used herein relates to naturally occurring membranes as well as to artificial membranes. Preferably, the membranes consist of lipid bilayers. As pointed out above, specific examples are cellular membranes and bio-membranes, like the plasma membrane of cells, the endoplasmic reticulum, mitochondrial membrane, golgi vesicles, lysosomes, peroxisomes, but also cellular membranes of plant cells, like membranes of the chloroplasts or other organelles as well as vacuoles. The cellular or bio-membrane into which the chimeric peptide of the invention is inserted is the plasma membrane of an animal cell, most preferably of a mammalian cell, but also of amphibian cells, like frog oocytes. Yet, as also discussed herein, membrane preparations, like crude membrane preparations or liposomes are envisaged as "membranes" wherein the chimeric peptide of the present invention is inserted The term "at least two detectable labels" as used herein means that the chimeric peptide of the invention may comprise two, three, four, five or more detectable labels, most preferred, however, are constructs comprising two detectable labels. The detectable labels will be detailed herein below and may, in particular comprise fluorophores as well as bio-luminescent substances. In accordance with the appended examples, however, most preferred are two detectable labels on one chimeric peptide of the invention.

The term "said label is located at" as employed herein means that the label is positioned at either the carboxy- or amino terminus of the cAMP binding moiety. As already indicated above, the fusion may be direct or via an intervening linker and it is also envisaged and documented herein that at least one of said at least two detectable labels are located within the cAMP binding moieties (interchalating or inserted into said cAMP-binding moiety). Corresponding examples are given, inter alia, in SEQ ID Nos: 14 (also 53), 15 (also 55), 20 and 65 (also 73) and are illustrated in FIG. 1.

As far as insertion of detectable labels are concerned, it is apparent to the person skilled in the art that said insertions can be variable. Yet, it is to be noted that insertions of the detectable label may lead to a deletion/replacement of naturally occurring amino acids in the cAMP binding moiety, however, without affecting cAMP binding to the cAMP binding site.

The terms "amino terminus" or "carboxy terminus" as used herein refers to the amino terminus and carboxy terminus of the cAMP binding moiety of the chimeric peptide of the invention or (where explicitly stated) the chimeric peptide of the invention.

The detectable labels to be introduced into the chimeric peptide of the present invention are preferably fluorescent labels or bioluminescent labels. The detectable labels also comprise genetically encoded fluorophores as well as synthetic fluorophores that specifically bind to a genetically encoded and engineered site, (Flash-technology; see, inter alia, Adams (2002), J. Am. Chem. Soc. 124, 6063-6076 or Griffin (2000), Meth. Enzym. 327, 565-578.

As discussed herein, the inventive constructs are particularly useful in the direct determination of cAMP concentration in vitro and/or in vivo. Accordingly, the detection portions/labels present in the chimeric peptide of the invention facilitate the detection of a conformational change within the chimeric peptide of the invention upon cAMP binding, which, in turn, is indicative for change of the energy emitted by the detection portions/detectable labels. Accordingly, the term "direct determination of cAMP concentration" relates to the fact that the chimeric peptide of the invention provides a monomolecular tool particularly feasible to directly determine the cAMP levels in a sample. For example, the chimeric peptide as defined above, may be added to a sample and by measuring and/or recording FRET or BRET the cAMP concentration in the sample can be measured by comparing values of the fluorescence emission with a standard curve obtained with defined concentrations of cAMP. The "chimeric indicators" provided in this invention may be ubiquitously applied to studying, e.g., cAMP, its physiological role as well as spatio-temporal regulations.

The term "direct determination" as used herein indicates that cAMP binds directly to a cAMP binding site of the chimeric protein of the invention which then produces a detectable signal. Thus, and in contrast to the prior art, only one protein is needed to detect cAMP in vivo or to determine cAMP concentration in vitro, without the need of any further tools such as auxiliary proteins, antibodies, labels, tracers or the like. In this context it is of note that cAMP sensors of the prior art are relying on cAMP dependent interactions between/of two proteins.

The sample as defined herein may be for instance a cell, a cell lysate, a crude cell extract, a membrane preparation, a tissue or biofluids. Biofluids as used herein preferably refer to body fluids such as semen, lymph, sera, plasma, urine, synovial fluid or spinal fluid.

Moreover, the chimeric peptide of the invention can be used for monitoring over space and time the amount, distribution, location, or fluctuation of cAMP in a living cell or tissue. For instance, a cell or tissue may be transfected or transformed with the nucleic acid or vector of the invention and FRET or BRET in the living cell or tissue may be measured/recorded.

In one embodiment of the chimeric peptide of the invention, these detection labels are portions of a split fluorescent protein. Preferably, this split fluorescent portions is a split green fluorescent protein (split GFP). The term "green fluorescent protein" or "GFP" as used throughout the present application refers to the GFP initially cloned by Prasher (Gene 111 (1992), 229-233) from *Aequorea victoria* and mutants thereof showing GFP activity. The term "GFP activity" refers to the known properties of a GFP, i.e. fluorescence emission upon excitation by a suitable light, the capacity of autocatalytic maturation involving folding into tertiary structure and the formation of the chromophore and the independence of any co-factors or metabolic energy supply for carrying out fluorescence as well as autocatalytic maturation. These properties are well known in the art and for example reviewed by Tsien (Ann. Rev. Biochem. 67 (1998), 509-544). For the purposes of the present invention, unless otherwise stated, any detectable emission wavelength of a GFP mutant can be useful for applying the chimeric peptide of the invention. In the prior art, many GFP mutants are described, wherein specific amino acid residues are substituted with the effect of an improved fluorescence efficiency and/or a shifted excitation and/or emission wavelength (see, e.g., Heim, Methods Enzymol. 302 (1999), 408-423; Heikal et al., PNAS 97 (2000), 11996-12001). Particularly, mutating glutamine in position 69 to methionine can reduce the inherent pH and halide sensitivity of eYFP (Griesbeck et al., J. Biol. Chem. (2001) 276, 29188-29194). Thus, if eYFP, or a derivative thereof having substantially the same excitation and emission spectrum, is used as one detection portion of the fusion protein of the invention, it is preferred that the eYFP or derivative thereof shows this mutation. Yet, as shown in the appended examples, YFP is also useful in accordance with this invention. Examples for GFP mutants useful for applying the invention include (enhanced) yellow fluorescent protein ((e)YFP), (enhanced) cyan fluorescent protein ((e)CFP), (enhanced) blue fluorescent protein ((e)BFP), (enhanced) green fluorescent protein ((e)GFP), DsRED, Citrine and Sapphire. Within the scope of the present invention, any GFP mutant or functional analog of GFP may be used as long as it shows fluorescent activity. Preferably, such GFP variants/mutants are encoded by a nucleic acid molecule that hybridizes, preferably under stringent conditions, with the nucleotide sequence encoding the wild-type GFP, or with polynucleotides encoding variants/mutants as the sequence depicted under SEQ ID NOS: 23 and 24. These GFP-mutants/variants showing the polypeptide sequence as depicted in SEQ ID NOS: 21 and 22 relate to the most preferred GFP variants to be employed in this invention, namely enhanced cyan fluorescent protein (eCFP) and yellow fluorescent protein (YFP). Suitable preferred hybridization conditions and sequence identity values for preferred hybridizing nucleotide sequences encoding a mutant GFP are mentioned below.

In this context, the term "hybridization" means hybridization under conventional hybridization conditions. They may be low stringent, preferably stringent (i.e. high stringent) hybridization conditions, as for instance described in Sambrook at al., Molecular Cloning, A Laboratory Manual, loc. cit. In an especially preferred embodiment the term "hybridization" means that hybridization occurs under "stringent hybridization conditions" referring to an overnight incubation at 42 degree C. in a solution comprising 50% formamide, 5×SSC (750 mM NaCl, 75 mM trisodium citrate), 50 mM sodium phosphate (pH 7.6), 5×Denhardt's solution, 10% dextran sulfate, and 20 μg/ml denatured, sheared salmon sperm DNA, followed by washing the filters in 0.1×SSC at about 65 degree C.

The term "split fluorescent protein" refers to a fluorescent protein the amino acid sequence of which is divided into two portions, whereby upon secondary spatial joining of these portions, the split fluorescent protein assumes a three-dimensional structure which allows it to emit fluorescence when excited by light of a suitable wavelength. It is for example contemplated that the split fluorescent protein is a split GFP, as it has been described by Baird (Proc. Natl. Acad. Sci. USA 96 (1999), 11241-11246). Following the teachings of the prior art, it is possible for a person skilled in the art to divide a GFP into two split GFP portions for fusing them to the chimeric peptide of the invention. It is furthermore conceivable that other fluorescent proteins than GFP, e.g. those mentioned infra, may be split so as to constitute two detection portions in the same manner as split GFP described herein.

In another embodiment of the present invention, the first detection label is an energy-emitting protein portion and the second detection portion is a fluorescent protein label or vice versa. In connection with this embodiment, it is unimportant on which part of the chimeric peptide the first detection portion is located with respect to the other part defined herein, i.e. whether said detection label is located on the N- or the C-terminus of the cAMP binding moiety of the chimeric peptide of the invention, fused directly or via a linker as set forth above. As discussed above, one of the detection labels may also be placed within the cAMP binding domain/moiety as described herein; see, e.g. examples given in FIG. 1 or sequences as provided, inter alia, in SEQ ID Nos: 14, 15 or 20. The term "energy-emitting protein portion" refers to proteins capable of radiative energy emission which can (i) take up energy in a suitable form and (ii) transmit at least part of this energy by resonance energy transfer (RET) to the second detection label being a fluorescent protein portion which is thereby elicited to energy emission. The form of energy uptake may be anything that is conceivable to the person skilled in the art and may involve, e.g., a chemical reaction (chemiluminescence or bioluminescence) or absorption of radiation (fluorescence or phosphorescence).

The term "fluorescent protein portion" refers to proteins that are capable of fluorescence, i.e. to absorb energy from radiation of a certain wave length, e.g. ultra-violet or visible light, and to emit this energy or a part thereof by radiation, wherein the emitted radiation has a higher wavelength than the eliciting radiation. There are many examples of fluorescent proteins described in the literature that may be useful in connection with the present invention such as GFPs as mentioned above, fluorescent proteins from non-bioluminescent organisms of the class Anthozoa (WO 00/34318, WO 00/34319, WO 00/34320, WO 00/34321, WO 00/34322, WO 00/34323, WO 00/34324, WO 00/34325, WO 00/34326, WO 00/34526) or the fluorescent protein bmFP from *Photobacterium phosphoreum* (Karatani, Photochem. Photobiol. 71 (2000), 230). Preferred, however, are fluorescent proteins being a YFP and eCFP as employed in the appended examples.

The term "resonance energy transfer" (RET) refers to a non-radiative transfer of excitation energy from a donor (first detection portion) to an acceptor molecule (second detection portion) as indicated above (Heyduk T. Measuring protein conformational changes by FRET/LRET. Curr Opin Biotechnol. 2002 August; 13(4):292-6. Review; Truong K, Ikura M. The use of FRET imaging microscopy to detect protein-protein interactions and protein conformational changes in vivo. Curr Opin Struct Biol. 2001 October; 11 (5):573-8. Review; Issad T, Boute N, Boubekeur S, Lacasa D, Pernet K. Looking for an insulin pill? Use the BRET methodology! Diabetes Metab. 2003 April; 29(2 Pt 1):111-7; Boute N, Jockers R, Issad T. The use of resonance energy transfer in high-throughput screening: BRET versus FRET. Trends Pharmacol Sci. 2002 August; 23(8):351-4. Review).

Moreover, FRET or BRET can be determined as shown in the following Figures and Examples.

Figure 13:
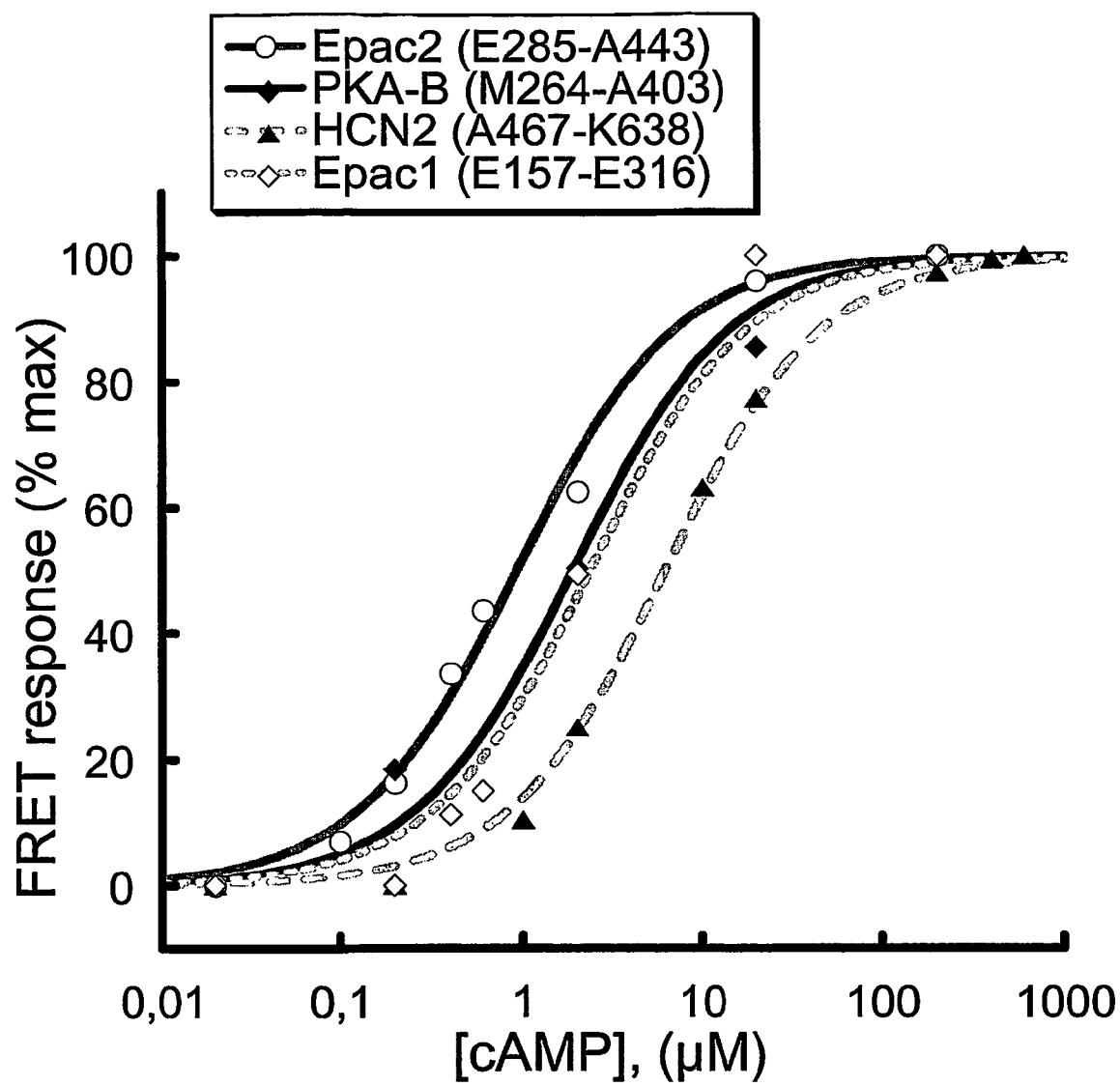

In a preferred embodiment of the chimeric peptide of the invention, the cAMP binding site of the cAMP binding moiety binds to CAMP with high affinity. Preferably, the cAMP binding site of the cAMP binding moiety binds cAMP with a $K_d$ in the range of 1 nM to 50 µM, more preferably in the range of 1 nM to 50 µM, more preferably in the range of 5 nM to 40 µM, more preferably in the range of 100 nM to 30 µM, more preferably in the range of 200 nM to 20 µM. As shown in the examples, a preferred range in this context is, e.g., 5 nM to 5 µM, but also 100 nM to 25 µM. A particular preferred range in this context is between 100 nM and 50 µM. As shown in FIG. 13, a most particular preferred range is between 10 nM and 50 µM, most particular preferred between 10 nM to 3 µM.

In another preferred embodiment of the chimeric peptide of the invention, the cAMP binding moiety is selected from the group consisting of the regulatory subunit (R) of a cAMP dependent protein kinase, a guanine nucleotide exchange factor catabolic gene activator protein, cAMP gated ion channel, a cyclic nucleotide-gated ion channel, neuropathy target esterase (NTE) and cAMP receptor of Dictyostelium.

The family of cAMP-binding proteins comprises over ten protein sequences which encode for proteins with known function, as well as several sequences derived from a search in databases for potential cyclic nucleotide binding sites (Dremier S, Kopperud R, Doskeland S O, Dumont J E, Maenhaut C. Search for new cyclic AMP-binding proteins. FEBS Lett. 2003 Jul. 3; 546(1):103-7). Until 1998 when EPAC1 was cloned and characterized (de Rooij J, Zwartkruis F J, Verheijen M H, Cool R H, Nijman S M, Wittinghofer A, Bos J L. Epac is a Rap1 guanine-nucleotide-exchange factor directly activated by cyclic AMP. Nature. 1998 Dec. 3; 396(6710): 474-7) protein kinase A (PKA) was accepted as a unique cAMP effector in the cell. To the present state of knowledge, several proteins bind cAMP and regulate cell function, e.g. EPAC 1 and 2, cyclic nucleotide gated channels (CNGC), catabolite genes activating protein in *E. coli* (CAP), neuropathy target esterase (NTE). There have been a number of sequences identified which encode for proteins with potential cAMP-binding activity, but their function remains elusive: a mouse embryo EST sequence (A1595216), KIAA0313 human sequence (AB002311), Im493605 sequence (Dremier S, Kopperud R, Doskeland S O, Dumont J E, Maenhaut C. Search for new cyclic AMP-binding proteins. FEBS Lett. 2003 Jul. 3; 546(1):103-7). As apparent to a person skilled in the art, also these sequences can be used for the construction of the chimeric peptide of the invention.

Preferably, the cAMP binding moiety is from PKA, EPAC1, EPAC2, catabolic gene activator protein of *E. coli*, said cAMP gated ion channel, like HCN2 (hyperpolarization-activated, cyclic nucleotide-gated $K^+$ channel 2), neuropathy target esterase (NTE) and cAMP receptor of Dictyostelium. The cAMP binding moiety of PKA, EPAC1 or EPAC2 is preferably of bacterial, mouse, rat or human origin.

In another preferred embodiment of the chimeric peptide of the invention, the detectable labels are fluorescent labels, bioluminescent labels or spin labels (Jahnke W. Spin labels as a tool to identify and characterize protein-ligand interactions by NMR spectroscopy. Chembiochem. 2002 Mar. 1; 3(2-3): 167-73. Review). Preferably, said fluorescent labels are selected from the group consisting of GFP, YFP, CFP, BFP, cytrine, sapphire, and dsRed. The bioluminescent label is preferably luciferase, such as renilla luciferase or firefly luciferase.

As discussed above, in a most preferred embodiment of the chimeric peptide of the invention, the cAMP binding moiety is selected from the following group. These constructs are also particularly useful in the methods provided herein and may be comprised in the kits described below. The preferred constructs comprise cAMP binding moieties selected from the group consisting of:

(a) a cAMP binding moiety of a polypeptide as shown in SEQ ID NOs: 1 to 7 and 74;

(f) a cAMP-binding moiety as shown or as comprised in any one of SEQ ID Nos: 27, 29, 31, 33, 34, 35, 36 and 37;

(g) a cAMP-binding moiety as comprised in any one of SEQ ID Nos: 8 to 20;

(h) a cAMP-binding moiety as comprised in any one of SEQ ID Nos: 39, 41, 43, 45, 47, 49, 51, 53, 55, 57, 59, 61, 63, 65, 67, 69, 71 and 73; and (i) a cAMP binding moiety which is at least 70%, 80%, 90% or 95% identical to a cAMP binding moiety as defined in any one of claims 1 to 8 or the cAMP-binding moiety of (a) to (d).

Accordingly, particularly preferred chimeric peptides of the invention may be selected from (a) a chimeric peptide is encoded by a nucleic acid molecule as shown in any one of SEQ ID Nos: 38, 40, 42, 44, 46, 48, 50, 52, 54, 56, 58, 70 and 72;

(b) a chimeric peptide comprising an amino acid sequence as shown in any one of SEQ ID Nos: 39, 41, 43, 45, 47, 49, 51, 53, 55, 57, 59, 61, 63, 65, 67, 69, 71 and 73;

(c) a chimeric peptide encoded by a nucleic acid molecule which encodes a polypeptide which is at least 70% identical to a polypeptide as defined in (a) or (b) and which can be used for direct determination of cAMP concentration in vitro and/or in vivo; and (d) a chimeric peptide which is encoded by a nucleic acid molecule which is degenerate to a DNA sequence as defined in (a) and (c).

The invention furthermore relates to a nucleic acid molecule encoding the above defined chimeric peptide. Such nucleic acid molecules comprise, but are not limited to DNA molecules as shown in SEQ ID Nos: 38, 40, 42, 44, 46, 48, 50, 52, 54, 56, 58, 60, 62, 64, 66, 68, 70 and 72.

The term "nucleic acid molecule" as used herein means DNA or RNA or both in combination or any modification thereof that is known in the state of the art (see, e.g., U.S. Pat. No. 5,525,711, U.S. Pat. No. 4,711,955, U.S. Pat. No. 5,792,608 or EP 302175 for examples of modifications). Such nucleic acid molecule(s) are single- or double-stranded, linear or circular and without any size limitation. The nucleic acid molecules of the invention can be obtained for instance from natural sources or may be produced synthetically or by recombinant techniques, such as PCR. In a preferred embodiment, the nucleic acid molecules of the invention are DNA molecules, in particular genomic DNA or cDNA, or RNA molecules. Preferably, the nucleic acid molecule is double-stranded DNA. Particular inventive nucleic acid molecules are nucleic acid molecules encoding the polypeptide sequences depicted in SEQ ID NOS: 8 to 20 as well as polypeptide sequences shown in SEQ ID Nos: 39, 41, 43, 45, 47, 49, 51, 53, 55, 57, 59, 61, 63, 65, 67, 69, 71 and 73 and illustrated in FIGS. 1 and 11.

The nucleic acid molecule comprising a nucleotide sequence encoding it is a recombinant nucleic acid molecule, i.e. a nucleic acid molecule that has been produced by a technique useful for artificially combining nucleic acid molecules or parts thereof that were beforehand not connected as in the resulting chimeric peptide. Suitable techniques are for example available from the prior art, as represented by Sambrook and Russell (2001), Molecular Cloning: A Laboratory Manual, CSH Press and Ausubel, Current Protocols in Molecular Biology, Green Publishing Associates and Wiley Interscience, N.Y. (1989) as well as Vilardaga (1995), Biotechniques 18, 605-606. Furthermore, the corresponding techniques are illustrated in the appended examples. Said techniques comprise in particular site-directed mutagenesis.

For the construction of the chimeric peptide of the invention, a polynucleotide sequence encoding a cAMP binding moiety may be used, wherein the polynucleotide sequence is at least 70%, 80%, 90% or 95% identical to a nucleotide sequence encoding the cAMP binding moiety of a polypeptide sequence as comprised in SEQ ID NOS: 1 to 7 or 74 or as listed above. By a nucleic acid having a nucleotide sequence at least, for example, 95% "identical" to a reference nucleotide sequence described in the present invention, it is intended that the nucleotide sequence of the nucleic acid is identical to the reference sequence except that the nucleotide sequence may include up to five point mutations per each 100 nucleotides of the reference nucleotide sequence encoding the polypeptide. In other words, to obtain a nucleic acid having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence.

As pointed out above, the person skilled in the art is readily in the position to deduce from a given amino acid sequence or a given nucleotide sequence a "cAMP binding moiety/domain" and/or the "cAMP binding site". Corresponding methods comprise the method disclosed, inter alia, in Dremier (2003) FEBS Letters 546, 103-107; Rehmann (2003), Nat. Str. Biol. 10, 25-32 or Kawasaki (1998), Science 282, 2275-2279. The corresponding methods comprise, accordingly, databank searches, either alone or in combination with biological, and/or biochemical assays, e.g., restriction enzyme digestion assays (and following binding studies of expressed protein stretches/fragments to cAMP in vivo and/or in vitro), binding assays, competition assays (for example with labelled, e.g., radioactive cAMP) and the like. It is of note that a "cAMP binding site" is also known in the literature as "PBC" or "phosphate binding cassette". A corresponding "cAMP binding site" can be deduced by analogous methods and normally comprises a rather short stretch of amino acid residues (preferably between 13 to 15 amino acids, mostly 14) and normally start with "F" (phenylalanin) and end with an "A" (alanin); see also FIG. 14 or Rehmann (2003), loc.cit. A preferred computer program in context of determination of functional parts of a given amino acid sequence is TBLASTN; see also the algorithm as known from Dremier (2003), loc. cit.

Like the determination of "cAMP binding domains/moieties" and/or "cAMP binding sites", the identification of nucleic acid molecules and/or polypeptides, which are at least 70%, 80%, 90% or 95% identical to a nucleotide sequence or amino acid sequence described in the present invention can also comprise conventional determination using known computer programs. A preferred method for determining the best overall match between a query sequence (a sequence of the present invention) and a subject sequence, also referred to as a global sequence alignment, can be determined using the FASTDB computer program based on the algorithm of Brutlag et al. (Comp. App. Biosci. 6:237-245 (1990)). In a sequence alignment the query and subject sequences are both DNA sequences. An RNA sequence can be compared by converting U's to T's. The result of said global sequence alignment is in percent identity. Preferred parameters used in a FASTDB alignment of DNA sequences to calculate percent identity are: Matrix=Unitary, k-tuple=4, Mismatch Penalty=1, Joining Penalty=30, Randomization Group Length=0, Cutoff Score=1, Gap Penalty=5, Gap Size Penalty 0.05, Window Size=500 or the length of the subject nucleotide sequence, whichever is shorter.

In accordance to the above, for the generation of the chimeric peptide of the invention, a cAMP binding moiety may be used which is at least 70%, 80%, 90% or 95% identical to a cAMP binding moiety of a polypeptide as shown in SEQ ID NOs: 1 to 7 or 74 or as listed above. Particularly preferred are given herein above and comprise, inter alia, amino acid residues 281-445 of EPAC2 (domain B), amino acid residues 203-323 of EPAC1, amino acid residues 274-416 of regulatory II beta subunit of PKA, amino acid residues 544-661 of cyclic-gated potassium channel 2, amino acid residues 12-98 of catabolite gene activating protein, amino acid residues 473-568 of neuropathy target esterase or amino acid residues 628-767 of cyclic nucleotide gated cation channel 4 (CNG-4).

The term "at least 70%" as used herein refers to 70% or more percent sequence identity.

Moreover, the invention relates to a vector comprising the nucleic acid molecule as defined above.

In a preferred embodiment of the vector of the invention, said vector is an expression vector.

The present invention also relates to cloning vectors and expression vectors, particularly plasmids, cosmids, viruses (such as adenoviruses or retroviruses) and bacteriophages used conventionally in genetic engineering, that comprise a nucleic acid molecule or an expression cassette of the invention.

In a preferred embodiment of the invention, the vectors of the invention are suitable for the transformation of fungal cells, plant cells, cells of microorganisms (i.e. bacteria, protists, yeasts, algae etc.) or animal cells, in particular mammalian cells. Preferably, such vectors are suitable for the transformation of human cells. Methods which are well known to those skilled in the art can be used to construct recombinant vectors; see, for example, the techniques described in Sambrook and Russell (2001), loc. cit. Alternatively, the vectors may be liposomes into which the nucleic acid molecules or expression cassettes of the invention can be reconstituted for delivery to target cells. Likewise, the term "vector" refers to complexes containing such nucleic acid molecules or expression cassettes which furthermore comprise compounds that are known to facilitate gene transfer into cells such as polycations, cationic peptides and the like.

In addition to the nucleic acid molecule or expression cassette of the invention, the vector may contain further genes such as marker genes which allow for the selection of said vector in a suitable host cell and under suitable conditions. Generally, the vector also contains one or more origins of replication.

Advantageously, the nucleic acid molecules contained in the vectors are operably linked to expression control sequences allowing expression, i.e. ensuring transcription and synthesis of a translatable RNA, in prokaryotic or eukaryotic cells.

In one aspect, the expression of the nucleic acid molecules of the invention in prokaryotic or eukaryotic cells is interesting because it permits the production of the chimeric peptide of the invention. In addition, it is possible to insert different additional mutations into the nucleic acid molecules by methods usual in molecular biology (see for instance Sambrook and Russell (2001), loc. cit.), leading to the synthesis of proteins possibly having modified properties, e.g. as concerns binding affinity or energy emission (e.g. RET) efficiency. In this regard, it is possible to mutate the nucleic acid molecules present in the vector by inserting or deleting coding sequences or to introduce amino acid substitutions by replacing the corresponding codon triplets.

For genetic engineering, e.g. in prokaryotic cells, the nucleic acid molecules of the invention or parts of these molecules can be introduced into plasmids which permit mutagenesis or sequence modification by recombination of DNA sequences. Standard methods (see Sambrook and Russell (2001), loc. cit.) allow base exchanges to be performed or natural or synthetic sequences to be added. Similarly, for expression in eukaryotic cells, corresponding expression vectors, like pcDNA3 may be employed. DNA fragments can be connected to each other by applying adapters and linkers to the fragments. Moreover, engineering measures which provide suitable restriction sites or remove surplus DNA or restriction sites can be used. In those cases, in which insertions, deletions or substitutions are possible, in vitro mutagenesis, "primer repair", restriction or ligation can be used. In general, sequence analysis, restriction analysis and other methods of biochemistry and molecular biology are carried out as analysis methods. The expression of the nucleic acid molecule of the present invention is preferably in a stable cell line. Procedure for selection of stably transfected cell lines are known in the art; see, inter alia, Vilardaga (2001), JBC 276, 33435-33443. Preferred host cells are CHO-cells, HEK 293, Cos 7, HeLa, PC12 or NIH3T3 cells or even primary cells like primary cardiomyocytes, fibroblasts, endothelial or embryonic stem cells.

Furthermore, the present invention relates to expression cassettes comprising the above-described nucleic acid molecule of the invention and operably linked thereto control sequences allowing expression in prokaryotic or eukaryotic cells.

Suitable expression control sequences include promoters that are applicable in the target host organism or host cell. Such promoters are well known to the person skilled in the art for diverse hosts from prokaryotic and eukaryotic organisms and are described in the literature. For example, such promoters can be isolated from naturally occurring genes or can be synthetic or chimeric promoters. Likewise, the promoter can already be present in the target genome and will be linked to the nucleic acid molecule by a suitable technique known in the art, such as for example homologous recombination. Specific examples of expression control sequences and sources from where they can be derived are given further below and in the appended examples.

Expression cassettes according to the invention are particularly meant for an easy to use insertion into target nucleic acid molecules such as vectors or genomic DNA. For this purpose, the expression cassette is preferably provided with nucleotide sequences at its 5'- and 3'-flanks facilitating its removal from and insertion into specific sequence positions like, for instance, restriction enzyme recognition sites or target sequences for homologous recombination as, e.g. catalyzed by recombinases.

The invention also relates to a host transformed with the vector or nucleic acid molecule as set forth above.

Another embodiment of the invention relates to host cells, in particular prokaryotic or eukaryotic cells, genetically engineered with an above-described nucleic acid molecule, expression cassette or vector of the invention, and to cells descended from such transformed cells and containing a nucleic acid molecule, expression cassette or vector of the invention and to cells obtainable by the above-mentioned method for producing the same. As pointed out below, the invention also relates to non-human transgenic animals comprising nucleic acid sequences encoding the chimeric peptide of the invention.

Preferably, host cells are bacterial, fungal, insect, plant or animal host cells. In a preferred embodiment, the host cell is genetically engineered in such a way that it contains the introduced nucleic acid molecule stably integrated into the genome. More preferably the nucleic acid molecule can be expressed so as to lead to the production of the chimeric peptide of the invention.

A classical overview of different expression systems is for instance contained in Methods in Enzymology 153 (1987), 385-516, in Bitter et al. (Methods in Enzymology 153 (1987), 516-544) and in Sawers et al. (Applied Microbiology and Biotechnology 46 (1996), 1-9), Billman-Jacobe (Current Opinion in Biotechnology 7 (1996), 500-4), Hockney (Trends in Biotechnology 12 (1994), 456-463), Griffiths et al., (Methods in Molecular Biology 75 (1997), 427-440). An overview of yeast expression systems is for instance given by Hensing et al. (Antoine von Leuwenhoek 67 (1995), 261-279), Bussineau (Developments in Biological Standardization 83 (1994), 13-19), Gellissen et al. (Antoine van Leuwenhoek 62 (1992), 79-93, Fleer (Current Opinion in Biotechnology 3 (1992), 486-496), Vedvick (Current Opinion in Biotechnology 2 (1991), 742-745) and Buckholz (Bio/Technology 9 (1991), 1067-1072). Particular preferred expression systems include, but are not limited to Sf9 cells, *E. coli* cells or mammalian cells such as CHO-cells, HEK 293, Cos 7, HeLa, PC12 or NIH3T3 cells.

Expression vectors have been widely described in the literature. As a rule, they contain not only a selection marker gene and a replication origin ensuring replication in the host selected, but also a bacterial or viral promoter and, in most cases, a termination signal for transcription. Between the promoter and the termination signal, there is in general at least one restriction site or a polylinker which enables the insertion of a coding nucleotide sequence. It is possible to use promoters ensuring constitutive expression of the gene and inducible promoters which permit a deliberate control of the expression of the gene. Bacterial and viral promoter sequences possessing these properties are described in detail in the literature. Regulatory sequences for the expression in microorganisms (for instance *E. coli, S. cerevisiae*) are sufficiently described in the literature. Promoters permitting a particularly high expression of a downstream sequence are for instance the T7 promoter (Studier et al., Methods in Enzymology 185 (1990), 60-89), lacUV5, trp, trp-lacUV5 (DeBoer et al., in Rodriguez and Chamberlin (Eds), Promoters, Structure and Function; Praeger, N.Y., (1982), 462-481; DeBoer et al., Proc. Natl. Acad. Sci. USA (1983), 21-25), Ip1, rac (Boros et al., Gene 42 (1986), 97-100). Inducible promoters are preferably used for the synthesis of proteins. These promoters often lead to higher protein yields than do constitutive promoters. In order to obtain an optimum amount of protein, a two-stage process is often used. First, the host cells are cultured under optimum conditions up to a relatively high cell density. In the second step, transcription is induced depending on the type of promoter used. In this regard, a tac promoter is particularly suitable which can be induced by lactose or IPTG (isopropyl-β-D-thiogalactopyranoside) (deBoer et al., Proc. Natl. Acad. Sci. USA 80 (1983), 21-25). Termination signals for transcription such as the SV40-poly-A site or the tk-poly-A site useful for applications in mammalian cells are also described in the literature. Suitable expression vectors are known in the art such as Okayama-Berg cDNA expression vector pcDV1 (Pharmacia), pCDM8, pRc/CMV, pcDNA1, pcDNA3 (Invitrogene; see also appended examples), pSPORT1 (GIBCO BRL)) or pCI (Promega).

The transformation of the host cell with a nucleic acid molecule or vector according to the invention can be carried out by standard methods, as for instance described in Sambrook and Russell (2001), loc. cit. The host cell is cultured in nutrient media meeting the requirements of the particular host cell used, in particular in respect of the pH value, temperature, salt concentration, aeration, antibiotics, vitamins, trace elements etc. The chimeric peptide according to the present invention can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromography and lectin chromatography. In case the chimeric peptide of the invention is expressed as a membrane protein, the protein may be purified applying detergents, like TritonX-100 or SDS. Protein refolding steps can be used, as necessary, in completing the configuration of the protein. Such a purified chimeric peptide may, inter alia, be reassembled and/or introduced into artificial biological membrane, like liposomes, crude membrane preparations or lipid bilayers.

Preferably, the host is a mammalian cell, an amphibian cell, a fish cell, an insect cell, a fungal cell, a plant cell or a bacterial cell, or a transgenic non-human animal.

The present invention furthermore relates to non-human transgenic organisms, i.e. multicellular organisms comprising a nucleic acid molecule encoding a chimeric peptide of the invention or an expression cassette or vector as described above, preferably stably integrated into its genome, at least in a subset of the cells of that organism, or to parts thereof such as tissues or organs. Most preferably, such non-human transgene origin is a mammal like mouse, a rat, a sheep, a goat, a pig, a dog, a rat or a horse.

The transgenic animal expressing the chimeric peptide of the present invention are particularly useful in pharmacological studies, screening and identification method as provided herein. It is of note that in particular for these studies not only cells but also organs or parts of organs of said non-human transgenic animals are particularly useful. It is envisaged that, for example, heart, blood vessel, muscle, gland, bone, kidney or liver, or brain or slice cultures of brain of the herein described non-human transgenic animal are employed in the screening and identification method provided herein. Besides the non-human transgenic animals which are mammals, it is also envisaged that said non-human transgenic organisms may be an amphibian, an insect, a fungi or even a plant. Particular preferred non-human transgenic animals in this context are *Drosphila, C. elegans, Xenopus* as well as yeasts like *S. pombe* or *S. cerevisae* or the *Aspergillus* species. Transgenic plants comprise, but are not limited to, wheat, tobacco, parsley or *Arabidopsis*.

As mentioned herein above and as in particular illustrated in the appended examples, the chimeric peptides defined herein are in particular useful in screening and identification methods for molecules or compounds which are capable of modifying the binding of cAMP to the chimeric peptide or the biological and/or pharmacological action of adenylyl cyclases and/or phosphodiesterases. As the examples show, adenosine as an agonist of Gs-protein coupled receptors can induce elevation of cAMP in the cell. Direct activators of adenylyl cyclase, such as forskolin also produce a detectable FRET-signal.

More preferably, said mammalian cell is a CHO-cell, HEK 293, HeLa, Cos 7, PC12 or NIH3T3 cell as well as primary cell cultures, like neuronal cultures. As apparent to the person skilled in the art, primary cells or transgenic animals expressing the chimeric peptide of the invention can also be utilized for said screening or identification methods.

In another preferred embodiment of the host of the invention, said amphibian cell is an oocyte, preferably a xenopus oocyte.

In a further embodiment, the invention relates to a method for producing cells or hosts capable of expressing the chimeric peptide of the invention comprising genetically engineering cells or hosts with an above-described nucleic acid molecule, expression cassette or vector of the invention.

In addition, the invention relates to a method for producing the chimeric peptide as defined above, comprising culturing/raising the above mentioned host, and optionally, isolating and/or purifying the produced chimeric peptide.

Moreover, the invention relates to chimeric peptides which are obtainable by a method for their production as described above. Accordingly, a further embodiment of the invention relates to a method for producing the chimeric peptide of the invention comprising culturing the above-described host cells under conditions allowing the expression of said chimeric peptide and recovering said chimeric peptide from the membranes of the host cell or host organism. In case the chimeric peptide is localized in the membranes of the host cells, the protein can be recovered from the cultured cells by detergent-treatment.

Moreover, the invention relates to an in vitro method for determining the concentration of cAMP in a sample, comprising adding the chimeric peptide as defined above, or obtainable by the mentioned method, to the sample and measuring/recording FRET or BRET and determining cAMP concentration in the sample by comparing values of the fluorescence emission with a standard curve obtained with defined concentrations of cAMP.

As already explained herein above, the detection portions/labels present in the chimeric peptide of the invention facilitate the detection of a conformational change within the chimeric peptide of the invention upon cAMP binding, which, in turn, leads to a change of the energy emitted by the detection portions/detectable labels which can be monitored by FRET or BRET. The conformational change of the cAMP binding moiety upon cAMP binding results in a detectable change of RET between the detection portions/labels. Such a change can for instance be taken from a comparison of the emission spectra of a cAMP binding moiety in the absence of a suitable binding compound, i.e. cAMP, with the same cAMP binding moiety in the presence of such a compound. If, for example, RET is increased, the emission peak of the acceptor is raised and the emission peak of the donor is diminished. Thus, the ratio of the emission intensity of the acceptor to that of the donor is indicative for the degree of RET between the detection portions. The conformational change of the chimeric peptide upon binding of cAMP may result either in a decrease or an increase of the distance between the detection portions. Thus, the chimeric peptide of the invention provides a monomolecular tool particularly feasible to directly determining the cAMP levels in a sample. For example, the chimeric peptide as defined above, may be added to a sample and by measuring and/or recording FRET or BRET, the cAMP concentration in the sample, e.g., a cell, cell lysate, crude cell extract, membrane preparation or a tissue can be measured by comparing values of the fluorescence emission with a standard curve obtained with defined concentrations of cAMP. To exemplify a possible assay for cAMP measurements in vitro, cells can be transiently transfected with a plasmid encoding, e.g., an EPAC2-based chimeric peptide carrying CFP and YFP as described above. 24 h post transfection, cell lysates can be prepared and emission spectra can be taken after addition of different cAMP concentrations as indicated in the Examples. Decrease in the intensity at 525 nm with its increase at 475 nm represents a loss in FRET-signal between CFP and YFP. The relation of the signal intensity 475 nm/intensity 525 nm to cAMP concentration can be plotted into a saturation curve for subsequent precise measurements of cAMP concentration in different unknown samples.

In an alternate in vitro assay which may be used for the determination of cAMP concentration in a sample, for example, a His-tagged EPAC-cAMP FRET sensor of the invention is expressed in Sf9 or *E. coli* cells. Subsequently, the protein is isolated by suitable purification methods, e.g. by using a nickel column. In the following, a defined volume of a buffer solution containing a specific concentration of the chimeric peptide of the invention is added to a defined volume of the sample. The change in FRET of the sample is detected by the use of a photometer which is suitable for FRET detection, for example as a 96-well reader. At the same time, a calibration curve is monitored by using aliquots of the sample to which defined amounts of cAMP are added. Changes in FRET are monitored caused by cAMP binding with the chimeric peptide of the invention which reduces FRET.

In accordance with the above, the sample as defined herein may be for instance a cell, a cell lysate, a crude cell extract, a membrane preparation, a tissue or biofluids. Biofluids as used herein preferably refer to body fluids such as semen, lymph, sera, plasma, urine, synovial fluid or spinal fluid.

The above described assay using the chimeric peptide of the invention shows various advantages. For example, said assays are sensitive for samples derived from various sources. Fluorescence is detected in accordance with industry standard. Furthermore, the rate of detection is very high, i.e. <10 min compared to >1 h by common radio-immunoassays (RIA). Furthermore, the above assay shows high selectivity for cAMP compared to ATP, which is not the case by many RIA assays. Moreover, it is cost-efficient and the FRET sensor can be produced in large-scale by expressing in SF9/*E. coli*, which is not the case for antibodies. In addition, the above described assay is applicable for HTS. Finally, if the fluorophores are replaced with luciferase the above assay can be adapted for BRET.

As apparent for those skilled in the art, the chimeric peptides of the invention may also be in vitro-labeled by using chemical fluorescence labelings.

The invention also relates to a method for monitoring over space and time the amount, distribution, location, or fluctuation of cAMP in a living cell or tissue, comprising transforming a cell or tissue with the nucleic acid or vector of the invention and measuring/recording FRET or BRET in the living cell or tissue, as well as in living (non-human) transgenic animals.

By measuring FRET changes by using the chimeric peptide of the invention, it is possible to monitor cAMP concentration changes in single cells with a high spatial- and time— (i.e. ms temporal) resolution. This new methodology is uniquely suited for temporal and topographical mapping of cAMP signalling and has the potential to uncover new aspects of this transduction system as well as to delineate the fine details of cAMP biochemistry in vivo.

Moreover, the chimeric peptide of the invention may be utilized to investigate how the cAMP signalling pathway is organized and regulated within the three dimensional matrix of cells, to analyze its temporal dynamics and to delineate adaptation/alteration mechanisms implemented in physiopathological conditions in various cell types. For instance, it is possible to analyse cell types where cAMP plays a key role, such as cardiac myocytes. It has been recently shown that in neonatal cardiac myocytes, β-adrenergic receptor stimulation generates local microdomains of high cAMP that are maintained by the activity of phosphodiesterases (Zaccolo M, Pozzan T. Discrete microdomains with high concentration of cAMP in stimulated rat neonatal cardiac myocytes. Science. 2002 Mar. 1; 295(5560):1711-5). The chimeric peptide of the invention may be used to extend such analysis in order to generate detailed information on the kinetics of cAMP, the spatio-temporal dynamics of 7-transmembrane receptor-, adenylyl cyclase- or phosphodiesterase-activation and the regulatory mechanisms involved. Subsequently, pathological conditions where a possible role for cAMP signalling has been suggested may be analysed. Said disease conditions include, but are not limited to such diabetes mellitus, cardiac hypertrophy, cardiac insufficiency, or hypertension. Moreover, it is well described that cAMP signaling is involved in learning, memory and immune responses as already set forth above.

In addition, it is widely accepted that the cAMP pathway plays a key role in proliferation control, however the molecular details of cAMP-dependent cell cycle regulation are still poorly understood due to the difficulty to follow in vivo the specific molecular event affected by cAMP. Thus, the chimeric peptide of the invention may be used for FRET/BRET-based monitoring of cAMP in prokaryotic or eukaryotic, preferably mammalian cells in order to study the role of the cAMP signalling pathway in the cell cycle control and in cell proliferation. For instance, stable mammalian cell line clones may be established expressing the chimeric peptide of the invention and cAMP changes may be measured by monitoring cAMP dynamics during the cell cycle of synchronized cells. Subsequently, the same type of analyses may be extended to unperturbed single cells.

The chimeric peptide of the invention may also be used for monitoring over space and time the amount, distribution, location, or fluctuation of cAMP in tissues, for example, in organs of transgenic animal expressing the chimeric peptide of the invention. For instance, by using tissue-specific promoters, the chimeric peptide may be expressed in a particular tissue or organ of transgenic animals to study cAMP signaling in organogenesis or pathogenesis of diseases of that organ. Of course, these are only non-limiting examples without restricting the embodiments of the invention.

Thus, the chimeric peptide of the invention provides a cAMP sensor which is particularly suitable for the detection of intracellular cAMP concentration in living cells, tissues and transgenic animals using a photometer with ms time resolution. Said assays show various advantages compared to the PKA-FRET assay described in the art (Zaccolo et al., loc. cit). So far, the PKA-FRET assay is the only one which is suitable for the application in living cells. The PKA-FRET assay is based on the detection of FRET between two subunits of protein kinase A, which is activated via the binding of 4 cAMP molecules. The binding mechanism is very complicated since all of the four binding sites are cooperatively regulated. Therefore, the inventors use a chimeric peptide containing only one cAMP binding site as a intramolecular FRET system. Basically, there are differences in handling and application of the two types of assays mentioned above which lead to advantages of the method of the present invention. The chimeric peptide of the present invention is biologically inactive since regulatory domains of the protein have been deleted, except the cAMP binding domain. Therefore, the sensor of the invention can be expressed in every cell without causing problems, for example, it does not interfere with cell biology or cell physiology. Thus, it is possible to generate stable cell lines and transgenic organisms. Furthermore feedback-mechanisms, which have an effect on the production of cAMP, are not actively modified in contrast to the PKA-FRET method described in the art. Moreover, the stoichiometry of fluorophores is always 1:1 in the intramolecular FRET system. In contrast, in the PKA-FRET system, the stoichiometry of fluorophores is variable and, therefore, can not be regulated.

The invention also relates to a method for identifying molecules or compounds which are capable of activating or inhibiting binding of cAMP to the chimeric peptide of the invention, comprising the steps of:
(a) transfecting the nucleic acid or the vector of the invention into a cell thereby expressing the chimeric peptide of the invention;
(b) contacting said cell with (a) molecule(s) or compound(s) to be tested; and
(c) measuring whether said molecule(s) or compound(s) to be tested lead(s) to a change in energy emitted by said two detectable labels comprised in the chimeric peptide as defined above.

As mentioned herein above and as in particular illustrated in the appended examples, the chimeric peptides defined herein are particularly useful in screening and identification methods for molecules or compounds which are capable of modifying, i.e. activating or inhibiting the binding of cAMP to the cAMP binding site of the chimeric peptide of the invention. For instance, cells as set forth above may be transfected with the nucleic acid or the vector of the invention resulting in the expression of the chimeric peptide of the invention. In a following step, these cells are contacted with (a) molecule(s) or compound(s) to be tested. By measuring whether said molecule(s) or compound(s) to be tested lead(s) to a change in energy emitted by said two detectable labels comprised in the chimeric peptide, it is possible to identify molecules or compounds which are capable of activating or inhibiting binding of cAMP to the chimeric peptide of the invention. As the examples show, the present invention is based on the surprising finding that intramolecular RET-analysis can be carried out on the chimeric peptide of the invention, based on a conformational change upon cAMP binding, resulting in a change in energy (measurable by FRET or BRET). Accordingly, the present invention provides for the first time means and methods whereby activation (as well as de-activation) or inhibition of cAMP binding to the chimeric peptide of the invention may be observed with a high resolution and within physiological kinetics. In particular, high resolution assays for conformational changes/switches of activation or inhibition of the chimeric peptide of the invention in living cells are provided. Therefore, the present invention provides for distinct screening as well as identification methods for agonists, partial agonists, inverse agonists as well as antagonists of the chimeric peptide of the invention. In context of this invention as well as in accordance with the pharmacological sciences, the term "agonist" can be confined as a molecule or a compound that activates binding of cAMP to the chimeric peptide of the invention. As "partial agonists" the art defines molecules/compounds that behave like agonists, but that, even at high concentrations, cannot activate the binding of cAMP to the chimeric peptide of the invention to the same maximal extend as full agonists. The term "antagonist" relates to molecules/compounds that inhibit binding of cAMP to the chimeric peptide of the invention.

The identification and/or characterization of molecules which are capable of activating or inhibiting the cAMP binding to the chimeric peptide of the invention, may be, inter alia, achieved by transfecting an appropriate host with a nucleic acid molecule encoding the chimeric peptide of the invention. Said hosts comprise, but are not limited to CHO-cells, HEK 293, HeLa, Cos 7, PC12 or NIH3T3 cell, (primary) cardiomyocytes, fibroblasts, endothelial or embryonic stem cells, (primary) cultured nerve cells, muscle cells or frog oocytes. The transfection may be in the form of a transient transfection. Alternatively, stable cell lines expressing the chimeric peptide of the invention may be used. The cells are then contacted with (a) molecule(s) or compound(s) to be tested and it is measured whether said molecule(s) or compound(s) lead(s) to a change in energy emitted by said two detectable labels comprised in the chimeric peptide as defined above. As the appended examples illustrate, the particular preferred measurement methods comprise the FRET- or BRET-measurements.

The invention further relates to a method for identifying molecules or compounds which are capable of activating, deactivating or inactivating the biological/pharmacological function of an adenylyl cyclase or a phosphodiesterase, comprising the steps of:
(a) transfecting the nucleic acid or the vector of the invention into a cell expressing an adenylyl cyclase or a phosphodiesterase;
(b) contacting said cell with (a) molecule(s) or compound(s) to be tested; and
(c) measuring whether said molecule(s) or compound(s) to be tested lead(s) to a change in energy emitted by said two detectable labels comprised in the chimeric peptide as defined above.

The chimeric peptide defined herein are particularly useful in screening and identification methods for molecules or compounds which are capable of modifying the biological and/or pharmacological action of adenylyl cyclases or phosphodiesterases. Briefly discussed, ligand binding to a number of Gs-protein coupled receptors (e.g. adrenergic $\beta 1$ and $\beta 2$, adenosine A2, prostaglandin E2) activates adenylyl cyclase, a cAMP producing enzyme, which is an ubiquitous second messenger capable of regulating various cell processes through activation of its targets protein kinase A, EPAC and cyclic nucleotid gated channels. Intracellular levels of cAMP are negatively regulated by specific phosphodiesterases that determine strength and spatial organisation of the signal. Pathologic and therapy-induced changes in cAMP signaling could result in several chronic diseases or side effects (heart failure, bronchial asthma, inflammatory diseases, cancer) (Cooper D M. Regulation and organization of adenylyl cyclases and cAMP. Biochem J. 2003 Nov. 1; 375(Pt 3):517-29; Conti M, Richter W, Mehats C, Livera G, Park J Y, Jin C. Cyclic AMP-specific PDE4 phosphodiesterases as critical components of cyclic AMP signaling. J Biol. Chem. 2003 Feb. 21; 278(8):5493-6).

As the examples show, the present invention is based on the surprising finding that intramolecular RET-analysis can be carried out on the chimeric peptide of the invention, based on a conformational change upon cAMP binding, resulting in a charge in energy (measurable by FRET or BRET). Accordingly, the present invention provides for the first time means and methods whereby activation (as well as de-activation) of the chimeric peptide of the invention may be observed with a high resolution and within physiological kinetics. In particular, high resolution assays for regulation of adenylyl cyclases or phosphodiesterases in living cells are provided.

According to the methods provided herein, the invention provides for identifying, characterizing, screening compounds or molecules which are capable of activating, deactivating or inactivating adenylyl cyclases or phosphodiesterases whereby said interaction may lead to an activation, a partial activation, an inhibition or a partial inhibition of the biological and/or pharmacological function of said adenylyl cyclases or phosphodiesterases. Therefore, the present invention provides for distinct screening as well as identification methods for agonists, partial agonists, inverse agonists as well as antagonists of adenylyl cyclases or phosphodiesterases. In context of this invention as well as in accordance with the pharmacological sciences, the term "agonist" can be confined as a molecule or a compound that binds to and activates adenylyl cyclases or phosphodiesterases. As "partial agonists" the art defines molecules/compounds that behave like agonists, but that, even at high concentrations, cannot activate the adenylyl cyclases or phosphodiesterases to the same maximal extend as full agonists. The term "inverse agonist" relates to molecules/compounds that bind to and inhibit activity of the corresponding adenylyl cyclases or phosphodiesterases. These inverse agonists are of particular importance and visible, when the adenylyl cyclases or phosphodiesterases exhibit intrinsic agonist-independent activity. The term "antagonist" relates to molecules/compounds that bind to the adenylyl cyclases or phosphodiesterases but do not alter the intrinsic activity of said enzymes. They may also prevent binding of the corresponding ligand of the adenylyl cyclases or phosphodiesterases and they may prevent the binding and activation of the adenylyl cyclases or phosphodiesterases by their agonists or partial agonists.

In accordance with the present invention, the term "antagonist" denotes molecules/substances, which are capable of inhibiting and/or reducing an agonistic effect. The term "antagonist" comprises competitive, non-competitive, functional and chemical antagonists as described, inter alia, in Mutschler, "Arzneimittelwirkungen" (1986), Wissenschaftliche Verlagsgesellschaft mbH, Stuttgart, Germany. The term "partial antagonist" in accordance with the present invention means a molecule/substance that is capable of incompletely blocking the action of agonists through, inter alia, a non-competitive mechanism. As "agonist", in accordance with this invention, molecules/substances are denoted which have an affinity as well as an intrinsic activity. Mostly, said intrinsic activity ($\alpha$) is defined as being proportional to the quotient of the effect, triggered by said agonist ($E_A$) and the effect which can be maximally obtained in a given biological system ($E_{max}$): therefore, the intrinsic activity can be defined as $$\alpha \sim \frac{E_A}{E_{max}}$$

The highest relative intrinsic activity results from $E_A/E_{max}=1$. Agonists with an intrinsic activity of 1 are full agonists, whereas substances/molecules with an intrinsic activity of >0 and <1 are partial agonists. Partial agonists show a dualistic effect, i.e. they comprise agonistic as well as antagonistic effects.

The person skilled in the art can, therefore, easily employ the compounds and the methods of this invention in order to elucidate the agonistic and/or antagonistic effects and/or characteristics of a compound/molecule/substance to be identified and/or characterized in accordance with any of the above described methods.

The identification and/or characterization of molecules which are capable of activating, deactivating or inactivating the chimeric peptide, may be, inter alia, achieved by transfecting an appropriate host stably or transiently expressing adenylyl cyclases or phosphodiesterases with a nucleic acid molecule encoding the chimeric peptide of the invention. Said hosts comprise, but are not limited to CHO-cell, HEK 293, HeLa, Cos 7, PC12 or NIH3T3 cell, frog oocytes or primary cells like primary cardiomyocytes, fibroblasts, muscle, endothelial or embryonic stem cells. Of course, it is also possible to use cell lines stably transfected with the chimeric peptide encoding nucleic acid in which nucleic acids encoding adenylyl cyclases or phosphodiesterases are transfected. The cells are then contacted with (a) molecule(s) or compound(s) to be tested and it is measured whether said molecule(s) or compound(s) lead(s) to a change in energy emitted by said two detectable labels comprised in the chimeric peptide as defined above. As set forth above, the particular preferred measurement methods comprise the FRET- or BRET-measurements.

Moreover, the invention relates to a method of screening for molecules or compounds which are activators/agonists, inverse agonists or inhibitors/antagonists of the biological/pharmacological function of an adenylyl cyclase or a phosphodiesterase, comprising the steps of (a) transfecting the nucleic acid or vector of the invention into a cell expressing an adenylyl cyclase or a phosphodiesterase;

(b) contacting said cell with the molecule(s) or compound(s) to be tested;

(c) measuring and/or detecting a change in energy emitted by said two detectable labels comprised in the chimeric peptide as defined above; and (d) comparing said change in energy to a standard response as measured in the absence of said candidate molecule(s)/compound(s).

The term "standard response" as used herein refers to a signal, i.e. change in FRET, which is induced by routinely used activators/inhibitors of adenylyl cyclase or phosphodiestetase or agonists/partial agonists/reverse agonists/antagonists of G-protein coupled receptors, used as so called reference compounds. For in vitro measurements, the "standard response" as defined herein refers to a signal, i.e. change in FRET, which is induced by addition of a known cAMP concentration, also termed standard concentration or reference concentration.

In addition, the invention relates to a method for identifying molecules or compounds which are capable of eliciting a biological/pharmacological response of an adenylyl cyclase or a phosphodiesterase, comprising the steps of:
(a) transfecting the nucleic acid or vector of the invention into a cell expressing an adenylyl cyclase or a phosphodiesterase;
(b) contacting said cell with the molecule(s) or compound(s) to be tested; and
(c) identifying among these molecules/compounds the molecules/compounds which are capable of eliciting a change in energy emitted by said two detectable labels comprised in the chimeric peptide of the invention.

Potential candidate molecules or candidate mixtures of molecules may be, inter alia, substances, compounds or compositions which are of chemical or biological origin, which are naturally occurring and/or which are synthetically, recombinantly and/or chemically produced. Thus, candidate molecules may be antibodies, proteins, protein-fragments, peptides, amino acids and/or derivatives thereof or other compounds, such as ions, which bind to and/or interact with, inter alia, the chimeric peptide of the invention, adenylyl cyclases or phosphodiesterases.

A person skilled in the art will immediately appreciate that the methods of the invention may present an important contribution to pharmacological research, in particular in the field of drug screening. Thus, corresponding techniques for drug screening described in the literature are incorporated herein by reference. This includes for instance Kyranos (Curr. Opin. Drug. Discov. Devel. 4 (2001), 719-728), Pochapsky (Curr. Top. Med. Chem. 1 (2001), 427-441) and Bohets (Curr. Top. Med. Chem. 1 (2001), 367-383).

According to the present embodiment, in principle any kind of cell, membrane, membrane preparation or liposome may be used for the present method that is amenable to optical detection. The cell to be used can be transformed so as to express the chimeric peptide of the present invention. Thus, the cells may be single cells such as bacteria, yeasts, protozoa or cultured cells, e.g., of vertebrate, preferably mammalian, more preferably human origin. For certain applications, it may be useful to take pathogenetically affected cells such as tumor cells or cells infected by an infectious agent, e.g. a virus, wherein preferentially measurements are conducted in comparison with corresponding healthy cells. Likewise, the cells may be part of a tissue, organ or organism, in particular of a non-human transgenic animal defined above.

The candidate compounds or test compounds can in principle be taken from any source. They may be naturally occurring substances, modified naturally occurring substance, chemically synthesized substances or substances produced by a transgenic organism and optionally purified to a certain degree and/or further modified. Practically, the candidate compound may be taken from a compound library as they are routinely applied for screening processes.

The term "contacting" refers to the addition of a candidate compound/test compounds to the analyzed cell in a way that the compound may become effective to the cell at the cell surface or upon cellular uptake. Typically, the candidate compound or a solution containing it may be added to the assay mixture. Step (a) of the methods of the present invention, i.e. the "contacting step" may likewise be accomplished by adding a sample containing said candidate compound or a plurality of candidate compounds to the assay mixture. If such a sample or plurality of compounds is identified by the present method to contain a compound of interest, then it is either possible to isolate the compound from the original sample or to further subdivide the original sample, for example, if it consists of a plurality of different compounds, so as to reduce the number of different substances per sample and repeat the method with the subdivisions of the original sample. Depending on the complexity of the sample, the steps described herein can be performed several times, preferably until the sample identified according to the method of the invention only comprises a limited number of or only one substance(s). Preferably said sample comprises substances of similar chemical and/or physical properties, and most preferably said substances are identical.

Step (b), i.e. the "measuring or identification step" may be carried out in accordance with the explanations regarding measuring a change in energy emission of the fusion proteins, i.e. the chimeric peptides of the invention as given hereinabove. Particularly preferred are optical measurement techniques that allow a resolution of fluorescence on the level of single cells, preferably at the subcellular level. Suitable imaging techniques are described in the literature such as in Periasamy A., Methods in Cellular Imaging, 2001, Oxford University Press or in Fluorescence Imaging Spectroscopy and Microscopy, 1996, edited by: X. F. Wang; Brian Herman. John Wiley and Sons. They may involve fluorescence, preferably confocal, microscopy, digital image recording, e.g. by way of a CCD camera, and suitable picture analysis software. The appended examples also provide for useful settings for measuring candidate compounds. Preferentially, step (b) is carried out by running parallel control experiments. For instance, a corresponding cell expressing the same chimeric peptide may be observed under corresponding conditions as in steps (a) and (b), however, without contacting a candidate compound.

Accordingly, potential candidate molecules may be contacted with a cell as referred to above which express a chimeric peptide of the invention or with a membrane patch, a membrane preparation, comprising a chimeric peptide of the invention and measuring a corresponding response (inter alia, a dose-response, a current-response, or a concentration response) in order to elucidate any effect said candidate molecule causes. Said response is most preferably measured by methods provided herein and in particular by FRET or BRET technology.

Within the scope of the present invention are also methods for identifying, characterizing and for screening of molecules which are capable of interacting with adenylyl cyclases or phosphodiesterases which comprise so-called high-throughput screening methods and similar approaches which are known in the art (Spencer, Biotechnol. Bioeng. 61 (1998), 61-67; Oldenburg, Annu. Rep. Med. Chem. 33 (1998), 301-311; Milligan, Trends Pharmacol. Sci. 20 (1999), 118-124) carried out using 96-well, 384-well, 1536-well (and other) commercially available plates. Further methods to be employed in accordance with the present invention comprise, but are not limited to, homogenous fluorescence readouts in high-throughput screenings (as described, inter alia, in Pope, Drug Discovery Today 4 (1999), 350-362). The method of the present invention for identification, characterization and/or screening of molecules capable of interacting with adenylyl cyclases or phosphodiesterases, can, inter alia, employ hosts as defined herein which express the chimeric peptide of the present invention. Cell-based assays, instrumentation for said assays and/or measurements are well-known in the art and described, inter alia, in Gonzalez, Drug Discovery Today 4 (1999), 431-439 or Ramm, Drug Discovery Today 4 (1999), 401-410.

In a preferred embodiment of the screening methods of the invention, said energy change is an increase or decrease of fluorescence resonance energy transfer (FRET) or bioluminescence resonance energy transfer (BRET).

In a preferred embodiment, the response or energy changes to be measured in the methods provided herein correspond to an increase or a decrease of fluorescence resonance energy transfer (FRET). In FRET, both donor and acceptor, i.e. both detection portions, are fluorescent protein portions and, for measuring FRET, the fusion protein is supplied with energy, i.e. radiation, appropriate for exciting energy emission by the first detection portion.

Accordingly, it is a preferred embodiment of the chimeric peptide of the present invention, that the first detection label is a fluorescent protein portion.

The efficiency of FRET is dependent on the distance between the two fluorescent partners. The mathematical formula describing FRET is the following: $E=R_0^6/(R_0^6+r^6)$, where E is the efficiency of FRET, r is the actual distance between the fluorescent partners, and $R_0$ is the Förster distance at which FRET is 50% of the maximal FRET value which is possible for a given pair of FRET partners. $R_0$, which can be determined experimentally, is dependent on the relative orientation between the fluorescent partners ($\kappa$), refractive index of the media (n), integral overlap of the emission of the donor with the excitation of the acceptor partner ($J(\lambda)$), and the quantum yield of the fluorescent donor partner ($Q_D$) ($R_0^6=8.79\times10^{-25}[\kappa^2 n^{-4} Q_D J(\lambda)]$ (in cm$^6$)). In classical FRET based applications the orientation factor $\kappa^2$ is assumed to equal ⅔, which is the value for donors and acceptors that randomize by rotational diffusion prior to energy transfer (Lakovicz, Principles of Fluorescence spectroscopy, second edition, page 370). Thus, at randomized rotational diffusion, the change in ratio is assumed to be only due to a change in distance between the chromophores. For perpendicular dipoles $\kappa^2$ is 0.

In accordance with the appended examples, a decrease in FRET-signal can be determined by the following equation: $r(t)=A\times(1-e^{-t/\tau})$, where $\tau$ is the time constant (s) and A is the magnitude of the signal. When necessary for calculating $\tau$, agonist-independent changes in FRET due to photobleaching were subtracted.

In order to apply FRET for detection of agonists, antagonists, partial agonists and partial antagonists as well as inverse agonists, the person skilled in the art is capable of selecting suitable detection labels (defined above) for the chimeric protein of the invention that show a detectable FRET and a detectable change of FRET upon a conformational change in its structure. Preferably, maximum FRET efficiency is at least 5%, more preferably at least 50% and most preferably 80% of the energy released by the first detection label upon excitation. Additionally, the two detection labels need to have a spectral overlap. The greater the overlap of the emission spectrum of the donor with the absorption spectrum of the acceptor, the higher is the value of $R_0$. Acceptors with larger extinction coefficients lead to higher $R_0$ values. In contrast, the overlap in excitation spectra of both detection portions should be small enough to prevent coexcitation of the acceptor chromophore. Likewise, the spectra of both detection portions should only overlap to an extent that discrimination between the two emission signals is still possible.

As detailed in the appended examples, in a particularly preferred embodiment, the first detection portion is cyan fluorescent protein (CFP) and the second detection portion is enhanced yellow fluorescent protein (eYFP).

It has been shown that CFP and YFP are particularly well suited for the chimeric peptide of the present invention since they show an efficient change in FRET. CFP and eYFP are well known in the art and nucleic acid molecules containing corresponding coding sequences are commercially available e.g. from Clonetech. Said nucleic acid sequences are also shown in appended SEQ ID NOS: 23 and 24, whereas the corresponding amino acid sequences are shown in SEQ ID NOS: 21 and 22, respectively.

In a further preferred embodiment of the present invention the methods provided herein are based on the detection of responses or energy changes which comprise an increase or a decrease of bioluminescent resonance energy transfer (BRET). BRET-technology is very well known in the art and, inter alia, described in Angars, (2000) PNAS 97, 3684-3689; in Mercier (2002), JBC 277, 44925-44931; in Barcock, (2003), JBC 278, 3378-3385 or in WO 99/66324. As pointed out herein above a preferred bioluminescent protein is renilla luciferase but also firefly luciferase may be employed. As a preferred fluorescent protein portion in the chimeric peptide of the present invention comprising renilla luciferase as a first detection system, enhanced yellow fluorescent protein or yellow fluorescent protein may be employed.

In accordance with the methods provided herein in a most preferred embodiment, the chimeric peptide of the present invention is located, respectively inserted, into a biological membrane. Most preferably, said biological membrane is a plasma membrane of a cultured cell or is a membrane in (a) cell(s) of an organ or tissue of a non-human transgenic animal expressing the chimeric peptide of the present invention. Further embodiments of the remaining and/or identification methods of the present invention are given and illustrated in the appended examples. It is of note that in context of the present invention several control as already briefly discussed herein above may be employed. For example, chimeric peptides comprising only one detectable label may be used as controls. Such chimeric peptides will not provide for any change in energy emitted or to a detectable response which may be measured. Accordingly, the test molecules or test compounds or samples comprised either alone or in combination such molecules or compounds may be tested in parallel experiment on chimeric peptides of the present invention, capable of eliciting a distinct response upon conformational change and chimeric peptides which only comprise one of the above-identified detectable labels and are, accordingly, not capable of eliciting a corresponding signal, in particular of eliciting an resonance energy transfer. Another control protein to be employed in accordance with the method of the present invention is the chimeric peptide which comprises both detectable labels on the C-terminus.

The invention also provides for a diagnostic composition comprising the chimeric peptide, the nucleic acid molecule, the vector, the host cell or the organs or cells of the non-human transgenic animal of the invention. Such a diagnostic composition is particularly useful in the methods of the present invention.

The invention also relates to a kit comprising the chimeric peptide, the nucleic acid molecule, the vector or the host cell of the invention or organs or cells of the non-human transgenic animal as characterized above.

The embodiments disclosed in connection with the method of the present invention apply, mutatis mutandis, to the kit of the present invention.

Advantageously, the kit of the present invention further comprises, optionally (a) reaction buffer(s), storage solutions, wash solutions and/or remaining reagents or materials required for the conduction of scientific, pharmacological and drug screening assays or the like as described herein.

Furthermore, parts of the kit of the invention can be packaged individually in vials or bottles or in combination in containers or multicontainer units.

The kit of the present invention may be advantageously used, inter alia, for carrying out the method for detecting cAMP concentrations, cAMP spatio-temporal distributions as described herein and/or it could be employed in a variety of applications referred herein, e.g., screening reagents for compounds capable of activating or inhibiting cAMP binding, as well screening methods for compounds capable of influencing biological molecules, like adenylyl cyclase or phosphodiesterase. Additionally, the kit of the invention may contain means for detection suitable for scientific, medical and/or diagnostic purposes. The manufacture of the kits follows preferably standard procedures which are known to the person skilled in the art. The kit of the present invention is preferably useful in a detection assays as provided herein.

Similarly, kits are provided which comprise the compounds of the invention, in particular, the chimeric peptide, the nucleic acid molecule, the vector, the host cell or the organs or cells of the non-human transgenic animal of the invention. These kits as provided herein are particularly useful in the methods of the present invention and in particular in the determination of cAMP concentrations in vivo and/or in vitro. These kits as well as the methods provided herein are also useful in pharmaceutical screenings, also comprising "high-throughput" screening. The technical advantage of the chimeric peptide, the nucleic acid molecule, the vector, the host cell or the organs or cells of the non-human transgenic animal, the kits and methods of the present invention is the use of the chimeric constructs/peptides of the invention as functional biosensors. Accordingly, the compounds and methods of the present invention are also useful in basic scientific, preferably biomedical and/or biochemical research, and in drug screenings. The invention also allows the use of specific devices which can be employed to monitor the cAMP concentration in living cells and/or organisms. These devices are useful in measuring cAMP with the help of the chimeric peptides/constructs of the invention. The devices comprise, inter alia, light sources, filter systems, light detections systems, in particular emission detectors.

In addition, the invention relates to the use of the chimeric peptide, the nucleic acid molecule, the vector or the host cell of the invention or organs or cells of the non-human transgenic animal as defined above for the detection of (a) modifier(s) of the biological activity of an adenylyl cyclase or a phosphodiesterase in vivo/in vitro.

The invention also relates to the use of the chimeric peptide or the nucleic acid molecule, the vector, the host cell or the organs or cells of the non-human transgenic animal of the invention for the detection of (a) modifier(s) of cAMP binding to the chimeric peptide of the invention or the biological activity of adenylyl cyclases or phosphodiesterases in vivo or in vitro.

Additionally, the present invention relates to a method for the production of a pharmaceutical composition comprising the steps of the method of the invention for identifying, characterizing and/or screening of molecules which are capable of interacting with the chimeric peptide of the invention, adenylyl cyclases or phosphodiesterases, and further comprising a step, wherein a derivative of said identified, characterized and/or screened molecule is generated. Such a derivative may be generated by, inter alia, peptidomimetics.

The invention furthermore relates to a method for the production of a pharmaceutical composition comprising the steps of the method of the invention for identifying, characterizing, screening and/or derivatizing of molecules which are capable of interacting with the chimeric peptide of the invention, adenylyl cyclases or phosphodiesterases and formulating the molecules identified, characterized, screened and/or derivatized in pharmaceutically acceptable form.

The figures show:

FIG. 1: Construction of GFP-tagged cAMP-binding proteins. Sequences encoding for 1 or 2 binding domains of PKA or EPAC were amplified using PCR and fused with those of EYFP and ECFP with subsequent subcloning and expression in pcDNA3 (mammalian expression) or pVL1393 (Sf9 insect cell expression) as described in Example 1. A relative FRET-signal for each chimeric protein is indicated. Chimeras containing both cAMP-binding domains of PKA and EPAC2 or a low affinity domain A of EPAC2 were inactive, whereas constructs with a single high-affinity cAMP-binding domain gained powerful sensing proteins.

FIG. 2: Crystal structure of the B cAMP-binding domain of protein kinase A (PKA) regulatory subunit and EPAC2. cAMP-binding cassettes are shown in yellow. Fluorophores (GFP variants) were inserted at the labeled positions of adjacent alpha-helecies to produce functional cAMP-sensing proteins. Upon binding the agonist a conformational change in B domains is assumed, which leads to change of distance between GFPs and of FRET-signal.

Figure 3:
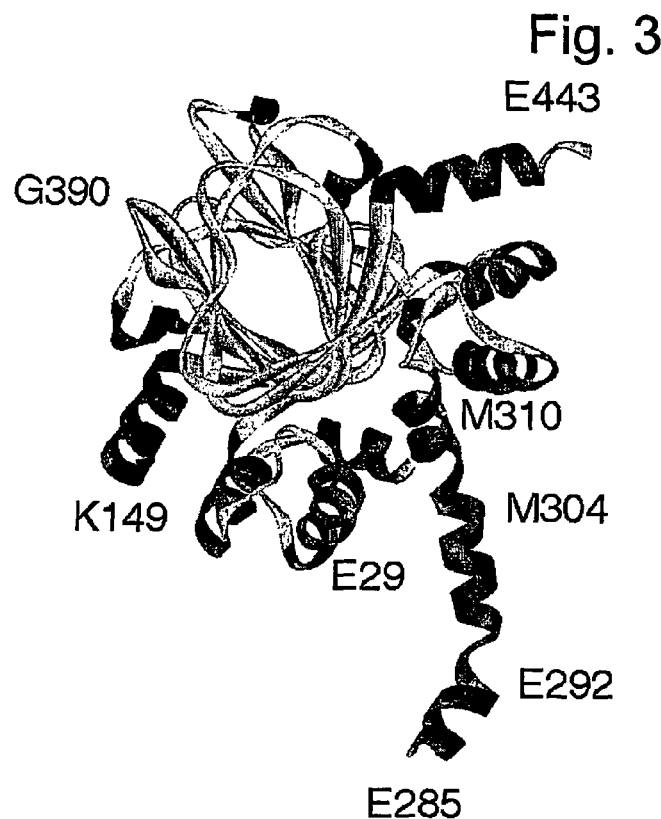

FIG. 3: Crystal structure of EPAC2 containing both cAMP-binding domains. Domain A (a.a. 12-151) binds the ligand with very little affinity that does not allow a sensor protein with GFPs inserted at blue marked positions (EYFP-E29-K149-ECFP) to change its conformation in presence of physiologically relevant amounts of cAMP, producing a FRET signal. Different green marked positions of high affinity domain B, however, are suitable to obtain a highly sensitive cAMP-sensor, which exhibit a robust change in FRET-signal upon binding the ligand.

Figure 4:
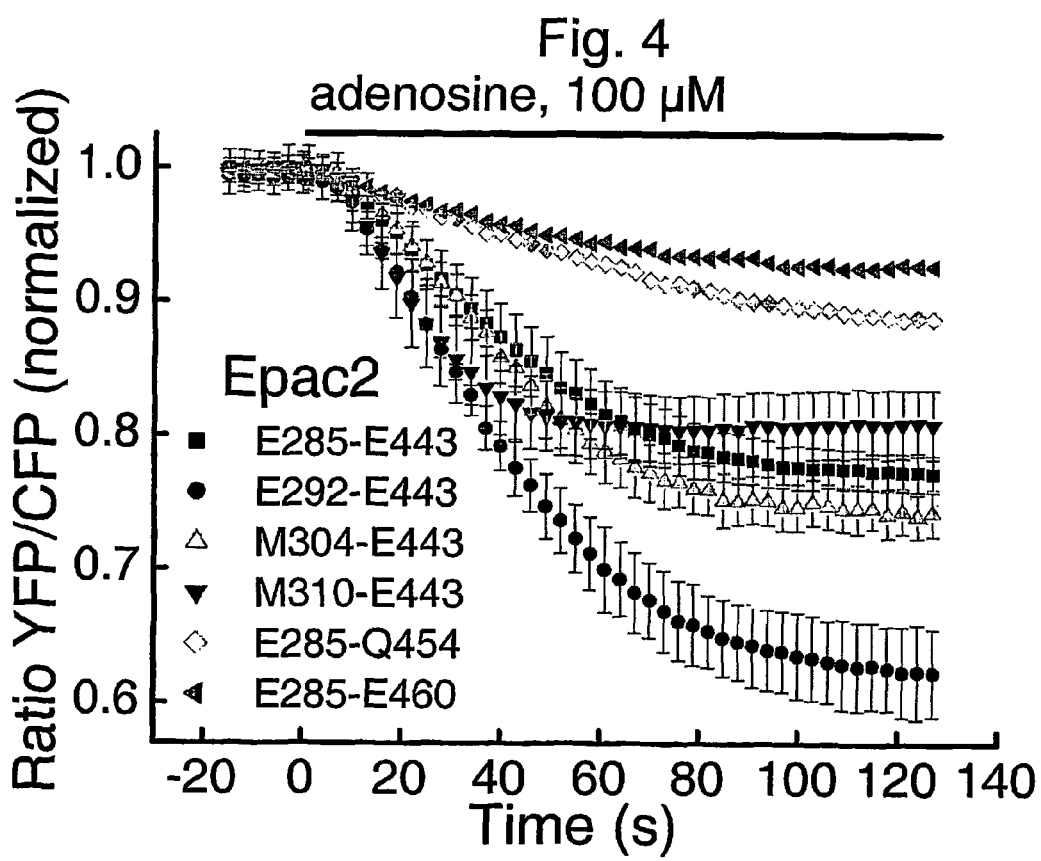

FIG. 4: Activation kinetics of various cAMP-sensor proteins that contained a single binding domain of EPAC2. CHO cells stably expressing adenosine A2B receptor, which couples to Gs protein and activates cAMP production via adenylyl cyclase, were transiently transfected with plasmids encoding for different sensor proteins, bearing GFP variants on the signed positions of cAMP-binding domain B of EPAC2. 24 hours after transfection FRET was measured in single living cells as described in Materials and Methods section and the influence of agonist (adenosine) was assessed in real time. Addition of adenosine to the cells resulted in decrease of FRET between YFP and CFP, implying a cAMP-induced conformational change that led to an increase in the distance between CFP and YFP. Depending on the structure of the protein amplitude and speed of the signal were different, allowing us to optimize the sensor finding the amino acid positions producing the most prominent signal.

Figure 5:
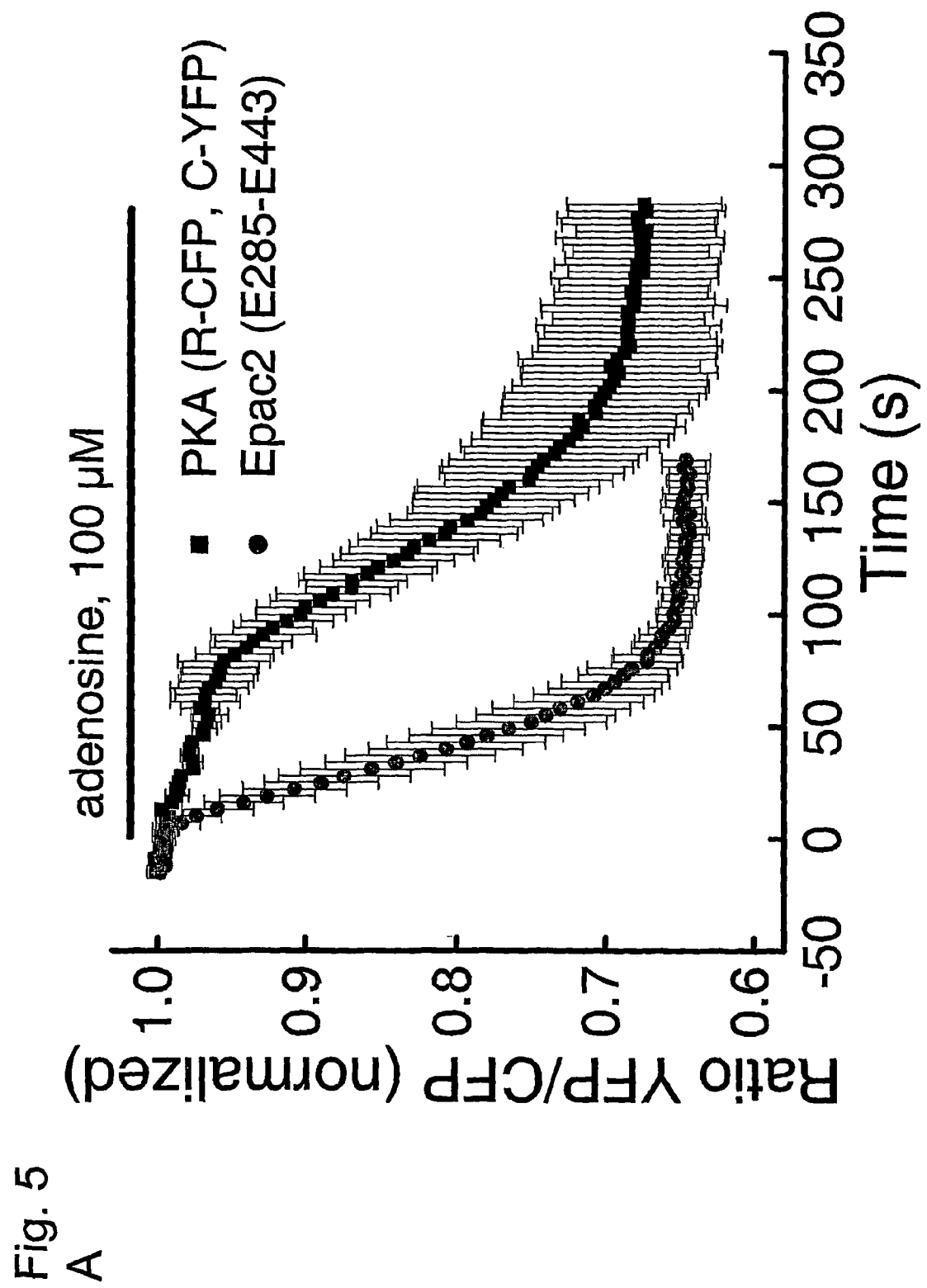
Figure 5B:
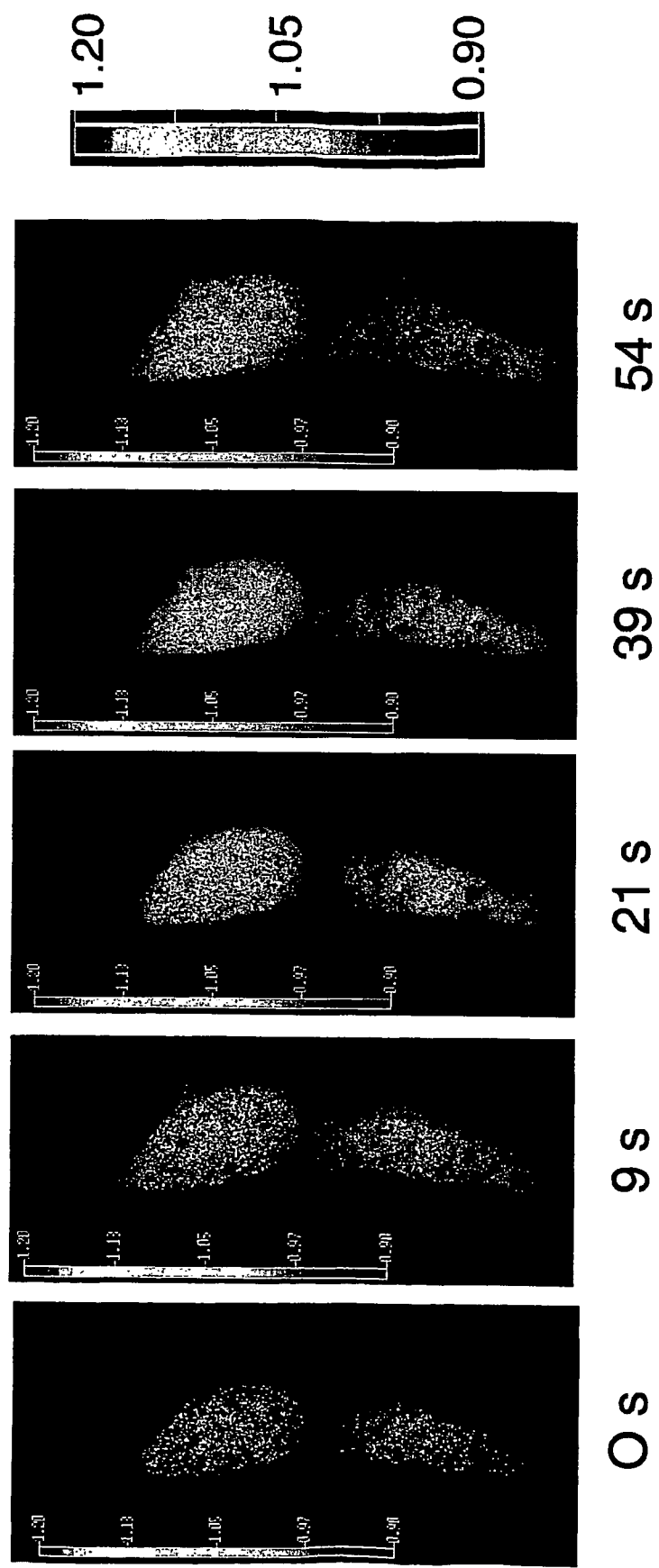

FIG. 5: A: Activation kinetics of cAMP-sensor proteins based on a single binding domain of EPAC2 (EYFP-E285-E443-ECFP) in CHOA2B cells compared to that of previously described PKA-sensor (Zaccolo et. al., Nat. Cell. Biol. 2000). Novel EPAC2-sensor shows a more rapid activation signal that could be due to presence of only 1 high-affinity cAMP-binding domain and absence of catalytic activity (induction of desensitization via phosphodiesterase activation) in contrast to PKA, having 4 cooperatively acting binding sites and possessing phosphodiesterase activating properties. B. Cell-imaging pictures of CHO cells at different times after addition of agonist. Decrease in monitored ratio (loss of red color) represents an increase in intracellular cAMP concentration. Experiments have been conducted as described in Materials and Methods and legend to FIG. 3.

FIG. 6: cAMP measurements in vitro. A. Fluorescence emission spectra of TSA-HEK293 cell lysate. Cells were transiently transfected with a plasmid encoding an EPAC2-based sensor (EYFP-E285-E443-ECFP). 24 h post transfection cell lysates were prepared and emission spectra were taken after addition of different agonist concentration as described in Materials and Methods. Decrease in the intensity at 525 nm with its increase at 475 nm represents a loss in FRET-signal between CFP and YFP. B. Relation of the signal intensity 475 nm/intensity 525 nm to cAMP concentration could be plotted into a saturation curve for subsequent precise measurements of cAMP concentration in different unknown samples.

Figure 7:
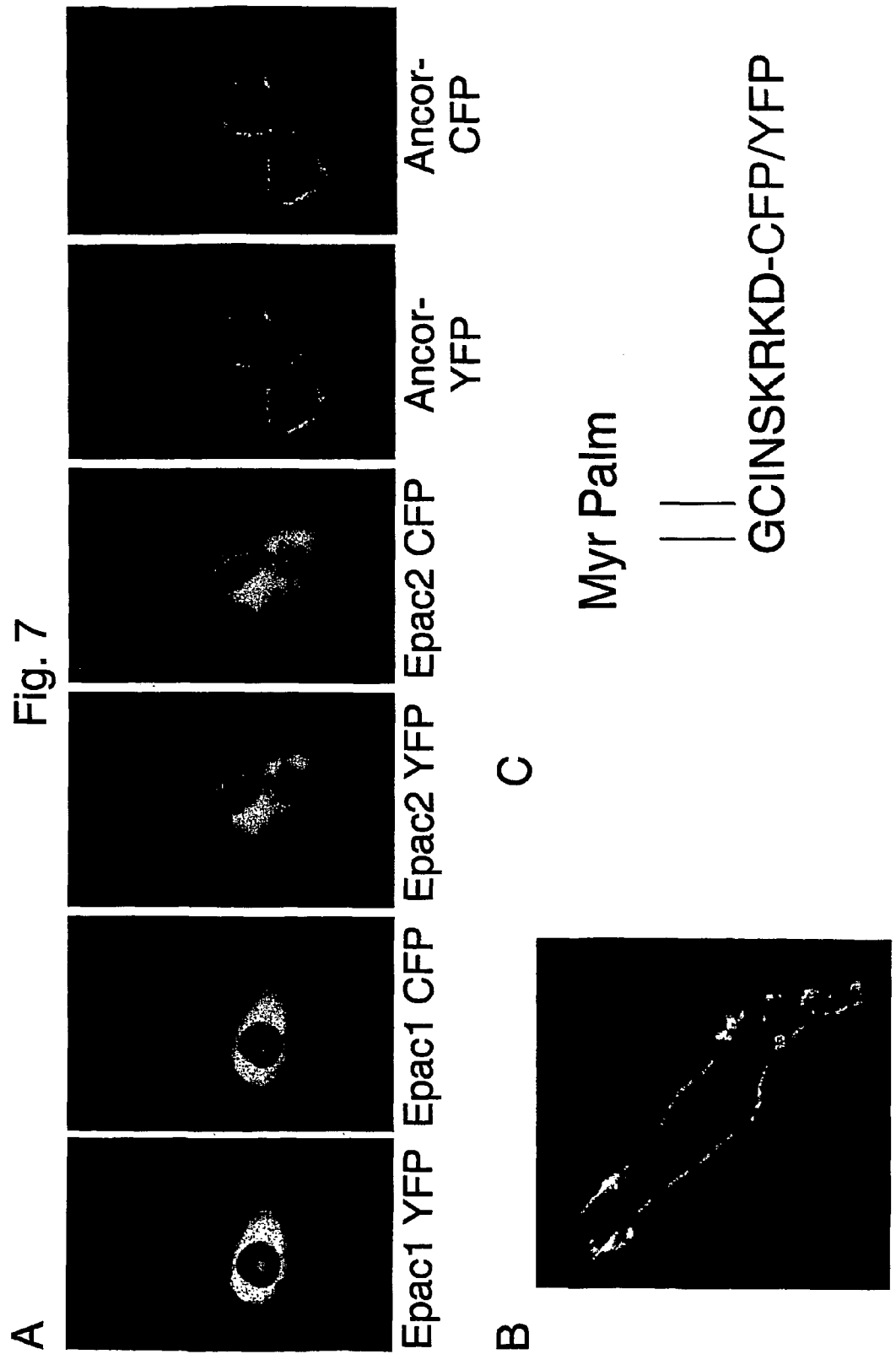

FIG. 7: Development of plasma membrane-anchored cAMP-sensor based on EPAC2 (E285-E443) construct. A. Fluorescent microscopy pictures of CHOA2B cells transfected with different constructs encoding for cAMP-sensing proteins. Fluorescence emission at 535±15 nm (YFP) and 480±20 nm (CFP) are represented. Introduction of a short N-terminal sequence of Lyn-kinase shown in FIG. 7C leads to targeting of fluorescent sensor-protein to distinct locations on the plasma membrane as revealed by confocal microscopy (FIG. 7B).

FIG. 8: A. Activation kinetics of cAMP-sensor proteins based on a single binding domain of EPAC1 (EYFP-E157-E316-ECFP) and PKA (EYFP-M264-A403-ECFP) in CHOA2B cells compared to that of EPAC2 construct (EYFP-E285-E443-ECFP). Homologous sequences of EPAC1 and PKA exhibit similar kinetic properties as EPAC2 binding domain, that allows to use them to produce a cAMP-sensing protein. B. Positioning EYPF in the position G390 of EPAC2 binding domain gains a sensor protein with larger amplitude than that of previously described mutants. Experiments have been conducted as described in Materials and Methods and legend to FIG. 3.

Figure 9:
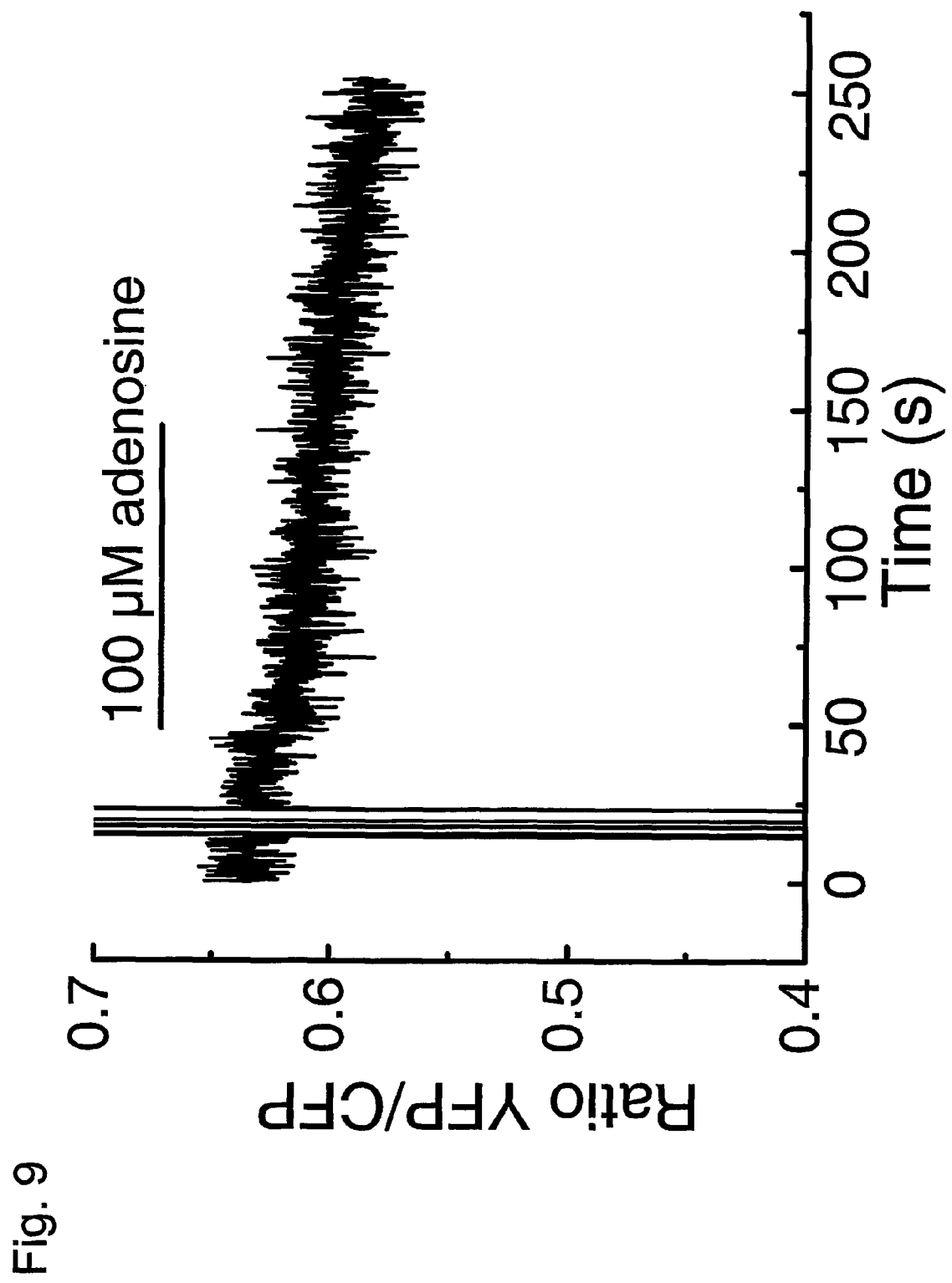

FIG. 9: No agonist dependent FRET changes were observed in CHOA2B cells expressing a fusion protein containing two cAMP binding sites of PKA RII subunits (PKA-construct-1: EYFP-E103-RII-A+B-A416-HAtag-ECFP) as determined by single cell photometric FRET detection.

Figure 10:
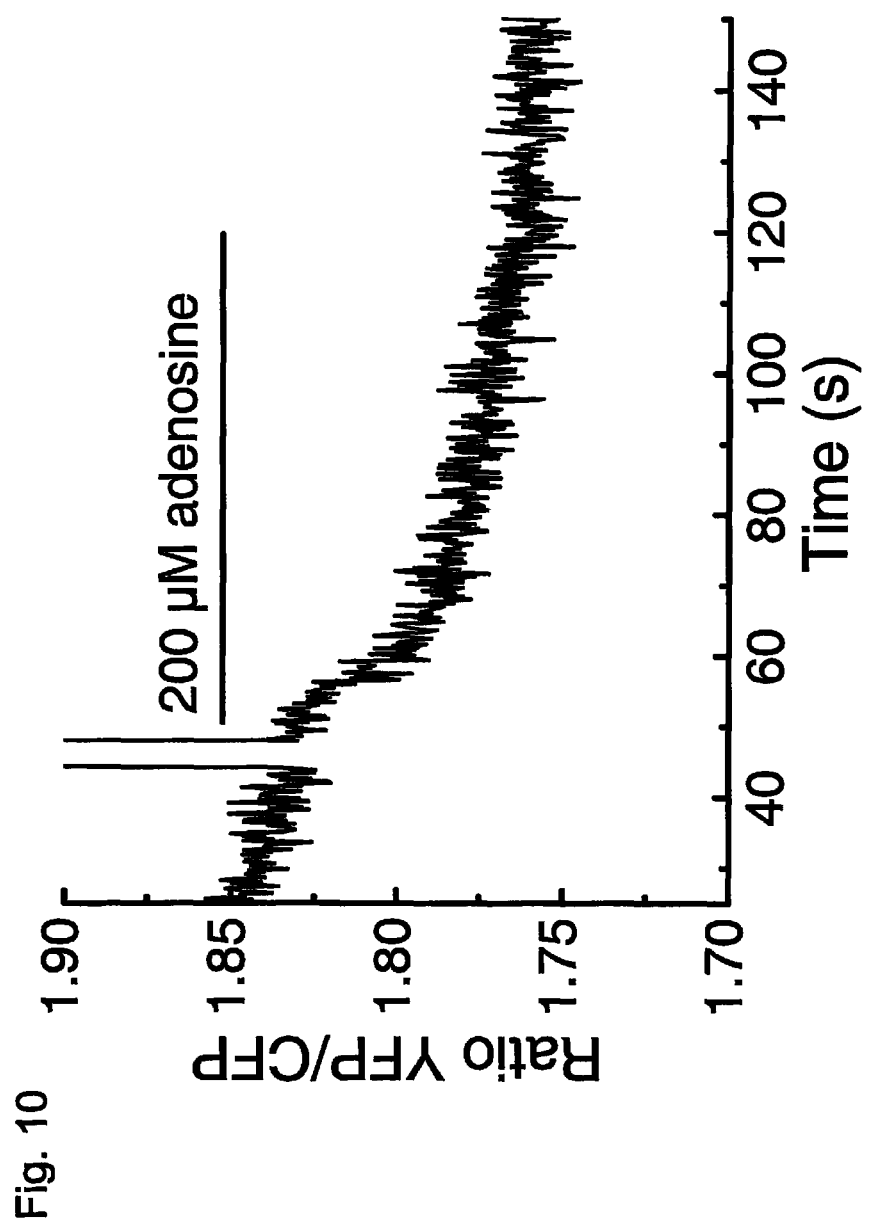

FIG. 10: Detectable agonist-dependent FRET changes were observed in CHOA2B cells expressing a fusion protein containing just one cAMP binding site (site B; PKA-construct 2, EYFP-M264—RII B-A416-HAtag-ECFP) of PKA RII subunits as determined by single cell photometric FRET detection.

FIG. 11. Construction of cAMP sensors based on a single binding domain of cAMP-regulated HCN2 ion channel. Clonings were performed as described in the legend to FIG. 1. Relative change in FRET upon agonist stimulation is indicated.

FIG. 12. Measurements of cAMP using the construct based on murine HCN2 (A467-K638). A. Crystal structure of the binding domain of HCN2 with bound cAMP (Zagotta, Nature. 2003; 425: 200-205). Position of GFP insertions showed in blue gained functional constructs (FIG. 11). B. FRET measurements in living HEK293 cells stimulated with 10 µM isoproterenol via endogenous beta2-adrenergic receptors. Cells were transfected with HCN2-based (A467-K638) sensor. A cAMP-dependent decrease in FRET is demonstrated.

FIG. 13. Concentration-response dependencies (measured as described in the legend to FIG. 6) for the sensors based on different cAMP-binding domains. Different constructs exhibit different affinities for cAMP, thereby allowing measurements of this second messenger in a broad range of physiologically relevant concentrations: from 20 nM to 100 µM.

FIG. 14. Multiple alignment of cAMP binding amino acid sequences of Epac1 (SEQ ID NO: 34), Epac2 (SEQ ID NO: 35), regulatory IIβ subunit of PKA (SEQ ID NO: 36) and HCN2 (SEQ ID NO: 37) ion channel. Highly conserved residues incl. glycins (G) and arginine (R) participating in cAMP binding are shown in bold. As documented, a "cAMP binding domain" (a minimal backbone for an inventive sensor, underlined) is a part of a sequence comprising residues directly involved in an interaction with cAMP and stabilizing the architecture of the binding site. Without being bound by theory, these include all β-sheets starting with a conserved L for Epac1,2 and HCN2 (under β1) or with IGT motive for PKA and a part of C-terminal α-B helix including highly conserved F residue, which is supposed to interact with highly conserved L (shown by bracket) to stabilize the domain architecture (as described in Rehmann et al. *Nat. Struct. Biol.* 2003, 10: 26-32). In case of HCN the cAMP binding domain is extenended to residue I636, since said residue is involved in the ligand binding (Zagotta, *Nature.* 2003; 425: 200-205). Additionally FIG. 14 shows cAMP binding sites as defined in accordance with this invention. These are shown in italic (14 amino acids from "FG" to "A") and comprise, preferably, 14 amino acids.

The present invention is illustrated by the following non-limiting Examples.

EXAMPLES

Example 1

Construction and Expression of Fluorescent Indicators

The DNA constructs encoding for cAMP-sensing proteins were generated by PCR using human EPAC1, murine EPAC2 or murine PICA regulatory II subunit cDNA as a template. GFP variants (EYFP and ECFP) were amplified with standard primers from pEYFP-Tub and pECFP plasmids (Clontech). Sequences for cAMP binding domains were cloned together with those of EYFP and ECFP in pcDNA3 vector (Invitrogen) for transient expression in mammalian cells (see FIG. 1 for structure details). For plasma membrane targeting of EPAC-construct additional N-terminal sequence MBCINSKRKD (SEQ ID NO: 75) encoding for myristolation and palmitoylation sites was inserted using oligonucleotides 5'-GATC-CGATATCATGGGATGTATCAATAG-CAAGCGCAAAGATG-3' (SEQ ID NO: 76) and 5'-CTAGCATCTTTGCGCTTGCTATTGATA-CATCCCATGATATCG-3' (SEQ ID NO: 77).

Example 2

Cell Culture

CHO-cells stably expressing adenosine A2B receptor and TSA-HEK293 cells were maintained in DMEM/F12 (37%, 5% $CO_2$) or DMEM (37%, 7% $CO_2$) medium, respectively, plated onto 24-mm glass coverslips for imaging experiments or 90 mm Petri dishes for cuvette fluorometric measurements and transfected with 3 µg or 30 µg DNA for each construct using calcium phosphate method. Transfected cells were analyzed 24 h later.

Example 3

FRET Measurements and Cell Imaging

For fluorescent microscopy glass coverslips with adherent cells were transferred to the experimental chamber in buffer, containing 144 mM NaCl, 5 mM KCl, 1 mM CaCl$_2$, 1 mM MgCl$_2$, 20 mM HEPES, pH=7.3, at room temperature and placed on a Zeiss Axiovert 200 inverted microscope equipped with an oil immersion 63× Plan-Neofluoran objective, dual-emission photometric system (Till Photonics) and "CooIS-NAP Photometrics" CCD-camera. Samples were excited with a light from Polychrom IV (Till Photonics). FRET was monitored using MetaFluor 5.0r6 software (Universal Imaging Corp.) as the emission ratio at 535±15 nm and 480±20 nm upon excitation at 436±10 nm. The imaging data were analyzed by MetaMorph 5.0r6 software (Universal Imaging Corp.) and corrected for spillover of CFP into 535 nm channel, as well as for acceptor photobleaching to give a corrected ratio F535 nm/F480 nm. To study agonist-induced changes in FRET, cells were continuously superfused with measuring buffer and adenosine (Sigma) solution.

Example 4

Fluorescence Measurements In Vitro

TSA-HEK293 cells 24 h post-transfection were washed with chilled PBS, scraped from the plate and resuspended in 5 mM Tris, 2 mM EDTA buffer at pH=7.3. After 40 s turrax on ice and 20 min centrifugation at 80000 prm fluorescence emission spectra of the supernatant (excitation at 436 nm, emission range 460-550 nm) were measured with a luminescence spectrometer LS50B (Perkin Elmer) before and after addition varying cAMP, cGMP and ATP (Sigma) concentrations. cAMP-saturation curves were plotted using Kaleida-Graph 3.0.5 software (Abelback) and fitted into the 100*m0/m3+m0 (m3=50, $EC_{50}$ mean) equation.

Example 5

Measurement of cAMP Concentrations

Measurements of cAMP may be performed using an optical method based on FRET between two fluorophores (e.g. ECFP and EYFP), fused directly to a single cAMP binding domain of cAMP-regulated proteins. As shown in FIG. 1 and FIG. 11, functional sensors could be constructed from Epac1, Epac2, PKA regulatory subunit or HCN2 ion channel. These proteins have a cAMP-binding sequence, characterized by several highly conserved amino acids, participating in the binding of cAMP (FIG. 14, residues in bold). FRET-based measurements of cAMP using said inventive constructs are possible due to a conformational change in the cAMP-binding domain, which leads to a decrease in distance between fluorophores resulting in a loss of FRET that could be visualized in single living cells (FIG. 5, FIG. 8, FIG. 12B) or in vitro (FIG. 6). Loss of FRET is measured as a decrease of the ratio YFP/CFP intensity, the binding of cAMP to the sensor results in a decrease in YFP intensity with a simultaneous increase in CFP, giving a decrease in ratio YFP/CFP. Using constructs based on single cAMP-binding domains (comprising merely one cAMP binding site), the cAMP concentration may be measured in a broad physiological range from 1 nM to 100 μM, in particular 200 nM to 50 μM; see, e.g., FIG. 13.

---

The invention claimed is:

1. A chimeric peptide having an amino acid sequence selected from the group consisting of SEQ ID NOs: 17, 41, 43, 45, and 47.

2. The chimeric peptide of claim 1, having the amino acid sequence of SEQ ID NO: 17.

3. The chimeric peptide of claim 1, having the amino acid sequence of SEQ ID NO: 41.

4. The chimeric peptide of claim 1, having the amino acid sequence of SEQ ID NO: 43.

5. The chimeric peptide of claim 1, having the amino acid sequence of SEQ ID NO: 45.

* * * * *

SEQUENCE LISTING

<160> NUMBER OF SEQ ID NOS: 79

<210> SEQ ID NO 1
<211> LENGTH: 416
<212> TYPE: PRT
<213> ORGANISM: Mus musculus

<400> SEQUENCE: 1

```
Met Ser Ile Glu Ile Pro Ala Gly Leu Thr Glu Leu Leu Gln Gly Phe
 1               5                  10                  15

Thr Val Glu Val Leu Arg His Gln Pro Ala Asp Leu Leu Glu Phe Ala
            20                  25                  30

Leu Gln His Phe Thr Arg Leu Gln Gln Glu Asn Glu Arg Lys Gly Ala
        35                  40                  45

Ala Arg Phe Gly His Glu Gly Arg Thr Trp Gly Asp Ala Gly Ala Ala
    50                  55                  60

Ala Gly Gly Thr Pro Ser Lys Gly Val Asn Phe Ala Glu Glu Pro
65                  70                  75                  80

Met Arg Ser Asp Ser Glu Asn Gly Glu Glu Glu Ala Ala Glu Ala
                85                  90                  95

Gly Ala Phe Asn Ala Pro Val Ile Asn Arg Phe Thr Arg Arg Ala Ser
                100                 105                 110

Val Cys Ala Glu Ala Tyr Asn Pro Asp Glu Glu Glu Asp Asp Ala Glu
            115                 120                 125

Ser Arg Ile Ile His Pro Lys Thr Asp Asp Gln Arg Asn Arg Leu Gln
        130                 135                 140

Glu Ala Cys Lys Asp Ile Leu Leu Phe Lys Asn Leu Asp Pro Glu Gln
145                 150                 155                 160

Met Ser Gln Val Leu Asp Ala Met Phe Glu Lys Leu Val Lys Glu Gly
```

```
            165                 170                 175
Glu His Val Ile Asp Gln Gly Asp Gly Asp Asn Phe Tyr Val Ile
            180                 185                 190

Asp Arg Gly Thr Phe Asp Ile Tyr Val Lys Cys Asp Val Gly Arg
            195                 200                 205

Cys Val Gly Asn Tyr Asp Asn Arg Gly Ser Phe Gly Glu Leu Ala Leu
    210                 215                 220

Met Tyr Asn Thr Pro Arg Ala Ala Thr Ile Thr Ala Thr Ser Pro Gly
225                 230                 235                 240

Ala Leu Trp Gly Leu Asp Arg Val Thr Phe Arg Arg Ile Ile Val Lys
                245                 250                 255

Asn Asn Ala Lys Lys Arg Lys Met Tyr Glu Ser Phe Ile Glu Ser Leu
                260                 265                 270

Pro Phe Leu Lys Ser Leu Glu Val Ser Glu Arg Leu Lys Val Val Asp
                275                 280                 285

Val Ile Gly Thr Lys Val Tyr Asn Asp Gly Glu Gln Ile Ile Ala Gln
            290                 295                 300

Gly Asp Ser Ala Asp Ser Phe Phe Ile Val Glu Ser Gly Glu Val Arg
305                 310                 315                 320

Ile Thr Met Lys Arg Lys Gly Lys Ser Asp Ile Glu Glu Asn Gly Ala
                325                 330                 335

Val Glu Ile Ala Arg Cys Leu Arg Gly Gln Tyr Phe Gly Glu Leu Ala
            340                 345                 350

Leu Val Thr Asn Lys Pro Arg Ala Ala Ser Ala His Ala Ile Gly Thr
                355                 360                 365

Val Lys Cys Leu Ala Met Asp Val Gln Ala Phe Glu Arg Leu Leu Gly
    370                 375                 380

Pro Cys Met Glu Ile Met Lys Arg Asn Ile Ala Thr Tyr Glu Glu Gln
385                 390                 395                 400

Leu Val Ala Leu Phe Gly Thr Asn Met Asp Ile Val Glu Pro Thr Ala
                405                 410                 415

<210> SEQ ID NO 2
<211> LENGTH: 881
<212> TYPE: PRT
<213> ORGANISM: Homo sapiens

<400> SEQUENCE: 2

Met Val Leu Arg Arg Met His Arg Pro Arg Ser Cys Ser Tyr Gln Leu
 1               5                  10                  15

Leu Leu Glu His Gln Arg Pro Ser Cys Ile Gln Gly Leu Arg Trp Thr
                20                  25                  30

Pro Leu Thr Asn Ser Glu Glu Ser Leu Asp Phe Ser Glu Ser Leu Glu
            35                  40                  45

Gln Ala Ser Thr Glu Arg Val Leu Arg Ala Gly Arg Gln Leu His Arg
        50                  55                  60

His Leu Leu Ala Thr Cys Pro Asn Leu Ile Arg Asp Arg Lys Tyr His
 65                  70                  75                  80

Leu Arg Leu Tyr Arg Gln Cys Cys Ser Gly Arg Glu Leu Val Asp Gly
                85                  90                  95

Ile Leu Ala Leu Gly Leu Gly Val His Ser Arg Ser Gln Val Val Gly
            100                 105                 110

Ile Cys Gln Val Leu Leu Asp Glu Gly Ala Leu Cys His Val Lys His
        115                 120                 125
```

-continued

```
Asp Trp Ala Phe Gln Asp Arg Asp Ala Gln Phe Tyr Arg Phe Pro Gly
    130                 135                 140

Pro Glu Pro Glu Pro Val Gly Thr His Glu Met Glu Glu Glu Leu Ala
145                 150                 155                 160

Glu Ala Val Ala Leu Leu Ser Gln Arg Gly Pro Asp Ala Leu Leu Thr
                165                 170                 175

Val Ala Leu Arg Lys Pro Pro Gly Gln Arg Thr Asp Glu Glu Leu Asp
            180                 185                 190

Leu Ile Phe Glu Glu Leu Leu His Ile Lys Ala Val Ala His Leu Ser
        195                 200                 205

Asn Ser Val Lys Arg Glu Leu Ala Ala Val Leu Leu Phe Glu Pro His
210                 215                 220

Ser Lys Ala Gly Thr Val Leu Phe Ser Gln Gly Asp Lys Gly Thr Ser
225                 230                 235                 240

Trp Tyr Ile Ile Trp Lys Gly Ser Val Asn Val Val Thr His Gly Lys
                245                 250                 255

Gly Leu Val Thr Thr Leu His Glu Gly Asp Asp Phe Gly Gln Leu Ala
            260                 265                 270

Leu Val Asn Asp Ala Pro Arg Ala Ala Thr Ile Ile Leu Arg Glu Asp
        275                 280                 285

Asn Cys His Phe Leu Arg Val Asp Lys Gln Asp Phe Asn Arg Ile Ile
290                 295                 300

Lys Asp Val Glu Ala Lys Thr Met Arg Leu Glu His Gly Lys Val
305                 310                 315                 320

Val Leu Val Leu Glu Arg Ala Ser Gln Gly Ala Gly Pro Ser Arg Pro
                325                 330                 335

Pro Thr Pro Gly Arg Asn Arg Tyr Thr Val Met Ser Gly Thr Pro Glu
            340                 345                 350

Lys Ile Leu Glu Leu Leu Glu Ala Met Gly Pro Asp Ser Ser Ala
        355                 360                 365

His Asp Pro Thr Glu Thr Phe Leu Ser Asp Phe Leu Leu Thr His Arg
370                 375                 380

Val Phe Met Pro Ser Ala Gln Leu Cys Ala Ala Leu Leu His Phe
385                 390                 395                 400

His Val Glu Pro Ala Gly Gly Ser Gln Glu Arg Ser Thr Tyr Val
                405                 410                 415

Cys Asn Lys Arg Gln Gln Ile Leu Arg Leu Val Ser Gln Trp Val Ala
            420                 425                 430

Leu Tyr Gly Ser Met Leu His Thr Asp Pro Val Ala Thr Ser Phe Leu
        435                 440                 445

Gln Lys Leu Ser Asp Leu Val Gly Arg Asp Thr Arg Leu Ser Asn Leu
450                 455                 460

Leu Arg Glu Gln Trp Pro Glu Arg Arg Cys His Arg Leu Glu Asn
465                 470                 475                 480

Gly Cys Gly Asn Ala Ser Pro Gln Met Lys Ala Arg Asn Leu Pro Val
                485                 490                 495

Trp Leu Pro Asn Gln Asp Glu Pro Leu Pro Gly Ser Ser Cys Ala Ile
            500                 505                 510

Gln Val Gly Asp Lys Val Pro Tyr Asp Ile Cys Arg Pro Asp His Ser
        515                 520                 525

Val Leu Thr Leu Gln Leu Pro Val Thr Ala Ser Val Arg Glu Val Met
530                 535                 540

Ala Ala Leu Ala Gln Glu Asp Gly Trp Thr Lys Gly Gln Val Leu Val
```

```
            545                 550                 555                 560
Lys Val Asn Ser Ala Gly Asp Ala Ile Gly Leu Gln Pro Asp Ala Arg
                565                 570                 575
Gly Val Ala Thr Ser Leu Gly Leu Asn Glu Arg Leu Phe Val Val Asn
                580                 585                 590
Pro Gln Glu Val His Glu Leu Ile Pro His Pro Asp Gln Leu Gly Pro
                595                 600                 605
Thr Val Gly Ser Ala Glu Gly Leu Asp Leu Val Ser Ala Lys Asp Leu
                610                 615                 620
Ala Gly Gln Leu Thr Asp His Asp Trp Ser Leu Phe Asn Ser Ile His
625                 630                 635                 640
Gln Val Glu Leu Ile His Tyr Val Leu Gly Pro Gln His Leu Arg Asp
                645                 650                 655
Val Thr Thr Ala Asn Leu Glu Arg Phe Met Arg Arg Phe Asn Glu Leu
                660                 665                 670
Gln Tyr Trp Val Ala Thr Glu Leu Cys Leu Cys Pro Val Pro Gly Pro
                675                 680                 685
Arg Ala Gln Leu Leu Arg Lys Phe Ile Lys Leu Ala Ala His Leu Lys
                690                 695                 700
Glu Gln Lys Asn Leu Asn Ser Phe Phe Ala Val Met Phe Gly Leu Ser
705                 710                 715                 720
Asn Ser Ala Ile Ser Arg Leu Ala His Thr Trp Glu Arg Leu Pro His
                725                 730                 735
Lys Val Arg Lys Leu Tyr Ser Ala Leu Glu Arg Leu Leu Asp Pro Ser
                740                 745                 750
Trp Asn His Arg Val Tyr Arg Leu Ala Leu Ala Lys Leu Ser Pro Pro
                755                 760                 765
Val Ile Pro Phe Met Pro Leu Leu Leu Lys Asp Met Thr Phe Ile His
                770                 775                 780
Glu Gly Asn His Thr Leu Val Glu Asn Leu Ile Asn Phe Glu Lys Met
785                 790                 795                 800
Arg Met Met Ala Arg Ala Ala Arg Met Leu His His Cys Arg Ser His
                805                 810                 815
Asn Pro Val Pro Leu Ser Pro Leu Arg Ser Arg Val Ser His Leu His
                820                 825                 830
Glu Asp Ser Gln Val Ala Arg Ile Ser Thr Cys Ser Glu Gln Ser Leu
                835                 840                 845
Ser Thr Arg Ser Pro Ala Ser Thr Trp Ala Tyr Val Gln Gln Leu Lys
                850                 855                 860
Val Ile Asp Asn Gln Arg Glu Leu Ser Arg Leu Ser Arg Glu Leu Glu
865                 870                 875                 880
Pro

<210> SEQ ID NO 3
<211> LENGTH: 993
<212> TYPE: PRT
<213> ORGANISM: Mus musculus

<400> SEQUENCE: 3

Met Val Ala Ala His Ala Ala His Ser Gln Ser Ser Ala Glu Trp Ile
1               5                   10                  15
Ala Cys Leu Asp Lys Arg Pro Leu Glu Arg Ser Ser Glu Asp Val Asp
                20                  25                  30
Ile Ile Phe Thr Arg Leu Lys Gly Val Lys Ala Phe Glu Lys Phe His
```

```
                  35                  40                  45
Pro Asn Leu Arg Gln Ile Cys Leu Cys Gly Tyr Tyr Glu Asn Leu
             50                  55                  60
Glu Lys Gly Ile Thr Leu Phe Arg Gln Gly Asp Ile Gly Thr Asn Trp
 65                  70                  75                  80
Tyr Ala Val Leu Ala Gly Ser Leu Asp Val Lys Val Ser Glu Thr Ser
                 85                  90                  95
Ser His Gln Asp Ala Val Thr Ile Cys Thr Leu Gly Ile Gly Thr Ala
            100                 105                 110
Phe Gly Glu Ser Ile Leu Asp Asn Thr Pro Arg His Ala Thr Ile Val
            115                 120                 125
Thr Arg Glu Ser Ser Glu Leu Leu Arg Ile Glu Gln Glu Asp Phe Lys
            130                 135                 140
Ala Leu Trp Glu Lys Tyr Arg Gln Tyr Met Ala Gly Leu Leu Ala Pro
145                 150                 155                 160
Pro Tyr Gly Val Met Glu Thr Gly Ser Asn Asn Asp Arg Ile Pro Asp
                165                 170                 175
Lys Glu Asn Val Pro Ser Glu Lys Ile Leu Arg Ala Gly Lys Ile Leu
            180                 185                 190
Arg Ile Ala Ile Leu Ser Arg Ala Pro His Met Ile Arg Asp Arg Lys
            195                 200                 205
Tyr His Leu Lys Thr Tyr Arg Gln Cys Val Gly Thr Glu Leu Val
210                 215                 220
Asp Trp Met Ile Gln Gln Thr Ser Cys Val His Ser Arg Thr Gln Ala
225                 230                 235                 240
Val Gly Met Trp Gln Val Leu Leu Glu Asp Gly Val Leu Asn His Val
                245                 250                 255
Asp Gln Glu Arg His Phe Gln Asp Lys Tyr Leu Phe Tyr Arg Phe Leu
            260                 265                 270
Asp Asp Glu Arg Glu Asp Ala Pro Leu Pro Thr Glu Glu Lys Lys
            275                 280                 285
Glu Cys Asp Glu Glu Leu Gln Asp Thr Met Leu Leu Leu Ser Gln Met
290                 295                 300
Gly Pro Asp Ala His Met Arg Met Ile Leu Arg Lys Pro Pro Gly Gln
305                 310                 315                 320
Arg Thr Val Asp Asp Leu Glu Ile Ile Tyr Asp Glu Leu Leu His Ile
                325                 330                 335
Lys Ala Leu Ser His Leu Ser Thr Thr Val Lys Arg Glu Leu Ala Gly
            340                 345                 350
Val Leu Ile Phe Glu Ser His Ala Lys Gly Gly Thr Val Leu Phe Asn
            355                 360                 365
Gln Gly Glu Glu Gly Thr Ser Trp Tyr Ile Ile Leu Lys Gly Ser Val
            370                 375                 380
Asn Val Val Ile Tyr Gly Lys Gly Val Val Cys Thr Leu His Glu Gly
385                 390                 395                 400
Asp Asp Phe Gly Lys Leu Ala Leu Val Asn Asp Ala Pro Arg Ala Ala
                405                 410                 415
Ser Ile Val Leu Arg Glu Asp Asn Cys His Phe Leu Arg Val Asp Lys
            420                 425                 430
Glu Asp Phe Asn Arg Ile Leu Arg Asp Val Glu Ala Asn Thr Val Arg
            435                 440                 445
Leu Lys Glu His Asp Gln Asp Val Leu Val Leu Glu Lys Val Pro Ala
            450                 455                 460
```

```
Gly Asn Arg Ala Ala Asn Gln Gly Asn Ser Gln Pro Gln Gln Lys Tyr
465                 470                 475                 480

Thr Val Met Ser Gly Thr Pro Glu Lys Ile Leu Glu His Phe Leu Glu
            485                 490                 495

Thr Ile Arg Leu Glu Pro Ser Leu Asn Glu Ala Thr Asp Ser Val Leu
            500                 505                 510

Asn Asp Phe Val Met Met His Cys Val Phe Met Pro Asn Thr Gln Leu
            515                 520                 525

Cys Pro Ala Leu Val Ala His Tyr His Ala Gln Pro Ser Gln Gly Thr
            530                 535                 540

Glu Gln Glu Arg Met Asp Tyr Ala Leu Asn Asn Lys Arg Arg Val Ile
545                 550                 555                 560

Arg Leu Val Leu Gln Trp Ala Ala Met Tyr Gly Asp Leu Leu Gln Glu
                565                 570                 575

Asp Asp Val Ala Met Ala Phe Leu Glu Glu Phe Tyr Val Ser Val Ser
            580                 585                 590

Asp Asp Ala Arg Met Met Ala Ala Phe Lys Glu Gln Leu Pro Glu Leu
            595                 600                 605

Glu Lys Ile Val Lys Gln Ile Ser Glu Asp Ala Lys Ala Pro Gln Lys
610                 615                 620

Lys His Lys Val Leu Leu Gln Gln Phe Asn Thr Gly Asp Glu Arg Ala
625                 630                 635                 640

Gln Lys Arg Gln Pro Ile Arg Gly Ser Asp Glu Val Leu Phe Lys Val
                645                 650                 655

Tyr Cys Ile Asp His Thr Tyr Thr Thr Ile Arg Val Pro Val Ala Ala
                660                 665                 670

Ser Val Lys Glu Val Ile Ser Ala Val Ala Asp Lys Leu Gly Ser Gly
            675                 680                 685

Glu Gly Leu Ile Ile Val Lys Met Asn Ser Gly Gly Glu Lys Val Val
            690                 695                 700

Leu Lys Ser Asn Asp Val Ser Val Phe Thr Thr Leu Thr Ile Asn Gly
705                 710                 715                 720

Arg Leu Phe Ala Cys Pro Arg Glu Gln Phe Asp Ser Leu Thr Pro Leu
                725                 730                 735

Pro Glu Gln Glu Gly Pro Thr Thr Gly Thr Val Gly Thr Phe Glu Leu
            740                 745                 750

Met Ser Ser Lys Asp Leu Ala Tyr Gln Met Thr Thr Tyr Asp Trp Glu
            755                 760                 765

Leu Phe Asn Cys Val His Glu Leu Glu Leu Ile Tyr His Thr Phe Gly
            770                 775                 780

Arg His Asn Phe Lys Lys Thr Thr Ala Asn Leu Asp Leu Phe Leu Arg
785                 790                 795                 800

Arg Phe Asn Glu Ile Gln Phe Trp Val Val Thr Glu Val Cys Leu Cys
                805                 810                 815

Ser Gln Leu Ser Lys Arg Val Gln Leu Leu Lys Lys Phe Ile Lys Ile
            820                 825                 830

Ala Ala His Cys Lys Glu Tyr Lys Asn Leu Asn Ser Phe Phe Ala Ile
            835                 840                 845

Val Met Gly Leu Ser Asn Val Ala Val Ser Arg Leu Ala Leu Thr Trp
            850                 855                 860

Glu Lys Leu Pro Ser Lys Phe Lys Lys Phe Tyr Ala Glu Phe Glu Ser
865                 870                 875                 880
```

```
Leu Met Asp Pro Ser Arg Asn His Arg Ala Tyr Arg Leu Thr Ala Ala
                885                 890                 895

Lys Leu Glu Pro Pro Leu Ile Pro Phe Met Pro Leu Leu Ile Lys Asp
            900                 905                 910

Met Thr Phe Thr His Glu Gly Asn Lys Thr Phe Ile Asp Asn Leu Val
        915                 920                 925

Asn Phe Glu Lys Met Arg Met Ile Ala Asn Thr Ala Arg Thr Val Arg
    930                 935                 940

Tyr Tyr Arg Ser Gln Pro Phe Asn Pro Asp Ala Ala Gln Ala Asn Lys
945                 950                 955                 960

Asn His Gln Asp Val Arg Ser Tyr Val Arg Gln Leu Asn Val Ile Asp
                965                 970                 975

Asn Gln Arg Thr Leu Ser Gln Met Ser His Arg Leu Glu Pro Arg Arg
            980                 985                 990

Pro

<210> SEQ ID NO 4
<211> LENGTH: 889
<212> TYPE: PRT
<213> ORGANISM: Homo sapiens

<400> SEQUENCE: 4

Met Asp Ala Arg Gly Gly Gly Arg Pro Gly Glu Ser Pro Gly Ala
 1               5                  10                  15

Thr Pro Ala Pro Gly Pro Pro Pro Pro Pro Ala Pro Pro Gln
            20                  25                  30

Gln Gln Pro Pro Pro Pro Pro Ala Pro Pro Gly Pro Gly
        35                  40                  45

Pro Ala Pro Pro Gln His Pro Arg Ala Glu Ala Leu Pro Pro Glu
    50                  55                  60

Ala Ala Asp Glu Gly Gly Pro Arg Gly Arg Leu Arg Ser Arg Asp Ser
65                  70                  75                  80

Ser Cys Gly Arg Pro Gly Thr Pro Gly Ala Ala Ser Thr Ala Lys Gly
                85                  90                  95

Ser Pro Asn Gly Glu Cys Gly Arg Gly Glu Pro Gln Cys Ser Pro Ala
            100                 105                 110

Gly Pro Glu Gly Pro Ala Arg Gly Pro Lys Val Ser Phe Ser Cys Arg
        115                 120                 125

Gly Ala Ala Ser Gly Pro Ala Pro Gly Pro Gly Pro Ala Glu Glu Ala
130                 135                 140

Gly Ser Glu Glu Ala Gly Pro Ala Gly Glu Pro Arg Gly Ser Gln Ala
145                 150                 155                 160

Ser Phe Met Gln Arg Gln Phe Gly Ala Leu Leu Gln Pro Gly Val Asn
                165                 170                 175

Lys Phe Ser Leu Arg Met Phe Gly Ser Gln Lys Ala Val Glu Arg Glu
            180                 185                 190

Gln Glu Arg Val Lys Ser Ala Gly Ala Trp Ile Ile His Pro Tyr Ser
        195                 200                 205

Asp Phe Arg Phe Tyr Trp Asp Phe Thr Met Leu Leu Phe Met Val Gly
    210                 215                 220

Asn Leu Ile Ile Ile Pro Val Gly Ile Thr Phe Phe Lys Asp Glu Thr
225                 230                 235                 240

Thr Ala Pro Trp Ile Val Phe Asn Val Val Ser Asp Thr Phe Phe Leu
                245                 250                 255
```

```
Met Asp Leu Val Leu Asn Phe Arg Thr Gly Ile Val Ile Glu Asp Asn
                260                 265                 270

Thr Glu Ile Ile Leu Asp Pro Glu Lys Ile Lys Lys Lys Tyr Leu Arg
            275                 280                 285

Thr Trp Phe Val Val Asp Phe Val Ser Ser Ile Pro Val Asp Tyr Ile
        290                 295                 300

Phe Leu Ile Val Glu Lys Gly Ile Asp Ser Glu Val Tyr Lys Thr Ala
305                 310                 315                 320

Arg Ala Leu Arg Ile Val Arg Phe Thr Lys Ile Leu Ser Leu Leu Arg
                325                 330                 335

Leu Leu Arg Leu Ser Arg Leu Ile Arg Tyr Ile His Gln Trp Glu Glu
            340                 345                 350

Ile Phe His Met Thr Tyr Asp Leu Ala Ser Ala Val Met Arg Ile Cys
        355                 360                 365

Asn Leu Ile Ser Met Met Leu Leu Leu Cys His Trp Asp Gly Cys Leu
    370                 375                 380

Gln Phe Leu Val Pro Met Leu Gln Asp Phe Pro Arg Asn Cys Trp Val
385                 390                 395                 400

Ser Ile Asn Gly Met Val Asn His Ser Trp Ser Glu Leu Tyr Ser Phe
                405                 410                 415

Ala Leu Phe Lys Ala Met Ser His Met Leu Cys Ile Gly Tyr Gly Arg
            420                 425                 430

Gln Ala Pro Glu Ser Met Thr Asp Ile Trp Leu Thr Met Leu Ser Met
        435                 440                 445

Ile Val Gly Ala Thr Cys Tyr Ala Met Phe Ile Gly His Ala Thr Ala
    450                 455                 460

Leu Ile Gln Ser Leu Asp Ser Ser Arg Arg Gln Tyr Gln Glu Lys Tyr
465                 470                 475                 480

Lys Gln Val Glu Gln Tyr Met Ser Phe His Lys Leu Pro Ala Asp Phe
                485                 490                 495

Arg Gln Lys Ile His Asp Tyr Tyr Glu His Arg Tyr Gln Gly Lys Met
            500                 505                 510

Phe Asp Glu Asp Ser Ile Leu Gly Glu Leu Asn Gly Pro Leu Arg Glu
        515                 520                 525

Glu Ile Val Asn Phe Asn Cys Arg Lys Leu Val Ala Ser Met Pro Leu
    530                 535                 540

Phe Ala Asn Ala Asp Pro Asn Phe Val Thr Ala Met Leu Thr Lys Leu
545                 550                 555                 560

Lys Phe Glu Val Phe Gln Pro Gly Asp Tyr Ile Ile Arg Glu Gly Thr
                565                 570                 575

Ile Gly Lys Lys Met Tyr Phe Ile Gln His Gly Val Val Ser Val Leu
            580                 585                 590

Thr Lys Gly Asn Lys Glu Met Lys Leu Ser Asp Gly Ser Tyr Phe Gly
        595                 600                 605

Glu Ile Cys Leu Leu Thr Arg Gly Arg Arg Thr Ala Ser Val Arg Ala
    610                 615                 620

Asp Thr Tyr Cys Arg Leu Tyr Ser Leu Ser Val Asp Asn Phe Asn Glu
625                 630                 635                 640

Val Leu Glu Glu Tyr Pro Met Met Arg Arg Ala Phe Glu Thr Val Ala
                645                 650                 655

Ile Asp Arg Leu Asp Arg Ile Gly Lys Lys Asn Ser Ile Leu Leu His
            660                 665                 670

Lys Val Gln His Asp Leu Asn Ser Gly Val Phe Asn Asn Gln Glu Asn
```

```
                675                 680                 685
Ala Ile Ile Gln Glu Ile Val Lys Tyr Asp Arg Glu Met Val Gln Gln
        690                 695                 700
Ala Glu Leu Gly Gln Arg Val Gly Leu Phe Pro Pro Pro Pro Pro
705                 710                 715                 720
Pro Gln Val Thr Ser Ala Ile Ala Thr Leu Gln Gln Ala Ala Ala Met
                725                 730                 735
Ser Phe Cys Pro Gln Val Ala Arg Pro Leu Val Gly Pro Leu Ala Leu
                740                 745                 750
Gly Ser Pro Arg Leu Val Arg Arg Pro Pro Gly Pro Ala Pro Ala
                755                 760                 765
Ala Ala Ser Pro Gly Pro Pro Pro Ala Ser Pro Pro Gly Ala Pro
        770                 775                 780
Ala Ser Pro Arg Ala Pro Arg Thr Ser Pro Tyr Gly Gly Leu Pro Ala
785                 790                 795                 800
Ala Pro Leu Ala Gly Pro Ala Leu Pro Ala Arg Arg Leu Ser Arg Ala
                805                 810                 815
Ser Arg Pro Leu Ser Ala Ser Gln Pro Ser Leu Pro His Gly Ala Pro
                820                 825                 830
Gly Pro Ala Ala Ser Thr Arg Pro Ala Ser Ser Ser Thr Pro Arg Leu
                835                 840                 845
Arg Pro Thr Pro Ala Ala Arg Ala Ala Ala Pro Ser Pro Asp Arg Arg
        850                 855                 860
Asp Ser Ala Ser Pro Gly Ala Ala Gly Gly Leu Asp Pro Gln Asp Ser
865                 870                 875                 880
Ala Arg Ser Arg Leu Ser Ser Asn Leu
                885

<210> SEQ ID NO 5
<211> LENGTH: 909
<212> TYPE: PRT
<213> ORGANISM: Homo sapiens

<400> SEQUENCE: 5

Met Pro Arg Glu Leu Ser Arg Ile Glu Glu Lys Glu Asp Glu Glu
  1               5                  10                  15
Glu Glu Glu Glu Glu Glu Glu Glu Glu Glu Glu Glu Glu Val Thr Glu
                 20                  25                  30
Val Leu Leu Asp Ser Cys Val Val Ser Gln Val Gly Val Gly Gln Ser
             35                  40                  45
Glu Glu Asp Gly Thr Arg Pro Gln Ser Thr Ser Asp Gln Lys Leu Trp
         50                  55                  60
Glu Glu Val Gly Glu Glu Ala Lys Lys Glu Ala Glu Glu Lys Ala Lys
 65                  70                  75                  80
Glu Glu Ala Glu Glu Val Ala Glu Glu Glu Ala Glu Lys Glu Pro Gln
                 85                  90                  95
Asp Trp Ala Glu Thr Lys Glu Glu Pro Glu Ala Glu Ala Ala Ala
             100                 105                 110
Ser Ser Gly Val Pro Ala Thr Lys Gln His Pro Glu Val Gln Val Glu
         115                 120                 125
Asp Thr Asp Ala Asp Ser Cys Pro Leu Met Ala Glu Asn Pro Pro
     130                 135                 140
Ser Thr Val Leu Pro Pro Pro Ser Pro Ala Lys Ser Asp Thr Leu Ile
145                 150                 155                 160
```

```
Val Pro Ser Ser Ala Ser Gly Thr His Arg Lys Lys Leu Pro Ser Glu
                165                 170                 175
Asp Asp Glu Ala Glu Glu Leu Lys Ala Leu Ser Pro Ala Glu Ser Pro
            180                 185                 190
Val Val Ala Trp Ser Asp Pro Thr Thr Pro Lys Asp Thr Asp Gly Gln
        195                 200                 205
Asp Arg Ala Ala Ser Thr Ala Ser Thr Asn Ser Ala Ile Ile Asn Asp
    210                 215                 220
Arg Leu Gln Glu Leu Val Lys Leu Phe Lys Glu Arg Thr Glu Lys Val
225                 230                 235                 240
Lys Glu Lys Leu Ile Asp Pro Asp Val Thr Ser Asp Glu Glu Ser Pro
                245                 250                 255
Lys Pro Ser Pro Ala Lys Lys Ala Pro Glu Pro Ala Pro Asp Thr Lys
            260                 265                 270
Pro Ala Glu Ala Glu Pro Val Glu Glu Glu His Tyr Cys Asp Met Leu
        275                 280                 285
Cys Cys Lys Phe Lys His Arg Pro Trp Lys Lys Tyr Gln Phe Pro Gln
    290                 295                 300
Ser Ile Asp Pro Leu Thr Asn Leu Met Tyr Val Leu Trp Leu Phe Phe
305                 310                 315                 320
Val Val Met Ala Trp Asn Trp Asn Cys Trp Leu Ile Pro Val Arg Trp
                325                 330                 335
Ala Phe Pro Tyr Gln Thr Pro Asp Asn Ile His His Trp Leu Leu Met
            340                 345                 350
Asp Tyr Leu Cys Asp Leu Ile Tyr Phe Leu Asp Ile Thr Val Phe Gln
        355                 360                 365
Thr Arg Leu Gln Phe Val Arg Gly Gly Asp Ile Ile Thr Asp Lys Lys
    370                 375                 380
Asp Met Arg Asn Asn Tyr Leu Lys Ser Arg Arg Phe Lys Met Asp Leu
385                 390                 395                 400
Leu Ser Leu Leu Pro Leu Asp Phe Leu Tyr Leu Lys Val Gly Val Asn
                405                 410                 415
Pro Leu Leu Arg Leu Pro Arg Cys Leu Lys Tyr Met Ala Phe Phe Glu
            420                 425                 430
Phe Asn Ser Arg Leu Glu Ser Ile Leu Ser Lys Ala Tyr Val Tyr Arg
        435                 440                 445
Val Ile Arg Thr Thr Ala Tyr Leu Leu Tyr Ser Leu His Leu Asn Ser
    450                 455                 460
Cys Leu Tyr Tyr Trp Ala Ser Ala Tyr Gln Gly Leu Gly Ser Thr His
465                 470                 475                 480
Trp Val Tyr Asp Gly Val Gly Asn Ser Tyr Ile Arg Cys Tyr Tyr Phe
                485                 490                 495
Ala Val Lys Thr Leu Ile Thr Ile Gly Gly Leu Pro Asp Pro Lys Thr
            500                 505                 510
Leu Phe Glu Ile Val Phe Gln Leu Leu Asn Tyr Phe Thr Gly Val Phe
        515                 520                 525
Ala Phe Ser Val Met Ile Gly Gln Met Arg Asp Val Val Gly Ala Ala
    530                 535                 540
Thr Ala Gly Gln Thr Tyr Tyr Arg Ser Cys Met Asp Ser Thr Val Lys
545                 550                 555                 560
Tyr Met Asn Phe Tyr Lys Ile Pro Lys Ser Val Gln Asn Arg Val Lys
                565                 570                 575
Thr Trp Tyr Glu Tyr Thr Trp His Ser Gln Gly Met Leu Asp Glu Ser
```

```
                    580                 585                 590
Glu Leu Met Val Gln Leu Pro Asp Lys Met Arg Leu Asp Leu Ala Ile
            595                 600                 605

Asp Val Asn Tyr Asn Ile Val Ser Lys Val Ala Leu Phe Gln Gly Cys
        610                 615                 620

Asp Arg Gln Met Ile Phe Asp Met Leu Lys Arg Leu Arg Ser Val Val
625                 630                 635                 640

Tyr Leu Pro Asn Asp Tyr Val Cys Lys Lys Gly Glu Ile Gly Arg Glu
                645                 650                 655

Met Tyr Ile Ile Gln Ala Gly Gln Val Gln Val Leu Gly Gly Pro Asp
            660                 665                 670

Gly Lys Ser Val Leu Val Thr Leu Lys Ala Gly Ser Val Phe Gly Glu
        675                 680                 685

Ile Ser Leu Leu Ala Val Gly Gly Gly Asn Arg Arg Thr Ala Asn Val
    690                 695                 700

Val Ala His Gly Phe Thr Asn Leu Phe Ile Leu Asp Lys Lys Asp Leu
705                 710                 715                 720

Asn Glu Ile Leu Val His Tyr Pro Glu Ser Gln Lys Leu Leu Arg Lys
                725                 730                 735

Lys Ala Arg Arg Met Leu Arg Ser Asn Asn Lys Pro Lys Glu Glu Lys
            740                 745                 750

Ser Val Leu Ile Leu Pro Pro Arg Ala Gly Thr Pro Lys Leu Phe Asn
        755                 760                 765

Ala Ala Leu Ala Met Thr Gly Lys Met Gly Gly Lys Gly Ala Lys Gly
    770                 775                 780

Gly Lys Leu Ala His Leu Arg Ala Arg Leu Lys Glu Leu Ala Ala Leu
785                 790                 795                 800

Glu Ala Ala Ala Lys His Glu Glu Leu Val Glu Gln Ala Lys Ser Ser
                805                 810                 815

Gln Asp Val Lys Gly Glu Glu Gly Ser Ala Ala Pro Asp Gln His Thr
            820                 825                 830

His Pro Lys Glu Ala Ala Thr Asp Pro Pro Ala Pro Arg Thr Pro Pro
        835                 840                 845

Glu Pro Pro Gly Ser Pro Pro Ser Ser Pro Pro Ala Ser Leu Gly
    850                 855                 860

Ser Cys Glu Gly Glu Glu Gly Pro Ala Glu Pro Glu His Ser
865                 870                 875                 880

Val Arg Ile Cys Met Ser Pro Gly Pro Glu Pro Gly Glu Gln Ile Leu
                885                 890                 895

Ser Val Lys Met Pro Glu Glu Arg Glu Glu Lys Ala Glu
            900                 905

<210> SEQ ID NO 6
<211> LENGTH: 210
<212> TYPE: PRT
<213> ORGANISM: Escherichia coli

<400> SEQUENCE: 6

Met Val Leu Gly Lys Pro Gln Thr Asp Pro Thr Leu Glu Trp Phe Leu
1               5                   10                  15

Ser His Cys His Ile His Lys Tyr Pro Ser Lys Ser Thr Leu Ile His
            20                  25                  30

Gln Gly Glu Lys Ala Glu Thr Leu Tyr Tyr Ile Val Lys Gly Ser Val
        35                  40                  45
```

```
Ala Val Leu Ile Lys Asp Glu Gly Lys Glu Met Ile Leu Ser Tyr
         50                  55                  60

Leu Asn Gln Gly Asp Phe Ile Gly Glu Leu Gly Leu Phe Glu Glu Gly
 65                  70                  75                  80

Gln Glu Arg Ser Ala Trp Val Arg Ala Lys Thr Ala Cys Glu Val Ala
                 85                  90                  95

Glu Ile Ser Tyr Lys Lys Phe Arg Gln Leu Ile Gln Val Asn Pro Asp
                100                 105                 110

Ile Leu Met Arg Leu Ser Ala Gln Met Ala Arg Arg Leu Gln Val Thr
             115                 120                 125

Ser Glu Lys Val Gly Asn Leu Ala Phe Leu Asp Val Thr Gly Arg Ile
130                 135                 140

Ala Gln Thr Leu Leu Asn Leu Ala Lys Gln Pro Asp Ala Met Thr His
145                 150                 155                 160

Pro Asp Gly Met Gln Ile Lys Ile Thr Arg Gln Glu Ile Gly Gln Ile
                165                 170                 175

Val Gly Cys Ser Arg Glu Thr Val Gly Arg Ile Leu Lys Met Leu Glu
            180                 185                 190

Asp Gln Asn Leu Ile Ser Ala His Gly Lys Thr Ile Val Val Tyr Gly
        195                 200                 205

Thr Arg
    210

<210> SEQ ID NO 7
<211> LENGTH: 1327
<212> TYPE: PRT
<213> ORGANISM: Homo sapiens

<400> SEQUENCE: 7

Met Glu Ala Pro Leu Gln Thr Gly Met Val Leu Gly Val Met Ile Gly
  1               5                  10                  15

Ala Gly Val Ala Val Val Thr Ala Val Leu Ile Leu Leu Val Val
                 20                  25                  30

Arg Arg Leu Arg Val Pro Lys Thr Pro Ala Pro Asp Gly Pro Arg Tyr
             35                  40                  45

Arg Phe Arg Lys Arg Asp Lys Val Leu Phe Tyr Gly Arg Lys Ile Met
 50                  55                  60

Arg Lys Val Ser Gln Ser Thr Ser Ser Leu Val Asp Thr Ser Val Ser
 65                  70                  75                  80

Ala Thr Ser Arg Pro Arg Met Arg Lys Lys Leu Lys Met Leu Asn Ile
                 85                  90                  95

Ala Lys Lys Ile Leu Arg Ile Gln Lys Glu Thr Pro Thr Leu Gln Arg
                100                 105                 110

Lys Glu Pro Pro Pro Ala Val Leu Glu Ala Asp Leu Thr Glu Gly Asp
            115                 120                 125

Leu Ala Asn Ser His Leu Pro Ser Glu Val Leu Tyr Met Leu Lys Asn
130                 135                 140

Val Arg Val Leu Gly His Phe Glu Lys Pro Leu Phe Leu Glu Leu Cys
145                 150                 155                 160

Arg His Met Val Phe Gln Arg Leu Gly Gln Gly Asp Tyr Val Phe Arg
                165                 170                 175

Pro Gly Gln Pro Asp Ala Ser Ile Tyr Val Val Gln Asp Gly Leu Leu
            180                 185                 190

Glu Leu Cys Leu Pro Gly Pro Asp Gly Lys Glu Cys Val Val Lys Glu
        195                 200                 205
```

```
Val Val Pro Gly Asp Ser Val Asn Ser Leu Leu Ser Ile Leu Asp Val
    210                 215                 220

Ile Thr Gly His Gln His Pro Gln Arg Thr Val Ser Ala Arg Ala Ala
225                 230                 235                 240

Arg Asp Ser Thr Val Leu Arg Leu Pro Val Glu Ala Phe Ser Ala Val
                    245                 250                 255

Phe Thr Lys Tyr Pro Glu Ser Leu Val Arg Val Val Gln Ile Ile Met
                260                 265                 270

Val Arg Leu Gln Arg Val Thr Phe Leu Ala Leu His Asn Tyr Leu Gly
            275                 280                 285

Leu Thr Asn Glu Leu Phe Ser His Glu Ile Gln Pro Leu Arg Leu Phe
    290                 295                 300

Pro Ser Pro Gly Leu Pro Thr Arg Thr Ser Pro Val Arg Gly Ser Lys
305                 310                 315                 320

Arg Met Val Ser Thr Ser Ala Thr Asp Glu Pro Arg Glu Thr Pro Gly
                325                 330                 335

Arg Pro Pro Asp Pro Thr Gly Ala Pro Leu Pro Gly Pro Thr Gly Asp
                340                 345                 350

Pro Val Lys Pro Thr Ser Leu Glu Thr Pro Ser Ala Pro Leu Leu Ser
            355                 360                 365

Arg Cys Val Ser Met Pro Gly Asp Ile Ser Gly Leu Gln Gly Gly Pro
370                 375                 380

Arg Ser Asp Phe Asp Met Ala Tyr Glu Arg Gly Arg Ile Ser Val Ser
385                 390                 395                 400

Leu Gln Glu Glu Ala Ser Gly Gly Ser Leu Ala Ala Pro Ala Arg Thr
                405                 410                 415

Pro Thr Gln Glu Pro Arg Glu Gln Pro Ala Gly Ala Cys Glu Tyr Ser
                420                 425                 430

Tyr Cys Glu Asp Glu Ser Ala Thr Gly Gly Cys Pro Phe Gly Pro Tyr
            435                 440                 445

Gln Gly Arg Gln Thr Ser Ser Ile Phe Glu Ala Ala Lys Gln Glu Leu
    450                 455                 460

Ala Lys Leu Met Arg Ile Glu Asp Pro Ser Leu Leu Asn Ser Arg Val
465                 470                 475                 480

Leu Leu His His Ala Lys Ala Gly Thr Ile Ile Ala Arg Gln Gly Asp
                485                 490                 495

Gln Asp Val Ser Leu His Phe Val Leu Trp Gly Cys Leu His Val Tyr
            500                 505                 510

Gln Arg Met Ile Asp Lys Ala Glu Asp Val Cys Leu Phe Val Ala Gln
    515                 520                 525

Pro Gly Glu Leu Val Gly Gln Leu Ala Val Leu Thr Gly Glu Pro Leu
530                 535                 540

Ile Phe Thr Leu Arg Ala Gln Arg Asp Cys Thr Phe Leu Arg Ile Ser
545                 550                 555                 560

Lys Ser Asp Phe Tyr Glu Ile Met Arg Ala Gln Pro Ser Val Val Leu
                565                 570                 575

Ser Ala Ala His Thr Val Ala Ala Arg Met Ser Pro Phe Val Arg Gln
                580                 585                 590

Met Asp Phe Ala Ile Asp Trp Thr Ala Val Glu Ala Gly Arg Ala Leu
            595                 600                 605

Tyr Arg Gln Gly Asp Arg Ser Asp Cys Thr Tyr Ile Val Leu Asn Gly
    610                 615                 620
```

```
Arg Leu Arg Ser Val Ile Gln Arg Gly Ser Gly Lys Lys Glu Leu Val
625                 630                 635                 640

Gly Glu Tyr Gly Arg Gly Asp Leu Ile Gly Val Val Glu Ala Leu Thr
            645                 650                 655

Arg Gln Pro Arg Ala Thr Thr Val His Ala Val Arg Asp Thr Glu Leu
        660                 665                 670

Ala Lys Leu Pro Glu Gly Thr Leu Gly His Ile Lys Arg Arg Tyr Pro
    675                 680                 685

Gln Val Val Thr Arg Leu Ile His Leu Leu Ser Gln Lys Ile Leu Gly
690                 695                 700

Asn Leu Gln Gln Leu Gln Gly Pro Phe Pro Ala Gly Ser Gly Leu Gly
705                 710                 715                 720

Val Pro Pro His Ser Glu Leu Thr Asn Pro Ala Ser Asn Leu Ala Thr
                725                 730                 735

Val Ala Ile Leu Pro Val Cys Ala Glu Val Pro Met Val Ala Phe Thr
            740                 745                 750

Leu Glu Leu Gln His Ala Leu Gln Ala Ile Gly Pro Thr Leu Leu Leu
        755                 760                 765

Asn Ser Asp Ile Ile Arg Ala Arg Leu Gly Ala Ser Ala Leu Asp Ser
770                 775                 780

Ile Gln Glu Phe Arg Leu Ser Gly Trp Leu Ala Gln Gln Glu Asp Ala
785                 790                 795                 800

His Arg Ile Val Leu Tyr Gln Thr Asp Ala Ser Leu Thr Pro Trp Thr
                805                 810                 815

Val Arg Cys Leu Arg Gln Ala Asp Cys Ile Leu Ile Val Gly Leu Gly
            820                 825                 830

Asp Gln Glu Pro Thr Leu Gly Gln Leu Glu Gln Met Leu Glu Asn Thr
        835                 840                 845

Ala Val Arg Ala Leu Lys Gln Leu Val Leu Leu His Arg Glu Glu Gly
    850                 855                 860

Ala Gly Pro Thr Arg Thr Val Glu Trp Leu Asn Met Arg Ser Trp Cys
865                 870                 875                 880

Ser Gly His Leu His Leu Arg Cys Pro Arg Arg Leu Phe Ser Arg Arg
                885                 890                 895

Ser Pro Ala Lys Leu His Glu Leu Tyr Glu Lys Val Phe Ser Arg Arg
            900                 905                 910

Ala Asp Arg His Ser Asp Phe Ser Arg Leu Ala Arg Val Leu Thr Gly
        915                 920                 925

Asn Thr Ile Ala Leu Val Leu Gly Gly Gly Ala Arg Gly Cys Ser
    930                 935                 940

His Ile Gly Val Leu Lys Ala Leu Glu Glu Ala Gly Val Pro Val Asp
945                 950                 955                 960

Leu Val Gly Gly Thr Ser Ile Gly Ser Phe Ile Gly Ala Leu Tyr Ala
                965                 970                 975

Glu Glu Arg Ser Ala Ser Arg Thr Lys Gln Arg Ala Arg Glu Trp Ala
            980                 985                 990

Lys Ser Met Thr Ser Val Leu Glu Pro Val Leu Asp Leu Thr Tyr Pro
        995                 1000                1005

Val Thr Ser Met Phe Thr Gly Ser Ala Phe Asn Arg Ser Ile His Arg
    1010                1015                1020

Val Phe Gln Asp Lys Gln Ile Glu Asp Leu Trp Leu Pro Tyr Phe Asn
1025                1030                1035                1040

Val Thr Thr Asp Ile Thr Ala Ser Ala Met Arg Val His Lys Asp Gly
```

```
                1045                1050                1055
Ser Leu Trp Arg Tyr Val Arg Ala Ser Met Thr Leu Ser Gly Tyr Leu
            1060                1065                1070

Pro Pro Leu Cys Asp Pro Lys Asp Gly His Leu Leu Met Asp Gly Gly
        1075                1080                1085

Tyr Ile Asn Asn Leu Pro Ala Asp Ile Ala Arg Ser Met Gly Ala Lys
    1090                1095                1100

Thr Val Ile Ala Ile Asp Val Gly Ser Gln Asp Glu Thr Asp Leu Ser
1105                1110                1115                1120

Thr Tyr Gly Asp Ser Leu Ser Gly Trp Trp Leu Leu Trp Lys Arg Leu
            1125                1130                1135

Asn Pro Trp Ala Asp Lys Val Lys Val Pro Asp Met Ala Glu Ile Gln
        1140                1145                1150

Ser Arg Leu Ala Tyr Val Ser Cys Val Arg Gln Leu Glu Val Val Lys
    1155                1160                1165

Ser Ser Ser Tyr Cys Glu Tyr Leu Arg Pro Pro Ile Asp Cys Phe Lys
1170                1175                1180

Thr Met Asp Phe Gly Lys Phe Asp Gln Ile Tyr Asp Val Gly Tyr Gln
1185                1190                1195                1200

Tyr Gly Lys Ala Val Phe Gly Gly Trp Ser Arg Gly Asn Val Ile Glu
        1205                1210                1215

Lys Met Leu Thr Asp Arg Arg Ser Thr Asp Leu Asn Glu Ser Arg Arg
    1220                1225                1230

Ala Asp Val Leu Ala Phe Pro Ser Ser Gly Phe Thr Asp Leu Ala Glu
1235                1240                1245

Ile Val Ser Arg Ile Glu Pro Pro Thr Ser Tyr Val Ser Asp Gly Cys
        1250                1255                1260

Ala Asp Gly Glu Glu Ser Asp Cys Leu Thr Gly Tyr Glu Glu Asp Ala
1265                1270                1275                1280

Gly Pro Asp Cys Ser Arg Asp Glu Gly Gly Ser Pro Glu Gly Ala Ser
            1285                1290                1295

Pro Ser Thr Ala Ser Glu Met Glu Glu Glu Lys Ser Ile Leu Arg Gln
        1300                1305                1310

Arg Arg Cys Leu Pro Gln Glu Pro Pro Gly Ser Ala Thr Asp Ala
    1315                1320                1325

<210> SEQ ID NO 8
<211> LENGTH: 640
<212> TYPE: PRT
<213> ORGANISM: Mus musculus

<400> SEQUENCE: 8

Met Val Ser Lys Gly Glu Glu Leu Phe Thr Gly Val Val Pro Ile Leu
 1               5                  10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Phe Gly Tyr Gly Leu Gln Cys Phe Ala Arg Tyr Pro Asp His Met Lys
65                  70                  75                  80

Gln His Asp Phe Phe Lys Ser Ala Met Pro Glu Gly Tyr Val Gln Glu
                85                  90                  95
```

```
Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
        180                 185                 190

Pro Val Leu Leu Pro Asp Asn His Tyr Leu Ser Tyr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys Glu
225                 230                 235                 240

Phe Glu Glu Lys Lys Glu Cys Asp Glu Leu Gln Asp Thr Met Leu
                245                 250                 255

Leu Leu Ser Gln Met Gly Pro Asp Ala His Met Arg Met Ile Leu Arg
            260                 265                 270

Lys Pro Pro Gly Gln Arg Thr Val Asp Asp Leu Glu Ile Tyr Glu
            275                 280                 285

Glu Leu Leu His Ile Lys Ala Leu Ser His Leu Ser Thr Thr Val Lys
    290                 295                 300

Arg Glu Leu Ala Gly Val Leu Ile Phe Glu Ser His Ala Lys Gly Gly
305                 310                 315                 320

Thr Val Leu Phe Asn Gln Gly Glu Glu Gly Thr Ser Trp Tyr Ile Ile
                325                 330                 335

Leu Lys Gly Ser Val Asn Val Val Ile Tyr Gly Lys Gly Val Val Cys
            340                 345                 350

Thr Leu His Glu Gly Asp Asp Phe Gly Lys Leu Ala Leu Val Asn Asp
        355                 360                 365

Ala Pro Arg Ala Ala Ser Ile Val Leu Arg Glu Asp Asn Cys His Phe
    370                 375                 380

Leu Arg Val Asp Lys Glu Asp Phe Asn Arg Ile Leu Arg Asp Val Glu
385                 390                 395                 400

Ser Arg Val Ser Lys Gly Glu Glu Leu Phe Thr Gly Val Val Pro Ile
                405                 410                 415

Leu Val Glu Leu Asp Gly Asp Val Asn Gly His Arg Phe Ser Val Ser
            420                 425                 430

Gly Glu Gly Glu Gly Asp Ala Thr Tyr Gly Lys Leu Thr Leu Lys Phe
        435                 440                 445

Ile Cys Thr Thr Gly Lys Leu Pro Val Pro Trp Pro Thr Leu Val Thr
    450                 455                 460

Thr Leu Thr Trp Gly Val Gln Cys Phe Ser Arg Tyr Pro Asp His Met
465                 470                 475                 480

Lys Gln His Asp Phe Phe Lys Ser Ala Met Pro Glu Gly Tyr Val Gln
                485                 490                 495

Glu Arg Thr Ile Phe Phe Lys Asp Asp Gly Asn Tyr Lys Thr Arg Ala
            500                 505                 510

Glu Val Lys Phe Glu Gly Asp Thr Leu Val Asn Arg Ile Glu Leu Lys
```

```
            515                 520                 525
Gly Ile Asp Phe Lys Glu Asp Gly Asn Ile Leu Gly His Lys Leu Glu
    530                 535                 540

Tyr Asn Tyr Ile Ser His Asn Val Tyr Ile Thr Ala Asp Lys Gln Lys
545                 550                 555                 560

Asn Gly Ile Lys Ala His Phe Lys Ile Arg His Asn Ile Glu Asp Gly
                565                 570                 575

Ser Val Gln Leu Ala Asp His Tyr Gln Gln Asn Thr Pro Ile Gly Asp
            580                 585                 590

Gly Pro Val Leu Leu Pro Asp Asn His Tyr Leu Ser Thr Gln Ser Ala
        595                 600                 605

Leu Ser Lys Asp Pro Asn Glu Lys Arg Asp His Met Val Leu Leu Glu
    610                 615                 620

Phe Val Thr Ala Ala Gly Ile Thr Leu Gly Met Asp Glu Leu Tyr Lys
625                 630                 635                 640

<210> SEQ ID NO 9
<211> LENGTH: 633
<212> TYPE: PRT
<213> ORGANISM: Mus musculus

<400> SEQUENCE: 9

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Phe Gly Tyr Gly Leu Gln Cys Phe Ala Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys Glu
225                 230                 235                 240

Phe Glu Glu Leu Gln Asp Thr Met Leu Leu Leu Ser Gln Met Gly Pro
                245                 250                 255
```

```
Asp Ala His Met Arg Met Ile Leu Arg Lys Pro Pro Gly Gln Arg Thr
                260                 265                 270

Val Asp Asp Leu Glu Ile Ile Tyr Glu Glu Leu Leu His Ile Lys Ala
            275                 280                 285

Leu Ser His Leu Ser Thr Thr Val Lys Arg Glu Leu Ala Gly Val Leu
        290                 295                 300

Ile Phe Glu Ser His Ala Lys Gly Gly Thr Val Leu Phe Asn Gln Gly
305                 310                 315                 320

Glu Glu Gly Thr Ser Trp Tyr Ile Ile Leu Lys Gly Ser Val Asn Val
                325                 330                 335

Val Ile Tyr Gly Lys Gly Val Val Cys Thr Leu His Glu Gly Asp Asp
            340                 345                 350

Phe Gly Lys Leu Ala Leu Val Asn Asp Ala Pro Arg Ala Ala Ser Ile
        355                 360                 365

Val Leu Arg Glu Asp Asn Cys His Phe Leu Arg Val Asp Lys Glu Asp
370                 375                 380

Phe Asn Arg Ile Leu Arg Asp Val Glu Ser Arg Val Ser Lys Gly Glu
385                 390                 395                 400

Glu Leu Phe Thr Gly Val Val Pro Ile Leu Val Glu Leu Asp Gly Asp
                405                 410                 415

Val Asn Gly His Arg Phe Ser Val Ser Gly Glu Gly Glu Gly Asp Ala
            420                 425                 430

Thr Tyr Gly Lys Leu Thr Leu Lys Phe Ile Cys Thr Thr Gly Lys Leu
        435                 440                 445

Pro Val Pro Trp Pro Thr Leu Val Thr Thr Leu Thr Trp Gly Val Gln
450                 455                 460

Cys Phe Ser Arg Tyr Pro Asp His Met Lys Gln His Asp Phe Phe Lys
465                 470                 475                 480

Ser Ala Met Pro Glu Gly Tyr Val Gln Glu Arg Thr Ile Phe Phe Lys
                485                 490                 495

Asp Asp Gly Asn Tyr Lys Thr Arg Ala Glu Val Lys Phe Glu Gly Asp
            500                 505                 510

Thr Leu Val Asn Arg Ile Glu Leu Lys Gly Ile Asp Phe Lys Glu Asp
        515                 520                 525

Gly Asn Ile Leu Gly His Lys Leu Glu Tyr Asn Tyr Ile Ser His Asn
530                 535                 540

Val Tyr Ile Thr Ala Asp Lys Gln Lys Asn Gly Ile Lys Ala His Phe
545                 550                 555                 560

Lys Ile Arg His Asn Ile Glu Asp Gly Ser Val Gln Leu Ala Asp His
                565                 570                 575

Tyr Gln Gln Asn Thr Pro Ile Gly Asp Gly Pro Val Leu Leu Pro Asp
            580                 585                 590

Asn His Tyr Leu Ser Thr Gln Ser Ala Leu Ser Lys Asp Pro Asn Glu
        595                 600                 605

Lys Arg Asp His Met Val Leu Leu Glu Phe Val Thr Ala Ala Gly Ile
610                 615                 620

Thr Leu Gly Met Asp Glu Leu Tyr Lys
625                 630

<210> SEQ ID NO 10
<211> LENGTH: 621
<212> TYPE: PRT
<213> ORGANISM: Mus musculus

<400> SEQUENCE: 10
```

```
Met Val Ser Lys Gly Glu Glu Leu Phe Thr Gly Val Pro Ile Leu
 1               5                  10                  15

Val Glu Leu Asp Gly Asp Val Asn Gly His Lys Phe Ser Val Ser Gly
             20                  25                  30

Glu Gly Glu Gly Asp Ala Thr Tyr Gly Lys Leu Thr Leu Lys Phe Ile
         35                  40                  45

Cys Thr Thr Gly Lys Leu Pro Val Pro Trp Pro Thr Leu Val Thr Thr
         50                  55                  60

Phe Gly Tyr Gly Leu Gln Cys Phe Ala Arg Tyr Pro Asp His Met Lys
 65                  70                  75                  80

Gln His Asp Phe Phe Lys Ser Ala Met Pro Glu Gly Tyr Val Gln Glu
                 85                  90                  95

Arg Thr Ile Phe Phe Lys Asp Asp Gly Asn Tyr Lys Thr Arg Ala Glu
                100                 105                 110

Val Lys Phe Glu Gly Asp Thr Leu Val Asn Arg Ile Glu Leu Lys Gly
            115                 120                 125

Ile Asp Phe Lys Glu Asp Gly Asn Ile Leu Gly His Lys Leu Glu Tyr
        130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Ala Leu
        195                 200                 205

Ser Lys Asp Pro Asn Glu Lys Arg Asp His Met Val Leu Leu Glu Phe
210                 215                 220

Val Thr Ala Ala Gly Ile Thr Leu Gly Met Asp Glu Leu Tyr Lys Glu
225                 230                 235                 240

Phe Met Gly Pro Asp Ala His Met Arg Met Ile Leu Arg Lys Pro Pro
                245                 250                 255

Gly Gln Arg Thr Val Asp Asp Leu Glu Ile Ile Tyr Glu Glu Leu Leu
            260                 265                 270

His Ile Lys Ala Leu Ser His Leu Ser Thr Thr Val Lys Arg Glu Leu
        275                 280                 285

Ala Gly Val Leu Ile Phe Glu Ser His Ala Lys Gly Thr Val Leu
290                 295                 300

Phe Asn Gln Gly Glu Gly Thr Ser Trp Tyr Ile Ile Leu Lys Gly
305                 310                 315                 320

Ser Val Asn Val Val Ile Tyr Gly Lys Gly Val Val Cys Thr Leu His
                325                 330                 335

Glu Gly Asp Asp Phe Gly Lys Leu Ala Leu Val Asn Asp Ala Pro Arg
            340                 345                 350

Ala Ala Ser Ile Val Leu Arg Glu Asp Asn Cys His Phe Leu Arg Val
        355                 360                 365

Asp Lys Glu Asp Phe Asn Arg Ile Leu Arg Asp Val Glu Ser Arg Val
370                 375                 380

Ser Lys Gly Glu Glu Leu Phe Thr Gly Val Val Pro Ile Leu Val Glu
385                 390                 395                 400

Leu Asp Gly Asp Val Asn Gly His Arg Phe Ser Val Ser Gly Glu Gly
                405                 410                 415
```

Glu Gly Asp Ala Thr Tyr Gly Lys Leu Thr Leu Lys Phe Ile Cys Thr
                420                 425                 430

Thr Gly Lys Leu Pro Val Pro Trp Pro Thr Leu Val Thr Leu Thr
            435                 440                 445

Trp Gly Val Gln Cys Phe Ser Arg Tyr Pro Asp His Met Lys Gln His
450                 455                 460

Asp Phe Phe Lys Ser Ala Met Pro Glu Gly Tyr Val Gln Glu Arg Thr
465                 470                 475                 480

Ile Phe Phe Lys Asp Asp Gly Asn Tyr Lys Thr Arg Ala Glu Val Lys
                485                 490                 495

Phe Glu Gly Asp Thr Leu Val Asn Arg Ile Glu Leu Lys Gly Ile Asp
            500                 505                 510

Phe Lys Glu Asp Gly Asn Ile Leu Gly His Lys Leu Glu Tyr Asn Tyr
        515                 520                 525

Ile Ser His Asn Val Tyr Ile Thr Ala Asp Lys Gln Lys Asn Gly Ile
530                 535                 540

Lys Ala His Phe Lys Ile Arg His Asn Ile Glu Asp Gly Ser Val Gln
545                 550                 555                 560

Leu Ala Asp His Tyr Gln Gln Asn Thr Pro Ile Gly Asp Gly Pro Val
                565                 570                 575

Leu Leu Pro Asp Asn His Tyr Leu Ser Thr Gln Ser Ala Leu Ser Lys
            580                 585                 590

Asp Pro Asn Glu Lys Arg Asp His Met Val Leu Leu Glu Phe Val Thr
        595                 600                 605

Ala Ala Gly Ile Thr Leu Gly Met Asp Glu Leu Tyr Lys
610                 615                 620

<210> SEQ ID NO 11
<211> LENGTH: 615
<212> TYPE: PRT
<213> ORGANISM: Mus musculus

<400> SEQUENCE: 11

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Phe Gly Tyr Gly Leu Gln Cys Phe Ala Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

```
Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Ala Leu
            195                 200             205

Ser Lys Asp Pro Asn Glu Lys Arg Asp His Met Val Leu Leu Glu Phe
210                 215                 220

Val Thr Ala Ala Gly Ile Thr Leu Gly Met Asp Glu Leu Tyr Lys Glu
225                 230                 235                 240

Phe Met Arg Met Ile Leu Arg Lys Pro Pro Gly Gln Arg Thr Val Asp
                245                 250                 255

Asp Leu Glu Ile Ile Tyr Glu Glu Leu Leu His Ile Lys Ala Leu Ser
            260                 265                 270

His Leu Ser Thr Thr Val Lys Arg Glu Leu Ala Gly Val Leu Ile Phe
            275                 280                 285

Glu Ser His Ala Lys Gly Gly Thr Val Leu Phe Asn Gln Gly Glu Glu
            290                 295                 300

Gly Thr Ser Trp Tyr Ile Ile Leu Lys Gly Ser Val Asn Val Val Ile
305                 310                 315                 320

Tyr Gly Lys Gly Val Val Cys Thr Leu His Glu Gly Asp Asp Phe Gly
                325                 330                 335

Lys Leu Ala Leu Val Asn Asp Ala Pro Arg Ala Ala Ser Ile Val Leu
            340                 345                 350

Arg Glu Asp Asn Cys His Phe Leu Arg Val Asp Lys Glu Asp Phe Asn
            355                 360                 365

Arg Ile Leu Arg Asp Val Glu Ser Arg Val Ser Lys Gly Glu Glu Leu
            370                 375                 380

Phe Thr Gly Val Val Pro Ile Leu Val Glu Leu Asp Gly Asp Val Asn
385                 390                 395                 400

Gly His Arg Phe Ser Val Ser Gly Glu Gly Glu Gly Asp Ala Thr Tyr
                405                 410                 415

Gly Lys Leu Thr Leu Lys Phe Ile Cys Thr Thr Gly Lys Leu Pro Val
            420                 425                 430

Pro Trp Pro Thr Leu Val Thr Thr Leu Thr Trp Gly Val Gln Cys Phe
            435                 440                 445

Ser Arg Tyr Pro Asp His Met Lys Gln His Asp Phe Phe Lys Ser Ala
450                 455                 460

Met Pro Glu Gly Tyr Val Gln Glu Arg Thr Ile Phe Phe Lys Asp Asp
465                 470                 475                 480

Gly Asn Tyr Lys Thr Arg Ala Glu Val Lys Phe Glu Gly Asp Thr Leu
                485                 490                 495

Val Asn Arg Ile Glu Leu Lys Gly Ile Asp Phe Lys Glu Asp Gly Asn
            500                 505                 510

Ile Leu Gly His Lys Leu Glu Tyr Asn Tyr Ile Ser His Asn Val Tyr
            515                 520                 525

Ile Thr Ala Asp Lys Gln Lys Asn Gly Ile Lys Ala His Phe Lys Ile
            530                 535                 540

Arg His Asn Ile Glu Asp Gly Ser Val Gln Leu Ala Asp His Tyr Gln
545                 550                 555                 560

Gln Asn Thr Pro Ile Gly Asp Gly Pro Val Leu Leu Pro Asp Asn His
                565                 570                 575

Tyr Leu Ser Thr Gln Ser Ala Leu Ser Lys Asp Pro Asn Glu Lys Arg
            580                 585                 590
```

Asp His Met Val Leu Leu Glu Phe Val Thr Ala Ala Gly Ile Thr Leu
        595                 600                 605

Gly Met Asp Glu Leu Tyr Lys
    610                 615

<210> SEQ ID NO 12
<211> LENGTH: 653
<212> TYPE: PRT
<213> ORGANISM: Mus musculus

<400> SEQUENCE: 12

Met Val Ser Lys Gly Glu Glu Leu Phe Thr Gly Val Val Pro Ile Leu
 1               5                  10                  15

Val Glu Leu Asp Gly Asp Val Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
        50                  55                  60

Phe Gly Tyr Gly Leu Gln Cys Phe Ala Arg Tyr Pro Asp His Met Lys
 65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys Glu
225                 230                 235                 240

Phe Glu Glu Lys Lys Glu Cys Asp Glu Glu Leu Gln Asp Thr Met Leu
                245                 250                 255

Leu Leu Ser Gln Met Gly Pro Asp Ala His Met Arg Met Ile Leu Arg
            260                 265                 270

Lys Pro Pro Gly Gln Arg Thr Val Asp Asp Leu Glu Ile Ile Tyr Glu
        275                 280                 285

Glu Leu Leu His Ile Lys Ala Leu Ser His Leu Ser Thr Thr Val Lys
    290                 295                 300

Arg Glu Leu Ala Gly Val Leu Ile Phe Glu Ser His Ala Lys Gly Gly
305                 310                 315                 320

Thr Val Leu Phe Asn Gln Gly Glu Gly Thr Ser Trp Tyr Ile Ile
                325                 330                 335

Leu Lys Gly Ser Val Asn Val Val Ile Tyr Gly Lys Val Val Cys
            340                 345                 350

```
Thr Leu His Glu Gly Asp Asp Phe Gly Lys Leu Ala Leu Val Asn Asp
            355                 360                 365

Ala Pro Arg Ala Ala Ser Ile Val Leu Arg Glu Asp Asn Cys His Phe
    370                 375                 380

Leu Arg Val Asp Lys Glu Asp Phe Asn Arg Ile Leu Arg Asp Val Glu
385                 390                 395                 400

Ala Asn Thr Val Arg Leu Lys Glu His Asp Gln Phe Cys Ser Arg Val
                405                 410                 415

Ser Lys Gly Glu Glu Leu Phe Thr Gly Val Val Pro Ile Leu Val Glu
            420                 425                 430

Leu Asp Gly Asp Val Asn Gly His Arg Phe Ser Val Ser Gly Glu Gly
            435                 440                 445

Glu Gly Asp Ala Thr Tyr Gly Lys Leu Thr Leu Lys Phe Ile Cys Thr
    450                 455                 460

Thr Gly Lys Leu Pro Val Pro Trp Pro Thr Leu Val Thr Thr Leu Thr
465                 470                 475                 480

Trp Gly Val Gln Cys Phe Ser Arg Tyr Pro Asp His Met Lys Gln His
                485                 490                 495

Asp Phe Phe Lys Ser Ala Met Pro Glu Gly Tyr Val Gln Glu Arg Thr
            500                 505                 510

Ile Phe Phe Lys Asp Asp Gly Asn Tyr Lys Thr Arg Ala Glu Val Lys
            515                 520                 525

Phe Glu Gly Asp Thr Leu Val Asn Arg Ile Glu Leu Lys Gly Ile Asp
    530                 535                 540

Phe Lys Glu Asp Gly Asn Ile Leu Gly His Lys Leu Glu Tyr Asn Tyr
545                 550                 555                 560

Ile Ser His Asn Val Tyr Ile Thr Ala Asp Lys Gln Lys Asn Gly Ile
                565                 570                 575

Lys Ala His Phe Lys Ile Arg His Asn Ile Glu Asp Gly Ser Val Gln
            580                 585                 590

Leu Ala Asp His Tyr Gln Gln Asn Thr Pro Ile Gly Asp Gly Pro Val
            595                 600                 605

Leu Leu Pro Asp Asn His Tyr Leu Ser Thr Gln Ser Ala Leu Ser Lys
    610                 615                 620

Asp Pro Asn Glu Lys Arg Asp His Met Val Leu Leu Glu Phe Val Thr
625                 630                 635                 640

Ala Ala Gly Ile Thr Leu Gly Met Asp Glu Leu Tyr Lys
                645                 650

<210> SEQ ID NO 13
<211> LENGTH: 657
<212> TYPE: PRT
<213> ORGANISM: Mus musculus

<400> SEQUENCE: 13

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
    50                  55                  60

Phe Gly Tyr Gly Leu Gln Cys Phe Ala Arg Tyr Pro Asp His Met Lys
```

```
              65                  70                  75                  80

Gln His Asp Phe Phe Lys Ser Ala Met Pro Glu Gly Tyr Val Gln Glu
                    85                  90                  95

Arg Thr Ile Phe Phe Lys Asp Asp Gly Asn Tyr Lys Thr Arg Ala Glu
                    100                 105                 110

Val Lys Phe Glu Gly Asp Thr Leu Val Asn Arg Ile Glu Leu Lys Gly
                    115                 120                 125

Ile Asp Phe Lys Glu Asp Gly Asn Ile Leu Gly His Lys Leu Glu Tyr
                    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                    165                 170                 175

Val Gln Leu Ala Asp His Tyr Gln Gln Asn Thr Pro Ile Gly Asp Gly
                    180                 185                 190

Pro Val Leu Leu Pro Asp Asn His Tyr Leu Ser Tyr Gln Ser Ala Leu
                    195                 200                 205

Ser Lys Asp Pro Asn Glu Lys Arg Asp His Met Val Leu Leu Glu Phe
210                 215                 220

Val Thr Ala Ala Gly Ile Thr Leu Gly Met Asp Glu Leu Tyr Lys Glu
225                 230                 235                 240

Phe Glu Glu Lys Lys Glu Cys Asp Glu Glu Leu Gln Asp Thr Met Leu
                    245                 250                 255

Leu Leu Ser Gln Met Gly Pro Asp Ala His Met Arg Met Ile Leu Arg
                    260                 265                 270

Lys Pro Pro Gly Gln Arg Thr Val Asp Asp Leu Glu Ile Ile Tyr Glu
                    275                 280                 285

Glu Leu Leu His Ile Lys Ala Leu Ser His Leu Ser Thr Thr Val Lys
                    290                 295                 300

Arg Glu Leu Ala Gly Val Leu Ile Phe Glu Ser His Ala Lys Gly Gly
305                 310                 315                 320

Thr Val Leu Phe Asn Gln Gly Glu Glu Gly Thr Ser Trp Tyr Ile Ile
                    325                 330                 335

Leu Lys Gly Ser Val Asn Val Val Ile Tyr Gly Lys Gly Val Val Cys
                    340                 345                 350

Thr Leu His Glu Gly Asp Asp Phe Gly Lys Leu Ala Leu Val Asn Asp
                    355                 360                 365

Ala Pro Arg Ala Ala Ser Ile Val Leu Arg Glu Asp Asn Cys His Phe
370                 375                 380

Leu Arg Val Asp Lys Glu Asp Phe Asn Arg Ile Leu Arg Asp Val Glu
385                 390                 395                 400

Ala Asn Thr Val Arg Leu Lys Glu His Asp Gln Asp Val Leu Val Leu
                    405                 410                 415

Glu Ser Arg Val Ser Lys Gly Glu Glu Leu Phe Thr Gly Val Val Pro
                    420                 425                 430

Ile Leu Val Glu Leu Asp Gly Asp Val Asn Gly His Arg Phe Ser Val
                    435                 440                 445

Ser Gly Glu Gly Glu Gly Asp Ala Thr Tyr Gly Lys Leu Thr Leu Lys
                    450                 455                 460

Phe Ile Cys Thr Thr Gly Lys Leu Pro Val Pro Trp Pro Thr Leu Val
465                 470                 475                 480

Thr Thr Leu Thr Trp Gly Val Gln Cys Phe Ser Arg Tyr Pro Asp His
                    485                 490                 495
```

```
Met Lys Gln His Asp Phe Phe Lys Ser Ala Met Pro Glu Gly Tyr Val
            500                 505                 510

Gln Glu Arg Thr Ile Phe Phe Lys Asp Asp Gly Asn Tyr Lys Thr Arg
            515                 520                 525

Ala Glu Val Lys Phe Glu Gly Asp Thr Leu Val Asn Arg Ile Glu Leu
530                 535                 540

Lys Gly Ile Asp Phe Lys Glu Asp Gly Asn Ile Leu Gly His Lys Leu
545                 550                 555                 560

Glu Tyr Asn Tyr Ile Ser His Asn Val Tyr Ile Thr Ala Asp Lys Gln
                565                 570                 575

Lys Asn Gly Ile Lys Ala His Phe Lys Ile Arg His Asn Ile Glu Asp
            580                 585                 590

Gly Ser Val Gln Leu Ala Asp His Tyr Gln Gln Asn Thr Pro Ile Gly
            595                 600                 605

Asp Gly Pro Val Leu Leu Pro Asp Asn His Tyr Leu Ser Thr Gln Ser
            610                 615                 620

Ala Leu Ser Lys Asp Pro Asn Glu Lys Arg Asp His Met Val Leu Leu
625                 630                 635                 640

Glu Phe Val Thr Ala Ala Gly Ile Thr Leu Gly Met Asp Glu Leu Tyr
                645                 650                 655

Lys

<210> SEQ ID NO 14
<211> LENGTH: 641
<212> TYPE: PRT
<213> ORGANISM: Mus musculus

<400> SEQUENCE: 14

Met Glu Glu Lys Lys Glu Cys Asp Glu Glu Leu Gln Asp Thr Met Leu
  1               5                  10                  15

Leu Leu Ser Gln Met Gly Pro Asp Ala His Met Arg Met Ile Leu Arg
                 20                  25                  30

Lys Pro Pro Gly Gln Arg Thr Val Asp Asp Leu Glu Ile Ile Tyr Glu
             35                  40                  45

Glu Leu Leu His Ile Lys Ala Leu Ser His Leu Ser Thr Thr Val Lys
          50                  55                  60

Arg Glu Leu Ala Gly Val Leu Ile Phe Glu Ser His Ala Lys Gly Gly
 65                  70                  75                  80

Thr Val Leu Phe Asn Gln Gly Glu Gly Thr Ser Trp Tyr Ile Ile
                 85                  90                  95

Leu Lys Gly Ser Val Asn Val Val Ile Ala Ser Val Ser Lys Gly Glu
                100                 105                 110

Glu Leu Phe Thr Gly Val Val Pro Ile Leu Val Glu Leu Asp Gly Asp
            115                 120                 125

Val Asn Gly His Lys Phe Ser Val Ser Gly Glu Gly Glu Gly Asp Ala
            130                 135                 140

Thr Tyr Gly Lys Leu Thr Leu Lys Phe Ile Cys Thr Thr Gly Lys Leu
145                 150                 155                 160

Pro Val Pro Trp Pro Thr Leu Val Thr Thr Phe Gly Tyr Gly Leu Gln
                165                 170                 175

Cys Phe Ala Arg Tyr Pro Asp His Met Lys Gln His Asp Phe Phe Lys
            180                 185                 190

Ser Ala Met Pro Glu Gly Tyr Val Gln Glu Arg Thr Ile Phe Phe Lys
            195                 200                 205
```

```
Asp Asp Gly Asn Tyr Lys Thr Arg Ala Glu Val Lys Phe Glu Gly Asp
210                 215                 220

Thr Leu Val Asn Arg Ile Glu Leu Lys Gly Ile Asp Phe Lys Glu Asp
225                 230                 235                 240

Gly Asn Ile Leu Gly His Lys Leu Glu Tyr Asn Tyr Asn Ser His Asn
            245                 250                 255

Val Tyr Ile Met Ala Asp Lys Gln Lys Asn Gly Ile Lys Val Asn Phe
            260                 265                 270

Lys Ile Arg His Asn Ile Glu Asp Gly Ser Val Gln Leu Ala Asp His
        275                 280                 285

Tyr Gln Gln Asn Thr Pro Ile Gly Asp Gly Pro Val Leu Leu Pro Asp
290                 295                 300

Asn His Tyr Leu Ser Tyr Gln Ser Ala Leu Ser Lys Asp Pro Asn Glu
305                 310                 315                 320

Lys Arg Asp His Met Val Leu Leu Glu Phe Val Thr Ala Ala Gly Ile
            325                 330                 335

Thr Leu Gly Met Asp Glu Leu Tyr Lys Glu Phe Gly Lys Gly Val Val
            340                 345                 350

Cys Thr Leu His Glu Gly Asp Asp Phe Gly Lys Leu Ala Leu Val Asn
        355                 360                 365

Asp Ala Pro Arg Ala Ala Ser Ile Val Leu Arg Glu Asp Asn Cys His
370                 375                 380

Phe Leu Arg Val Asp Lys Glu Asp Phe Asn Arg Ile Leu Arg Asp Val
385                 390                 395                 400

Glu Ser Arg Val Ser Lys Gly Glu Glu Leu Phe Thr Gly Val Val Pro
            405                 410                 415

Ile Leu Val Glu Leu Asp Gly Asp Val Asn Gly His Arg Phe Ser Val
            420                 425                 430

Ser Gly Glu Gly Glu Gly Asp Ala Thr Tyr Gly Lys Leu Thr Leu Lys
        435                 440                 445

Phe Ile Cys Thr Thr Gly Lys Leu Pro Val Pro Trp Pro Thr Leu Val
450                 455                 460

Thr Thr Leu Thr Trp Gly Val Gln Cys Phe Ser Arg Tyr Pro Asp His
465                 470                 475                 480

Met Lys Gln His Asp Phe Phe Lys Ser Ala Met Pro Glu Gly Tyr Val
            485                 490                 495

Gln Glu Arg Thr Ile Phe Phe Lys Asp Asp Gly Asn Tyr Lys Thr Arg
            500                 505                 510

Ala Glu Val Lys Phe Glu Gly Asp Thr Leu Val Asn Arg Ile Glu Leu
        515                 520                 525

Lys Gly Ile Asp Phe Lys Glu Asp Gly Asn Ile Leu Gly His Lys Leu
530                 535                 540

Glu Tyr Asn Tyr Ile Ser His Asn Val Tyr Ile Thr Ala Asp Lys Gln
545                 550                 555                 560

Lys Asn Gly Ile Lys Ala His Phe Lys Ile Arg His Asn Ile Glu Asp
            565                 570                 575

Gly Ser Val Gln Leu Ala Asp His Tyr Gln Gln Asn Thr Pro Ile Gly
            580                 585                 590

Asp Gly Pro Val Leu Leu Pro Asp Asn His Tyr Leu Ser Thr Gln Ser
        595                 600                 605

Ala Leu Ser Lys Asp Pro Asn Glu Lys Arg Asp His Met Val Leu Leu
610                 615                 620
```

-continued

```
Glu Phe Val Thr Ala Ala Gly Ile Thr Leu Gly Met Asp Glu Leu Tyr
625                 630                 635                 640

Lys

<210> SEQ ID NO 15
<211> LENGTH: 658
<212> TYPE: PRT
<213> ORGANISM: Mus musculus

<400> SEQUENCE: 15

Met Glu Glu Lys Lys Glu Cys Asp Glu Leu Gln Asp Thr Met Leu
  1               5                  10                  15

Leu Leu Ser Gln Met Gly Pro Asp Ala His Met Arg Met Ile Leu Arg
             20                  25                  30

Lys Pro Pro Gly Gln Arg Thr Val Asp Asp Leu Glu Ile Ile Tyr Glu
         35                  40                  45

Glu Leu Leu His Ile Lys Ala Leu Ser His Leu Ser Thr Thr Val Lys
 50                  55                  60

Arg Glu Leu Ala Gly Val Leu Ile Phe Glu Ser His Ala Lys Gly Gly
 65                  70                  75                  80

Thr Val Leu Phe Asn Gln Gly Glu Glu Gly Thr Ser Trp Tyr Ile Ile
                 85                  90                  95

Leu Lys Gly Ser Val Asn Val Val Ile Ala Ser Val Ser Lys Gly Glu
            100                 105                 110

Glu Leu Phe Thr Gly Val Val Pro Ile Leu Val Glu Leu Asp Gly Asp
        115                 120                 125

Val Asn Gly His Lys Phe Ser Val Ser Gly Glu Gly Glu Gly Asp Ala
130                 135                 140

Thr Tyr Gly Lys Leu Thr Leu Lys Phe Ile Cys Thr Thr Gly Lys Leu
145                 150                 155                 160

Pro Val Pro Trp Pro Thr Leu Val Thr Thr Phe Gly Tyr Gly Leu Gln
                165                 170                 175

Cys Phe Ala Arg Tyr Pro Asp His Met Lys Gln His Asp Phe Phe Lys
            180                 185                 190

Ser Ala Met Pro Glu Gly Tyr Val Gln Glu Arg Thr Ile Phe Phe Lys
        195                 200                 205

Asp Asp Gly Asn Tyr Lys Thr Arg Ala Glu Val Lys Phe Glu Gly Asp
210                 215                 220

Thr Leu Val Asn Arg Ile Glu Leu Lys Gly Ile Asp Phe Lys Glu Asp
225                 230                 235                 240

Gly Asn Ile Leu Gly His Lys Leu Glu Tyr Asn Tyr Asn Ser His Asn
                245                 250                 255

Val Tyr Ile Met Ala Asp Lys Gln Lys Asn Gly Ile Lys Val Asn Phe
            260                 265                 270

Lys Ile Arg His Asn Ile Glu Asp Gly Ser Val Gln Leu Ala Asp His
        275                 280                 285

Tyr Gln Gln Asn Thr Pro Ile Gly Asp Gly Pro Val Leu Leu Pro Asp
290                 295                 300

Asn His Tyr Leu Ser Tyr Gln Ser Ala Leu Ser Lys Asp Pro Asn Glu
305                 310                 315                 320

Lys Arg Asp His Met Val Leu Leu Glu Phe Val Thr Ala Ala Gly Ile
                325                 330                 335

Thr Leu Gly Met Asp Glu Leu Tyr Lys Glu Phe Gly Lys Gly Val Val
            340                 345                 350
```

Cys Thr Leu His Glu Gly Asp Asp Phe Gly Lys Leu Ala Leu Val Asn
            355                 360                 365

Asp Ala Pro Arg Ala Ala Ser Ile Val Leu Arg Glu Asp Asn Cys His
    370                 375                 380

Phe Leu Arg Val Asp Lys Glu Asp Phe Asn Arg Ile Leu Arg Asp Val
385                 390                 395                 400

Glu Ala Asn Thr Val Arg Leu Lys Glu His Asp Gln Asp Val Leu Val
                405                 410                 415

Leu Glu Ser Arg Val Ser Lys Gly Glu Leu Phe Thr Gly Val Val
                420                 425                 430

Pro Ile Leu Val Glu Leu Asp Gly Asp Val Asn Gly His Arg Phe Ser
            435                 440                 445

Val Ser Gly Glu Gly Glu Gly Asp Ala Thr Tyr Gly Lys Leu Thr Leu
    450                 455                 460

Lys Phe Ile Cys Thr Thr Gly Lys Leu Pro Val Pro Trp Pro Thr Leu
465                 470                 475                 480

Val Thr Thr Leu Thr Trp Gly Val Gln Cys Phe Ser Arg Tyr Pro Asp
                485                 490                 495

His Met Lys Gln His Asp Phe Phe Lys Ser Ala Met Pro Glu Gly Tyr
                500                 505                 510

Val Gln Glu Arg Thr Ile Phe Phe Lys Asp Asp Gly Asn Tyr Lys Thr
            515                 520                 525

Arg Ala Glu Val Lys Phe Glu Gly Asp Thr Leu Val Asn Arg Ile Glu
    530                 535                 540

Leu Lys Gly Ile Asp Phe Lys Glu Asp Gly Asn Ile Leu Gly His Lys
545                 550                 555                 560

Leu Glu Tyr Asn Tyr Ile Ser His Asn Val Tyr Ile Thr Ala Asp Lys
                565                 570                 575

Gln Lys Asn Gly Ile Lys Ala His Phe Lys Ile Arg His Asn Ile Glu
            580                 585                 590

Asp Gly Ser Val Gln Leu Ala Asp His Tyr Gln Gln Asn Thr Pro Ile
    595                 600                 605

Gly Asp Gly Pro Val Leu Leu Pro Asp Asn His Tyr Leu Ser Thr Gln
610                 615                 620

Ser Ala Leu Ser Lys Asp Pro Asn Glu Lys Arg Asp His Met Val Leu
625                 630                 635                 640

Leu Glu Phe Val Thr Ala Ala Gly Ile Thr Leu Gly Met Asp Glu Leu
                645                 650                 655

Tyr Lys

<210> SEQ ID NO 16
<211> LENGTH: 651
<212> TYPE: PRT
<213> ORGANISM: Mus musculus

<400> SEQUENCE: 16

Met Gly Cys Ile Asn Ser Lys Arg Lys Asp Ala Ser Val Ser Lys Gly
1               5                   10                  15

Glu Glu Leu Phe Thr Gly Val Val Pro Ile Leu Val Glu Leu Asp Gly
            20                  25                  30

Asp Val Asn Gly His Lys Phe Ser Val Ser Gly Glu Gly Glu Gly Asp
        35                  40                  45

Ala Thr Tyr Gly Lys Leu Thr Leu Lys Phe Ile Cys Thr Thr Gly Lys
    50                  55                  60

```
Leu Pro Val Pro Trp Pro Thr Leu Val Thr Thr Phe Gly Tyr Gly Leu
 65                  70                  75                  80

Gln Cys Phe Ala Arg Tyr Pro Asp His Met Lys Gln His Asp Phe Phe
                 85                  90                  95

Lys Ser Ala Met Pro Glu Gly Tyr Val Gln Glu Arg Thr Ile Phe Phe
            100                 105                 110

Lys Asp Asp Gly Asn Tyr Lys Thr Arg Ala Glu Val Lys Phe Glu Gly
        115                 120                 125

Asp Thr Leu Val Asn Arg Ile Glu Leu Lys Gly Ile Asp Phe Lys Glu
    130                 135                 140

Asp Gly Asn Ile Leu Gly His Lys Leu Glu Tyr Asn Tyr Asn Ser His
145                 150                 155                 160

Asn Val Tyr Ile Met Ala Asp Lys Gln Lys Asn Gly Ile Lys Val Asn
                165                 170                 175

Phe Lys Ile Arg His Asn Ile Glu Asp Gly Ser Val Gln Leu Ala Asp
            180                 185                 190

His Tyr Gln Gln Asn Thr Pro Ile Gly Asp Gly Pro Val Leu Leu Pro
        195                 200                 205

Asp Asn His Tyr Leu Ser Tyr Gln Ser Ala Leu Ser Lys Asp Pro Asn
    210                 215                 220

Glu Lys Arg Asp His Met Val Leu Leu Glu Phe Val Thr Ala Ala Gly
225                 230                 235                 240

Ile Thr Leu Gly Met Asp Glu Leu Tyr Lys Glu Phe Glu Glu Lys Lys
                245                 250                 255

Glu Cys Asp Glu Glu Leu Gln Asp Thr Met Leu Leu Leu Ser Gln Met
            260                 265                 270

Gly Pro Asp Ala His Met Arg Met Ile Leu Arg Lys Pro Pro Gly Gln
        275                 280                 285

Arg Thr Val Asp Asp Leu Glu Ile Ile Tyr Glu Glu Leu His Ile
    290                 295                 300

Lys Ala Leu Ser His Leu Ser Thr Thr Val Lys Arg Glu Leu Ala Gly
305                 310                 315                 320

Val Leu Ile Phe Glu Ser His Ala Lys Gly Gly Thr Val Leu Phe Asn
                325                 330                 335

Gln Gly Glu Glu Gly Thr Ser Trp Tyr Ile Ile Leu Lys Gly Ser Val
            340                 345                 350

Asn Val Val Ile Tyr Gly Lys Gly Val Val Cys Thr Leu His Glu Gly
        355                 360                 365

Asp Asp Phe Gly Lys Leu Ala Leu Val Asn Asp Ala Pro Arg Ala Ala
    370                 375                 380

Ser Ile Val Leu Arg Glu Asp Asn Cys His Phe Leu Arg Val Asp Lys
385                 390                 395                 400

Glu Asp Phe Asn Arg Ile Leu Arg Asp Val Glu Ser Arg Val Ser Lys
                405                 410                 415

Gly Glu Glu Leu Phe Thr Gly Val Pro Ile Leu Val Glu Leu Asp
            420                 425                 430

Gly Asp Val Asn Gly His Arg Phe Ser Val Ser Gly Glu Gly Glu Gly
        435                 440                 445

Asp Ala Thr Tyr Gly Lys Leu Thr Leu Lys Phe Ile Cys Thr Thr Gly
    450                 455                 460

Lys Leu Pro Val Pro Trp Pro Thr Leu Val Thr Thr Leu Thr Trp Gly
465                 470                 475                 480

Val Gln Cys Phe Ser Arg Tyr Pro Asp His Met Lys Gln His Asp Phe
```

```
                        485                 490                 495
Phe Lys Ser Ala Met Pro Glu Gly Tyr Val Gln Glu Arg Thr Ile Phe
                    500                 505                 510

Phe Lys Asp Asp Gly Asn Tyr Lys Thr Arg Ala Glu Val Lys Phe Glu
                515                 520                 525

Gly Asp Thr Leu Val Asn Arg Ile Glu Leu Lys Gly Ile Asp Phe Lys
            530                 535                 540

Glu Asp Gly Asn Ile Leu Gly His Lys Leu Glu Tyr Asn Tyr Ile Ser
545                 550                 555                 560

His Asn Val Tyr Ile Thr Ala Asp Lys Gln Lys Asn Gly Ile Lys Ala
                565                 570                 575

His Phe Lys Ile Arg His Asn Ile Glu Asp Gly Ser Val Gln Leu Ala
                580                 585                 590

Asp His Tyr Gln Gln Asn Thr Pro Ile Gly Asp Gly Pro Val Leu Leu
                595                 600                 605

Pro Asp Asn His Tyr Leu Ser Thr Gln Ser Ala Leu Ser Lys Asp Pro
            610                 615                 620

Asn Glu Lys Arg Asp His Met Val Leu Leu Glu Phe Val Thr Ala Ala
625                 630                 635                 640

Gly Ile Thr Leu Gly Met Asp Glu Leu Tyr Lys
                645                 650

<210> SEQ ID NO 17
<211> LENGTH: 641
<212> TYPE: PRT
<213> ORGANISM: Homo sapiens

<400> SEQUENCE: 17

Met Val Ser Lys Gly Glu Glu Leu Phe Thr Gly Val Val Pro Ile Leu
  1               5                  10                  15

Val Glu Leu Asp Gly Asp Val Asn Gly His Lys Phe Ser Val Ser Gly
                 20                  25                  30

Glu Gly Glu Gly Asp Ala Thr Tyr Gly Lys Leu Thr Leu Lys Phe Ile
             35                  40                  45

Cys Thr Thr Gly Lys Leu Pro Val Pro Trp Pro Thr Leu Val Thr Thr
         50                  55                  60

Phe Gly Tyr Gly Leu Gln Cys Phe Ala Arg Tyr Pro Asp His Met Lys
 65                  70                  75                  80

Gln His Asp Phe Phe Lys Ser Ala Met Pro Glu Gly Tyr Val Gln Glu
                 85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Ala Leu
        195                 200                 205
```

```
Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys Glu
225                 230                 235                 240

Phe Glu Glu Leu Ala Glu Ala Val Ala Leu Leu Ser Gln Arg Gly Pro
                245                 250                 255

Asp Ala Leu Leu Thr Val Ala Leu Arg Lys Pro Pro Gly Gln Arg Thr
            260                 265                 270

Asp Glu Glu Leu Asp Leu Ile Phe Glu Glu Leu Leu His Ile Lys Ala
                275                 280                 285

Val Ala His Leu Ser Asn Ser Val Lys Arg Glu Leu Ala Ala Val Leu
        290                 295                 300

Leu Phe Glu Pro His Ser Lys Ala Gly Thr Val Leu Phe Ser Gln Gly
305                 310                 315                 320

Asp Lys Gly Thr Ser Trp Tyr Ile Ile Trp Lys Gly Ser Val Asn Val
                325                 330                 335

Val Thr His Gly Lys Gly Leu Val Thr Thr Leu His Glu Gly Asp Asp
            340                 345                 350

Phe Gly Gln Leu Ala Leu Val Asn Asp Ala Pro Arg Ala Ala Thr Ile
                355                 360                 365

Ile Leu Arg Glu Asp Asn Cys His Phe Leu Arg Val Asp Lys Gln Asp
    370                 375                 380

Phe Asn Arg Ile Ile Lys Asp Val Glu Ala Lys Thr Met Arg Leu Glu
385                 390                 395                 400

Glu Ser Arg Val Ser Lys Gly Glu Glu Leu Phe Thr Gly Val Val Pro
                405                 410                 415

Ile Leu Val Glu Leu Asp Gly Asp Val Asn Gly His Arg Phe Ser Val
            420                 425                 430

Ser Gly Glu Gly Glu Gly Asp Ala Thr Tyr Gly Lys Leu Thr Leu Lys
        435                 440                 445

Phe Ile Cys Thr Thr Gly Lys Leu Pro Val Pro Trp Pro Thr Leu Val
        450                 455                 460

Thr Thr Leu Thr Trp Gly Val Gln Cys Phe Ser Arg Tyr Pro Asp His
465                 470                 475                 480

Met Lys Gln His Asp Phe Phe Lys Ser Ala Met Pro Glu Gly Tyr Val
                485                 490                 495

Gln Glu Arg Thr Ile Phe Phe Lys Asp Asp Gly Asn Tyr Lys Thr Arg
            500                 505                 510

Ala Glu Val Lys Phe Glu Gly Asp Thr Leu Val Asn Arg Ile Glu Leu
        515                 520                 525

Lys Gly Ile Asp Phe Lys Glu Asp Gly Asn Ile Leu Gly His Lys Leu
    530                 535                 540

Glu Tyr Asn Tyr Ile Ser His Asn Val Tyr Ile Thr Ala Asp Lys Gln
545                 550                 555                 560

Lys Asn Gly Ile Lys Ala His Phe Lys Ile Arg His Asn Ile Glu Asp
                565                 570                 575

Gly Ser Val Gln Leu Ala Asp His Tyr Gln Gln Asn Thr Pro Ile Gly
            580                 585                 590

Asp Gly Pro Val Leu Leu Pro Asp Asn His Tyr Leu Ser Thr Gln Ser
        595                 600                 605

Ala Leu Ser Lys Asp Pro Asn Glu Lys Arg Asp His Met Val Leu Leu
    610                 615                 620

Glu Phe Val Thr Ala Ala Gly Ile Thr Leu Gly Met Asp Glu Leu Tyr
```

```
                  625                 630                 635                 640
Lys

<210> SEQ ID NO 18
<211> LENGTH: 645
<212> TYPE: PRT
<213> ORGANISM: Mus musculus

<400> SEQUENCE: 18

Met Val Ser Lys Gly Glu Glu Leu Phe Thr Gly Val Val Pro Ile Leu
 1               5                  10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Phe Gly Tyr Gly Leu Gln Cys Phe Ala Arg Tyr Pro Asp His Met Lys
 65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys Glu
225                 230                 235                 240

Phe Met Tyr Glu Ser Phe Ile Glu Ser Leu Pro Phe Leu Lys Ser Leu
                245                 250                 255

Glu Val Ser Glu Arg Leu Lys Val Val Asp Val Ile Gly Thr Lys Val
            260                 265                 270

Tyr Asn Asp Gly Glu Gln Ile Ile Ala Gln Gly Asp Ser Ala Asp Ser
        275                 280                 285

Phe Phe Ile Val Glu Ser Gly Glu Val Arg Ile Thr Met Lys Arg Lys
    290                 295                 300

Gly Lys Ser Asp Ile Glu Glu Asn Gly Ala Val Glu Ile Ala Arg Cys
305                 310                 315                 320

Leu Arg Gly Gln Tyr Phe Gly Glu Leu Ala Leu Val Thr Asn Lys Pro
                325                 330                 335

Arg Ala Ala Ser Ala His Ala Ile Gly Thr Val Lys Cys Leu Ala Met
            340                 345                 350

Asp Val Gln Ala Phe Glu Arg Leu Leu Gly Pro Cys Met Glu Ile Met
```

```
        355                 360                 365
Lys Arg Asn Ile Ala Thr Tyr Glu Glu Gln Leu Val Ala Leu Phe Gly
    370                 375                 380

Thr Asn Met Asp Ile Val Glu Pro Thr Ala Lys Leu Tyr Pro Tyr Asp
385                 390                 395                 400

Val Pro Asp Tyr Ala Ser Arg Met Val Ser Lys Gly Glu Glu Leu Phe
                405                 410                 415

Thr Gly Val Val Pro Ile Leu Val Glu Leu Asp Gly Asp Val Asn Gly
            420                 425                 430

His Arg Phe Ser Val Ser Gly Glu Gly Glu Gly Asp Ala Thr Tyr Gly
        435                 440                 445

Lys Leu Thr Leu Lys Phe Ile Cys Thr Thr Gly Lys Leu Pro Val Pro
    450                 455                 460

Trp Pro Thr Leu Val Thr Thr Leu Thr Trp Gly Val Gln Cys Phe Ser
465                 470                 475                 480

Arg Tyr Pro Asp His Met Lys Gln His Asp Phe Phe Lys Ser Ala Met
                485                 490                 495

Pro Glu Gly Tyr Val Gln Glu Arg Thr Ile Phe Phe Lys Asp Asp Gly
            500                 505                 510

Asn Tyr Lys Thr Arg Ala Glu Val Lys Phe Glu Gly Asp Thr Leu Val
        515                 520                 525

Asn Arg Ile Glu Lys Gly Ile Asp Phe Lys Glu Asp Gly Asn Ile Leu
    530                 535                 540

Gly His Lys Leu Glu Tyr Asn Tyr Ile Ser His Asn Val Tyr Ile Thr
545                 550                 555                 560

Ala Asp Lys Gln Lys Asn Gly Ile Lys Ala His Phe Lys Ile Arg His
                565                 570                 575

Asn Ile Glu Asp Gly Ser Val Gln Leu Ala Asp His Tyr Gln Gln Asn
            580                 585                 590

Thr Pro Ile Gly Asp Gly Pro Val Leu Leu Pro Asp Asn His Tyr Leu
        595                 600                 605

Ser Thr Gln Ser Ala Leu Ser Lys Asp Pro Asn Glu Lys Arg Asp His
    610                 615                 620

Met Val Leu Leu Glu Phe Val Thr Ala Ala Gly Ile Thr Leu Gly Met
625                 630                 635                 640

Asp Glu Leu Tyr Lys
                645

<210> SEQ ID NO 19
<211> LENGTH: 621
<212> TYPE: PRT
<213> ORGANISM: Mus musculus

<400> SEQUENCE: 19

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Phe Gly Tyr Gly Leu Gln Cys Phe Ala Arg Tyr Pro Asp His Met Lys
65                  70                  75                  80
```

```
Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys Glu
225                 230                 235                 240

Phe Met Tyr Glu Ser Phe Ile Glu Ser Leu Pro Phe Leu Lys Ser Leu
                245                 250                 255

Glu Val Ser Glu Arg Leu Lys Val Val Asp Val Ile Gly Thr Lys Val
            260                 265                 270

Tyr Asn Asp Gly Glu Gln Ile Ile Ala Gln Gly Asp Ser Ala Asp Ser
        275                 280                 285

Phe Phe Ile Val Glu Ser Gly Glu Val Arg Ile Thr Met Lys Arg Lys
    290                 295                 300

Gly Lys Ser Asp Ile Glu Glu Asn Gly Ala Val Glu Ile Ala Arg Cys
305                 310                 315                 320

Leu Arg Gly Gln Tyr Phe Gly Glu Leu Ala Leu Val Thr Asn Lys Pro
                325                 330                 335

Arg Ala Ala Ser Ala His Ala Ile Gly Thr Val Lys Cys Leu Ala Met
            340                 345                 350

Asp Val Gln Ala Phe Glu Arg Leu Leu Gly Pro Cys Met Glu Ile Met
        355                 360                 365

Lys Arg Asn Ile Ala Thr Tyr Glu Glu Gln Leu Val Ala Ser Arg Val
    370                 375                 380

Ser Lys Gly Glu Glu Leu Phe Thr Gly Val Val Pro Ile Leu Val Glu
385                 390                 395                 400

Leu Asp Gly Asp Val Asn Gly His Arg Phe Ser Val Ser Gly Glu Gly
                405                 410                 415

Glu Gly Asp Ala Thr Tyr Gly Lys Leu Thr Leu Lys Phe Ile Cys Thr
            420                 425                 430

Thr Gly Lys Leu Pro Val Pro Trp Pro Thr Leu Val Thr Thr Leu Thr
        435                 440                 445

Trp Gly Val Gln Cys Phe Ser Arg Tyr Pro Asp His Met Lys Gln His
    450                 455                 460

Asp Phe Phe Lys Ser Ala Met Pro Glu Gly Tyr Val Gln Glu Arg Thr
465                 470                 475                 480

Ile Phe Phe Lys Asp Asp Gly Asn Tyr Lys Thr Arg Ala Glu Val Lys
                485                 490                 495

Phe Glu Gly Asp Thr Leu Val Asn Arg Ile Glu Leu Lys Gly Ile Asp
```

```
                  500                 505                 510
Phe Lys Glu Asp Gly Asn Ile Leu Gly His Lys Leu Glu Tyr Asn Tyr
            515                 520                 525

Ile Ser His Asn Val Tyr Ile Thr Ala Asp Lys Gln Lys Asn Gly Ile
            530                 535                 540

Lys Ala His Phe Lys Ile Arg His Asn Ile Glu Asp Gly Ser Val Gln
545                 550                 555                 560

Leu Ala Asp His Tyr Gln Gln Asn Thr Pro Ile Gly Asp Gly Pro Val
                565                 570                 575

Leu Leu Pro Asp Asn His Tyr Leu Ser Thr Gln Ser Ala Leu Ser Lys
            580                 585                 590

Asp Pro Asn Glu Lys Arg Asp His Met Val Leu Leu Glu Phe Val Thr
            595                 600                 605

Ala Ala Gly Ile Thr Leu Gly Met Asp Glu Leu Tyr Lys
610                 615                 620
```

<210> SEQ ID NO 20
<211> LENGTH: 621
<212> TYPE: PRT
<213> ORGANISM: Mus musculus

<400> SEQUENCE: 20

```
Met Tyr Glu Ser Phe Ile Glu Ser Leu Pro Phe Leu Lys Ser Leu Glu
1               5                   10                  15

Val Ser Glu Arg Leu Lys Val Val Asp Val Ile Gly Thr Lys Val Tyr
            20                  25                  30

Asn Asp Gly Glu Gln Ile Ile Ala Gln Gly Asp Ser Ala Asp Ser Phe
        35                  40                  45

Phe Ile Val Glu Ser Gly Glu Val Arg Ile Thr Met Lys Arg Lys Gly
    50                  55                  60

Lys Ser Asp Ile Ala Ser Val Ser Lys Gly Glu Glu Leu Phe Thr Gly
65                  70                  75                  80

Val Val Pro Ile Leu Val Glu Leu Asp Gly Asp Val Asn Gly His Lys
                85                  90                  95

Phe Ser Val Ser Gly Glu Gly Glu Gly Asp Ala Thr Tyr Gly Lys Leu
            100                 105                 110

Thr Leu Lys Phe Ile Cys Thr Thr Gly Lys Leu Pro Val Pro Trp Pro
        115                 120                 125

Thr Leu Val Thr Thr Phe Gly Tyr Gly Leu Gln Cys Phe Ala Arg Tyr
    130                 135                 140

Pro Asp His Met Lys Gln His Asp Phe Phe Lys Ser Ala Met Pro Glu
145                 150                 155                 160

Gly Tyr Val Gln Glu Arg Thr Ile Phe Phe Lys Asp Asp Gly Asn Tyr
                165                 170                 175

Lys Thr Arg Ala Glu Val Lys Phe Glu Gly Asp Thr Leu Val Asn Arg
            180                 185                 190

Ile Glu Leu Lys Gly Ile Asp Phe Lys Glu Asp Gly Asn Ile Leu Gly
        195                 200                 205

His Lys Leu Glu Tyr Asn Tyr Asn Ser His Asn Val Tyr Ile Met Ala
    210                 215                 220

Asp Lys Gln Lys Asn Gly Ile Lys Val Asn Phe Lys Ile Arg His Asn
225                 230                 235                 240

Ile Glu Asp Gly Ser Val Gln Leu Ala Asp His Tyr Gln Gln Asn Thr
                245                 250                 255
```

```
Pro Ile Gly Asp Gly Pro Val Leu Leu Pro Asp Asn His Tyr Leu Ser
            260                 265                 270

Tyr Gln Ser Ala Leu Ser Lys Asp Pro Asn Glu Lys Arg Asp His Met
        275                 280                 285

Val Leu Leu Glu Phe Val Thr Ala Ala Gly Ile Thr Leu Gly Met Asp
    290                 295                 300

Glu Leu Tyr Lys Glu Phe Glu Asn Gly Ala Val Glu Ile Ala Arg Cys
305                 310                 315                 320

Leu Arg Gly Gln Tyr Phe Gly Glu Leu Ala Leu Val Thr Asn Lys Pro
                325                 330                 335

Arg Ala Ala Ser Ala His Ala Ile Gly Thr Val Lys Cys Leu Ala Met
                340                 345                 350

Asp Val Gln Ala Phe Glu Arg Leu Leu Gly Pro Cys Met Glu Ile Met
            355                 360                 365

Lys Arg Asn Ile Ala Thr Tyr Glu Glu Gln Leu Val Ala Ser Arg Val
370                 375                 380

Ser Lys Gly Glu Glu Leu Phe Thr Gly Val Val Pro Ile Leu Val Glu
385                 390                 395                 400

Leu Asp Gly Asp Val Asn Gly His Arg Phe Ser Val Ser Gly Glu Gly
                405                 410                 415

Glu Gly Asp Ala Thr Tyr Gly Lys Leu Thr Leu Lys Phe Ile Cys Thr
            420                 425                 430

Thr Gly Lys Leu Pro Val Pro Trp Pro Thr Leu Val Thr Thr Leu Thr
        435                 440                 445

Trp Gly Val Gln Cys Phe Ser Arg Tyr Pro Asp His Met Lys Gln His
450                 455                 460

Asp Phe Phe Lys Ser Ala Met Pro Glu Gly Tyr Val Gln Glu Arg Thr
465                 470                 475                 480

Ile Phe Phe Lys Asp Asp Gly Asn Tyr Lys Thr Arg Ala Glu Val Lys
                485                 490                 495

Phe Glu Gly Asp Thr Leu Val Asn Arg Ile Glu Leu Lys Gly Ile Asp
            500                 505                 510

Phe Lys Glu Asp Gly Asn Ile Leu Gly His Lys Leu Glu Tyr Asn Tyr
        515                 520                 525

Ile Ser His Asn Val Tyr Ile Thr Ala Asp Lys Gln Lys Asn Gly Ile
530                 535                 540

Lys Ala His Phe Lys Ile Arg His Asn Ile Glu Asp Gly Ser Val Gln
545                 550                 555                 560

Leu Ala Asp His Tyr Gln Gln Asn Thr Pro Ile Gly Asp Gly Pro Val
                565                 570                 575

Leu Leu Pro Asp Asn His Tyr Leu Ser Thr Gln Ser Ala Leu Ser Lys
            580                 585                 590

Asp Pro Asn Glu Lys Arg Asp His Met Val Leu Leu Glu Phe Val Thr
        595                 600                 605

Ala Ala Gly Ile Thr Leu Gly Met Asp Glu Leu Tyr Lys
            610                 615                 620

<210> SEQ ID NO 21
<211> LENGTH: 239
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21
```

Met Val Ser Lys Gly Glu Glu Leu Phe Thr Gly Val Pro Ile Leu
1               5                   10                  15

Val Glu Leu Asp Gly Asp Val Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
        50                  55                  60

Phe Gly Tyr Gly Leu Gln Cys Phe Ala Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235

<210> SEQ ID NO 22
<211> LENGTH: 239
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Met Val Ser Lys Gly Glu Glu Leu Phe Thr Gly Val Pro Ile Leu
1               5                   10                  15

Val Glu Leu Asp Gly Asp Val Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
        50                  55                  60

Leu Thr Trp Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly

```
              115                 120                 125
Ile Asp Phe Lys Glu Asp Gly Asn Ile Leu Gly His Lys Leu Glu Tyr
    130                 135                 140

Asn Tyr Ile Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235

<210> SEQ ID NO 23
<211> LENGTH: 717
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagtt catctgcacc accggcaagc tgcccgtgcc ctggcccacc     180
ctcgtgacca ccttcggcta cggcctgcag tgcttcgccc gctaccccga ccacatgaag     240
cagcacgact tcttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggagg acggcaacat cctggggcac     420
aagctggagt acaactacaa cagccacaac gtctatatca tggccgacaa gcagaagaac     480
ggcatcaagg tgaacttcaa gatccgccac aacatcgagg acggcagcgt gcagctcgcc     540
gaccactacc agcagaacac ccccatcggc gacggccccg tgctgctgcc cgacaaccac     600
tacctgagct accagtccgc cctgagcaaa gaccccaacg agaagcgcga tcacatggtc     660
ctgctggagt tcgtgaccgc cgccgggatc actctcggca tggacgagct gtacaag       717

<210> SEQ ID NO 24
<211> LENGTH: 717
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 24
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagtt catctgcacc accggcaagc tgcccgtgcc ctggcccacc     180
ctcgtgacca ccttcgacct gggcgtgcag tgcttcagcc gctaccccga ccacatgaag     240
cagcacgact tcttcaagtc cgccatgccc gaaggctacg tccaggagcg caccatcttc     300
```

| | |
|---|---|
| ttcaaggacg acggcaacta caagacccgc gccgaggtga agttcgaggg cgacaccctg | 360 |
| gtgaaccgca tcgagctgaa gggcatcgac ttcaaggagg acggcaacat cctgggcac | 420 |
| aagctggagt acaactacat cagccacaac gtctatatca ccgccgacaa gcagaagaac | 480 |
| ggcatcaagg ccaacttcaa gatccgccac aacatcgagg acggcagcgt gcagctcgcc | 540 |
| gaccactacc agcagaacac ccccatcggc gacggccccg tgctgctgcc cgacaaccac | 600 |
| tacctgagca cccagtccgc cctgagcaaa gaccccaacg agaagcgcga tcacatggtc | 660 |
| ctgctggagt tcgtgaccgc cgccgggatc actctcggca tggacgagct gtacaag | 717 |

<210> SEQ ID NO 25
<211> LENGTH: 2982
<212> TYPE: DNA
<213> ORGANISM: Mus musculus

<400> SEQUENCE: 25

| | |
|---|---|
| atggtcgctg cgcacgctgc acactctcag tcctcggccg agtggatcgc ctgcctggat | 60 |
| aaaaggccgt tggagcgatc tagtgaagat gtggacataa ttttcacgcg gctgaaagga | 120 |
| gttaaagctt ttgagaaatt tcacccaaac ctccttcgtc agatttgttt atgcggttac | 180 |
| tatgagaacc tggaaaaagg aatcacactg ttttcgccaag gggatattgg aaccaactgg | 240 |
| tatgctgtcc tggctgggtc tttggatgtt aaagtgtctg agaccagcag tcaccaggat | 300 |
| gcggtgacca tctgcactct gggaattggg acagcctttg gagagtccat tctggataac | 360 |
| acccctcgcc atgcaaccat cgttaccagg gagagcagcg aacttctccg cattgagcag | 420 |
| gaggacttca aggcactatg ggagaaatac cgacagtata tggccggact tctggctcct | 480 |
| ccctatggtg ttatggaaac gggctctaac aatgacagga ttcctgacaa ggagaatgtc | 540 |
| ccttcagaga agatcctcag agctggaaaa attttacgaa ttgccattct ctctcgagct | 600 |
| ccccacatga aagagacag aaagtaccac ctaaagacat acagacaatg ctgtgttggg | 660 |
| actgagctgg tagactggat gatacagcag acatcctgtg ttcactcgcg gactcaagct | 720 |
| gttggcatgt ggcaagtctt gctggaagat ggtgtcctca accatgtgga ccaggagcgc | 780 |
| catttccaag acaaatattt attttatcga tttctggatg acgagcgtga ggatgcccct | 840 |
| ttgcctactg aggaagagaa gaggagtgt gatgaagaac ttcaggacac catgctgctg | 900 |
| ctctcacaga tgggccctga cgcccacatg agaatgatcc tgcgaaaacc acctggccag | 960 |
| aggactgtgg atgacctaga gattatctac gacgagctcc ttcatattaa agccttatcc | 1020 |
| catctctcta ccacagtgaa acgggagtta gcaggtgttc tcattttttga gtctcacgcc | 1080 |
| aaaggaggaa ctgtgttgtt taaccagggg gaagaaggta cctcctggta catcattctg | 1140 |
| aaaggatccg tgaatgtagt catttatggc aagggtgtgg tctgcaccct gcacgaagga | 1200 |
| gatgactttg gcaagttagc tctagtgaac gatgctccaa gagctgcctc cattgttctt | 1260 |
| cgggaagata ttgtcacttt cctaagagtc gacaaggaag acttcaatcg gattctgagg | 1320 |
| gacgttgagg cgaatacagt cagacttaaa gaacatgacc aagatgtctt ggtactggag | 1380 |
| aaggtcccag cagggaacag agctgctaat caaggaaact cacagcctca gcaaaagtat | 1440 |
| actgtgatgt caggaacacc tgaaaagatt ttagagcatt ttctagaaac aatacgcctt | 1500 |
| gagccatcgt tgaatgaagc aacagattcg gtttttaaatg actttgttat gatgcactgt | 1560 |
| gttttttatgc caaatacccca gctttgccct gcccttgtgg cccattacca cgcacagcct | 1620 |
| tctcaaggta ccgagcagga gagaatggat tatgccctca acaacaagag gcgggtcatc | 1680 |
| cgcttggtcc tgcagtgggc ggccatgtat ggcgatctcc tccaagaaga tgatgtggcc | 1740 |

```
atggccttcc tggaggagtt ctatgtgtct gtatcagatg acgcacggat gatggctgcc    1800
ttcaaggagc agctgccaga gctggagaag attgtcaagc aaatctcaga agacgcaaaa    1860
gctccacaga agaagcacaa ggtgcttttg caacagttca acacaggtga cgagagggcc    1920
cagaagcgtc agcctattcg tggctctgat gaggttttgt tcaaggtcta ctgcatcgac    1980
cacacctata ctaccattcg tgtgccggta gctgcctcgg tgaaggaagt catcagtgca    2040
gtagctgaca aactgggctc aggggaaggc ctgatcatcg tcaagatgaa ctctggagga    2100
gaaaaggtgg tgctgaaatc taatgatgtt tcagtattta cgacgctcac cattaatgga    2160
cgcctgtttg cctgcccgag agagcaattc gactcactga ctcccttgcc ggaacaggaa    2220
ggcccgacca ctgggacagt gggaacattt gagctgatga gctcgaaaga cctggcgtac    2280
cagatgacaa cctacgattg gaactcttc aactgtgtgc atgagctgga gctaatctac    2340
cacacatttg aaggcataa ttttaaaaag accacggcaa acttggattt gttcctgagg    2400
aggtttaatg aaattcagtt ttgggttgtc actgaggtct gcctttgttc ccagctcagc    2460
aaacgtgttc agcttttgaa aaaatttatc aagatagcgg ctcactgcaa ggagtacaaa    2520
aatctaaatt ccttttttcgc catcgtcatg ggactcagca acgtggccgt gagccgcttg    2580
gcactaacgt gggagaaact gccgagcaag tttaagaagt ctatgcgga gtttgagagc    2640 ttgatggatc cttccagaaa ccacagggca tacaggctga cagcagccaa gctggagccc    2700
cctctcatcc ctttcatgcc cttgcttatt aaagatatga catttactca tgagggaac    2760 aagacgttca ttgacaatct agtaaacttt gaaaaaatgc gcatgattgc aaacactgcc    2820
agaacagtac ggtactacag gagccagccc ttcaatccgg atgccgctca gctaataag    2880 aaccatcagg atgtccggag ttatgtacgg caattaaatg tgattgacaa ccagagaact    2940
ttatcacaga tgtcacacag attagagcct cgaaggccat ag                       2982
```

<210> SEQ ID NO 26  
<211> LENGTH: 246  
<212> TYPE: DNA  
<213> ORGANISM: Homo sapiens

<400> SEQUENCE: 26

```
ctgctctttg aaccacacag caaggcaggg accgtgttgt tcagccaggg ggacaagggc     60
acttcgtggt acattatctg gaagggatct gtcaacgtgg tgacccatgg caaggggctg    120
gtgaccaccc tgcatgaggg agatgatttt ggacagctgg ctctggtgaa tgatgcaccc    180
cgggcagcca ccatcatcct gcgagaagac aactgtcatt tcctgcgtgt ggacaagcag    240
gacttc                                                                246
```

<210> SEQ ID NO 27  
<211> LENGTH: 82  
<212> TYPE: PRT  
<213> ORGANISM: Homo sapiens

<400> SEQUENCE: 27

```
Leu Leu Phe Glu Pro His Ser Lys Ala Gly Thr Val Leu Phe Ser Gln
  1               5                  10                  15

Gly Asp Lys Gly Thr Ser Trp Tyr Ile Ile Trp Lys Gly Ser Val Asn
             20                  25                  30

Val Val Thr His Gly Lys Gly Leu Val Thr Thr Leu His Glu Gly Asp
         35                  40                  45

Asp Phe Gly Gln Leu Ala Leu Val Asn Asp Ala Pro Arg Ala Ala Thr
```

```
                     50                  55                  60
Ile Ile Leu Arg Glu Asp Asn Cys His Phe Leu Arg Val Asp Lys Gln
                 65                  70                  75                  80

Asp Phe

<210> SEQ ID NO 28
<211> LENGTH: 233
<212> TYPE: DNA
<213> ORGANISM: Mus musculus

<400> SEQUENCE: 28
ctcacgccaa aggaggaact gtgttgttta accaggggga agaaggtacc tcctggtaca     60
tcattctgaa aggatccgtg aatgtagtca tttatggcaa gggtgtggtc tgcaccctgc    120
acgaaggaga tgactttggc aagttagctc tagtgaacga tgctccaaga gctgcctcca    180
ttgttcttcg ggaagataat tgtcacttcc taagagtcga caaggaagac ttc           233

<210> SEQ ID NO 29
<211> LENGTH: 82
<212> TYPE: PRT
<213> ORGANISM: Mus musculus

<400> SEQUENCE: 29

Leu Ile Phe Glu Ser His Ala Lys Gly Gly Thr Val Leu Phe Asn Gln
 1                5                  10                  15

Gly Glu Glu Gly Thr Ser Trp Tyr Ile Ile Leu Lys Gly Ser Val Asn
                 20                  25                  30

Val Val Ile Tyr Gly Lys Gly Val Cys Thr Leu His Glu Gly Asp
             35                  40                  45

Asp Phe Gly Lys Leu Ala Leu Val Asn Asp Ala Pro Arg Ala Ala Ser
     50                  55                  60

Ile Val Leu Arg Glu Asp Asn Cys His Phe Leu Arg Val Asp Lys Glu
 65                  70                  75                  80

Asp Phe

<210> SEQ ID NO 30
<211> LENGTH: 270
<212> TYPE: DNA
<213> ORGANISM: Mus musculus

<400> SEQUENCE: 30
attggcacca aagtttacaa cgatggagaa cagatcattg ctcagggaga ctcggcggat     60
tcgttcttca ttgtagaatc tggagaagtg agaattacta tgaagagaaa gggtaaatca    120
gacatcgaag agaacggtgc tgtggaaatc gctcggtgtc tccggggaca gtattttgga    180
gagcttgccc tggtcactaa caagccaaga gcagcatctg cacacgccat tgggactgtc    240
aaatgcttag ccatggatgt gcaagcattt                                      270

<210> SEQ ID NO 31
<211> LENGTH: 90
<212> TYPE: PRT
<213> ORGANISM: Mus musculus

<400> SEQUENCE: 31

Ile Gly Thr Lys Val Tyr Asn Asp Gly Glu Gln Ile Ile Ala Gln Gly
 1                5                  10                  15

Asp Ser Ala Asp Ser Phe Phe Ile Val Glu Ser Gly Glu Val Arg Ile
             20                  25                  30
```

```
Thr Met Lys Arg Lys Gly Lys Ser Asp Ile Glu Glu Asn Gly Ala Val
            35                  40                  45

Glu Ile Ala Arg Cys Leu Arg Gly Gln Tyr Phe Gly Glu Leu Ala Leu
 50                  55                  60

Val Thr Asn Lys Pro Arg Ala Ala Ser Ala His Ala Ile Gly Thr Val
 65                  70                  75                  80

Lys Cys Leu Ala Met Asp Val Gln Ala Phe
                85                  90

<210> SEQ ID NO 32
<211> LENGTH: 312
<212> TYPE: DNA
<213> ORGANISM: Mus musculus

<400> SEQUENCE: 32
ctcaaatttg aggtcttcca gcctggagat tacatcatcc gagagggac catcgggaag    60 aagatgtact tcatccagca tggggtggtg agcgtgctca ccaagggcaa caaggagatg   120
aagctgtcgg atggctccta tttcggggag atctgcttgc tcacgagggg ccggcgtacg   180
gccagcgtgc gagctgacac ctactgtcgc ctctactcac tgagtgtgga caatttcaac   240
gaggtgctgg aggaataccc catgatgcgg cgtgcctttg agactgtggc tattgaccgg   300
ctagatcgca ta                                                      312

<210> SEQ ID NO 33
<211> LENGTH: 104
<212> TYPE: PRT
<213> ORGANISM: Mus musculus

<400> SEQUENCE: 33

Leu Lys Phe Glu Val Phe Gln Pro Gly Asp Tyr Ile Ile Arg Glu Gly
 1               5                  10                  15

Thr Ile Gly Lys Lys Met Tyr Phe Ile Gln His Gly Val Val Ser Val
             20                  25                  30

Leu Thr Lys Gly Asn Lys Glu Met Lys Leu Ser Asp Gly Ser Tyr Phe
         35                  40                  45

Gly Glu Ile Cys Leu Leu Thr Arg Gly Arg Arg Thr Ala Ser Val Arg
     50                  55                  60

Ala Asp Thr Tyr Cys Arg Leu Tyr Ser Leu Ser Val Asp Asn Phe Asn
 65                  70                  75                  80

Glu Val Leu Glu Glu Tyr Pro Met Met Arg Arg Ala Phe Glu Thr Val
                85                  90                  95

Ala Ile Asp Arg Leu Asp Arg Ile
            100

<210> SEQ ID NO 34
<211> LENGTH: 160
<212> TYPE: PRT
<213> ORGANISM: Homo sapiens

<400> SEQUENCE: 34

Glu Glu Leu Ala Glu Ala Val Ala Leu Leu Ser Gln Arg Gly Pro Asp
 1               5                  10                  15

Ala Leu Leu Thr Val Ala Leu Arg Lys Pro Pro Gly Gln Arg Thr Asp
             20                  25                  30

Glu Glu Leu Asp Leu Ile Phe Glu Glu Leu Leu His Ile Lys Ala Val
         35                  40                  45
```

```
Ala His Leu Ser Asn Ser Val Lys Arg Glu Leu Ala Val Leu Leu
 50                  55                  60

Phe Glu Pro His Ser Lys Ala Gly Thr Val Leu Phe Ser Gln Gly Asp
 65                  70                  75                  80

Lys Gly Thr Ser Trp Tyr Ile Ile Trp Lys Gly Ser Val Asn Val Val
                 85                  90                  95

Thr His Gly Lys Gly Leu Val Thr Thr Leu His Glu Gly Asp Asp Phe
                100                 105                 110

Gly Gln Leu Ala Leu Val Asn Asp Ala Pro Arg Ala Ala Thr Ile Ile
            115                 120                 125

Leu Arg Glu Asp Asn Cys His Phe Leu Arg Val Asp Lys Gln Asp Phe
130                 135                 140

Asn Arg Ile Ile Lys Asp Val Glu Ala Lys Thr Met Arg Leu Glu Glu
145                 150                 155                 160
```

<210> SEQ ID NO 35
<211> LENGTH: 159
<212> TYPE: PRT
<213> ORGANISM: Mus musculus

<400> SEQUENCE: 35

```
Glu Glu Lys Lys Glu Cys Asp Glu Glu Leu Gln Asp Thr Met Leu Leu
  1               5                  10                  15

Leu Ser Gln Met Gly Pro Asp Ala His Met Arg Met Ile Leu Arg Lys
                 20                  25                  30

Pro Pro Gly Gln Arg Thr Val Asp Asp Leu Glu Ile Ile Tyr Asp Glu
             35                  40                  45

Leu Leu His Ile Lys Ala Leu Ser His Leu Ser Thr Thr Val Lys Arg
         50                  55                  60

Glu Leu Ala Gly Val Leu Ile Phe Glu Ser His Ala Lys Gly Gly Thr
 65                  70                  75                  80

Val Leu Phe Asn Gln Gly Glu Glu Gly Thr Ser Trp Tyr Ile Ile Leu
                 85                  90                  95

Lys Gly Ser Val Asn Val Val Ile Tyr Gly Lys Gly Val Val Cys Thr
                100                 105                 110

Leu His Glu Gly Asp Asp Phe Gly Lys Leu Ala Leu Val Asn Asp Ala
            115                 120                 125

Pro Arg Ala Ala Ser Ile Val Leu Arg Glu Asp Asn Cys His Phe Leu
130                 135                 140

Arg Val Asp Lys Glu Asp Phe Asn Arg Ile Leu Arg Asp Val Glu
145                 150                 155
```

<210> SEQ ID NO 36
<211> LENGTH: 140
<212> TYPE: PRT
<213> ORGANISM: Mus musculus

<400> SEQUENCE: 36

```
Met Tyr Glu Ser Phe Ile Glu Ser Leu Pro Phe Leu Lys Ser Leu Glu
  1               5                  10                  15

Val Ser Glu Arg Leu Lys Val Val Asp Val Ile Gly Thr Lys Val Tyr
                 20                  25                  30

Asn Asp Gly Glu Gln Ile Ile Ala Gln Gly Asp Ser Ala Asp Ser Phe
             35                  40                  45

Phe Ile Val Glu Ser Gly Glu Val Arg Ile Thr Met Lys Arg Lys Gly
         50                  55                  60
```

```
Lys Ser Asp Ile Glu Glu Asn Gly Ala Val Glu Ile Ala Arg Cys Leu
 65                  70                  75                  80

Arg Gly Gln Tyr Phe Gly Glu Leu Ala Leu Val Thr Asn Lys Pro Arg
                 85                  90                  95

Ala Ala Ser Ala His Ala Ile Gly Thr Val Lys Cys Leu Ala Met Asp
            100                 105                 110

Val Gln Ala Phe Glu Arg Leu Leu Gly Pro Cys Met Glu Ile Met Lys
        115                 120                 125

Arg Asn Ile Ala Thr Tyr Glu Glu Gln Leu Val Ala
    130                 135                 140

<210> SEQ ID NO 37
<211> LENGTH: 172
<212> TYPE: PRT
<213> ORGANISM: Mus musculus

<400> SEQUENCE: 37

Ala Asp Phe Arg Gln Lys Ile His Asp Tyr Tyr Glu His Arg Tyr Gln
  1               5                  10                  15

Gly Lys Met Phe Asp Glu Asp Ser Ile Leu Gly Glu Leu Asn Gly Pro
             20                  25                  30

Leu Arg Glu Glu Ile Val Asn Phe Asn Cys Arg Lys Leu Val Ala Ser
         35                  40                  45

Met Pro Leu Phe Ala Asn Ala Asp Pro Asn Phe Val Thr Ala Met Leu
     50                  55                  60

Thr Lys Leu Lys Phe Glu Val Phe Gln Pro Gly Asp Tyr Ile Ile Arg
 65                  70                  75                  80

Glu Gly Thr Ile Gly Lys Lys Met Tyr Phe Ile Gln His Gly Val Val
                 85                  90                  95

Ser Val Leu Thr Lys Gly Asn Lys Glu Met Lys Leu Ser Asp Gly Ser
            100                 105                 110

Tyr Phe Gly Glu Ile Cys Leu Leu Thr Arg Gly Arg Arg Thr Ala Ser
        115                 120                 125

Val Arg Ala Asp Thr Tyr Cys Arg Leu Tyr Ser Leu Ser Val Asp Asn
    130                 135                 140

Phe Asn Glu Val Leu Glu Glu Tyr Pro Met Met Arg Arg Ala Phe Glu
145                 150                 155                 160

Thr Val Ala Ile Asp Arg Leu Asp Arg Ile Gly Lys
            165                 170

<210> SEQ ID NO 38
<211> LENGTH: 1929
<212> TYPE: DNA
<213> ORGANISM: Artificial Sequence
<220> FEATURE:
<223> OTHER INFORMATION: Description of Artificial Sequence: Synthetic
      fusion construct

<400> SEQUENCE: 38
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagtt catctgcacc accggcaagc tgcccgtgcc ctggcccacc     180
ctcgtgacca ccttcggcta cggcctgcag tgcttcgccc gctaccccga ccacatgaag     240
cagcacgact tcttcaagtc cgccatgccc gaaggctacg tccaggagcg caccatcttc     300
ttcaaggacg acggcaacta caagacccgc gccgaggtga agttcgaggg cgacaccctg     360
```

-continued

```
gtgaaccgca tcgagctgaa gggcatcgac ttcaaggagg acggcaacat cctggggcac      420
aagctggagt acaactacaa cagccacaac gtctatatca tggccgacaa gcagaagaac      480
ggcatcaagg tgaacttcaa gatccgccac aacatcgagg acggcagcgt gcagctcgcc      540
gaccactacc agcagaacac ccccatcggc gacggccccg tgctgctgcc cgacaaccac      600
tacctgagct accagtccgc cctgagcaaa gaccccaacg agaagcgcga tcacatggtc      660
ctgctggagt tcgtgaccgc cgccgggatc actctcggca tggacgagct gtacaaggaa      720
ttcgaggagt tggccgaagc tgtggccctg ctctcccagc gggggcctga cgccctgctc      780
actgtggcac ttcgaaagcc cccaggtcag cgcacggatg aagagctgga cctcatcttt      840
gaggagctgc tgcacatcaa ggctgtggcc cacctctcca actcggtgaa gcgagaatta      900
gcggctgttc tgctctttga accacacagc aaggcaggga ccgtgttgtt cagccagggg      960
gacaagggca cttcgtggta cattatctgg aagggatctg tcaacgtggt gacccatggc     1020
aaggggctgg tgaccaccct gcatgaggga atgattttg acagctggc tctggtgaat       1080 gatgcacccc gggcagccac catcatcctg cgagaagaca actgtcattt cctgcgtgtg     1140
gacaagcagg acttcaaccg tatcatcaag gatgtggagg caaagaccat gcggctggaa     1200
gaatctagaa tggtgagcaa gggcgaggag ctgttcaccg gggtggtgcc catcctggtc     1260
gagctggacg gcgacgtaaa cggccacaag ttcagcgtgt ccggcgaggg cgagggcgat     1320
gccacctacg gcaagctgac cctgaagttc atctgcacca ccggcaagct gcccgtgccc     1380
tggcccaccc tcgtgaccac cctgacctgg ggcgtgcagt gcttcagccg ctaccccgac     1440
cacatgaagc agcacgactt cttcaagtcc gccatgcccg aaggctacgt ccaggagcgc     1500
accatcttct tcaaggacga cggcaactac aagacccgcg ccgaggtgaa gttcgagggc     1560
gacaccctgg tgaaccgcat cgagctgaag ggcatcgact tcaaggagga cggcaacatc     1620
ctggggcaca agctggagta caactacatc agccacaacg tctatatcac cgccgacaag     1680
cagaagaacg gcatcaaggc caacttcaag atccgccaca acatcgagga cggcagcgtg     1740
cagctcgccg accactacca gcagaacacc cccatcggcg acggccccgt gctgctgccc     1800
gacaaccact acctgagcac ccagtccgcc ctgagcaaag accccaacga gaagcgcgat     1860
cacatggtcc tgctggagtt cgtgaccgcc gccgggatca ctctcggcat ggacgagctg     1920
tacaagtaa                                                             1929
```

<210> SEQ ID NO 39
<211> LENGTH: 645
<212> TYPE: PRT
<213> ORGANISM: Artificial Sequence
<220> FEATURE:
<223> OTHER INFORMATION: Description of Artificial Sequence: Synthetic
      fusion construct

<400> SEQUENCE: 39

```
Met Val Ser Lys Gly Glu Glu Leu Phe Thr Gly Val Val Pro Ile Leu
  1               5                  10                  15

Val Glu Leu Asp Gly Asp Val Asn Gly His Lys Phe Ser Val Ser Gly
                 20                  25                  30

Glu Gly Glu Gly Asp Ala Thr Tyr Gly Lys Leu Thr Leu Lys Phe Ile
             35                  40                  45

Cys Thr Thr Gly Lys Leu Pro Val Pro Trp Pro Thr Leu Val Thr Thr
         50                  55                  60

Phe Gly Tyr Gly Leu Gln Cys Phe Ala Arg Tyr Pro Asp His Met Lys
 65                  70                  75                  80
```

-continued

```
Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys Glu
225                 230                 235                 240

Phe Glu Glu Leu Ala Glu Ala Val Ala Leu Leu Ser Gln Arg Gly Pro
                245                 250                 255

Asp Ala Leu Leu Thr Val Ala Leu Arg Lys Pro Pro Gly Gln Arg Thr
            260                 265                 270

Asp Glu Glu Leu Asp Leu Ile Phe Glu Glu Leu His Ile Lys Ala
    275                 280                 285

Val Ala His Leu Ser Asn Ser Val Lys Arg Glu Leu Ala Ala Val Leu
290                 295                 300

Leu Phe Glu Pro His Ser Lys Ala Gly Thr Val Leu Phe Ser Gln Gly
305                 310                 315                 320

Asp Lys Gly Thr Ser Trp Tyr Ile Ile Trp Lys Gly Ser Val Asn Val
                325                 330                 335

Val Thr His Gly Lys Gly Leu Val Thr Thr Leu His Glu Gly Asp Asp
            340                 345                 350

Phe Gly Gln Leu Ala Leu Val Asn Asp Ala Pro Arg Ala Ala Thr Ile
        355                 360                 365

Ile Leu Arg Glu Asp Asn Cys His Phe Leu Arg Val Asp Lys Gln Asp
    370                 375                 380

Phe Asn Arg Ile Ile Lys Asp Val Glu Ala Lys Thr Met Arg Leu Glu
385                 390                 395                 400

Glu His Gly Lys Val Ser Arg Val Ser Lys Gly Glu Glu Leu Phe Thr
                405                 410                 415

Gly Val Val Pro Ile Leu Val Glu Leu Asp Gly Asp Val Asn Gly His
            420                 425                 430

Arg Phe Ser Val Ser Gly Glu Gly Glu Gly Asp Ala Thr Tyr Gly Lys
        435                 440                 445

Leu Thr Leu Lys Phe Ile Cys Thr Thr Gly Lys Leu Pro Val Pro Trp
    450                 455                 460

Pro Thr Leu Val Thr Thr Leu Thr Trp Gly Val Gln Cys Phe Ser Arg
465                 470                 475                 480

Tyr Pro Asp His Met Lys Gln His Asp Phe Phe Lys Ser Ala Met Pro
                485                 490                 495
```

```
Glu Gly Tyr Val Gln Glu Arg Thr Ile Phe Phe Lys Asp Asp Gly Asn
                500                 505                 510
Tyr Lys Thr Arg Ala Glu Val Lys Phe Glu Gly Asp Thr Leu Val Asn
            515                 520                 525
Arg Ile Glu Leu Lys Gly Ile Asp Phe Lys Glu Asp Gly Asn Ile Leu
        530                 535                 540
Gly His Lys Leu Glu Tyr Asn Tyr Ile Ser His Asn Val Tyr Ile Thr
545                 550                 555                 560
Ala Asp Lys Gln Lys Asn Gly Ile Lys Ala His Phe Lys Ile Arg His
                565                 570                 575
Asn Ile Glu Asp Gly Ser Val Gln Leu Ala Asp His Tyr Gln Gln Asn
            580                 585                 590
Thr Pro Ile Gly Asp Gly Pro Val Leu Leu Pro Asp Asn His Tyr Leu
        595                 600                 605
Ser Thr Gln Ser Ala Leu Ser Lys Asp Pro Asn Glu Lys Arg Asp His
        610                 615                 620
Met Val Leu Leu Glu Phe Val Thr Ala Ala Gly Ile Thr Leu Gly Met
625                 630                 635                 640
Asp Glu Leu Tyr Lys
                645

<210> SEQ ID NO 40
<211> LENGTH: 1926
<212> TYPE: DNA
<213> ORGANISM: Artificial Sequence
<220> FEATURE:
<223> OTHER INFORMATION: Description of Artificial Sequence: Synthetic
      fusion construct

<400> SEQUENCE: 40
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagtt catctgcacc accggcaagc tgcccgtgcc ctggcccacc     180
ctcgtgacca ccttcggcta cggcctgcag tgcttcgccc gctacccega ccacatgaag     240 cagcacgact tcttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggagg acggcaacat cctggggcac     420
aagctggagt acaactacaa cagccacaac gtctatatca tggccgacaa gcagaagaac     480
ggcatcaagg tgaacttcaa gatccgccac aacatcgagg acggcagcgt gcagctcgcc     540
gaccactacc agcagaacac ccccatcggc gacggccccg tgctgctgcc cgacaaccac     600
tacctgagct accagtccgc cctgagcaaa gaccccaacg agaagcgcga tcacatggtc     660
ctgctggagt tcgtgaccgc cgccgggatc actctcggca tggacgagct gtacaaggaa     720
ttcgaagaga gaaggagtg tgatgaagaa cttcaggaca ccatgctgct gctctcacag     780
atgggccctg acgcccacat gagaatgatc ctgcgaaaac acctggcca gaggactgtg     840 gatgacctag agattatcta cgacgagctc cttcatatta agccttatc ccatctctct     900 accacagtga acgggagtt agcaggtgtt ctcattttg agtctcacgc aaaggagga     960 actgtgttgt taaccaggg ggaagaaggt acctcctggt acatcattct gaaaggatcc    1020
gtgaatgtag tcatttatgg caagggtgtg gtctgcaccc tgcacgaagg agatgacttt    1080
ggcaagttag ctctagtgaa cgatgctcca agagctgcct ccattgttct tcgggaagat    1140
```

```
aattgtcact tcctaagagt cgacaaggaa gacttcaatc ggattctgag ggacgttgag    1200
tctagaatgg tgagcaaggg cgaggagctg ttcaccgggg tggtgcccat cctggtcgag    1260
ctggacggcg acgtaaacgg ccacaagttc agcgtgtccg gcgagggcga gggcgatgcc    1320
acctacggca agctgaccct gaagttcatc tgcaccaccg gcaagctgcc cgtgccctgg    1380
cccaccctcg tgaccaccct gacctggggc gtgcagtgct tcagccgcta ccccgaccac    1440
atgaagcagc acgacttctt caagtccgcc atgcccgaag ctacgtcca ggagcgcacc     1500 atcttcttca aggacgacgg caactacaag acccgcgccg aggtgaagtt cgagggcgac    1560
accctggtga accgcatcga gctgaagggc atcgacttca aggaggacgg caacatcctg    1620
gggcacaagc tggagtacaa ctacatcagc cacaacgtct atatcaccgc cgacaagcag    1680
aagaacggca tcaaggccaa cttcaagatc cgccacaaca tcgaggacgg cagcgtgcag    1740
ctcgccgacc actaccagca gaacaccccc atcggcgacg gccccgtgct gctgcccgac    1800
aaccactacc tgagcaccca gtccgccctg agcaaagacc ccaacgagaa gcgcgatcac    1860
atggtcctgc tggagttcgt gaccgccgcc gggatcactc tcggcatgga cgagctgtac    1920
aagtaa                                                                1926
```

<210> SEQ ID NO 41
<211> LENGTH: 640
<212> TYPE: PRT
<213> ORGANISM: Artificial Sequence
<220> FEATURE:
<223> OTHER INFORMATION: Description of Artificial Sequence: Synthetic fusion construct

<400> SEQUENCE: 41

```
Met Val Ser Lys Gly Glu Glu Leu Phe Thr Gly Val Val Pro Ile Leu
 1               5                  10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Phe Gly Tyr Gly Leu Gln Cys Phe Ala Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Ala Leu
        195                 200                 205

Ser Lys Asp Pro Asn Glu Lys Arg Asp His Met Val Leu Leu Glu Phe
```

```
            210                 215                 220
Val Thr Ala Ala Gly Ile Thr Leu Gly Met Asp Glu Leu Tyr Lys Glu
225                 230                 235                 240

Phe Glu Glu Lys Lys Glu Cys Asp Glu Glu Leu Gln Asp Thr Met Leu
                245                 250                 255

Leu Leu Ser Gln Met Gly Pro Asp Ala His Met Arg Met Ile Leu Arg
            260                 265                 270

Lys Pro Pro Gly Gln Arg Thr Val Asp Asp Leu Glu Ile Ile Tyr Asp
                275                 280                 285

Glu Leu Leu His Ile Lys Ala Leu Ser His Leu Ser Thr Thr Val Lys
            290                 295                 300

Arg Glu Leu Ala Gly Val Leu Ile Phe Glu Ser His Ala Lys Gly Gly
305                 310                 315                 320

Thr Val Leu Phe Asn Gln Gly Glu Glu Gly Thr Ser Trp Tyr Ile Ile
                325                 330                 335

Leu Lys Gly Ser Val Asn Val Val Ile Tyr Gly Lys Gly Val Val Cys
            340                 345                 350

Thr Leu His Glu Gly Asp Asp Phe Gly Lys Leu Ala Leu Val Asn Asp
            355                 360                 365

Ala Pro Arg Ala Ala Ser Ile Val Leu Arg Glu Asp Asn Cys His Phe
            370                 375                 380

Leu Arg Val Asp Lys Glu Asp Phe Asn Arg Ile Leu Arg Asp Val Glu
385                 390                 395                 400

Ser Arg Val Ser Lys Gly Glu Glu Leu Phe Thr Gly Val Val Pro Ile
                405                 410                 415

Leu Val Glu Leu Asp Gly Asp Val Asn Gly His Arg Phe Ser Val Ser
            420                 425                 430

Gly Glu Gly Glu Gly Asp Ala Thr Tyr Gly Lys Leu Thr Leu Lys Phe
            435                 440                 445

Ile Cys Thr Thr Gly Lys Leu Pro Val Pro Trp Pro Thr Leu Val Thr
            450                 455                 460

Thr Leu Thr Trp Gly Val Gln Cys Phe Ser Arg Tyr Pro Asp His Met
465                 470                 475                 480

Lys Gln His Asp Phe Phe Lys Ser Ala Met Pro Glu Gly Tyr Val Gln
                485                 490                 495

Glu Arg Thr Ile Phe Phe Lys Asp Asp Gly Asn Tyr Lys Thr Arg Ala
                500                 505                 510

Glu Val Lys Phe Glu Gly Asp Thr Leu Val Asn Arg Ile Glu Leu Lys
            515                 520                 525

Gly Ile Asp Phe Lys Glu Asp Gly Asn Ile Leu Gly His Lys Leu Glu
            530                 535                 540

Tyr Asn Tyr Ile Ser His Asn Val Tyr Ile Thr Ala Asp Lys Gln Lys
545                 550                 555                 560

Asn Gly Ile Lys Ala His Phe Lys Ile Arg His Asn Ile Glu Asp Gly
                565                 570                 575

Ser Val Gln Leu Ala Asp His Tyr Gln Gln Asn Thr Pro Ile Gly Asp
            580                 585                 590

Gly Pro Val Leu Leu Pro Asp Asn His Tyr Leu Ser Thr Gln Ser Ala
            595                 600                 605

Leu Ser Lys Asp Pro Asn Glu Lys Arg Asp His Met Val Leu Leu Glu
            610                 615                 620

Phe Val Thr Ala Ala Gly Ile Thr Leu Gly Met Asp Glu Leu Tyr Lys
625                 630                 635                 640
```

<210> SEQ ID NO 42
<211> LENGTH: 1905
<212> TYPE: DNA
<213> ORGANISM: Artificial Sequence
<220> FEATURE:
<223> OTHER INFORMATION: Description of Artificial Sequence: Synthetic fusion construct

<400> SEQUENCE: 42

| | | | | | |
|---|---|---|---|---|---|
| atggtgagca | agggcgagga | gctgttcacc | ggggtggtgc | ccatcctggt | cgagctggac | 60 |
| ggcgacgtaa | acggccacaa | gttcagcgtg | tccggcgagg | gcgagggcga | tgccacctac | 120 |
| ggcaagctga | ccctgaagtt | catctgcacc | accggcaagc | tgcccgtgcc | ctggcccacc | 180 |
| ctcgtgacca | ccttcggcta | cggcctgcag | tgcttcgccc | gctacccga | ccacatgaag | 240 |
| cagcacgact | tcttcaagtc | cgccatgccc | gaaggctacg | tccaggagcg | caccatcttc | 300 |
| ttcaaggacg | acggcaacta | caagacccgc | gccgaggtga | agttcgaggg | cgacaccctg | 360 |
| gtgaaccgca | tcgagctgaa | gggcatcgac | ttcaaggag | acggcaacat | cctggggcac | 420 |
| aagctggagt | acaactacaa | cagccacaac | gtctatatca | tggccgacaa | gcagaagaac | 480 |
| ggcatcaagg | tgaacttcaa | gatccgccac | aacatcgagg | acggcagcgt | gcagctcgcc | 540 |
| gaccactacc | agcagaacac | ccccatcggc | gacggccccg | tgctgctgcc | cgacaaccac | 600 |
| tacctgagct | accagtccgc | cctgagcaaa | gaccccaacg | agaagcgcga | tcacatggtc | 660 |
| ctgctggagt | tcgtgaccgc | cgccgggatc | actctcggca | tggacgagct | gtacaaggaa | 720 |
| ttcgaagaac | ttcaggacac | catgctgctg | ctctcacaga | tgggccctga | cgcccacatg | 780 |
| agaatgatcc | tgcgaaaacc | acctggccag | aggactgtgg | atgacctaga | gattatctac | 840 |
| gacgagctcc | ttcatattaa | agccttatcc | catctctcta | ccacagtgaa | acgggagtta | 900 |
| gcaggtgttc | tcattttga | gtctcacgcc | aaaggaggaa | ctgtgttgtt | taaccagggg | 960 |
| gaagaaggta | cctcctggta | catcattctg | aaaggatccg | tgaatgtagt | catttatggc | 1020 |
| aagggtgtgg | tctgcaccct | gcacgaagga | gatgactttg | gcaagttagc | tctagtgaac | 1080 |
| gatgctccaa | gagctgcctc | cattgttctt | cgggaagata | attgtcactt | cctaagagtc | 1140 |
| gacaaggaag | acttcaatcg | gattctgagg | gacgttgagt | ctagaatggt | gagcaagggc | 1200 |
| gaggagctgt | tcaccggggt | ggtgcccatc | ctggtcgagc | tggacggcga | cgtaaacggc | 1260 |
| cacaagttca | gcgtgtccgg | cgagggcgag | ggcgatgcca | cctacggcaa | gctgaccctg | 1320 |
| aagttcatct | gcaccaccgg | caagctgccc | gtgccctggc | ccaccctcgt | gaccaccctg | 1380 |
| acctggggcg | tgcagtgctt | cagccgctac | cccgaccaca | tgaagcagca | cgacttcttc | 1440 |
| aagtccgcca | tgcccgaagg | ctacgtccag | gagcgcacca | tcttcttcaa | ggacgacggc | 1500 |
| aactacaaga | cccgcgccga | ggtgaagttc | gagggcgaca | ccctggtgaa | ccgcatcgag | 1560 |
| ctgaagggca | tcgacttcaa | ggaggacggc | aacatcctgg | ggcacaagct | ggagtacaac | 1620 |
| tacatcagcc | acaacgtcta | tatcaccgcc | gacaagcaga | agaacggcat | caaggccaac | 1680 |
| ttcaagatcc | gccacaacat | cgaggacggc | agcgtgcagc | tcgccgacca | ctaccagcag | 1740 |
| aacacccca | tcggcgacgg | ccccgtgctg | ctgcccgaca | accactacct | gagcacccag | 1800 |
| tccgccctga | gcaaagaccc | caacgagaag | cgcgatcaca | tggtcctgct | ggagttcgtg | 1860 |
| accgccgccg | ggatcactct | cggcatggac | gagctgtaca | agtaa | | 1905 |

<210> SEQ ID NO 43
<211> LENGTH: 633

```
<212> TYPE: PRT
<213> ORGANISM: Artificial Sequence
<220> FEATURE:
<223> OTHER INFORMATION: Description of Artificial Sequence: Synthetic
      fusion construct

<400> SEQUENCE: 43
```

Met Val Ser Lys Gly Glu Glu Leu Phe Thr Gly Val Val Pro Ile Leu
 1               5                  10                  15

Val Glu Leu Asp Gly Asp Val Asn Gly His Lys Phe Ser Val Ser Gly
             20                  25                  30

Glu Gly Glu Gly Asp Ala Thr Tyr Gly Lys Leu Thr Leu Lys Phe Ile
         35                  40                  45

Cys Thr Thr Gly Lys Leu Pro Val Pro Trp Pro Thr Leu Val Thr Thr
 50                  55                  60

Phe Gly Tyr Gly Leu Gln Cys Phe Ala Arg Tyr Pro Asp His Met Lys
 65                  70                  75                  80

Gln His Asp Phe Phe Lys Ser Ala Met Pro Glu Gly Tyr Val Gln Glu
                 85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Ala Leu
        195                 200                 205

Ser Lys Asp Pro Asn Glu Lys Arg Asp His Met Val Leu Leu Glu Phe
210                 215                 220

Val Thr Ala Ala Gly Ile Thr Leu Gly Met Asp Glu Leu Tyr Lys Glu
225                 230                 235                 240

Phe Glu Glu Leu Gln Asp Thr Met Leu Leu Ser Gln Met Gly Pro
                245                 250                 255

Asp Ala His Met Arg Met Ile Leu Arg Lys Pro Pro Gly Gln Arg Thr
            260                 265                 270

Val Asp Asp Leu Glu Ile Ile Tyr Asp Glu Leu Leu His Ile Lys Ala
        275                 280                 285

Leu Ser His Leu Ser Thr Thr Val Lys Arg Glu Leu Ala Gly Val Leu
        290                 295                 300

Ile Phe Glu Ser His Ala Lys Gly Gly Thr Val Leu Phe Asn Gln Gly
305                 310                 315                 320

Glu Glu Gly Thr Ser Trp Tyr Ile Ile Leu Lys Gly Ser Val Asn Val
                325                 330                 335

Val Ile Tyr Gly Lys Gly Val Val Cys Thr Leu His Glu Gly Asp Asp
            340                 345                 350

Phe Gly Lys Leu Ala Leu Val Asn Asp Ala Pro Arg Ala Ala Ser Ile
        355                 360                 365

Val Leu Arg Glu Asp Asn Cys His Phe Leu Arg Val Asp Lys Glu Asp
370                 375                 380

```
Phe Asn Arg Ile Leu Arg Asp Val Glu Ser Arg Val Ser Lys Gly Glu
385                 390                 395                 400

Glu Leu Phe Thr Gly Val Val Pro Ile Leu Val Glu Leu Asp Gly Asp
            405                 410                 415

Val Asn Gly His Arg Phe Ser Val Ser Gly Glu Gly Glu Gly Asp Ala
        420                 425                 430

Thr Tyr Gly Lys Leu Thr Leu Lys Phe Ile Cys Thr Thr Gly Lys Leu
    435                 440                 445

Pro Val Pro Trp Pro Thr Leu Val Thr Thr Leu Thr Trp Gly Val Gln
450                 455                 460

Cys Phe Ser Arg Tyr Pro Asp His Met Lys Gln His Asp Phe Phe Lys
465                 470                 475                 480

Ser Ala Met Pro Glu Gly Tyr Val Gln Glu Arg Thr Ile Phe Phe Lys
            485                 490                 495

Asp Asp Gly Asn Tyr Lys Thr Arg Ala Glu Val Lys Phe Glu Gly Asp
        500                 505                 510

Thr Leu Val Asn Arg Ile Glu Leu Lys Gly Ile Asp Phe Lys Glu Asp
    515                 520                 525

Gly Asn Ile Leu Gly His Lys Leu Glu Tyr Asn Tyr Ile Ser His Asn
530                 535                 540

Val Tyr Ile Thr Ala Asp Lys Gln Lys Asn Gly Ile Lys Ala His Phe
545                 550                 555                 560

Lys Ile Arg His Asn Ile Glu Asp Gly Ser Val Gln Leu Ala Asp His
            565                 570                 575

Tyr Gln Gln Asn Thr Pro Ile Gly Asp Gly Pro Val Leu Leu Pro Asp
        580                 585                 590

Asn His Tyr Leu Ser Thr Gln Ser Ala Leu Ser Lys Asp Pro Asn Glu
    595                 600                 605

Lys Arg Asp His Met Val Leu Leu Glu Phe Val Thr Ala Ala Gly Ile
    610                 615                 620

Thr Leu Gly Met Asp Glu Leu Tyr Lys
625                 630

<210> SEQ ID NO 44
<211> LENGTH: 1869
<212> TYPE: DNA
<213> ORGANISM: Artificial Sequence
<220> FEATURE:
<223> OTHER INFORMATION: Description of Artificial Sequence: Synthetic
      fusion construct

<400> SEQUENCE: 44
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagtt catctgcacc accggcaagc tgcccgtgcc ctggcccacc     180
ctcgtgacca ccttcggcta cggcctgcag tgcttcgccc gctaccccga ccacatgaag     240
cagcacgact tcttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggagg acggcaacat cctggggcac     420
aagctggagt acaactacaa cagccacaac gtctatatca tggccgacaa gcagaagaac     480
ggcatcaagg tgaacttcaa gatccgccac aacatcgagg acggcagcgt gcagctcgcc     540
gaccactacc agcagaacac ccccatcggc gacggccccg tgctgctgcc cgacaaccac     600
```

```
tacctgagct accagtccgc cctgagcaaa gaccccaacg agaagcgcga tcacatggtc    660
ctgctggagt tcgtgaccgc cgccgggatc actctcggca tggacgagct gtacaaggaa    720
ttcatgggcc ctgacgccca catgagaatg atcctgcgaa aaccacctgg ccagaggact    780
gtggatgacc tagagattat ctacgacgag ctccttcata ttaaagcctt atcccatctc    840
tctaccacag tgaaacggga gttagcaggt gttctcattt ttgagtctca cgccaaagga    900
ggaactgtgt tgtttaacca gggggaagaa ggtacctcct ggtacatcat tctgaaagga    960
tccgtgaatg tagtcattta tggcaagggt gtggtctgca ccctgcacga aggagatgac   1020
tttggcaagt tagctctagt gaacgatgct ccaagagctg cctccattgt tcttcgggaa   1080
gataattgtc acttcctaag agtcgacaag gaagacttca atcggattct gagggacgtt   1140
gagtctagaa tggtgagcaa gggcgaggag ctgttcaccg gggtggtgcc catcctggtc   1200
gagctggacg gcgacgtaaa cggccacaag ttcagcgtgt ccggcgaggg cgagggcgat   1260
gccacctacg gcaagctgac cctgaagttc atctgcacca ccggcaagct gcccgtgccc   1320
tggcccaccc tcgtgaccac cctgacctgg ggcgtgcagt gcttcagccg ctaccccgac   1380
cacatgaagc agcacgactt cttcaagtcc gccatgcccg aaggctacgt ccaggagcgc   1440
accatcttct tcaaggacga cggcaactac aagacccgcg ccgaggtgaa gttcgagggc   1500
gacaccctgg tgaaccgcat cgagctgaag ggcatcgact tcaaggagga cggcaacatc   1560
ctggggcaca agctggagta caactacatc agccacaacg tctatatcac cgccgacaag   1620
cagaagaacg gcatcaaggc caacttcaag atccgccaca acatcgagga cggcagcgtg   1680
cagctcgccg accactacca gcagaacacc cccatcggcg acggccccgt gctgctgccc   1740
gacaaccact acctgagcac ccagtccgcc ctgagcaaag accccaacga gaagcgcgat   1800
cacatggtcc tgctggagtt cgtgaccgcc gccgggatca ctctcggcat ggacgagctg   1860
tacaagtaa                                                            1869
```

<210> SEQ ID NO 45
<211> LENGTH: 621
<212> TYPE: PRT
<213> ORGANISM: Artificial Sequence
<220> FEATURE:
<223> OTHER INFORMATION: Description of Artificial Sequence: Synthetic
      fusion construct

<400> SEQUENCE: 45

Met Val Ser Lys Gly Glu Glu Leu Phe Thr Gly Val Val Pro Ile Leu
  1               5                  10                  15

Val Glu Leu Asp Gly Asp Val Asn Gly His Lys Phe Ser Val Ser Gly
                 20                  25                  30

Glu Gly Glu Gly Asp Ala Thr Tyr Gly Lys Leu Thr Leu Lys Phe Ile
             35                  40                  45

Cys Thr Thr Gly Lys Leu Pro Val Pro Trp Pro Thr Leu Val Thr Thr
         50                  55                  60

Phe Gly Tyr Gly Leu Gln Cys Phe Ala Arg Tyr Pro Asp His Met Lys
     65                  70                  75                  80

Gln His Asp Phe Phe Lys Ser Ala Met Pro Glu Gly Tyr Val Gln Glu
                 85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

```
Ile Asp Phe Lys Glu Asp Gly Asn Ile Leu Gly His Lys Leu Glu Tyr
130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
                180                 185                 190

Pro Val Leu Leu Pro Asp Asn His Tyr Leu Ser Tyr Gln Ser Ala Leu
            195                 200                 205

Ser Lys Asp Pro Asn Glu Lys Arg Asp His Met Val Leu Leu Glu Phe
210                 215                 220

Val Thr Ala Ala Gly Ile Thr Leu Gly Met Asp Glu Leu Tyr Lys Glu
225                 230                 235                 240

Phe Met Gly Pro Asp Ala His Met Arg Met Ile Leu Arg Lys Pro Pro
                245                 250                 255

Gly Gln Arg Thr Val Asp Asp Leu Glu Ile Ile Tyr Asp Glu Leu Leu
                260                 265                 270

His Ile Lys Ala Leu Ser His Leu Ser Thr Thr Val Lys Arg Glu Leu
                275                 280                 285

Ala Gly Val Leu Ile Phe Glu Ser His Ala Lys Gly Gly Thr Val Leu
290                 295                 300

Phe Asn Gln Gly Glu Glu Gly Thr Ser Trp Tyr Ile Ile Leu Lys Gly
305                 310                 315                 320

Ser Val Asn Val Val Ile Tyr Gly Lys Gly Val Val Cys Thr Leu His
                325                 330                 335

Glu Gly Asp Asp Phe Gly Lys Leu Ala Leu Val Asn Asp Ala Pro Arg
                340                 345                 350

Ala Ala Ser Ile Val Leu Arg Glu Asp Asn Cys His Phe Leu Arg Val
            355                 360                 365

Asp Lys Glu Asp Phe Asn Arg Ile Leu Arg Asp Val Glu Ser Arg Val
370                 375                 380

Ser Lys Gly Glu Glu Leu Phe Thr Gly Val Val Pro Ile Leu Val Glu
385                 390                 395                 400

Leu Asp Gly Asp Val Asn Gly His Arg Phe Ser Val Ser Gly Glu Gly
                405                 410                 415

Glu Gly Asp Ala Thr Tyr Gly Lys Leu Thr Leu Lys Phe Ile Cys Thr
                420                 425                 430

Thr Gly Lys Leu Pro Val Pro Trp Pro Thr Leu Val Thr Thr Leu Thr
            435                 440                 445

Trp Gly Val Gln Cys Phe Ser Arg Tyr Pro Asp His Met Lys Gln His
450                 455                 460

Asp Phe Phe Lys Ser Ala Met Pro Glu Gly Tyr Val Gln Glu Arg Thr
465                 470                 475                 480

Ile Phe Phe Lys Asp Asp Gly Asn Tyr Lys Thr Arg Ala Glu Val Lys
                485                 490                 495

Phe Glu Gly Asp Thr Leu Val Asn Arg Ile Glu Leu Lys Gly Ile Asp
                500                 505                 510

Phe Lys Glu Asp Gly Asn Ile Leu Gly His Lys Leu Glu Tyr Asn Tyr
            515                 520                 525

Ile Ser His Asn Val Tyr Ile Thr Ala Asp Lys Gln Lys Asn Gly Ile
530                 535                 540
```

```
Lys Ala His Phe Lys Ile Arg His Asn Ile Glu Asp Gly Ser Val Gln
545                 550                 555                 560

Leu Ala Asp His Tyr Gln Gln Asn Thr Pro Ile Gly Asp Gly Pro Val
                565                 570                 575

Leu Leu Pro Asp Asn His Tyr Leu Ser Thr Gln Ser Ala Leu Ser Lys
            580                 585                 590

Asp Pro Asn Glu Lys Arg Asp His Met Val Leu Leu Glu Phe Val Thr
        595                 600                 605

Ala Ala Gly Ile Thr Leu Gly Met Asp Glu Leu Tyr Lys
    610                 615                 620

<210> SEQ ID NO 46
<211> LENGTH: 1851
<212> TYPE: DNA
<213> ORGANISM: Artificial Sequence
<220> FEATURE:
<223> OTHER INFORMATION: Description of Artificial Sequence: Synthetic
      fusion construct

<400> SEQUENCE: 46
atggtgagca agggcgagga gctgttcacc ggggtggtgc ccatcctggt cgagctggac     60
ggcgacgtaa acggccacaa gttcagcgtg tccggcgagg gcgagggcga tgccacctac    120
ggcaagctga ccctgaagtt catctgcacc accggcaagc tgcccgtgcc ctggcccacc    180
ctcgtgacca ccttcggcta cggcctgcag tgcttcgccc gctaccccga ccacatgaag    240
cagcacgact tcttcaagtc cgccatgccc gaaggctacg tccaggagcg caccatcttc    300
ttcaaggacg acggcaacta caagacccgc gccgaggtga agttcgaggg cgacaccctg    360
gtgaaccgca tcgagctgaa gggcatcgac ttcaaggagg acggcaacat cctggggcac    420
aagctggagt acaactacaa cagccacaac gtctatatca tggccgacaa gcagaagaac    480
ggcatcaagg tgaacttcaa gatccgccac aacatcgagg acggcagcgt gcagctcgcc    540
gaccactacc agcagaacac ccccatcggc gacggccccg tgctgctgcc cgacaaccac    600
tacctgagct accagtccgc cctgagcaaa gaccccaacg agaagcgcga tcacatggtc    660
ctgctggagt tcgtgaccgc cgccgggatc actctcggca tggacgagct gtacaaggaa    720
ttcatgagaa tgatcctgcg aaaaccacct ggccagagga ctgtggatga cctagagatt    780
atctacgacg agctccttca tattaaagcc ttatcccatc tctctaccac agtgaaacgg    840
gagttagcag gtgttctcat ttttgagtct cacgccaaag gaggaactgt gttgtttaac    900
caggggaag aagtacctc ctggtacatc attctgaaag gatccgtgaa tgtagtcatt    960
tatggcaagg gtgtggtctg caccctgcac gaaggagatg actttggcaa gttagctcta   1020
gtgaacgatg ctccaagagc tgcctccatt gttcttcggg aagataattg tcacttccta   1080
agagtcgaca aggaagactt caatcggatt ctgagggacg ttgagtctag aatggtgagc   1140
aagggcgagg agctgttcac cggggtggtg cccatcctgg tcgagctgga cggcgacgta   1200
aacggccaca gttcagcgt gtccggcgag ggcgagggcg atgccaccta cggcaagctg   1260
accctgaagt tcatctgcac caccggcaag ctgcccgtgc cctggcccac cctcgtgacc   1320
accctgacct gggcgtgca gtgcttcagc cgctaccccg accacatgaa gcagcacgac   1380
ttcttcaagt ccgccatgcc cgaaggctac gtccaggagc gcaccatctt cttcaaggac   1440
gacggcaact acaagacccg cgccgaggtg aagttcgagg gcgacaccct ggtgaaccgc   1500
atcgagctga agggcatcga cttcaaggag gacggcaaca tcctgggcca caagctggag   1560
tacaactaca tcagccacaa cgtctatatc accgccgaca agcagaagaa cggcatcaag   1620
```

```
gccaacttca agatccgcca caacatcgag gacggcagcg tgcagctcgc cgaccactac    1680
cagcagaaca cccccatcgg cgacggcccc gtgctgctgc ccgacaacca ctacctgagc    1740
acccagtccg ccctgagcaa agaccccaac gagaagcgcg atcacatggt cctgctggag    1800
ttcgtgaccg ccgccgggat cactctcggc atggacgagc tgtacaagta a             1851
```

<210> SEQ ID NO 47
<211> LENGTH: 615
<212> TYPE: PRT
<213> ORGANISM: Artificial Sequence
<220> FEATURE:
<223> OTHER INFORMATION: Description of Artificial Sequence: Synthetic
      fusion construct

<400> SEQUENCE: 47

```
Met Val Ser Lys Gly Glu Glu Leu Phe Thr Gly Val Val Pro Ile Leu
 1               5                  10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Phe Gly Tyr Gly Leu Gln Cys Phe Ala Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys Glu
225                 230                 235                 240

Phe Met Arg Met Ile Leu Arg Lys Pro Pro Gly Gln Arg Thr Val Asp
                245                 250                 255

Asp Leu Glu Ile Ile Tyr Asp Glu Leu Leu His Ile Lys Ala Leu Ser
            260                 265                 270

His Leu Ser Thr Thr Val Lys Arg Glu Leu Ala Gly Val Leu Ile Phe
        275                 280                 285

Glu Ser His Ala Lys Gly Gly Thr Val Leu Phe Asn Gln Gly Glu Glu
    290                 295                 300

Gly Thr Ser Trp Tyr Ile Ile Leu Lys Gly Ser Val Asn Val Val Ile
305                 310                 315                 320
```

```
Tyr Gly Lys Gly Val Val Cys Thr Leu His Glu Gly Asp Asp Phe Gly
            325                 330                 335

Lys Leu Ala Leu Val Asn Asp Ala Pro Arg Ala Ala Ser Ile Val Leu
            340                 345                 350

Arg Glu Asp Asn Cys His Phe Leu Arg Val Lys Glu Asp Phe Asn
            355                 360                 365

Arg Ile Leu Arg Asp Val Glu Ser Arg Val Ser Lys Gly Glu Glu Leu
            370                 375                 380

Phe Thr Gly Val Val Pro Ile Leu Val Glu Leu Asp Gly Asp Val Asn
385                 390                 395                 400

Gly His Arg Phe Ser Val Ser Gly Glu Gly Glu Gly Asp Ala Thr Tyr
            405                 410                 415

Gly Lys Leu Thr Leu Lys Phe Ile Cys Thr Thr Gly Lys Leu Pro Val
            420                 425                 430

Pro Trp Pro Thr Leu Val Thr Thr Leu Thr Trp Gly Val Gln Cys Phe
            435                 440                 445

Ser Arg Tyr Pro Asp His Met Lys Gln His Asp Phe Phe Lys Ser Ala
            450                 455                 460

Met Pro Glu Gly Tyr Val Gln Glu Arg Thr Ile Phe Phe Lys Asp Asp
465                 470                 475                 480

Gly Asn Tyr Lys Thr Arg Ala Glu Val Lys Phe Glu Gly Asp Thr Leu
            485                 490                 495

Val Asn Arg Ile Glu Leu Lys Gly Ile Asp Phe Lys Glu Asp Gly Asn
            500                 505                 510

Ile Leu Gly His Lys Leu Glu Tyr Asn Tyr Ile Ser His Asn Val Tyr
            515                 520                 525

Ile Thr Ala Asp Lys Gln Lys Asn Gly Ile Lys Ala His Phe Lys Ile
            530                 535                 540

Arg His Asn Ile Glu Asp Gly Ser Val Gln Leu Ala Asp His Tyr Gln
545                 550                 555                 560

Gln Asn Thr Pro Ile Gly Asp Gly Pro Val Leu Leu Pro Asp Asn His
                    565                 570                 575

Tyr Leu Ser Thr Gln Ser Ala Leu Ser Lys Asp Pro Asn Glu Lys Arg
            580                 585                 590

Asp His Met Val Leu Leu Glu Phe Val Thr Ala Ala Gly Ile Thr Leu
            595                 600                 605

Gly Met Asp Glu Leu Tyr Lys
610                 615

<210> SEQ ID NO 48
<211> LENGTH: 1965
<212> TYPE: DNA
<213> ORGANISM: Artificial Sequence
<220> FEATURE:
<223> OTHER INFORMATION: Description of Artificial Sequence: Synthetic
      fusion construct

<400> SEQUENCE: 48
atggtgagca agggcgagga gctgttcacc ggggtggtgc ccatcctggt cgagctggac     60
ggcgacgtaa acggccacaa gttcagcgtg tccggcgagg gcgagggcga tgccacctac    120
ggcaagctga ccctgaagtt catctgcacc accggcaagc tgcccgtgcc ctggcccacc    180
ctcgtgacca ccttcggcta cggcctgcag tgcttcgccc gctaccccga ccacatgaag    240
cagcacgact tcttcaagtc cgccatgccc gaaggctacg tccaggagcg caccatcttc    300
```

-continued

| | |
|---|---|
| ttcaaggacg acggcaacta caagacccgc gccgaggtga agttcgaggg cgacaccctg | 360 |
| gtgaaccgca tcgagctgaa gggcatcgac ttcaaggagg acggcaacat cctggggcac | 420 |
| aagctggagt acaactacaa cagccacaac gtctatatca tggccgacaa gcagaagaac | 480 |
| ggcatcaagg tgaacttcaa gatccgccac aacatcgagg acggcagcgt gcagctcgcc | 540 |
| gaccactacc agcagaacac ccccatcggc gacggccccg tgctgctgcc cgacaaccac | 600 |
| tacctgagct accagtccgc cctgagcaaa gaccccaacg agaagcgcga tcacatggtc | 660 |
| ctgctggagt tcgtgaccgc cgccgggatc actctcggca tggacgagct gtacaaggaa | 720 |
| ttcgaagaga agaaggagtg tgatgaagaa cttcaggaca ccatgctgct gctctcacag | 780 |
| atgggccctg acgcccacat gagaatgatc ctgcgaaaac acctggcca gaggactgtg | 840 |
| gatgacctag agattatcta cgacgagctc cttcatatta agccttatc ccatctctct | 900 |
| accacagtga acgggagtt agcaggtgtt ctcattttg agtctcacgc aaaggagga | 960 |
| actgtgttgt taaccaggg ggaagaaggt acctcctggt acatcattct gaaaggatcc | 1020 |
| gtgaatgtag tcatttatgg caagggtgtg gtctgcaccc tgcacgaagg agatgacttt | 1080 |
| ggcaagttag ctctagtgaa cgatgctcca agagctgcct ccattgttct tcgggaagat | 1140 |
| aattgtcact tcctaagagt cgacaaggaa gacttcaatc ggattctgag gacgttgag | 1200 |
| gcgaatacag tcagacttaa agaacatgac caattctgtt ctagaatggt gagcaagggc | 1260 |
| gaggagctgt tcaccggggt ggtgcccatc ctggtcgagc tggacggcga cgtaaacggc | 1320 |
| cacaagttca gcgtgtccgg cgagggcgag ggcgatgcca cctacggcaa gctgaccctg | 1380 |
| aagttcatct gcaccaccgg caagctgccc gtgcccggc ccaccctcgt gaccaccctg | 1440 |
| acctggggcg tgcagtgctt cagccgctac cccgaccaca tgaagcagca cgacttcttc | 1500 |
| aagtccgcca tgcccgaagg ctacgtccag gagcgcacca tcttcttcaa ggacgacggc | 1560 |
| aactacaaga cccgcgccga ggtgaagttc gagggcgaca ccctggtgaa ccgcatcgag | 1620 |
| ctgaagggca tcgacttcaa ggaggacggc aacatcctgg gcacaagct ggagtacaac | 1680 |
| tacatcagcc acaacgtcta tatcaccgcc gacaagcaga gaacggcat caaggccaac | 1740 |
| ttcaagatcc gccacaacat cgaggacggc agcgtgcagc tcgccgacca ctaccagcag | 1800 |
| aacacccca tcggcgacgg ccccgtgctg ctgcccgaca ccactacct gagcacccag | 1860 |
| tccgccctga gcaaagaccc caacgagaag cgcgatcaca tggtcctgct ggagttcgtg | 1920 |
| accgccgccg ggatcactct cggcatggac gagctgtaca agtaa | 1965 |

<210> SEQ ID NO 49
<211> LENGTH: 666
<212> TYPE: PRT
<213> ORGANISM: Artificial Sequence
<220> FEATURE:
<223> OTHER INFORMATION: Description of Artificial Sequence: Synthetic
      fusion construct

<400> SEQUENCE: 49

Met Val Ser Lys Gly Glu Glu Leu Phe Thr Gly Val Val Pro Ile Leu
 1               5                  10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

-continued

```
Phe Gly Tyr Gly Leu Gln Cys Phe Ala Arg Tyr Pro Asp His Met Lys
 65                  70                  75                  80

Gln His Asp Phe Phe Lys Ser Ala Met Pro Glu Gly Tyr Val Gln Glu
                 85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Ala Leu
        195                 200                 205

Ser Lys Asp Pro Asn Glu Lys Arg Asp His Met Val Leu Leu Glu Phe
210                 215                 220

Val Thr Ala Ala Gly Ile Thr Leu Gly Met Asp Glu Leu Tyr Lys Glu
225                 230                 235                 240

Phe Glu Glu Lys Lys Glu Cys Asp Glu Glu Leu Gln Asp Thr Met Leu
                245                 250                 255

Leu Leu Ser Gln Met Gly Pro Asp Ala His Met Arg Met Ile Leu Arg
            260                 265                 270

Lys Pro Pro Gly Gln Arg Thr Val Asp Asp Leu Glu Ile Ile Tyr Asp
        275                 280                 285

Glu Leu Leu His Ile Lys Ala Leu Ser His Leu Ser Thr Thr Val Lys
290                 295                 300

Arg Glu Leu Ala Gly Val Leu Ile Phe Glu Ser His Ala Lys Gly Gly
305                 310                 315                 320

Thr Val Leu Phe Asn Gln Gly Glu Glu Gly Thr Ser Trp Tyr Ile Ile
                325                 330                 335

Leu Lys Gly Ser Val Asn Val Val Ile Tyr Gly Lys Gly Val Val Cys
            340                 345                 350

Thr Leu His Glu Gly Asp Asp Phe Gly Lys Leu Ala Leu Val Asn Asp
        355                 360                 365

Ala Pro Arg Ala Ala Ser Ile Val Leu Arg Glu Asp Asn Cys His Phe
370                 375                 380

Leu Arg Val Asp Lys Glu Asp Phe Asn Arg Ile Leu Arg Asp Val Glu
385                 390                 395                 400

Asp Lys Glu Asp Phe Asn Arg Ile Leu Arg Asp Val Glu Ala Asn Thr
                405                 410                 415

Val Arg Leu Lys Glu His Asp Gln Phe Cys Ser Arg Val Ser Lys Gly
            420                 425                 430

Glu Glu Leu Phe Thr Gly Val Val Pro Ile Leu Val Glu Leu Asp Gly
        435                 440                 445

Asp Val Asn Gly His Arg Phe Ser Val Ser Gly Glu Gly Glu Gly Asp
450                 455                 460

Ala Thr Tyr Gly Lys Leu Thr Leu Lys Phe Ile Cys Thr Thr Gly Lys
465                 470                 475                 480

Leu Pro Val Pro Trp Pro Thr Leu Val Thr Thr Leu Thr Trp Gly Val
```

```
                485                 490                 495
Gln Cys Phe Ser Arg Tyr Pro Asp His Met Lys Gln His Asp Phe Phe
                500                 505                 510

Lys Ser Ala Met Pro Glu Gly Tyr Val Gln Glu Arg Thr Ile Phe Phe
                515                 520                 525

Lys Asp Asp Gly Asn Tyr Lys Thr Arg Ala Glu Val Lys Phe Glu Gly
            530                 535                 540

Asp Thr Leu Val Asn Arg Ile Glu Leu Lys Gly Ile Asp Phe Lys Glu
545                 550                 555                 560

Asp Gly Asn Ile Leu Gly His Lys Leu Glu Tyr Asn Tyr Ile Ser His
                565                 570                 575

Asn Val Tyr Ile Thr Ala Asp Lys Gln Lys Asn Gly Ile Lys Ala His
                580                 585                 590

Phe Lys Ile Arg His Asn Ile Glu Asp Gly Ser Val Gln Leu Ala Asp
                595                 600                 605

His Tyr Gln Gln Asn Thr Pro Ile Gly Asp Gly Pro Val Leu Leu Pro
                610                 615                 620

Asp Asn His Tyr Leu Ser Thr Gln Ser Ala Leu Ser Lys Asp Pro Asn
625                 630                 635                 640

Glu Lys Arg Asp His Met Val Leu Leu Glu Phe Val Thr Ala Ala Gly
                645                 650                 655

Ile Thr Leu Gly Met Asp Glu Leu Tyr Lys
                660                 665

<210> SEQ ID NO 50
<211> LENGTH: 1977
<212> TYPE: DNA
<213> ORGANISM: Artificial Sequence
<220> FEATURE:
<223> OTHER INFORMATION: Description of Artificial Sequence: Synthetic
      fusion construct

<400> SEQUENCE: 50
atggtgagca agggcgagga gctgttcacc ggggtggtgc ccatcctggt cgagctggac         60
ggcgacgtaa acggccacaa gttcagcgtg tccggcgagg gcgagggcga tgccacctac        120
ggcaagctga ccctgaagtt catctgcacc accggcaagc tgcccgtgcc ctggcccacc        180
ctcgtgacca ccttcggcta cggcctgcag tgcttcgccc gctaccccga ccacatgaag        240
cagcacgact tcttcaagtc cgccatgccc gaaggctacg tccaggagcg caccatcttc        300
ttcaaggacg acggcaacta caagacccgc gccgaggtga agttcgaggg cgacaccctg        360
gtgaaccgca tcgagctgaa gggcatcgac ttcaaggagg acggcaacat cctggggcac        420
aagctggagt acaactacaa cagccacaac gtctatatca tggccgacaa gcagaagaac        480
ggcatcaagg tgaacttcaa gatccgccac aacatcgagg acggcagcgt gcagctcgcc        540
gaccactacc agcagaacac ccccatcggc gacggccccg tgctgctgcc cgacaaccac        600
tacctgagct accagtccgc cctgagcaaa gaccccaacg agaagcgcga tcacatggtc        660
ctgctggagt tcgtgaccgc cgccgggatc actctcggca tggacgagct gtacaaggaa        720
ttcgaagaga agaaggagtg tgatgaagaa cttcaggaca ccatgctgct gctctcacag        780
atgggccctg acgcccacat gagaatgatc ctgcgaaaac acctggcca  gaggactgtg        840 gatgacctag agattatcta cgacgagctc cttcatatta aagccttatc ccatctctct        900
accacagtga acggragtt agcaggtgtt ctcatttttg agtctcacgc caaggagga         960 actgtgttgt taaccaggg ggaagaaggt acctcctggt acatcattct gaaaggatcc       1020
```

-continued

```
gtgaatgtag tcatttatgg caagggtgtg gtctgcaccc tgcacgaagg agatgacttt    1080
ggcaagttag ctctagtgaa cgatgctcca agagctgcct ccattgttct tcgggaagat    1140
aattgtcact tcctaagagt cgacaaggaa gacttcaatc ggattctgag ggacgttgag    1200
gcgaatacag tcagacttaa agaacatgac caagatgtct tggtactgga gtctagaatg    1260
gtgagcaagg gcgaggagct gttcaccggg gtggtgccca tcctggtcga gctggacggc    1320
gacgtaaacg gccacaagtt cagcgtgtcc ggcgagggcg agggcgatgc cacctacggc    1380
aagctgaccc tgaagttcat ctgcaccacc ggcaagctgc ccgtgccctg gcccaccctc    1440
gtgaccaccc tgacctgggg cgtgcagtgc ttcagccgct accccgacca catgaagcag    1500
cacgacttct tcaagtccgc catgcccgaa ggctacgtcc aggagcgcac catcttcttc    1560
aaggacgacg gcaactacaa gacccgcgcc gaggtgaagt tcgagggcga caccctggtg    1620
aaccgcatcg agctgaaggg catcgacttc aaggaggacg gcaacatcct ggggcacaag    1680
ctggagtaca actacatcag ccacaacgtc tatatcaccg ccgacaagca gaagaacggc    1740
atcaaggcca acttcaagat ccgccacaac atcgaggacg gcagcgtgca gctcgccgac    1800
cactaccagc agaacacccc catcggcgac ggccccgtgc tgctgcccga caaccactac    1860
ctgagcaccc agtccgccct gagcaaagac cccaacgaga gcgcgatca catggtcctg    1920 ctggagttcg tgaccgccgc cgggatcact ctcggcatgg acgagctgta caagtaa      1977
```

<210> SEQ ID NO 51
<211> LENGTH: 657
<212> TYPE: PRT
<213> ORGANISM: Artificial Sequence
<220> FEATURE:
<223> OTHER INFORMATION: Description of Artificial Sequence: Synthetic fusion construct

<400> SEQUENCE: 51

```
Met Val Ser Lys Gly Glu Glu Leu Phe Thr Gly Val Val Pro Ile Leu
  1               5                  10                  15

Val Glu Leu Asp Gly Asp Val Asn Gly His Lys Phe Ser Val Ser Gly
             20                  25                  30

Glu Gly Glu Gly Asp Ala Thr Tyr Gly Lys Leu Thr Leu Lys Phe Ile
         35                  40                  45

Cys Thr Thr Gly Lys Leu Pro Val Pro Trp Pro Thr Leu Val Thr Thr
     50                  55                  60

Phe Gly Tyr Gly Leu Gln Cys Phe Ala Arg Tyr Pro Asp His Met Lys
 65                  70                  75                  80

Gln His Asp Phe Phe Lys Ser Ala Met Pro Glu Gly Tyr Val Gln Glu
                 85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190
```

```
Pro Val Leu Leu Pro Asp Asn His Tyr Leu Ser Tyr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys Glu
225                 230                 235                 240

Phe Glu Glu Lys Lys Glu Cys Asp Glu Glu Leu Gln Asp Thr Met Leu
                245                 250                 255

Leu Leu Ser Gln Met Gly Pro Asp Ala His Met Arg Met Ile Leu Arg
            260                 265                 270

Lys Pro Pro Gly Gln Arg Thr Val Asp Asp Leu Glu Ile Ile Tyr Asp
        275                 280                 285

Glu Leu Leu His Ile Lys Ala Leu Ser His Leu Ser Thr Thr Val Lys
    290                 295                 300

Arg Glu Leu Ala Gly Val Leu Ile Phe Glu Ser His Ala Lys Gly Gly
305                 310                 315                 320

Thr Val Leu Phe Asn Gln Gly Glu Gly Thr Ser Trp Tyr Ile Ile
                325                 330                 335

Leu Lys Gly Ser Val Asn Val Val Ile Tyr Gly Lys Gly Val Val Cys
            340                 345                 350

Thr Leu His Glu Gly Asp Asp Phe Gly Lys Leu Ala Leu Val Asn Asp
        355                 360                 365

Ala Pro Arg Ala Ala Ser Ile Val Leu Arg Glu Asp Asn Cys His Phe
    370                 375                 380

Leu Arg Val Asp Lys Glu Asp Phe Asn Arg Ile Leu Arg Asp Val Glu
385                 390                 395                 400

Ala Asn Thr Val Arg Leu Lys Glu His Asp Gln Asp Val Leu Val Leu
                405                 410                 415

Glu Ser Arg Val Ser Lys Gly Glu Glu Leu Phe Thr Gly Val Val Pro
            420                 425                 430

Ile Leu Val Glu Leu Asp Gly Asp Val Asn Gly His Arg Phe Ser Val
        435                 440                 445

Ser Gly Glu Gly Glu Gly Asp Ala Thr Tyr Gly Lys Leu Thr Leu Lys
    450                 455                 460

Phe Ile Cys Thr Thr Gly Lys Leu Pro Val Pro Trp Pro Thr Leu Val
465                 470                 475                 480

Thr Thr Leu Thr Trp Gly Val Gln Cys Phe Ser Arg Tyr Pro Asp His
                485                 490                 495

Met Lys Gln His Asp Phe Phe Lys Ser Ala Met Pro Glu Gly Tyr Val
            500                 505                 510

Gln Glu Arg Thr Ile Phe Phe Lys Asp Asp Gly Asn Tyr Lys Thr Arg
        515                 520                 525

Ala Glu Val Lys Phe Glu Gly Asp Thr Leu Val Asn Arg Ile Glu Leu
    530                 535                 540

Lys Gly Ile Asp Phe Lys Glu Asp Gly Asn Ile Leu Gly His Lys Leu
545                 550                 555                 560

Glu Tyr Asn Tyr Ile Ser His Asn Val Tyr Ile Thr Ala Asp Lys Gln
                565                 570                 575

Lys Asn Gly Ile Lys Ala His Phe Lys Ile Arg His Asn Ile Glu Asp
            580                 585                 590

Gly Ser Val Gln Leu Ala Asp His Tyr Gln Gln Asn Thr Pro Ile Gly
        595                 600                 605
```

```
Asp Gly Pro Val Leu Leu Pro Asp Asn His Tyr Leu Ser Thr Gln Ser
    610                 615                 620

Ala Leu Ser Lys Asp Pro Asn Glu Lys Arg Asp His Met Val Leu Leu
625                 630                 635                 640

Glu Phe Val Thr Ala Ala Gly Ile Thr Leu Gly Met Asp Glu Leu Tyr
                645                 650                 655

Lys

<210> SEQ ID NO 52
<211> LENGTH: 1929
<212> TYPE: DNA
<213> ORGANISM: Artificial Sequence
<220> FEATURE:
<223> OTHER INFORMATION: Description of Artificial Sequence: Synthetic
      fusion construct

<400> SEQUENCE: 52
```

| | | | | | |
|---|---|---|---|---|---|
| gaagagaaga | aggagtgtga | tgaagaactt | caggacacca | tgctgctgct | ctcacagatg | 60 |
| ggccctgacg | cccacatgag | aatgatcctg | cgaaaaccac | ctggccagag | gactgtggat | 120 |
| gacctagaga | ttatctacga | cgagctcctt | catattaaag | ccttatccca | tctctctacc | 180 |
| acagtgaaac | gggagttagc | aggtgttctc | atttttgagt | ctcacgccaa | aggaggaact | 240 |
| gtgttgttta | ccaggggga | agaaggtacc | tcctggtaca | tcattctgaa | aggatccgtg | 300 |
| aatgtagtca | ttgctagcat | ggtgagcaag | ggcgaggagc | tgttcaccgg | ggtggtgccc | 360 |
| atcctggtcg | agctggacgg | cgacgtaaac | ggccacaagt | tcagcgtgtc | cggcgagggc | 420 |
| gagggcgatg | ccacctacgg | caagctgacc | ctgaagttca | tctgcaccac | cggcaagctg | 480 |
| cccgtgccct | ggcccaccct | cgtgaccacc | ttcggctacg | gcctgcagtg | cttcgcccgc | 540 |
| taccccgacc | acatgaagca | gcacgacttc | ttcaagtccg | ccatgcccga | aggctacgtc | 600 |
| caggagcgca | ccatcttctt | caaggacgac | ggcaactaca | agacccgcgc | cgaggtgaag | 660 |
| ttcgagggcg | acaccctggt | gaaccgcatc | gagctgaagg | gcatcgactt | caaggaggac | 720 |
| ggcaacatcc | tggggcacaa | gctggagtac | aactacaaca | gccacaacgt | ctatatcatg | 780 |
| gccgacaagc | agaagaacgg | catcaaggtg | aacttcaaga | tccgccacaa | catcgaggac | 840 |
| ggcagcgtgc | agctcgccga | ccactaccag | cagaacaccc | ccatcggcga | cggccccgtg | 900 |
| ctgctgcccg | acaaccacta | cctgagctac | cagtccgccc | tgagcaaaga | ccccaacgag | 960 |
| aagcgcgatc | acatggtcct | gctggagttc | gtgaccgccg | ccgggatcac | tctcggcatg | 1020 |
| gacgagctgt | acaaggaatt | cggcaagggt | gtggtctgca | ccctgacgca | aggagatgac | 1080 |
| tttggcaagt | tagctctagt | gaacgatgct | ccaagagctg | cctccattgt | tcttcgggaa | 1140 |
| gataattgtc | acttcctaag | agtcgacaag | gaagacttca | atcggattct | gagggacgtt | 1200 |
| gagtctagaa | tggtgagcaa | gggcgaggag | ctgttcaccg | gggtggtgcc | catcctggtc | 1260 |
| gagctggacg | gcgacgtaaa | cggccacaag | ttcagcgtgt | ccggcgaggg | cgagggcgat | 1320 |
| gccacctacg | gcaagctgac | cctgaagttc | atctgcacca | ccggcaagct | gcccgtgccc | 1380 |
| tggcccaccc | tcgtgaccac | cctgacctgg | ggcgtgcagt | gcttcagccg | ctaccccgac | 1440 |
| cacatgaagc | agcacgactt | cttcaagtcc | gccatgcccg | aaggctacgt | ccaggagcgc | 1500 |
| accatcttct | tcaaggacga | cggcaactac | aagacccgcg | ccgaggtgaa | gttcgagggc | 1560 |
| gacaccctgg | tgaaccgcat | cgagctgaag | ggcatcgact | tcaaggagga | cggcaacatc | 1620 |
| ctggggcaca | agctggagta | caactacatc | agccacaacg | tctatatcac | cgccgacaag | 1680 |
| cagaagaacg | gcatcaaggc | caacttcaag | atccgccaca | acatcgagga | cggcagcgtg | 1740 |

-continued

```
cagctcgccg accactacca gcagaacacc cccatcggcg acggccccgt gctgctgccc    1800
gacaaccact acctgagcac ccagtccgcc ctgagcaaag accccaacga aagcgcgat     1860 cacatggtcc tgctggagtt cgtgaccgcc gccgggatca ctctcggcat ggacgagctg    1920
tacaagtaa                                                            1929
```

<210> SEQ ID NO 53
<211> LENGTH: 658
<212> TYPE: PRT
<213> ORGANISM: Artificial Sequence
<220> FEATURE:
<223> OTHER INFORMATION: Description of Artificial Sequence: Synthetic fusion construct

<400> SEQUENCE: 53

```
Met Glu Glu Lys Lys Glu Cys Asp Glu Glu Leu Gln Asp Thr Met Leu
 1               5                  10                  15

Leu Leu Ser Gln Met Gly Pro Asp Ala His Met Arg Met Ile Leu Arg
             20                  25                  30

Lys Pro Pro Gly Gln Arg Thr Val Asp Asp Leu Glu Ile Ile Tyr Glu
         35                  40                  45

Glu Leu Leu His Ile Lys Ala Leu Ser His Leu Ser Thr Thr Val Lys
     50                  55                  60

Arg Glu Leu Ala Gly Val Leu Ile Phe Glu Ser His Ala Lys Gly Gly
 65                  70                  75                  80

Thr Val Leu Phe Asn Gln Gly Glu Glu Gly Thr Ser Trp Tyr Ile Ile
                 85                  90                  95

Leu Lys Gly Ser Val Asn Val Val Ile Ala Ser Val Ser Lys Gly Glu
            100                 105                 110

Glu Leu Phe Thr Gly Val Val Pro Ile Leu Val Glu Leu Asp Gly Asp
        115                 120                 125

Val Asn Gly His Lys Phe Ser Val Ser Gly Glu Gly Glu Gly Asp Ala
    130                 135                 140

Thr Tyr Gly Lys Leu Thr Leu Lys Phe Ile Cys Thr Thr Gly Lys Leu
145                 150                 155                 160

Pro Val Pro Trp Pro Thr Leu Val Thr Thr Phe Gly Tyr Gly Leu Gln
                165                 170                 175

Cys Phe Ala Arg Tyr Pro Asp His Met Lys Gln His Asp Phe Phe Lys
            180                 185                 190

Ser Ala Met Pro Glu Gly Tyr Val Gln Glu Arg Thr Ile Phe Phe Lys
        195                 200                 205

Asp Asp Gly Asn Tyr Lys Thr Arg Ala Glu Val Lys Phe Glu Gly Asp
    210                 215                 220

Thr Leu Val Asn Arg Ile Glu Leu Lys Gly Ile Asp Phe Lys Glu Asp
225                 230                 235                 240

Gly Asn Ile Leu Gly His Lys Leu Glu Tyr Asn Tyr Asn Ser His Asn
                245                 250                 255

Val Tyr Ile Met Ala Asp Lys Gln Lys Asn Gly Ile Lys Val Asn Phe
            260                 265                 270

Lys Ile Arg His Asn Ile Glu Asp Gly Ser Val Gln Leu Ala Asp His
        275                 280                 285

Tyr Gln Gln Asn Thr Pro Ile Gly Asp Gly Pro Val Leu Leu Pro Asp
    290                 295                 300

Asn His Tyr Leu Ser Tyr Gln Ser Ala Leu Ser Lys Asp Pro Asn Glu
305                 310                 315                 320
```

Lys Arg Asp His Met Val Leu Leu Glu Phe Val Thr Ala Ala Gly Ile
            325                 330                 335

Thr Leu Gly Met Asp Glu Leu Tyr Lys Glu Phe Gly Lys Gly Val Val
            340                 345                 350

Cys Thr Leu His Glu Gly Asp Asp Phe Gly Lys Leu Ala Leu Val Asn
            355                 360                 365

Asp Ala Pro Arg Ala Ala Ser Ile Val Leu Arg Glu Asp Asn Cys His
            370                 375                 380

Phe Leu Arg Val Asp Lys Glu Asp Phe Asn Arg Ile Leu Arg Asp Val
385                 390                 395                 400

Glu Ala Asn Thr Val Arg Leu Lys Glu His Asp Gln Asp Val Leu Val
            405                 410                 415

Leu Glu Ser Arg Val Ser Lys Gly Glu Glu Leu Phe Thr Gly Val Val
            420                 425                 430

Pro Ile Leu Val Glu Leu Asp Gly Asp Val Asn Gly His Arg Phe Ser
            435                 440                 445

Val Ser Gly Glu Gly Glu Gly Asp Ala Thr Tyr Gly Lys Leu Thr Leu
            450                 455                 460

Lys Phe Ile Cys Thr Thr Gly Lys Leu Pro Val Pro Trp Pro Thr Leu
465                 470                 475                 480

Val Thr Thr Leu Thr Trp Gly Val Gln Cys Phe Ser Arg Tyr Pro Asp
            485                 490                 495

His Met Lys Gln His Asp Phe Phe Lys Ser Ala Met Pro Glu Gly Tyr
            500                 505                 510

Val Gln Glu Arg Thr Ile Phe Phe Lys Asp Asp Gly Asn Tyr Lys Thr
            515                 520                 525

Arg Ala Glu Val Lys Phe Glu Gly Asp Thr Leu Val Asn Arg Ile Glu
            530                 535                 540

Leu Lys Gly Ile Asp Phe Lys Glu Asp Gly Asn Ile Leu Gly His Lys
545                 550                 555                 560

Leu Glu Tyr Asn Tyr Ile Ser His Asn Val Tyr Ile Thr Ala Asp Lys
            565                 570                 575

Gln Lys Asn Gly Ile Lys Ala His Phe Lys Ile Arg His Asn Ile Glu
            580                 585                 590

Asp Gly Ser Val Gln Leu Ala Asp His Tyr Gln Gln Asn Thr Pro Ile
            595                 600                 605

Gly Asp Gly Pro Val Leu Leu Pro Asp Asn His Tyr Leu Ser Thr Gln
            610                 615                 620

Ser Ala Leu Ser Lys Asp Pro Asn Glu Lys Arg Asp His Met Val Leu
625                 630                 635                 640

Leu Glu Phe Val Thr Ala Ala Gly Ile Thr Leu Gly Met Asp Glu Leu
            645                 650                 655

Tyr Lys

<210> SEQ ID NO 54
<211> LENGTH: 1980
<212> TYPE: DNA
<213> ORGANISM: Artificial Sequence
<220> FEATURE:
<223> OTHER INFORMATION: Description of Artificial Sequence: Synthetic
      fusion construct

<400> SEQUENCE: 54
gaagagaaga aggagtgtga tgaagaactt caggacacca tgctgctgct ctcacagatg    60

```
ggccctgacg cccacatgag aatgatcctg cgaaaaccac ctggccagag gactgtggat      120
gacctagaga ttatctacga cgagctcctt catattaaag ccttatccca tctctctacc      180
acagtgaaac gggagttagc aggtgttctc attttttgagt ctcacgccaa aggaggaact     240
gtgttgttta accaggggga agaaggtacc tcctggtaca tcattctgaa aggatccgtg      300
aatgtagtca ttgctagcat ggtgagcaag ggcgaggagc tgttcaccgg ggtggtgccc      360
atcctggtcg agctggacgg cgacgtaaac ggccacaagt tcagcgtgtc cggcgagggc      420
gagggcgatg ccacctacgg caagctgacc ctgaagttca tctgcaccac cggcaagctg      480
cccgtgccct ggcccaccct cgtgaccacc ttcggctacg gcctgcagtg cttcgcccgc      540
taccccgacc acatgaagca gcacgacttc ttcaagtccg ccatgcccga aggctacgtc      600
caggagcgca ccatcttctt caaggacgac ggcaactaca agacccgcgc cgaggtgaag      660
ttcgagggcg acaccctggt gaaccgcatc gagctgaagg gcatcgactt caaggaggac      720
ggcaacatcc tggggcacaa gctggagtac aactacaaca gccacaacgt ctatatcatg      780
gccgacaagc agaagaacgg catcaaggtg aacttcaaga tccgccacaa catcgaggac      840
ggcagcgtgc agctcgccga ccactaccag cagaacaccc ccatcggcga cggccccgtg      900
ctgctgcccg acaaccacta cctgagctac cagtccgccc tgagcaaaga ccccaacgag      960
aagcgcgatc acatggtcct gctggagttc gtgaccgccg ccgggatcac tctcggcatg      1020
gacgagctgt acaaggaatt cggcaagggt gtggtctgca ccctgcacga aggagatgac      1080
tttggcaagt tagctctagt gaacgatgct ccaagagctg cctccattgt tcttcgggaa      1140
gataattgtc acttcctaag agtcgacaag gaagacttca atcggattct gagggacgtt      1200
gaggcgaata cagtcagact taaagaacat gaccaagatg tcttggtact ggagtctaga      1260
atggtgagca agggcgagga gctgttcacc ggggtggtgc ccatcctggt cgagctggac      1320
ggcgacgtaa acggccacaa gttcagcgtg tccggcgagg gcgagggcga tgccacctac      1380
ggcaagctga ccctgaagtt catctgcacc accggcaagc tgcccgtgcc ctggcccacc      1440
ctcgtgacca ccctgaccct gggcgtgcag tgcttcagcc gctaccccga ccacatgaag      1500
cagcacgact tcttcaagtc cgccatgccc gaaggctacg tccaggagcg caccatcttc      1560
ttcaaggacg acggcaacta caagacccgc gccgaggtga agttcgaggg cgacaccctg      1620
gtgaaccgca tcgagctgaa gggcatcgac ttcaaggagg acggcaacat cctggggcac      1680
aagctggagt acaactacat cagccacaac gtctatatca ccgccgacaa gcagaagaac      1740
ggcatcaagg ccaacttcaa gatccgccac aacatcgagg acggcagcgt gcagctcgcc      1800
gaccactacc agcagaacac ccccatcggc gacggccccg tgctgctgcc cgacaaccac      1860
tacctgagca cccagtccgc cctgagcaaa gaccccaacg agaagcgcga tcacatggtc      1920
ctgctggagt tcgtgaccgc cgccgggatc actctcggca tggacgagct gtacaagtaa      1980
```

<210> SEQ ID NO 55
<211> LENGTH: 658
<212> TYPE: PRT
<213> ORGANISM: Artificial Sequence
<220> FEATURE:
<223> OTHER INFORMATION: Description of Artificial Sequence: Synthetic
      fusion construct

<400> SEQUENCE: 55

```
Met Glu Glu Lys Lys Glu Cys Asp Glu Glu Leu Gln Asp Thr Met Leu
 1               5                  10                  15

Leu Leu Ser Gln Met Gly Pro Asp Ala His Met Arg Met Ile Leu Arg
```

-continued

```
            20                  25                  30
Lys Pro Pro Gly Gln Arg Thr Val Asp Asp Leu Glu Ile Ile Tyr Glu
            35                  40                  45
Glu Leu Leu His Ile Lys Ala Leu Ser His Leu Ser Thr Val Lys
        50                  55                  60
Arg Glu Leu Ala Gly Val Leu Ile Phe Glu Ser His Ala Lys Gly Gly
65                  70                  75                  80
Thr Val Leu Phe Asn Gln Gly Glu Gly Thr Ser Trp Tyr Ile Ile
                85                  90                  95
Leu Lys Gly Ser Val Asn Val Ile Ala Ser Val Ser Lys Gly Glu
            100                 105                 110
Glu Leu Phe Thr Gly Val Val Pro Ile Leu Val Glu Leu Asp Gly Asp
        115                 120                 125
Val Asn Gly His Lys Phe Ser Val Ser Gly Glu Gly Glu Gly Asp Ala
        130                 135                 140
Thr Tyr Gly Lys Leu Thr Leu Lys Phe Ile Cys Thr Thr Gly Lys Leu
145                 150                 155                 160
Pro Val Pro Trp Pro Thr Leu Val Thr Thr Phe Gly Tyr Gly Leu Gln
                165                 170                 175
Cys Phe Ala Arg Tyr Pro Asp His Met Lys Gln His Asp Phe Phe Lys
            180                 185                 190
Ser Ala Met Pro Glu Gly Tyr Val Gln Glu Arg Thr Ile Phe Phe Lys
            195                 200                 205
Asp Asp Gly Asn Tyr Lys Thr Arg Ala Glu Val Lys Phe Glu Gly Asp
        210                 215                 220
Thr Leu Val Asn Arg Ile Glu Leu Lys Gly Ile Asp Phe Lys Glu Asp
225                 230                 235                 240
Gly Asn Ile Leu Gly His Lys Leu Glu Tyr Asn Tyr Asn Ser His Asn
                245                 250                 255
Val Tyr Ile Met Ala Asp Lys Gln Lys Asn Gly Ile Lys Val Asn Phe
            260                 265                 270
Lys Ile Arg His Asn Ile Glu Asp Gly Ser Val Gln Leu Ala Asp His
        275                 280                 285
Tyr Gln Gln Asn Thr Pro Ile Gly Asp Gly Pro Val Leu Leu Pro Asp
        290                 295                 300
Asn His Tyr Leu Ser Tyr Gln Ser Ala Leu Ser Lys Asp Pro Asn Glu
305                 310                 315                 320
Lys Arg Asp His Met Val Leu Leu Glu Phe Val Thr Ala Ala Gly Ile
                325                 330                 335
Thr Leu Gly Met Asp Glu Leu Tyr Lys Glu Phe Gly Lys Gly Val Val
                340                 345                 350
Cys Thr Leu His Glu Gly Asp Asp Phe Gly Lys Leu Ala Leu Val Asn
            355                 360                 365
Asp Ala Pro Arg Ala Ala Ser Ile Val Leu Arg Glu Asp Asn Cys His
        370                 375                 380
Phe Leu Arg Val Asp Lys Glu Asp Phe Asn Arg Ile Leu Arg Asp Val
385                 390                 395                 400
Glu Ala Asn Thr Val Arg Leu Lys Glu His Asp Gln Asp Val Leu Val
                405                 410                 415
Leu Glu Ser Arg Val Ser Lys Gly Glu Glu Leu Phe Thr Gly Val Val
            420                 425                 430
Pro Ile Leu Val Glu Leu Asp Gly Asp Val Asn Gly His Arg Phe Ser
            435                 440                 445
```

Val Ser Gly Glu Gly Glu Gly Asp Ala Thr Tyr Gly Lys Leu Thr Leu
    450                 455                 460

Lys Phe Ile Cys Thr Thr Gly Lys Leu Pro Val Pro Trp Pro Thr Leu
465                 470                 475                 480

Val Thr Thr Leu Thr Trp Gly Val Gln Cys Phe Ser Arg Tyr Pro Asp
                485                 490                 495

His Met Lys Gln His Asp Phe Phe Lys Ser Ala Met Pro Glu Gly Tyr
                500                 505                 510

Val Gln Glu Arg Thr Ile Phe Phe Lys Asp Asp Gly Asn Tyr Lys Thr
            515                 520                 525

Arg Ala Glu Val Lys Phe Glu Gly Asp Thr Leu Val Asn Arg Ile Glu
        530                 535                 540

Leu Lys Gly Ile Asp Phe Lys Glu Asp Gly Asn Ile Leu Gly His Lys
545                 550                 555                 560

Leu Glu Tyr Asn Tyr Ile Ser His Asn Val Tyr Ile Thr Ala Asp Lys
                565                 570                 575

Gln Lys Asn Gly Ile Lys Ala His Phe Lys Ile Arg His Asn Ile Glu
                580                 585                 590

Asp Gly Ser Val Gln Leu Ala Asp His Tyr Gln Gln Asn Thr Pro Ile
            595                 600                 605

Gly Asp Gly Pro Val Leu Leu Pro Asp Asn His Tyr Leu Ser Thr Gln
        610                 615                 620

Ser Ala Leu Ser Lys Asp Pro Asn Glu Lys Arg Asp His Met Val Leu
625                 630                 635                 640

Leu Glu Phe Val Thr Ala Ala Gly Ile Thr Leu Gly Met Asp Glu Leu
                645                 650                 655

Tyr Lys

<210> SEQ ID NO 56
<211> LENGTH: 1962
<212> TYPE: DNA
<213> ORGANISM: Artificial Sequence
<220> FEATURE:
<223> OTHER INFORMATION: Description of Artificial Sequence: Synthetic
      fusion construct

<400> SEQUENCE: 56
atgggatgta tcaatagcaa gcgcaaagat gctagcatgg tgagcaaggg cgaggagctg      60
ttcaccgggg tggtgcccat cctggtcgag ctggacggcg acgtaaacgg ccacaagttc     120
agcgtgtccg gcgagggcga gggcgatgcc acctacggca agctgaccct gaagttcatc     180
tgcaccaccg gcaagctgcc cgtgccctgg cccaccctcg tgaccacctt cggctacggc     240
ctgcagtgct tcgcccgcta ccccgaccac atgaagcagc acgacttctt caagtccgcc     300
atgcccgaag gctacgtcca ggagcgcacc atcttcttca aggacgacgg caactacaag     360
acccgcgccg aggtgaagtt cgagggcgac accctggtga accgcatcga gctgaagggc     420
atcgacttca aggaggacgg caacatcctg ggcacaagc tggagtacaa ctacaacagc     480
cacaacgtct atatcatggc cgacaagcag aagaacggca tcaaggtgaa cttcaagatc     540
cgccacaaca tcgaggacgg cagcgtgcag ctcgccgacc actaccagca gaacaccccc     600
atcggcgacg gccccgtgct gctgcccgac aaccactacc tgagctacca gtccgccctg     660
agcaaagacc ccaacgagaa gcgcgatcac atggtcctgc tggagttcgt gaccgccgcc     720
gggatcactc tcggcatgga cgagctgtac aaggaattcg aagagaagaa ggagtgtgat     780

-continued

```
gaagaacttc aggacaccat gctgctgctc tcacagatgg gccctgacgc ccacatgaga    840
atgatcctgc gaaaaccacc tggccagagg actgtggatg acctagagat tatctacgac    900
gagctccttc atattaaagc cttatcccat ctctctacca cagtgaaacg ggagttagca    960
ggtgttctca tttttgagtc tcacgccaaa ggaggaactg tgttgtttaa ccaggggga   1020
gaaggtacct cctggtacat cattctgaaa ggatccgtga atgtagtcat ttatggcaag   1080
ggtgtggtct gcaccctgca cgaaggagat gactttggca agttagctct agtgaacgat   1140
gctccaagag ctgcctccat tgttcttcgg gaagataatt gtcacttcct aagagtcgac   1200
aaggaagact tcaatcggat tctgagggac gttgagtcta aatggtgag caagggcgag   1260
gagctgttca ccggggtggt gcccatcctg gtcgagctgg acggcgacgt aaacggccac   1320
aagttcagcg tgtccggcga gggcgagggc gatgccacct acggcaagct gaccctgaag   1380
ttcatctgca ccaccggcaa gctgcccgtg ccctggccca ccctcgtgac caccctgacc   1440
tgggcgtgc agtgcttcag ccgctacccc gaccacatga gcagcacga cttcttcaag   1500
tccgccatgc ccgaaggcta cgtccaggag cgcaccatct tcttcaagga cgacggcaac   1560
tacaagaccc gcgccgaggt gaagttcgag ggcgacaccc tggtgaaccg catcgagctg   1620
aagggcatcg acttcaagga ggacggcaac atcctggggc acaagctgga gtacaactac   1680
atcagccaca acgtctatat caccgccgac aagcagaaga acggcatcaa ggccaacttc   1740
aagatccgcc acaacatcga ggacggcagc gtgcagctcg ccgaccacta ccagcagaac   1800
accccatcg gcgacggccc cgtgctgctg cccgacaacc actacctgag cacccagtcc   1860
gccctgagca agaccccaa cgagaagcgc gatcacatgg tcctgctgga gttcgtgacc   1920
gccgccggga tcactctcgg catggacgag ctgtacaagt aa                     1962
```

<210> SEQ ID NO 57
<211> LENGTH: 652
<212> TYPE: PRT
<213> ORGANISM: Artificial Sequence
<220> FEATURE:
<223> OTHER INFORMATION: Description of Artificial Sequence: Synthetic fusion construct

<400> SEQUENCE: 57

```
Met Gly Cys Ile Asn Ser Lys Arg Lys Asp Ala Ser Met Val Ser Lys
  1               5                  10                  15

Gly Glu Glu Leu Phe Thr Gly Val Val Pro Ile Leu Val Glu Leu Asp
                 20                  25                  30

Gly Asp Val Asn Gly His Lys Phe Ser Val Ser Gly Glu Gly Glu Gly
             35                  40                  45

Asp Ala Thr Tyr Gly Lys Leu Thr Leu Lys Phe Ile Cys Thr Thr Gly
         50                  55                  60

Lys Leu Pro Val Pro Trp Pro Thr Leu Val Thr Thr Phe Gly Tyr Gly
 65                  70                  75                  80

Leu Gln Cys Phe Ala Arg Tyr Pro Asp His Met Lys Gln His Asp Phe
                 85                  90                  95

Phe Lys Ser Ala Met Pro Glu Gly Tyr Val Gln Glu Arg Thr Ile Phe
                100                 105                 110

Phe Lys Asp Asp Gly Asn Tyr Lys Thr Arg Ala Glu Val Lys Phe Glu
            115                 120                 125

Gly Asp Thr Leu Val Asn Arg Ile Glu Leu Lys Gly Ile Asp Phe Lys
        130                 135                 140

Glu Asp Gly Asn Ile Leu Gly His Lys Leu Glu Tyr Asn Tyr Asn Ser
```

```
            145                 150                 155                 160
        His Asn Val Tyr Ile Met Ala Asp Lys Gln Lys Asn Gly Ile Lys Val
                        165                 170                 175
        Asn Phe Lys Ile Arg His Asn Ile Glu Asp Gly Ser Val Gln Leu Ala
                        180                 185                 190
        Asp His Tyr Gln Gln Asn Thr Pro Ile Gly Asp Gly Pro Val Leu Leu
                        195                 200                 205
        Pro Asp Asn His Tyr Leu Ser Tyr Gln Ser Ala Leu Ser Lys Asp Pro
                        210                 215                 220
        Asn Glu Lys Arg Asp His Met Val Leu Leu Glu Phe Val Thr Ala Ala
        225                 230                 235                 240
        Gly Ile Thr Leu Gly Met Asp Glu Leu Tyr Lys Glu Phe Glu Glu Lys
                        245                 250                 255
        Lys Glu Cys Asp Glu Glu Leu Gln Asp Thr Met Leu Leu Leu Ser Gln
                        260                 265                 270
        Met Gly Pro Asp Ala His Met Arg Met Ile Leu Arg Lys Pro Pro Gly
                        275                 280                 285
        Gln Arg Thr Val Asp Asp Leu Glu Ile Ile Tyr Asp Glu Leu Leu His
                        290                 295                 300
        Ile Lys Ala Leu Ser His Leu Ser Thr Thr Val Lys Arg Glu Leu Ala
        305                 310                 315                 320
        Gly Val Leu Ile Phe Glu Ser His Ala Lys Gly Gly Thr Val Leu Phe
                        325                 330                 335
        Asn Gln Gly Glu Glu Gly Thr Ser Trp Tyr Ile Ile Leu Lys Gly Ser
                        340                 345                 350
        Val Asn Val Val Ile Tyr Gly Lys Gly Val Val Cys Thr Leu His Glu
                        355                 360                 365
        Gly Asp Asp Phe Gly Lys Leu Ala Leu Val Asn Asp Ala Pro Arg Ala
                        370                 375                 380
        Ala Ser Ile Val Leu Arg Glu Asp Asn Cys His Phe Leu Arg Val Asp
        385                 390                 395                 400
        Lys Glu Asp Phe Asn Arg Ile Leu Arg Asp Val Glu Ser Arg Val Ser
                        405                 410                 415
        Lys Gly Glu Glu Leu Phe Thr Gly Val Val Pro Ile Leu Val Glu Leu
                        420                 425                 430
        Asp Gly Asp Val Asn Gly His Arg Phe Ser Val Ser Gly Glu Gly Glu
                        435                 440                 445
        Gly Asp Ala Thr Tyr Gly Lys Leu Thr Leu Lys Phe Ile Cys Thr Thr
        450                 455                 460
        Gly Lys Leu Pro Val Pro Trp Pro Thr Leu Val Thr Thr Leu Thr Trp
        465                 470                 475                 480
        Gly Val Gln Cys Phe Ser Arg Tyr Pro Asp His Met Lys Gln His Asp
                        485                 490                 495
        Phe Phe Lys Ser Ala Met Pro Glu Gly Tyr Val Gln Glu Arg Thr Ile
                        500                 505                 510
        Phe Phe Lys Asp Asp Gly Asn Tyr Lys Thr Arg Ala Glu Val Lys Phe
                        515                 520                 525
        Glu Gly Asp Thr Leu Val Asn Arg Ile Glu Leu Lys Gly Ile Asp Phe
                        530                 535                 540
        Lys Glu Asp Gly Asn Ile Leu Gly His Lys Leu Glu Tyr Asn Tyr Ile
        545                 550                 555                 560
        Ser His Asn Val Tyr Ile Thr Ala Asp Lys Gln Lys Asn Gly Ile Lys
                        565                 570                 575
```

```
Ala His Phe Lys Ile Arg His Asn Ile Glu Asp Gly Ser Val Gln Leu
            580                 585                 590
Ala Asp His Tyr Gln Gln Asn Thr Pro Ile Gly Asp Gly Pro Val Leu
            595                 600                 605
Leu Pro Asp Asn His Tyr Leu Ser Thr Gln Ser Ala Leu Ser Lys Asp
610                 615                 620
Pro Asn Glu Lys Arg Asp His Met Val Leu Leu Glu Phe Val Thr Ala
625                 630                 635                 640
Ala Gly Ile Thr Leu Gly Met Asp Glu Leu Tyr Lys
                645                 650

<210> SEQ ID NO 58
<211> LENGTH: 1869
<212> TYPE: DNA
<213> ORGANISM: Artificial Sequence
<220> FEATURE:
<223> OTHER INFORMATION: Description of Artificial Sequence: Synthetic
      fusion construct

<400> SEQUENCE: 58
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagtt catctgcacc accggcaagc tgcccgtgcc ctggcccacc     180
ctcgtgacca ccttcggcta cggcctgcag tgcttcgccc gctaccccga ccacatgaag     240
cagcacgact tcttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggagg acggcaacat cctggggcac     420
aagctggagt acaactacaa cagccacaac gtctatatca tggccgacaa gcagaagaac     480
ggcatcaagg tgaacttcaa gatccgccac aacatcgagg acggcagcgt gcagctcgcc     540
gaccactacc agcagaacac ccccatcggc gacggccccg tgctgctgcc cgacaaccac     600
tacctgagct accagtccgc cctgagcaaa gaccccaacg agaagcgcga tcacatggtc     660
ctgctggagt tcgtgaccgc cgccgggatc actctcggca tggacgagct gtacaaggaa     720
ttcatgtacg agagctttat tgagtcactg ccattcctca agtctctgga ggtttctgaa     780
cgcctgaagg tggtagatgt gattggcacc aaagtttaca cgatggaga acagatcatt     840 gctcagggag actcggcgga ttcgttcttc attgtagaat ctggagaagt gagaattact     900
atgaagagaa agggtaaatc agacatcgaa gagaacggtg ctgtggaaat cgctcggtgt     960
ctccggggac agtattttgg agagcttgcc ctggtcacta caagccaag agcagcatct    1020 gcacacgcca ttgggactgt caaatgctta gccatggatg tgcaagcatt tgagaggctt    1080
ctgggacctt gcatggaaat tatgaagagg aatatcgcca cctatgagga gcaattagtt    1140
gcatctagaa tggtgagcaa gggcgaggag ctgttcaccg gggtggtgcc catcctggtc    1200
gagctggacg gcgacgtaaa cggccacaag ttcagcgtgt ccggcgaggg cgagggcgat    1260
gccacctacg gcaagctgac cctgaagttc atctgcacca ccggcaagct gcccgtgccc    1320
tggcccaccc tcgtgaccac cctgacctgg ggcgtgcagt gcttcagccg ctaccccgac    1380
cacatgaagc agcacgactt cttcaagtcc gccatgcccg aaggctacgt ccaggagcgc    1440
accatcttct tcaaggacga cggcaactac aagacccgcg ccgaggtgaa gttcgagggc    1500
gacaccctgg tgaaccgcat cgagctgaag ggcatcgact tcaaggagga cggcaacatc    1560
```

-continued

```
ctggggcaca agctggagta caactacatc agccacaacg tctatatcac cgccgacaag    1620
cagaagaacg gcatcaaggc caacttcaag atccgccaca acatcgagga cggcagcgtg    1680
cagctcgccg accactacca gcagaacacc cccatcggcg acggccccgt gctgctgccc    1740
gacaaccact acctgagcac ccagtccgcc ctgagcaaag accccaacga gaagcgcgat    1800
cacatggtcc tgctggagtt cgtgaccgcc gccgggatca ctctcggcat ggacgagctg    1860
tacaagtaa                                                             1869
```

<210> SEQ ID NO 59
<211> LENGTH: 621
<212> TYPE: PRT
<213> ORGANISM: Artificial Sequence
<220> FEATURE:
<223> OTHER INFORMATION: Description of Artificial Sequence: Synthetic fusion construct

<400> SEQUENCE: 59

```
Met Val Ser Lys Gly Glu Glu Leu Phe Thr Gly Val Val Pro Ile Leu
  1               5                  10                  15

Val Glu Leu Asp Gly Asp Val Asn Gly His Lys Phe Ser Val Ser Gly
             20                  25                  30

Glu Gly Glu Gly Asp Ala Thr Tyr Gly Lys Leu Thr Leu Lys Phe Ile
         35                  40                  45

Cys Thr Thr Gly Lys Leu Pro Val Pro Trp Pro Thr Leu Val Thr Thr
     50                  55                  60

Phe Gly Tyr Gly Leu Gln Cys Phe Ala Arg Tyr Pro Asp His Met Lys
 65                  70                  75                  80

Gln His Asp Phe Phe Lys Ser Ala Met Pro Glu Gly Tyr Val Gln Glu
                 85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys Glu
225                 230                 235                 240

Phe Met Tyr Glu Ser Phe Ile Glu Ser Leu Pro Phe Leu Lys Ser Leu
                245                 250                 255

Glu Val Ser Glu Arg Leu Lys Val Asp Val Ile Gly Thr Lys Val
            260                 265                 270

Tyr Asn Asp Gly Glu Gln Ile Ile Ala Gln Gly Asp Ser Ala Asp Ser
        275                 280                 285

Phe Phe Ile Val Glu Ser Gly Glu Val Arg Ile Thr Met Lys Arg Lys
    290                 295                 300
```

Gly Lys Ser Asp Ile Glu Glu Asn Gly Ala Val Glu Ile Ala Arg Cys
305                 310                 315                 320

Leu Arg Gly Gln Tyr Phe Gly Glu Leu Ala Leu Val Thr Asn Lys Pro
                325                 330                 335

Arg Ala Ala Ser Ala His Ala Ile Gly Thr Val Lys Cys Leu Ala Met
            340                 345                 350

Asp Val Gln Ala Phe Glu Arg Leu Leu Gly Pro Cys Met Glu Ile Met
        355                 360                 365

Lys Arg Asn Ile Ala Thr Tyr Glu Glu Gln Leu Val Ala Ser Arg Val
370                 375                 380

Ser Lys Gly Glu Glu Leu Phe Thr Gly Val Val Pro Ile Leu Val Glu
385                 390                 395                 400

Leu Asp Gly Asp Val Asn Gly His Arg Phe Ser Val Ser Gly Glu Gly
                405                 410                 415

Glu Gly Asp Ala Thr Tyr Gly Lys Leu Thr Leu Lys Phe Ile Cys Thr
            420                 425                 430

Thr Gly Lys Leu Pro Val Pro Trp Pro Thr Leu Val Thr Thr Leu Thr
        435                 440                 445

Trp Gly Val Gln Cys Phe Ser Arg Tyr Pro Asp His Met Lys Gln His
450                 455                 460

Asp Phe Phe Lys Ser Ala Met Pro Glu Gly Tyr Val Gln Glu Arg Thr
465                 470                 475                 480

Ile Phe Phe Lys Asp Asp Gly Asn Tyr Lys Thr Arg Ala Glu Val Lys
                485                 490                 495

Phe Glu Gly Asp Thr Leu Val Asn Arg Ile Glu Leu Lys Gly Ile Asp
            500                 505                 510

Phe Lys Glu Asp Gly Asn Ile Leu Gly His Lys Leu Glu Tyr Asn Tyr
        515                 520                 525

Ile Ser His Asn Val Tyr Ile Thr Ala Asp Lys Gln Lys Asn Gly Ile
530                 535                 540

Lys Ala His Phe Lys Ile Arg His Asn Ile Glu Asp Gly Ser Val Gln
545                 550                 555                 560

Leu Ala Asp His Tyr Gln Gln Asn Thr Pro Ile Gly Asp Gly Pro Val
                565                 570                 575

Leu Leu Pro Asp Asn His Tyr Leu Ser Thr Gln Ser Ala Leu Ser Lys
            580                 585                 590

Asp Pro Asn Glu Lys Arg Asp His Met Val Leu Leu Glu Phe Val Thr
        595                 600                 605

Ala Ala Gly Ile Thr Leu Gly Met Asp Glu Leu Tyr Lys
610                 615                 620

<210> SEQ ID NO 60
<211> LENGTH: 1954
<212> TYPE: DNA
<213> ORGANISM: Artificial Sequence
<220> FEATURE:
<223> OTHER INFORMATION: Description of Artificial Sequence: Synthetic
      fusion construct

<400> SEQUENCE: 60
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagtt catctgcacc accggcaagc tgcccgtgcc ctggcccacc     180
ctcgtgacca ccttcggcta cggcctgcag tgcttcgccc gctaccccga ccacatgaag     240

```
cagcacgact tcttcaagtc cgccatgccc gaaggctacg tccaggagcg caccatcttc    300
ttcaaggacg acggcaacta caagacccgc gccgaggtga agttcgaggg cgacaccctg    360
gtgaaccgca tcgagctgaa gggcatcgac ttcaaggagg acggcaacat cctggggcac    420
aagctggagt acaactacaa cagccacaac gtctatatca tggccgacaa gcagaagaac    480
ggcatcaagg tgaacttcaa gatccgccac aacatcgagg acggcagcgt gcagctcgcc    540
gaccactacc agcagaacac ccccatcggc gacggccccg tgctgctgcc cgacaaccac    600
tacctgagct accagtccgc cctgagcaaa gaccccaacg agaagcgcga tcacatggtc    660
ctgctggagt tcgtgaccgc cgccgggatc actctcggca tggacgagct gtacaaggaa    720
ttcgtaaaaa acaatgccaa aaatgtacga gagctttatt gagtcactgc cattcctcaa    780
gtctctggag gtttctgaac gcctgaaggt ggtagatgtg attggcacca agtttacaa     840 cgatggagaa cagatcattg ctcagggaga ctcggcggat tcgttcttca ttgtagaatc    900
tggagaagtg agaattacta tgaagagaaa gggtaaatca gacatcgaag agaacggtgc    960
tgtggaaatc gctcggtgtc tccggggaca gtattttgga gagcttgccc tggtcactaa   1020
caagccaaga gcagcatctg cacacgccat tgggactgtc aaatgcttag ccatggatgt   1080
gcaagcattt gagaggcttc tgggaccttg catggaaatt atgaagagga atatcgccac   1140
ctatgaggag caattagttg cactgtttgg gacaaacatg gatattgttg agcccactgc   1200
aaagctttat ccttatgatg ttcctgatta tgccatggtg agcaagggcg aggagctgtt   1260
caccggggtg gtgcccatcc tggtcgagct ggacggcgac gtaaacggcc acaagttcag   1320
cgtgtccggc gagggcgagg gcgatgccac ctacggcaag ctgaccctga agttcatctg   1380
caccaccggc aagctgcccg tgccctggcc caccctcgtg accaccctga cctggggcgt   1440
gcagtgcttc agccgctacc ccgaccacat gaagcagcac gacttcttca gtccgccat    1500 gcccgaaggc tacgtccagg agcgcaccat cttcttcaag gacgacggca actacaagac   1560
ccgcgccgag gtgaagttcg agggcgacac cctggtgaac cgcatcgagc tgaagggcat   1620
cgacttcaag gaggacggca acatcctggg gcacaagctg gagtacaact acatcagcca   1680
caacgtctat atcaccgccg acaagcagaa gaacggcatc aaggccaact tcaagatccg   1740
ccacaacatc gaggacggca gcgtgcagct cgccgaccac taccagcaga acacccccat   1800
cggcgacggc cccgtgctgc tgcccgacaa ccactacctg agcacccagt ccgccctgag   1860
caaagacccc aacgagaagc gcgatcacat ggtcctgctg gagttcgtga ccgccgccgg   1920
gatcactctc ggcatggacg agctgtacaa gtaa                               1954
```

<210> SEQ ID NO 61
<211> LENGTH: 652
<212> TYPE: PRT
<213> ORGANISM: Artificial Sequence
<220> FEATURE:
<223> OTHER INFORMATION: Description of Artificial Sequence: Synthetic
      fusion construct

<400> SEQUENCE: 61

Met Val Ser Lys Gly Glu Glu Leu Phe Thr Gly Val Val Pro Ile Leu
 1               5                  10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

-continued

```
Cys Thr Thr Gly Lys Leu Pro Val Pro Trp Pro Thr Leu Val Thr Thr
         50                  55                  60
Phe Gly Tyr Gly Leu Gln Cys Phe Ala Arg Tyr Pro Asp His Met Lys
 65                  70                  75                  80
Gln His Asp Phe Phe Lys Ser Ala Met Pro Glu Gly Tyr Val Gln Glu
                 85                  90                  95
Arg Thr Ile Phe Phe Lys Asp Asp Gly Asn Tyr Lys Thr Arg Ala Glu
            100                 105                 110
Val Lys Phe Glu Gly Asp Thr Leu Val Asn Arg Ile Glu Leu Lys Gly
            115                 120                 125
Ile Asp Phe Lys Glu Asp Gly Asn Ile Leu Gly His Lys Leu Glu Tyr
130                 135                 140
Asn Tyr Asn Ser His Asn Val Tyr Ile Met Ala Asp Lys Gln Lys Asn
145                 150                 155                 160
Gly Ile Lys Val Asn Phe Lys Ile Arg His Asn Ile Glu Asp Gly Ser
                165                 170                 175
Val Gln Leu Ala Asp His Tyr Gln Gln Asn Thr Pro Ile Gly Asp Gly
            180                 185                 190
Pro Val Leu Leu Pro Asp Asn His Tyr Leu Ser Tyr Gln Ser Ala Leu
            195                 200                 205
Ser Lys Asp Pro Asn Glu Lys Arg Asp His Met Val Leu Leu Glu Phe
210                 215                 220
Val Thr Ala Ala Gly Ile Thr Leu Gly Met Asp Glu Leu Tyr Lys Glu
225                 230                 235                 240
Phe Val Lys Asn Asn Ala Lys Lys Arg Lys Met Tyr Glu Ser Phe Ile
                245                 250                 255
Glu Ser Leu Pro Phe Leu Lys Ser Leu Glu Val Ser Glu Arg Leu Lys
            260                 265                 270
Val Val Asp Val Ile Gly Thr Lys Val Tyr Asn Asp Gly Glu Gln Ile
            275                 280                 285
Ile Ala Gln Gly Asp Ser Ala Asp Ser Phe Phe Ile Val Glu Ser Gly
290                 295                 300
Glu Val Arg Ile Thr Met Lys Arg Lys Gly Lys Ser Asp Ile Glu Glu
305                 310                 315                 320
Asn Gly Ala Val Glu Ile Ala Arg Cys Leu Arg Gly Gln Tyr Phe Gly
                325                 330                 335
Glu Leu Ala Leu Val Thr Asn Lys Pro Arg Ala Ala Ser Ala His Ala
            340                 345                 350
Ile Gly Thr Val Lys Cys Leu Ala Met Asp Val Gln Ala Phe Glu Arg
            355                 360                 365
Leu Leu Gly Pro Cys Met Glu Ile Met Lys Arg Asn Ile Ala Thr Tyr
370                 375                 380
Glu Glu Gln Leu Val Ala Leu Phe Gly Thr Asn Met Asp Ile Val Glu
385                 390                 395                 400
Pro Thr Ala Lys Leu Tyr Pro Tyr Asp Val Pro Asp Tyr Ala Met Val
                405                 410                 415
Ser Lys Gly Glu Glu Leu Phe Thr Gly Val Val Pro Ile Leu Val Glu
            420                 425                 430
Leu Asp Gly Asp Val Asn Gly His Arg Phe Ser Val Ser Gly Glu Gly
            435                 440                 445
Glu Gly Asp Ala Thr Tyr Gly Lys Leu Thr Leu Lys Phe Ile Cys Thr
450                 455                 460
Thr Gly Lys Leu Pro Val Pro Trp Pro Thr Leu Val Thr Thr Leu Thr
```

```
                  465                 470                 475                 480
            Trp Gly Val Gln Cys Phe Ser Arg Tyr Pro Asp His Met Lys Gln His
                                485                 490                 495
            Asp Phe Phe Lys Ser Ala Met Pro Glu Gly Tyr Val Gln Glu Arg Thr
                            500                 505                 510
            Ile Phe Phe Lys Asp Asp Gly Asn Tyr Lys Thr Arg Ala Glu Val Lys
                        515                 520                 525
            Phe Glu Gly Asp Thr Leu Val Asn Arg Ile Glu Lys Gly Ile Asp Phe
                    530                 535                 540
            Lys Glu Asp Gly Asn Ile Leu Gly His Lys Leu Glu Tyr Asn Tyr Ile
            545                 550                 555                 560
            Ser His Asn Val Tyr Ile Thr Ala Asp Lys Gln Lys Asn Gly Ile Lys
                                565                 570                 575
            Ala His Phe Lys Ile Arg His Asn Ile Glu Asp Gly Ser Val Gln Leu
                            580                 585                 590
            Ala Asp His Tyr Gln Gln Asn Thr Pro Ile Gly Asp Gly Pro Val Leu
                        595                 600                 605
            Leu Pro Asp Asn His Tyr Leu Ser Thr Gln Ser Ala Leu Ser Lys Asp
                    610                 615                 620
            Pro Asn Glu Lys Arg Asp His Met Val Leu Leu Glu Phe Val Thr Ala
            625                 630                 635                 640
            Ala Gly Ile Thr Leu Gly Met Asp Glu Leu Tyr Lys
                                645                 650

<210> SEQ ID NO 62
<211> LENGTH: 1935
<212> TYPE: DNA
<213> ORGANISM: Artificial Sequence
<220> FEATURE:
<223> OTHER INFORMATION: Description of Artificial Sequence: Synthetic
      fusion construct

<400> SEQUENCE: 62
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagtt catctgcacc accggcaagc tgcccgtgcc ctggcccacc     180
ctcgtgacca ccttcggcta cggcctgcag tgcttcgccc gctaccccga ccacatgaag     240
cagcacgact tcttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggagg acggcaacat cctggggcac     420
aagctggagt acaactacaa cagccacaac gtctatatca tggccgacaa gcagaagaac     480
ggcatcaagg tgaacttcaa gatccgccac aacatcgagg acggcagcgt gcagctcgcc     540
gaccactacc agcagaacac ccccatcggc gacggccccg tgctgctgcc cgacaaccac     600
tacctgagct accagtccgc cctgagcaaa gaccccaacg agaagcgcga tcacatggtc     660
ctgctggagt tcgtgaccgc cgccgggatc actctcggca tggacgagct gtacaaggaa     720
ttcatgtacg agagctttat tgagtcactg ccattcctca gtctctggag gtttctgaa      780 cgcctgaagg tggtagatgt gattggcacc aaagtttaca cgatggaga acagatcatt     840 gctcagggag actcggcgga ttcgttcttc attgtagaat ctggagaagt gagaattact     900
atgaagagaa agggtaaatc agacatcgaa gagaacggtg ctgtggaaat cgctcggtgt     960
ctccggggac agtattttgg agagcttgcc ctggtcacta caagccaag agcagcatct    1020
```

```
gcacacgcca ttgggactgt caaatgctta gccatggatg tgcaagcatt tgagaggctt   1080
ctgggacctt gcatggaaat tatgaagagg aatatcgcca cctatgagga gcaattagtt   1140
gcactgtttg gacaaacat ggatattgtt gagcccactg caaagcttta tccttatgat   1200
gttcctgatt atgccatggt gagcaagggc gaggagctgt tcaccggggt ggtgcccatc   1260
ctggtcgagc tggacggcga cgtaaacggc cacaagttca gcgtgtccgg cgagggcgag   1320
ggcgatgcca cctacggcaa gctgaccctg aagttcatct gcaccaccgg caagctgccc   1380
gtgccctggc ccaccctcgt gaccaccctg acctggggcg tgcagtgctt cagccgctac   1440
cccgaccaca tgaagcagca cgacttcttc aagtccgcca tgcccgaagg ctacgtccag   1500
gagcgcacca tcttcttcaa ggacgacggc aactacaaga cccgcgccga ggtgaagttc   1560
gagggcgaca ccctggtgaa ccgcatcgag ctgaagggca tcgacttcaa ggaggacggc   1620
aacatcctgg ggcacaagct ggagtacaac tacatcagcc acaacgtcta tatcaccgcc   1680
gacaagcaga agaacggcat caaggccaac ttcaagatcc gccacaacat cgaggacggc   1740
agcgtgcagc tcgccgacca ctaccagcag aacacccca tcggcgacgg ccccgtgctg   1800
ctgcccgaca accactacct gagcacccag tccgccctga gcaaagaccc caacgagaag   1860
cgcgatcaca tggtcctgct ggagttcgtg accgccgccg ggatcactct cggcatggac   1920
gagctgtaca agtaa                                                    1935

<210> SEQ ID NO 63
<211> LENGTH: 643
<212> TYPE: PRT
<213> ORGANISM: Artificial Sequence
<220> FEATURE:
<223> OTHER INFORMATION: Description of Artificial Sequence: Synthetic
      fusion construct

<400> SEQUENCE: 63

Met Val Ser Lys Gly Glu Glu Leu Phe Thr Gly Val Val Pro Ile Leu
  1               5                  10                  15

Val Glu Leu Asp Gly Asp Val Asn Gly His Lys Phe Ser Val Ser Gly
             20                  25                  30

Glu Gly Glu Gly Asp Ala Thr Tyr Gly Lys Leu Thr Leu Lys Phe Ile
         35                  40                  45

Cys Thr Thr Gly Lys Leu Pro Val Pro Trp Pro Thr Leu Val Thr Thr
     50                  55                  60

Phe Gly Tyr Gly Leu Gln Cys Phe Ala Arg Tyr Pro Asp His Met Lys
 65                  70                  75                  80

Gln His Asp Phe Phe Lys Ser Ala Met Pro Glu Gly Tyr Val Gln Glu
                 85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190
```

```
Pro Val Leu Leu Pro Asp Asn His Tyr Leu Ser Tyr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys Glu
225                 230                 235                 240

Phe Met Tyr Glu Ser Phe Ile Glu Ser Leu Pro Phe Leu Lys Ser Leu
                245                 250                 255

Glu Val Ser Glu Arg Leu Lys Val Val Asp Val Ile Gly Thr Lys Val
                260                 265                 270

Tyr Asn Asp Gly Glu Gln Ile Ile Ala Gln Gly Asp Ser Ala Asp Ser
            275                 280                 285

Phe Phe Ile Val Glu Ser Gly Glu Val Arg Ile Thr Met Lys Arg Lys
        290                 295                 300

Gly Lys Ser Asp Ile Glu Glu Asn Gly Ala Val Glu Ile Ala Arg Cys
305                 310                 315                 320

Leu Arg Gly Gln Tyr Phe Gly Glu Leu Ala Leu Val Thr Asn Lys Pro
                325                 330                 335

Arg Ala Ala Ser Ala His Ala Ile Gly Thr Val Lys Cys Leu Ala Met
            340                 345                 350

Asp Val Gln Ala Phe Glu Arg Leu Leu Gly Pro Cys Met Glu Ile Met
        355                 360                 365

Lys Arg Asn Ile Ala Thr Tyr Glu Glu Gln Leu Val Ala Leu Phe Gly
    370                 375                 380

Thr Asn Met Asp Ile Val Glu Pro Thr Ala Lys Leu Tyr Pro Tyr Asp
385                 390                 395                 400

Val Pro Asp Tyr Ala Met Val Ser Lys Gly Glu Glu Leu Phe Thr Gly
                405                 410                 415

Val Val Pro Ile Leu Val Glu Leu Asp Gly Asp Val Asn Gly His Arg
            420                 425                 430

Phe Ser Val Ser Gly Glu Gly Glu Gly Asp Ala Thr Tyr Gly Lys Leu
        435                 440                 445

Thr Leu Lys Phe Ile Cys Thr Thr Gly Lys Leu Pro Val Pro Trp Pro
    450                 455                 460

Thr Leu Val Thr Thr Leu Thr Trp Gly Val Gln Cys Phe Ser Arg Tyr
465                 470                 475                 480

Pro Asp His Met Lys Gln His Asp Phe Phe Lys Ser Ala Met Pro Glu
                485                 490                 495

Gly Tyr Val Gln Glu Arg Thr Ile Phe Phe Lys Asp Asp Gly Asn Tyr
            500                 505                 510

Lys Thr Arg Ala Glu Val Lys Phe Glu Gly Asp Thr Leu Val Asn Arg
        515                 520                 525

Ile Glu Lys Gly Ile Asp Phe Lys Glu Asp Gly Asn Ile Leu Gly His
    530                 535                 540

Lys Leu Glu Tyr Asn Tyr Ile Ser His Asn Val Tyr Ile Thr Ala Asp
545                 550                 555                 560

Lys Gln Lys Asn Gly Ile Lys Ala His Phe Lys Ile Arg His Asn Ile
                565                 570                 575

Glu Asp Gly Ser Val Gln Leu Ala Asp His Tyr Gln Gln Asn Thr Pro
            580                 585                 590

Ile Gly Asp Gly Pro Val Leu Leu Pro Asp Asn His Tyr Leu Ser Thr
        595                 600                 605
```

Gln Ser Ala Leu Ser Lys Asp Pro Asn Glu Lys Arg Asp His Met Val
610                 615                 620

Leu Leu Glu Phe Val Thr Ala Ala Gly Ile Thr Leu Gly Met Asp Glu
625                 630                 635                 640

Leu Tyr Lys

<210> SEQ ID NO 64
<211> LENGTH: 1902
<212> TYPE: DNA
<213> ORGANISM: Artificial Sequence
<220> FEATURE:
<223> OTHER INFORMATION: Description of Artificial Sequence: Synthetic fusion construct

<400> SEQUENCE: 64

| | | | | | |
|---|---|---|---|---|---|
| atggtaaaaa | acaatgccaa | aaagaggaag | atgtacgaga | gctttattga | gtcactgcca | 60 |
| ttcctcaagt | ctctggaggt | ttctgaacgc | ctgaaggtgg | tagatgtgat | tggcaccaaa | 120 |
| gtttacaacg | atggagaaca | gatcattgct | cagggagact | cggcggattc | gttcttcatt | 180 |
| gtagaatctg | gagaagtgag | aattactatg | aagagaaagg | gtaaatcaga | catcgctagc | 240 |
| atggtgagca | agggcgagga | gctgttcacc | ggggtggtgc | ccatcctggt | cgagctggac | 300 |
| ggcgacgtaa | acggccacaa | gttcagcgtg | tccggcgagg | gcgagggcga | tgccacctac | 360 |
| ggcaagctga | ccctgaagtt | catctgcacc | accggcaagc | tgcccgtgcc | ctggcccacc | 420 |
| ctcgtgacca | ccttcggcta | cggcctgcag | tgcttcgccc | gctaccccga | ccacatgaag | 480 |
| cagcacgact | tcttcaagtc | cgccatgccc | gaaggctacg | tccaggagcg | caccatcttc | 540 |
| ttcaaggacg | acggcaacta | caagacccgc | gccgaggtga | agttcgaggg | cgacaccctg | 600 |
| gtgaaccgca | tcgagctgaa | gggcatcgac | ttcaaggagg | acggcaacat | cctggggcac | 660 |
| aagctggagt | acaactacaa | cagccacaac | gtctatatca | tggccgacaa | gcagaagaac | 720 |
| ggcatcaagg | tgaacttcaa | gatccgccac | aacatcgagg | acggcagcgt | gcagctcgcc | 780 |
| gaccactacc | agcagaacac | ccccatcggc | gacggccccg | tgctgctgcc | cgacaaccac | 840 |
| tacctgagct | accagtccgc | cctgagcaaa | gaccccaacg | agaagcgcga | tcacatggtc | 900 |
| ctgctggagt | tcgtgaccgc | cgccgggatc | actctcggca | tggacgagct | gtacaaggaa | 960 |
| ttcgagaacg | tgctgtggaa | atcgctcgg | tgtctccggg | gacagtattt | tggagagctt | 1020 |
| gccctggtca | ctaacaagcc | aagagcagca | tctgcacacg | ccattgggac | tgtcaaatgc | 1080 |
| ttagccatgg | atgtgcaagc | atttgagagg | cttctgggac | cttgcatgga | aattatgaag | 1140 |
| aggaatatcg | ccacctatga | ggagcaatta | gttgcatcta | gaatggtgag | caagggcgag | 1200 |
| gagctgttca | ccggggtggt | gcccatcctg | gtcgagctgg | acggcgacgt | aaacggccac | 1260 |
| aagttcagcg | tgtccggcga | gggcgagggc | gatgccacct | acggcaagct | gaccctgaag | 1320 |
| ttcatctgca | ccaccggcaa | gctgcccgtg | ccctggccca | ccctcgtgac | caccctgacc | 1380 |
| tggggcgtgc | agtgcttcag | ccgctacccc | gaccacatga | agcagcacga | cttcttcaag | 1440 |
| tccgccatgc | ccgaaggcta | cgtccaggag | cgcaccatct | tcttcaagga | cgacggcaac | 1500 |
| tacaagaccc | gcgccgaggt | gaagttcgag | ggcgacaccc | tggtgaaccg | catcgagctg | 1560 |
| aagggcatcg | acttcaagga | ggacggcaac | atcctggggc | acaagctgga | gtacaactac | 1620 |
| atcagccaca | acgtctatat | caccgccgac | aagcagaaga | acggcatcaa | ggccaacttc | 1680 |
| aagatccgcc | acaacatcga | ggacggcagc | gtgcagctcg | ccgaccacta | ccagcagaac | 1740 |
| acccccatcg | gcgacggccc | cgtgctgctg | cccgacaacc | actacctgag | cacccagtcc | 1800 |

-continued

```
gccctgagca aagaccccaa cgagaagcgc gatcacatgg tcctgctgga gttcgtgacc    1860
gccgccggga tcactctcgg catggacgag ctgtacaagt aa                      1902
```

<210> SEQ ID NO 65
<211> LENGTH: 631
<212> TYPE: PRT
<213> ORGANISM: Artificial Sequence
<220> FEATURE:
<223> OTHER INFORMATION: Description of Artificial Sequence: Synthetic
      fusion construct

<400> SEQUENCE: 65

```
Met Val Lys Asn Asn Ala Lys Lys Arg Lys Met Tyr Glu Ser Phe Ile
 1               5                  10                  15

Glu Ser Leu Pro Phe Leu Lys Ser Leu Glu Val Ser Glu Arg Leu Lys
             20                  25                  30

Val Val Asp Val Ile Gly Thr Lys Val Tyr Asn Asp Gly Glu Gln Ile
         35                  40                  45

Ile Ala Gln Gly Asp Ser Ala Asp Ser Phe Phe Ile Val Glu Ser Gly
     50                  55                  60

Glu Val Arg Ile Thr Met Lys Arg Lys Gly Lys Ser Asp Ile Ala Ser
 65                  70                  75                  80

Val Ser Lys Gly Glu Glu Leu Phe Thr Gly Val Val Pro Ile Leu Val
                 85                  90                  95

Glu Leu Asp Gly Asp Val Asn Gly His Lys Phe Ser Val Ser Gly Glu
            100                 105                 110

Gly Glu Gly Asp Ala Thr Tyr Gly Lys Leu Thr Leu Lys Phe Ile Cys
        115                 120                 125

Thr Thr Gly Lys Leu Pro Val Pro Trp Pro Thr Leu Val Thr Thr Phe
    130                 135                 140

Gly Tyr Gly Leu Gln Cys Phe Ala Arg Tyr Pro Asp His Met Lys Gln
145                 150                 155                 160

His Asp Phe Phe Lys Ser Ala Met Pro Glu Gly Tyr Val Gln Glu Arg
                165                 170                 175

Thr Ile Phe Phe Lys Asp Asp Gly Asn Tyr Lys Thr Arg Ala Glu Val
            180                 185                 190

Lys Phe Glu Gly Asp Thr Leu Val Asn Arg Ile Glu Leu Lys Gly Ile
        195                 200                 205

Asp Phe Lys Glu Asp Gly Asn Ile Leu Gly His Lys Leu Glu Tyr Asn
    210                 215                 220

Tyr Asn Ser His Asn Val Tyr Ile Met Ala Asp Lys Gln Lys Asn Gly
225                 230                 235                 240

Ile Lys Val Asn Phe Lys Ile Arg His Asn Ile Glu Asp Gly Ser Val
                245                 250                 255

Gln Leu Ala Asp His Tyr Gln Gln Asn Thr Pro Ile Gly Asp Gly Pro
            260                 265                 270

Val Leu Leu Pro Asp Asn His Tyr Leu Ser Tyr Gln Ser Ala Leu Ser
        275                 280                 285

Lys Asp Pro Asn Glu Lys Arg Asp His Met Val Leu Leu Glu Phe Val
    290                 295                 300

Thr Ala Ala Gly Ile Thr Leu Gly Met Asp Glu Leu Tyr Lys Glu Phe
305                 310                 315                 320

Glu Asn Gly Ala Val Glu Ile Ala Arg Cys Leu Arg Gly Gln Tyr Phe
                325                 330                 335

Gly Glu Leu Ala Leu Val Thr Asn Lys Pro Arg Ala Ala Ser Ala His
```

```
                 340                 345                 350
Ala Ile Gly Thr Val Lys Cys Leu Ala Met Asp Val Gln Ala Phe Glu
            355                 360                 365

Arg Leu Leu Gly Pro Cys Met Glu Ile Met Lys Arg Asn Ile Ala Thr
        370                 375                 380

Tyr Glu Glu Gln Leu Val Ala Ser Arg Val Ser Lys Gly Glu Glu Leu
385                 390                 395                 400

Phe Thr Gly Val Val Pro Ile Leu Val Glu Leu Asp Gly Asp Val Asn
                405                 410                 415

Gly His Arg Phe Ser Val Ser Gly Glu Gly Glu Gly Asp Ala Thr Tyr
            420                 425                 430

Gly Lys Leu Thr Leu Lys Phe Ile Cys Thr Thr Gly Lys Leu Pro Val
        435                 440                 445

Pro Trp Pro Thr Leu Val Thr Thr Leu Thr Trp Gly Val Gln Cys Phe
    450                 455                 460

Ser Arg Tyr Pro Asp His Met Lys Gln His Asp Phe Phe Lys Ser Ala
465                 470                 475                 480

Met Pro Glu Gly Tyr Val Gln Glu Arg Thr Ile Phe Phe Lys Asp Asp
                485                 490                 495

Gly Asn Tyr Lys Thr Arg Ala Glu Val Lys Phe Glu Gly Asp Thr Leu
            500                 505                 510

Val Asn Arg Ile Glu Leu Lys Gly Ile Asp Phe Lys Glu Asp Gly Asn
        515                 520                 525

Ile Leu Gly His Lys Leu Glu Tyr Asn Tyr Ile Ser His Asn Val Tyr
    530                 535                 540

Ile Thr Ala Asp Lys Gln Lys Asn Gly Ile Lys Ala His Phe Lys Ile
545                 550                 555                 560

Arg His Asn Ile Glu Asp Gly Ser Val Gln Leu Ala Asp His Tyr Gln
                565                 570                 575

Gln Asn Thr Pro Ile Gly Asp Gly Pro Val Leu Leu Pro Asp Asn His
            580                 585                 590

Tyr Leu Ser Thr Gln Ser Ala Leu Ser Lys Asp Pro Asn Glu Lys Arg
        595                 600                 605

Asp His Met Val Leu Leu Glu Phe Val Thr Ala Ala Gly Ile Thr Leu
    610                 615                 620

Gly Met Asp Glu Leu Tyr Lys
625                 630

<210> SEQ ID NO 66
<211> LENGTH: 1965
<212> TYPE: DNA
<213> ORGANISM: Artificial Sequence
<220> FEATURE:
<223> OTHER INFORMATION: Description of Artificial Sequence: Synthetic
      fusion construct

<400> SEQUENCE: 66
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagtt catctgcacc accggcaagc tgcccgtgcc ctggcccacc     180
ctcgtgacca ccttcggcta cggcctgcag tgcttcgccc gctaccccga ccacatgaag     240
cagcacgact tcttcaagtc cgccatgccc gaaggctacg tccaggagcg caccatcttc     300
ttcaaggacg acggcaacta caagacccgc gccgaggtga agttcgaggg cgacaccctg     360
```

```
gtgaaccgca tcgagctgaa gggcatcgac ttcaaggagg acggcaacat cctggggcac    420
aagctggagt acaactacaa cagccacaac gtctatatca tggccgacaa gcagaagaac    480
ggcatcaagg tgaacttcaa gatccgccac aacatcgagg acggcagcgt gcagctcgcc    540
gaccactacc agcagaacac ccccatcggc gacggccccg tgctgctgcc cgacaaccac    600
tacctgagct accagtccgc cctgagcaaa gaccccaacg agaagcgcga tcacatggtc    660
ctgctggagt tcgtgaccgc cgccgggatc actctcggca tggacgagct gtacaaggaa    720
ttcgctgact tccgccagaa gatccacgat tactatgaac accggtacca agggaagatg    780
tttgatgagg acagcatcct tggggaactc aacgggccac tcgtgaggga gattgtgaac    840
ttcaactgcc ggaagctggt ggcttccatg ccgctgtttg ccaatgcaga ccccaacttc    900
gtcacagcca tgctgacaaa gctcaaattt gaggtcttcc agcctggaga ttacatcatc    960
cgagagggga ccatcgggaa gaagatgtac ttcatccagc atgggggtggt gagcgtgctc   1020 accaagggca caaggagat gaagctgtcg gatggctcct atttcgggga gatctgcttg    1080
ctcacgaggg gccggcgtac ggccagcgtg cgagctgaca cctactgtcg cctctactca    1140
ctgagtgtgg acaatttcaa cgaggtgctg gaggaatacc ccatgatgcg gcgtgcctttt   1200 gagactgtgc tattgaccg gctagatcgc ataggcaagt ctagaatggt gagcaagggc     1260
gaggagctgt tcaccggggt ggtgcccatc ctggtcgagc tggacggcga cgtaaacggc    1320
cacaagttca gcgtgtccgg cgagggcgag ggcgatgcca cctacggcaa gctgaccctg    1380
aagttcatct gcaccaccgg caagctgccc gtgccctggc ccaccctcgt gaccaccctg    1440
acctggggcg tgcagtgctt cagccgctac cccgaccaca tgaagcagca cgacttcttc    1500
aagtccgcca tgcccgaagg ctacgtccag gagcgcacca tcttcttcaa ggacgacggc    1560
aactacaaga cccgcgccga ggtgaagttc gagggcgaca ccctggtgaa ccgcatcgag    1620
ctgaagggca tcgacttcaa ggaggacggc aacatcctgg gcacaagct ggagtacaac     1680 tacatcagcc acaacgtcta tatcaccgcc gacaagcaga gaacggcat caaggccaac     1740 ttcaagatcc gccacaacat cgaggacggc agcgtgcagc tcgccgacca ctaccagcag    1800
aacaccccca tcggcgacgg ccccgtgctg ctgcccgaca ccactacct gagcacccag     1860 tccgccctga gcaaagaccc caacgagaag cgcgatcaca tggtcctgct ggagttcgtg    1920
accgccgccg ggatcactct cggcatggac gagctgtaca agtaa                   1965
```

```
<210> SEQ ID NO 67
<211> LENGTH: 653
<212> TYPE: PRT
<213> ORGANISM: Artificial Sequence
<220> FEATURE:
<223> OTHER INFORMATION: Description of Artificial Sequence: Synthetic
      fusion construct

<400> SEQUENCE: 67
```

Met Val Ser Lys Gly Glu Glu Leu Phe Thr Gly Val Val Pro Ile Leu
  1               5                  10                  15

Val Glu Leu Asp Gly Asp Val Asn Gly His Lys Phe Ser Val Ser Gly
             20                  25                  30

Glu Gly Glu Gly Asp Ala Thr Tyr Gly Lys Leu Thr Leu Lys Phe Ile
         35                  40                  45

Cys Thr Thr Gly Lys Leu Pro Val Pro Trp Pro Thr Leu Val Thr Thr
     50                  55                  60

Phe Gly Tyr Gly Leu Gln Cys Phe Ala Arg Tyr Pro Asp His Met Lys
 65                  70                  75                  80

```
Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys Glu
225                 230                 235                 240

Phe Ala Asp Phe Arg Gln Lys Ile His Asp Tyr Tyr Glu His Arg Tyr
                245                 250                 255

Gln Gly Lys Met Phe Asp Glu Asp Ser Ile Leu Gly Glu Leu Asn Gly
            260                 265                 270

Pro Leu Arg Glu Glu Ile Val Asn Phe Asn Cys Arg Lys Leu Val Ala
        275                 280                 285

Ser Met Pro Leu Phe Ala Asn Ala Asp Pro Asn Phe Val Thr Ala Met
    290                 295                 300

Leu Thr Lys Leu Lys Phe Glu Val Phe Gln Pro Gly Asp Tyr Ile Ile
305                 310                 315                 320

Arg Glu Gly Thr Ile Gly Lys Lys Met Tyr Phe Ile Gln His Gly Val
                325                 330                 335

Val Ser Val Leu Thr Lys Gly Asn Lys Glu Met Lys Leu Ser Asp Gly
            340                 345                 350

Ser Tyr Phe Gly Glu Ile Cys Leu Leu Thr Arg Gly Arg Arg Thr Ala
        355                 360                 365

Ser Val Arg Ala Asp Thr Tyr Cys Arg Leu Tyr Ser Leu Ser Val Asp
    370                 375                 380

Asn Phe Asn Glu Val Leu Glu Glu Tyr Pro Met Met Arg Arg Ala Phe
385                 390                 395                 400

Glu Thr Val Ala Ile Asp Arg Leu Asp Arg Ile Gly Lys Ser Arg Val
                405                 410                 415

Ser Lys Gly Glu Glu Leu Phe Thr Gly Val Val Pro Ile Leu Val Glu
            420                 425                 430

Leu Asp Gly Asp Val Asn Gly His Arg Phe Ser Val Ser Gly Glu Gly
        435                 440                 445

Glu Gly Asp Ala Thr Tyr Gly Lys Leu Thr Leu Lys Phe Ile Cys Thr
    450                 455                 460

Thr Gly Lys Leu Pro Val Pro Trp Pro Thr Leu Val Thr Thr Leu Thr
465                 470                 475                 480

Trp Gly Val Gln Cys Phe Ser Arg Tyr Pro Asp His Met Lys Gln His
                485                 490                 495
```

```
Asp Phe Phe Lys Ser Ala Met Pro Glu Gly Tyr Val Gln Glu Arg Thr
                500                 505                 510

Ile Phe Phe Lys Asp Asp Gly Asn Tyr Lys Thr Arg Ala Glu Val Lys
            515                 520                 525

Phe Glu Gly Asp Thr Leu Val Asn Arg Ile Glu Leu Lys Gly Ile Asp
        530                 535                 540

Phe Lys Glu Asp Gly Asn Ile Leu Gly His Lys Leu Glu Tyr Asn Tyr
545                 550                 555                 560

Ile Ser His Asn Val Tyr Ile Thr Ala Asp Lys Gln Lys Asn Gly Ile
                565                 570                 575

Lys Ala His Phe Lys Ile Arg His Asn Ile Glu Asp Gly Ser Val Gln
            580                 585                 590

Leu Ala Asp His Tyr Gln Gln Asn Thr Pro Ile Gly Asp Gly Pro Val
        595                 600                 605

Leu Leu Pro Asp Asn His Tyr Leu Ser Thr Gln Ser Ala Leu Ser Lys
    610                 615                 620

Asp Pro Asn Glu Lys Arg Asp His Met Val Leu Leu Glu Phe Val Thr
625                 630                 635                 640

Ala Ala Gly Ile Thr Leu Gly Met Asp Glu Leu Tyr Lys
                645                 650
```

<210> SEQ ID NO 68
<211> LENGTH: 1875
<212> TYPE: DNA
<213> ORGANISM: Artificial Sequence
<220> FEATURE:
<223> OTHER INFORMATION: Description of Artificial Sequence: Synthetic
      fusion construct

<400> SEQUENCE: 68

```
atggtgagca agggcgagga gctgttcacc ggggtggtgc ccatcctggt cgagctggac     60
ggcgacgtaa acggccacaa gttcagcgtg tccggcgagg gcgagggcga tgccacctac    120
ggcaagctga ccctgaagtt catctgcacc accggcaagc tgcccgtgcc ctggcccacc    180
ctcgtgacca ccttcggcta cggcctgcag tgcttcgccc gctaccccga ccacatgaag    240
cagcacgact tcttcaagtc cgccatgccc gaaggctacg tccaggagcg caccatcttc    300
ttcaaggacg acggcaacta caagacccgc gccgaggtga agttcgaggg cgacaccctg    360
gtgaaccgca tcgagctgaa gggcatcgac ttcaaggagg acggcaacat cctggggcac    420
aagctggagt acaactacaa cagccacaac gtctatatca tggccgacaa gcagaagaac    480
ggcatcaagg tgaacttcaa gatccgccac aacatcgagg acggcagcgt gcagctcgcc    540
gaccactacc agcagaacac ccccatcggc gacggccccg tgctgctgcc cgacaaccac    600
tacctgagct accagtccgc cctgagcaaa gaccccaacg agaagcgcga tcacatggtc    660
ctgctggagt tcgtgaccgc cgccgggatc actctcggca tggacgagct gtacaaggaa    720
ttcgggccac tgcgtgagga gattgtgaac ttcaactgcc ggaagctggt ggcttccatg    780
ccgctgtttg ccaatgcaga ccccaacttc gtcacagcca tgctgacaaa gctcaaattt    840
gaggtcttcc agcctggaga ttacatcatc cgagagggga ccatcgggaa gaagatgtac    900
ttcatccagc atgggtggt gagcgtgctc accaagggca caaggagat gaagctgtcg    960
gatggctcct atttcgggga gatctgcttg ctcacgaggg ccggcgtac ggccagcgtg   1020
cgagctgaca cctactgtcg cctctactca ctgagtgtgg acaatttcaa cgaggtgctg   1080
gaggaatacc ccatgatgcg cgcgtgcctt gagactgtgg ctattgaccg gctagatcgc   1140
```

```
ataggcaagt ctagaatggt gagcaagggc gaggagctgt tcaccggggt ggtgcccatc    1200
ctggtcgagc tggacggcga cgtaaacggc cacaagttca gcgtgtccgg cgagggcgag    1260
ggcgatgcca cctacggcaa gctgaccctg aagttcatct gcaccaccgg caagctgccc    1320
gtgccctggc ccaccctcgt gaccaccctg acctggggcg tgcagtgctt cagccgctac    1380
cccgaccaca tgaagcagca cgacttcttc aagtccgcca tgcccgaagg ctacgtccag    1440
gagcgcacca tcttcttcaa ggacgacggc aactacaaga cccgcgccga ggtgaagttc    1500
gagggcgaca ccctggtgaa ccgcatcgag ctgaagggca tcgacttcaa ggaggacggc    1560
aacatcctgg ggcacaagct ggagtacaac tacatcagcc acaacgtcta tatcaccgcc    1620
gacaagcaga agaacggcat caaggccaac ttcaagatcc gccacaacat cgaggacggc    1680
agcgtgcagc tcgccgacca ctaccagcag aacacccca tcggcgacgg ccccgtgctg    1740
ctgcccgaca accactacct gagcacccag tccgccctga gcaaagaccc caacgagaag    1800
cgcgatcaca tggtcctgct ggagttcgtg accgccgccg ggatcactct cggcatggac    1860
gagctgtaca agtaa                                                    1875
```

<210> SEQ ID NO 69
<211> LENGTH: 623
<212> TYPE: PRT
<213> ORGANISM: Artificial Sequence
<220> FEATURE:
<223> OTHER INFORMATION: Description of Artificial Sequence: Synthetic
      fusion construct

<400> SEQUENCE: 69

```
Met Val Ser Lys Gly Glu Glu Leu Phe Thr Gly Val Val Pro Ile Leu
  1               5                  10                  15

Val Glu Leu Asp Gly Asp Val Asn Gly His Lys Phe Ser Val Ser Gly
             20                  25                  30

Glu Gly Glu Gly Asp Ala Thr Tyr Gly Lys Leu Thr Leu Lys Phe Ile
         35                  40                  45

Cys Thr Thr Gly Lys Leu Pro Val Pro Trp Pro Thr Leu Val Thr Thr
     50                  55                  60

Phe Gly Tyr Gly Leu Gln Cys Phe Ala Arg Tyr Pro Asp His Met Lys
 65                  70                  75                  80

Gln His Asp Phe Phe Lys Ser Ala Met Pro Glu Gly Tyr Val Gln Glu
                 85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Ala Leu
        195                 200                 205

Ser Lys Asp Pro Asn Glu Lys Arg Asp His Met Val Leu Leu Glu Phe
    210                 215                 220
```

Val Thr Ala Ala Gly Ile Thr Leu Gly Met Asp Glu Leu Tyr Lys Glu
225                 230                 235                 240

Phe Gly Pro Leu Arg Glu Glu Ile Val Asn Phe Asn Cys Arg Lys Leu
            245                 250                 255

Val Ala Ser Met Pro Leu Phe Ala Asn Ala Asp Pro Asn Phe Val Thr
            260                 265                 270

Ala Met Leu Thr Lys Leu Lys Phe Glu Val Phe Gln Pro Gly Asp Tyr
            275                 280                 285

Ile Ile Arg Glu Gly Thr Ile Gly Lys Lys Met Tyr Phe Ile Gln His
            290                 295                 300

Gly Val Val Ser Val Leu Thr Lys Gly Asn Lys Glu Met Lys Leu Ser
305                 310                 315                 320

Asp Gly Ser Tyr Phe Gly Glu Ile Cys Leu Leu Thr Arg Gly Arg Arg
                325                 330                 335

Thr Ala Ser Val Arg Ala Asp Thr Tyr Cys Arg Leu Tyr Ser Leu Ser
                340                 345                 350

Val Asp Asn Phe Asn Glu Val Leu Glu Glu Tyr Pro Met Met Arg Arg
            355                 360                 365

Ala Phe Glu Thr Val Ala Ile Asp Arg Leu Asp Arg Ile Gly Lys Ser
370                 375                 380

Arg Val Ser Lys Gly Glu Glu Leu Phe Thr Gly Val Val Pro Ile Leu
385                 390                 395                 400

Val Glu Leu Asp Gly Asp Val Asn Gly His Arg Phe Ser Val Ser Gly
                405                 410                 415

Glu Gly Glu Gly Asp Ala Thr Tyr Gly Lys Leu Thr Leu Lys Phe Ile
            420                 425                 430

Cys Thr Thr Gly Lys Leu Pro Val Pro Trp Pro Thr Leu Val Thr Thr
            435                 440                 445

Leu Thr Trp Gly Val Gln Cys Phe Ser Arg Tyr Pro Asp His Met Lys
    450                 455                 460

Gln His Asp Phe Phe Lys Ser Ala Met Pro Glu Gly Tyr Val Gln Glu
465                 470                 475                 480

Arg Thr Ile Phe Phe Lys Asp Asp Gly Asn Tyr Lys Thr Arg Ala Glu
                485                 490                 495

Val Lys Phe Glu Gly Asp Thr Leu Val Asn Arg Ile Glu Leu Lys Gly
            500                 505                 510

Ile Asp Phe Lys Glu Asp Gly Asn Ile Leu Gly His Lys Leu Glu Tyr
            515                 520                 525

Asn Tyr Ile Ser His Asn Val Tyr Ile Thr Ala Asp Lys Gln Lys Asn
530                 535                 540

Gly Ile Lys Ala His Phe Lys Ile Arg His Asn Ile Glu Asp Gly Ser
545                 550                 555                 560

Val Gln Leu Ala Asp His Tyr Gln Gln Asn Thr Pro Ile Gly Asp Gly
                565                 570                 575

Pro Val Leu Leu Pro Asp Asn His Tyr Leu Ser Thr Gln Ser Ala Leu
            580                 585                 590

Ser Lys Asp Pro Asn Glu Lys Arg Asp His Met Val Leu Leu Glu Phe
            595                 600                 605

Val Thr Ala Ala Gly Ile Thr Leu Gly Met Asp Glu Leu Tyr Lys
            610                 615                 620

<210> SEQ ID NO 70
<211> LENGTH: 1796
<212> TYPE: DNA

<213> ORGANISM: Artificial Sequence
<220> FEATURE:
<223> OTHER INFORMATION: Description of Artificial Sequence: Synthetic fusion construct

<400> SEQUENCE: 70

```
atggtgagca agggcgagga gctgttcacc ggggtggtgc ccatcctggt cgagctggac    60
ggcgacgtaa acggccacaa gttcagcgtg tccggcgagg gcgagggcga tgccacctac   120
ggcaagctga ccctgaagtt catctgcacc accggcaagc tgcccgtgcc ctggcccacc   180
ctcgtgacca ccttcggcta cggcctgcag tgcttcgccc gctaccccga ccacatgaag   240
cagcacgact tcttcaagtc cgccatgccc gaaggctacg tccaggagcg caccatcttc   300
ttcaaggacg acggcaacta caagacccgc gccgaggtga agttcgaggg cgacaccctg   360
gtgaaccgca tcgagctgaa gggcatcgac ttcaaggagg acggcaacat cctggggcac   420
aagctggagt acaactacaa cagccacaac gtctatatca tggccgacaa gcagaagaac   480
ggcatcaagg tgaacttcaa gatccgccac aacatcgagg acggcagcgt gcagctcgcc   540
gaccactacc agcagaacac ccccatcggc gacggccccg tgctgctgcc cgacaaccac   600
tacctgagct accagtccgc cctgagcaaa gaccccaacg agaagcgcga tcacatggtc   660
ctgctggagt tcgtgaccgc cgccgggatc actctcggca tggacgagct gtacaaggaa   720
ttcccaactt cgtcacagcc atgctgacaa agctcaaatt tgaggtcttc agcctggag    780
attacatcat ccgagagggg accatcggga agaagatgta cttcatccag catggggtgg   840
tgagcgtgct caccaaggc aacaaggaga tgaagctgtc ggatggctcc tatttcgggg    900
agatctgctt gctcacgagg ggccggcgta cggccagcgt gcgagctgac acctactgtc   960
gcctctactc actgagtgtg acaatttca cgaggtgct ggaggaatac cccatgatgc    1020
ggcgtgcctt tgagactgtg ctattgacc ggctagatcg cataggcaag tctagaatgg   1080
tgagcaaggg cgaggagctg ttcaccgggg tggtgcccat cctggtcgag ctggacggcg   1140
acgtaaacgg ccacaagttc agcgtgtccg gcgagggcga gggcgatgcc acctacggca   1200
agctgacccct gaagttcatc tgcaccaccg gcaagctgcc cgtgccctgg cccaccctcg   1260
tgaccaccct gacctgggc gtgcagtgct tcagccgcta ccccgaccac atgaagcagc   1320
acgacttctt caagtccgcc atgcccgaag gctacgtcca ggagcgcacc atcttcttca   1380
aggacgacgg caactacaag acccgcgccg aggtgaagtt cgagggcgac accctggtga   1440
accgcatcga gctgaagggc atcgacttca aggaggacgg caacatcctg ggcacaagc   1500
tggagtacaa ctacatcagc cacaacgtct atatcaccgc cgacaagcag aagaacggca   1560
tcaaggccaa cttcaagatc cgccacaaca tcgaggacgg cagcgtgcag ctcgccgacc   1620
actaccagca gaacaccccc atcggcgacg gccccgtgct gctgcccgac aaccactacc   1680
tgagcaccca gtccgccctg agcaaagacc ccaacgagaa gcgcgatcac atggtcctgc   1740
tggagttcgt gaccgccgcc gggatcactc tcggcatgga cgagctgtac aagtaa      1796
```

<210> SEQ ID NO 71
<211> LENGTH: 597
<212> TYPE: PRT
<213> ORGANISM: Artificial Sequence
<220> FEATURE:
<223> OTHER INFORMATION: Description of Artificial Sequence: Synthetic fusion construct

<400> SEQUENCE: 71

Met Val Ser Lys Gly Glu Glu Leu Phe Thr Gly Val Val Pro Ile Leu

-continued

```
  1               5               10              15
Val Glu Leu Asp Gly Asp Val Asn Gly His Lys Phe Ser Val Ser Gly
                20                  25                  30
Glu Gly Glu Gly Asp Ala Thr Tyr Gly Lys Leu Thr Leu Lys Phe Ile
                35                  40                  45
Cys Thr Thr Gly Lys Leu Pro Val Pro Trp Pro Thr Leu Val Thr Thr
                50                  55                  60
Phe Gly Tyr Gly Leu Gln Cys Phe Ala Arg Tyr Pro Asp His Met Lys
 65                  70                  75                  80
Gln His Asp Phe Phe Lys Ser Ala Met Pro Glu Gly Tyr Val Gln Glu
                85                  90                  95
Arg Thr Ile Phe Phe Lys Asp Asp Gly Asn Tyr Lys Thr Arg Ala Glu
                100                 105                 110
Val Lys Phe Glu Gly Asp Thr Leu Val Asn Arg Ile Glu Leu Lys Gly
                115                 120                 125
Ile Asp Phe Lys Glu Asp Gly Asn Ile Leu Gly His Lys Leu Glu Tyr
                130                 135                 140
Asn Tyr Asn Ser His Asn Val Tyr Ile Met Ala Asp Lys Gln Lys Asn
145                 150                 155                 160
Gly Ile Lys Val Asn Phe Lys Ile Arg His Asn Ile Glu Asp Gly Ser
                165                 170                 175
Val Gln Leu Ala Asp His Tyr Gln Gln Asn Thr Pro Ile Gly Asp Gly
                180                 185                 190
Pro Val Leu Leu Pro Asp Asn His Tyr Leu Ser Tyr Gln Ser Ala Leu
                195                 200                 205
Ser Lys Asp Pro Asn Glu Lys Arg Asp His Met Val Leu Leu Glu Phe
210                 215                 220
Val Thr Ala Ala Gly Ile Thr Leu Gly Met Asp Glu Leu Tyr Lys Glu
225                 230                 235                 240
Phe Pro Asn Phe Val Thr Ala Met Leu Thr Lys Leu Lys Phe Glu Val
                245                 250                 255
Phe Gln Pro Gly Asp Tyr Ile Ile Arg Glu Gly Thr Ile Gly Lys Lys
                260                 265                 270
Met Tyr Phe Ile Gln His Gly Val Val Ser Val Leu Thr Lys Gly Asn
                275                 280                 285
Lys Glu Met Lys Leu Ser Asp Gly Ser Tyr Phe Gly Glu Ile Cys Leu
                290                 295                 300
Leu Thr Arg Gly Arg Arg Thr Ala Ser Val Arg Ala Asp Thr Tyr Cys
305                 310                 315                 320
Arg Leu Tyr Ser Leu Ser Val Asp Asn Phe Asn Glu Val Leu Glu Glu
                325                 330                 335
Tyr Pro Met Met Arg Arg Ala Phe Glu Thr Val Ala Ile Asp Arg Leu
                340                 345                 350
Asp Arg Ile Gly Lys Ser Arg Val Ser Lys Gly Glu Glu Leu Phe Thr
                355                 360                 365
Gly Val Val Pro Ile Leu Val Glu Leu Asp Gly Asp Val Asn Gly His
                370                 375                 380
Arg Phe Ser Val Ser Gly Glu Gly Glu Gly Asp Ala Thr Tyr Gly Lys
385                 390                 395                 400
Leu Thr Leu Lys Phe Ile Cys Thr Thr Gly Lys Leu Pro Val Pro Trp
                405                 410                 415
Pro Thr Leu Val Thr Thr Leu Thr Trp Gly Val Gln Cys Phe Ser Arg
                420                 425                 430
```

Tyr Pro Asp His Met Lys Gln His Asp Phe Phe Lys Ser Ala Met Pro
            435                 440                 445

Glu Gly Tyr Val Gln Glu Arg Thr Ile Phe Phe Lys Asp Asp Gly Asn
        450                 455                 460

Tyr Lys Thr Arg Ala Glu Val Lys Phe Glu Gly Asp Thr Leu Val Asn
465                 470                 475                 480

Arg Ile Glu Leu Lys Gly Ile Asp Phe Lys Glu Asp Gly Asn Ile Leu
                485                 490                 495

Gly His Lys Leu Glu Tyr Asn Tyr Ile Ser His Asn Val Tyr Ile Thr
            500                 505                 510

Ala Asp Lys Gln Lys Asn Gly Ile Lys Ala His Phe Lys Ile Arg His
            515                 520                 525

Asn Ile Glu Asp Gly Ser Val Gln Leu Ala Asp His Tyr Gln Gln Asn
        530                 535                 540

Thr Pro Ile Gly Asp Gly Pro Val Leu Leu Pro Asp Asn His Tyr Leu
545                 550                 555                 560

Ser Thr Gln Ser Ala Leu Ser Lys Asp Pro Asn Glu Lys Arg Asp His
                565                 570                 575

Met Val Leu Leu Glu Phe Val Thr Ala Ala Gly Ile Thr Leu Gly Met
            580                 585                 590

Asp Glu Leu Tyr Lys
        595

<210> SEQ ID NO 72
<211> LENGTH: 1896
<212> TYPE: DNA
<213> ORGANISM: Mus musculus

<400> SEQUENCE: 72
atggtaaaaa acaatgccaa aaagaggaag atgtacgaga gctttattga gtcactgcca      60
ttcctcaagt ctctggaggt ttctgaacgc ctgaaggtgg tagatgtgat tggcaccaaa     120
gtttacaacg atggagaaca gatcattgct cagggagact cggcggattc gttcttcatt     180
gtagaatctg gagaagtgag aattactatg aagagaaagg gtaaatcaga catcgctagc     240
gtgagcaagg gcgaggagct gttcaccggg gtggtgccca tcctggtcga gctggacggc     300
gacgtaaacg gccacaagtt cagcgtgtcc ggcgagggcg agggcgatgc cacctacggc     360
aagctgaccc tgaagttcat ctgcaccacc ggcaagctgc ccgtgccctg gcccaccctc     420
gtgaccaccc tcggctacgg cctgcagtgc ttcgcccgct accccgacca catgaagcag     480
cacgacttct tcaagtccgc catgcccgaa ggctacgtcc aggagcgcac catcttcttc     540
aaggacgacg gcaactacaa gacccgcgcc gaggtgaagt tcgagggcga caccctggtg     600
aaccgcatcg agctgaaggg catcgacttc aaggaggacg gcaacatcct ggggcacaag     660
ctggagtaca actacaacag ccacaacgtc tatatcatgg ccgacaagca gaagaacggc     720
atcaaggtga acttcaagat ccgccacaac atcgaggacg gcagcgtgca gctcgccgac     780
cactaccagc agaacacccc catcggcgac ggccccgtgc tgctgcccga caaccactac     840
ctgagctacc agtccgccct gagcaaagac cccaacgaga gcgcgatca catggtcctg     900 ctggagttcg tgaccgccgc cgggatcact ctcggcatgg acgagctgta caaggaattc     960
gagaacggtg ctgtggaaat cgctcggtgt ctccggggac agtatttggg agagcttgcc    1020
ctggtcacta caagccaag agcagcatct gcacacgcca ttgggactgt caatgcttta    1080
gccatggatg tgcaagcatt tgagaggctt ctgggacctt gcatggaaat tatgaagagg    1140

```
aatatcgcca cctatgagga gcaattagtt gcatctagag tgagcaaggg cgaggagctg   1200
ttcaccgggg tggtgcccat cctggtcgag ctggacggcg acgtaaacgg ccacaagttc   1260
agcgtgtccg gcgagggcga gggcgatgcc acctacggca agctgaccct gaagttcatc   1320
tgcaccaccg gcaagctgcc cgtgccctgg cccaccctcg tgaccaccct gacctggggc   1380
gtgcagtgct tcagccgcta ccccgaccac atgaagcagc acgacttctt caagtccgcc   1440
atgcccgaag ctacgtcca ggagcgcacc atcttcttca aggacgacgg caactacaag   1500
acccgcgccg aggtgaagtt cgagggcgac accctggtga accgcatcga gctgaagggc   1560
atcgacttca aggaggacgg caacatcctg gggcacaagc tggagtacaa ctacatcagc   1620
cacaacgtct atatcaccgc cgacaagcag aagaacggca tcaaggccaa cttcaagatc   1680
cgccacaaca tcgaggacgg cagcgtgcag ctcgccgacc actaccagca gaacaccccc   1740
atcggcgacg gccccgtgct gctgcccgac aaccactacc tgagcaccca gtccgccctg   1800
agcaaagacc ccaacgagaa gcgcgatcac atggtcctgc tggagttcgt gaccgccgcc   1860
gggatcactc tcggcatgga cgagctgtac aagtaa                             1896
```

<210> SEQ ID NO 73
<211> LENGTH: 631
<212> TYPE: PRT
<213> ORGANISM: Mus musculus

<400> SEQUENCE: 73

```
Met Val Lys Asn Asn Ala Lys Lys Arg Lys Met Tyr Glu Ser Phe Ile
  1               5                  10                  15

Glu Ser Leu Pro Phe Leu Lys Ser Leu Glu Val Ser Glu Arg Leu Lys
                 20                  25                  30

Val Val Asp Val Ile Gly Thr Lys Val Tyr Asn Asp Gly Glu Gln Ile
             35                  40                  45

Ile Ala Gln Gly Asp Ser Ala Asp Ser Phe Phe Ile Val Glu Ser Gly
         50                  55                  60

Glu Val Arg Ile Thr Met Lys Arg Lys Gly Lys Ser Asp Ile Ala Ser
 65                  70                  75                  80

Val Ser Lys Gly Glu Glu Leu Phe Thr Gly Val Val Pro Ile Leu Val
                 85                  90                  95

Glu Leu Asp Gly Asp Val Asn Gly His Lys Phe Ser Val Ser Gly Glu
            100                 105                 110

Gly Glu Gly Asp Ala Thr Tyr Gly Lys Leu Thr Leu Lys Phe Ile Cys
        115                 120                 125

Thr Thr Gly Lys Leu Pro Val Pro Trp Pro Thr Leu Val Thr Thr Phe
    130                 135                 140

Gly Tyr Gly Leu Gln Cys Phe Ala Arg Tyr Pro Asp His Met Lys Gln
145                 150                 155                 160

His Asp Phe Phe Lys Ser Ala Met Pro Glu Gly Tyr Val Gln Glu Arg
                165                 170                 175

Thr Ile Phe Phe Lys Asp Asp Gly Asn Tyr Lys Thr Arg Ala Glu Val
            180                 185                 190

Lys Phe Glu Gly Asp Thr Leu Val Asn Arg Ile Glu Leu Lys Gly Ile
        195                 200                 205

Asp Phe Lys Glu Asp Gly Asn Ile Leu Gly His Lys Leu Glu Tyr Asn
    210                 215                 220

Tyr Asn Ser His Asn Val Tyr Ile Met Ala Asp Lys Gln Lys Asn Gly
225                 230                 235                 240
```

```
Ile Lys Val Asn Phe Lys Ile Arg His Asn Ile Glu Asp Gly Ser Val
                245                 250                 255

Gln Leu Ala Asp His Tyr Gln Gln Asn Thr Pro Ile Gly Asp Gly Pro
            260                 265                 270

Val Leu Leu Pro Asp Asn His Tyr Leu Ser Tyr Gln Ser Ala Leu Ser
            275                 280                 285

Lys Asp Pro Asn Glu Lys Arg Asp His Met Val Leu Leu Glu Phe Val
            290                 295                 300

Thr Ala Ala Gly Ile Thr Leu Gly Met Asp Glu Leu Tyr Lys Glu Phe
305                 310                 315                 320

Glu Asn Gly Ala Val Glu Ile Ala Arg Cys Leu Arg Gly Gln Tyr Phe
                325                 330                 335

Gly Glu Leu Ala Leu Val Thr Asn Lys Pro Arg Ala Ala Ser Ala His
            340                 345                 350

Ala Ile Gly Thr Val Lys Cys Leu Ala Met Asp Val Gln Ala Phe Glu
            355                 360                 365

Arg Leu Leu Gly Pro Cys Met Glu Ile Met Lys Arg Asn Ile Ala Thr
370                 375                 380

Tyr Glu Glu Gln Leu Val Ala Ser Arg Val Ser Lys Gly Glu Glu Leu
385                 390                 395                 400

Phe Thr Gly Val Val Pro Ile Leu Val Glu Leu Asp Gly Asp Val Asn
                405                 410                 415

Gly His Arg Phe Ser Val Ser Gly Glu Gly Glu Gly Asp Ala Thr Tyr
            420                 425                 430

Gly Lys Leu Thr Leu Lys Phe Ile Cys Thr Thr Gly Lys Leu Pro Val
            435                 440                 445

Pro Trp Pro Thr Leu Val Thr Thr Leu Thr Trp Gly Val Gln Cys Phe
            450                 455                 460

Ser Arg Tyr Pro Asp His Met Lys Gln His Asp Phe Phe Lys Ser Ala
465                 470                 475                 480

Met Pro Glu Gly Tyr Val Gln Glu Arg Thr Ile Phe Phe Lys Asp Asp
                485                 490                 495

Gly Asn Tyr Lys Thr Arg Ala Glu Val Lys Phe Glu Gly Asp Thr Leu
            500                 505                 510

Val Asn Arg Ile Glu Leu Lys Gly Ile Asp Phe Lys Glu Asp Gly Asn
            515                 520                 525

Ile Leu Gly His Lys Leu Glu Tyr Asn Tyr Ile Ser His Asn Val Tyr
            530                 535                 540

Ile Thr Ala Asp Lys Gln Lys Asn Gly Ile Lys Ala His Phe Lys Ile
545                 550                 555                 560

Arg His Asn Ile Glu Asp Gly Ser Val Gln Leu Ala Asp His Tyr Gln
                565                 570                 575

Gln Asn Thr Pro Ile Gly Asp Gly Pro Val Leu Leu Pro Asp Asn His
            580                 585                 590

Tyr Leu Ser Thr Gln Ser Ala Leu Ser Lys Asp Pro Asn Glu Lys Arg
            595                 600                 605

Asp His Met Val Leu Leu Glu Phe Val Thr Ala Ala Gly Ile Thr Leu
            610                 615                 620

Gly Met Asp Glu Leu Tyr Lys
625                 630

<210> SEQ ID NO 74
<211> LENGTH: 863
```

<212> TYPE: PRT
<213> ORGANISM: Mus musculus

<400> SEQUENCE: 74

Met Asp Ala Arg Gly Gly Arg Pro Gly Asp Ser Pro Gly Thr
1               5                   10                  15

Thr Pro Ala Pro Gly Pro Pro Pro Pro Pro Ala Pro Pro
            20              25              30

Gln Pro Gln Pro Pro Ala Pro Pro Asn Pro Thr Thr Pro Ser
        35              40              45

His Pro Glu Ser Ala Asp Glu Pro Gly Pro Arg Ala Arg Leu Cys Ser
    50              55                  60

Arg Asp Ser Ala Cys Thr Pro Gly Ala Ala Lys Gly Gly Ala Asn Gly
65              70                  75                  80

Glu Cys Gly Arg Gly Glu Pro Gln Cys Ser Pro Glu Gly Pro Ala Arg
            85                  90                  95

Gly Pro Lys Val Ser Phe Ser Cys Arg Gly Ala Ala Ser Gly Pro Ser
            100                 105                 110

Ala Ala Glu Glu Ala Gly Ser Glu Glu Ala Gly Pro Ala Gly Glu Pro
            115                 120                 125

Arg Gly Ser Gln Ala Ser Phe Leu Gln Arg Gln Phe Gly Ala Leu Leu
    130                 135                 140

Gln Pro Gly Val Asn Lys Phe Ser Leu Arg Met Phe Gly Ser Gln Lys
145                 150                 155                 160

Ala Val Glu Arg Glu Gln Glu Arg Val Lys Ser Ala Gly Ala Trp Ile
                165                 170                 175

Ile His Pro Tyr Ser Asp Phe Arg Phe Tyr Trp Asp Phe Thr Met Leu
            180                 185                 190

Leu Phe Met Val Gly Asn Leu Ile Ile Ile Pro Val Gly Ile Thr Phe
            195                 200                 205

Phe Lys Asp Glu Thr Thr Ala Pro Trp Ile Val Phe Asn Val Val Ser
            210                 215                 220

Asp Thr Phe Phe Leu Met Asp Leu Val Leu Asn Phe Arg Thr Gly Ile
225                 230                 235                 240

Val Ile Glu Asp Asn Thr Glu Ile Ile Leu Asp Pro Glu Lys Ile Lys
                245                 250                 255

Lys Lys Tyr Leu Arg Thr Trp Phe Val Val Asp Phe Val Ser Ser Ile
            260                 265                 270

Pro Val Asp Tyr Ile Phe Leu Ile Val Glu Lys Gly Ile Asp Ser Glu
            275                 280                 285

Val Tyr Lys Thr Ala Arg Ala Leu Arg Ile Val Arg Phe Thr Lys Ile
    290                 295                 300

Leu Ser Leu Leu Arg Leu Leu Arg Leu Ser Arg Leu Ile Arg Tyr Ile
305                 310                 315                 320

His Gln Trp Glu Glu Ile Phe His Met Thr Tyr Asp Leu Ala Ser Ala
                325                 330                 335

Val Met Arg Ile Cys Asn Leu Ile Ser Met Met Leu Leu Leu Cys His
                340                 345                 350

Trp Asp Gly Cys Leu Gln Phe Leu Val Pro Met Leu Gln Asp Phe Pro
            355                 360                 365

Ser Asp Cys Trp Val Ser Ile Asn Asn Met Val Asn His Ser Trp Ser
    370                 375                 380

Glu Leu Tyr Ser Phe Ala Leu Phe Lys Ala Met Ser His Met Leu Cys
385                 390                 395                 400

```
Ile Gly Tyr Gly Arg Gln Ala Pro Glu Ser Met Thr Asp Ile Trp Leu
            405                 410                 415

Thr Met Leu Ser Met Ile Val Gly Ala Thr Cys Tyr Ala Met Phe Ile
            420                 425                 430

Gly His Ala Thr Ala Leu Ile Gln Ser Leu Asp Ser Ser Arg Arg Gln
            435                 440                 445

Tyr Gln Glu Lys Tyr Lys Gln Val Glu Gln Tyr Met Ser Phe His Lys
            450                 455                 460

Leu Pro Ala Asp Phe Arg Gln Lys Ile His Asp Tyr Glu His Arg
465                 470                 475                 480

Tyr Gln Gly Lys Met Phe Asp Glu Asp Ser Ile Leu Gly Glu Leu Asn
            485                 490                 495

Gly Pro Leu Arg Glu Glu Ile Val Asn Phe Asn Cys Arg Lys Leu Val
            500                 505                 510

Ala Ser Met Pro Leu Phe Ala Asn Ala Asp Pro Asn Phe Val Thr Ala
            515                 520                 525

Met Leu Thr Lys Leu Lys Phe Glu Val Phe Gln Pro Gly Asp Tyr Ile
            530                 535                 540

Ile Arg Glu Gly Thr Ile Gly Lys Lys Met Tyr Phe Ile Gln His Gly
545                 550                 555                 560

Val Val Ser Val Leu Thr Lys Gly Asn Lys Glu Met Lys Leu Ser Asp
            565                 570                 575

Gly Ser Tyr Phe Gly Glu Ile Cys Leu Leu Thr Arg Gly Arg Arg Thr
            580                 585                 590

Ala Ser Val Arg Ala Asp Thr Tyr Cys Arg Leu Tyr Ser Leu Ser Val
            595                 600                 605

Asp Asn Phe Asn Glu Val Leu Glu Glu Tyr Pro Met Met Arg Arg Ala
            610                 615                 620

Phe Glu Thr Val Ala Ile Asp Arg Leu Asp Arg Ile Gly Lys Lys Asn
625                 630                 635                 640

Ser Ile Leu Leu His Lys Val Gln His Asp Leu Ser Ser Gly Val Phe
            645                 650                 655

Asn Asn Gln Glu Asn Ala Ile Ile Gln Glu Ile Val Lys Tyr Asp Arg
            660                 665                 670

Glu Met Val Gln Gln Ala Glu Leu Gly Gln Arg Val Gly Leu Phe Pro
            675                 680                 685

Pro Pro Pro Pro Gln Val Thr Ser Ala Ile Ala Thr Leu Gln Gln
690                 695                 700

Ala Val Ala Met Ser Phe Cys Pro Gln Val Ala Arg Pro Leu Val Gly
705                 710                 715                 720

Pro Leu Ala Leu Gly Ser Pro Arg Leu Val Arg Arg Ala Pro Pro Gly
            725                 730                 735

Pro Leu Pro Pro Ala Ala Ser Pro Gly Pro Pro Ala Ala Ser Pro Pro
            740                 745                 750

Ala Ala Pro Ser Ser Pro Arg Ala Pro Arg Thr Ser Pro Tyr Gly Val
            755                 760                 765

Pro Gly Ser Pro Ala Thr Arg Val Gly Pro Ala Leu Pro Ala Arg Arg
            770                 775                 780

Leu Ser Arg Ala Ser Arg Pro Leu Ser Ala Ser Gln Pro Ser Leu Pro
785                 790                 795                 800

His Gly Val Pro Ala Pro Ser Pro Ala Ala Ser Ala Arg Pro Ala Ser
            805                 810                 815
```

```
Ser Ser Thr Pro Arg Leu Gly Pro Ala Pro Thr Ala Arg Thr Ala Ala
        820                 825                 830

Pro Ser Pro Asp Arg Arg Asp Ser Ala Ser Pro Gly Ala Ala Ser Gly
        835                 840                 845

Leu Asp Pro Leu Asp Ser Ala Arg Ser Arg Leu Ser Ser Asn Leu
        850                 855                 860

<210> SEQ ID NO 75
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Met Asx Cys Ile Asn Ser Lys Arg Lys Asp
  1               5                  10

<210> SEQ ID NO 76
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
gatccgatat catgggatgt atcaatagca agcgcaaaga tg                         42

<210> SEQ ID NO 77
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
ctagcatctt tgcgcttgct attgatacat cccatgatat cg                         42

<210> SEQ ID NO 78
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Gly Cys Ile Asn Ser Lys Arg Lys Asp
  1               5

<210> SEQ ID NO 79
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 79

His His His His His His
  1               5
```